US010919953B2

(12) United States Patent
Katada et al.

(10) Patent No.: US 10,919,953 B2
(45) Date of Patent: Feb. 16, 2021

(54) FCGAMMARIIB-SPECIFIC FC REGION VARIANT

(71) Applicant: Chugai Seiyaku Kabushiki Kaisha, Tokyo (JP)

(72) Inventors: Hitoshi Katada, Shizuoka (JP); Shojiro Kadono, Kanagawa (JP); Futa Mimoto, Shizuoka (JP); Tomoyuki Igawa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 629 days.

(21) Appl. No.: 14/423,269

(22) PCT Filed: Aug. 23, 2013

(86) PCT No.: PCT/JP2013/072507
§ 371 (c)(1),
(2) Date: Feb. 23, 2015

(87) PCT Pub. No.: WO2014/030728
PCT Pub. Date: Feb. 27, 2014

(65) Prior Publication Data
US 2015/0299296 A1  Oct. 22, 2015

(30) Foreign Application Priority Data
Aug. 24, 2012 (JP) .............................. JP2012-185868

(51) Int. Cl.
*C07K 16/00* (2006.01)
*C12P 21/08* (2006.01)
*A61K 39/395* (2006.01)
*C07K 16/30* (2006.01)
*C07K 16/28* (2006.01)
*C07K 1/00* (2006.01)
*A61K 9/00* (2006.01)
*A61K 39/00* (2006.01)

(52) U.S. Cl.
CPC .............. *C07K 16/00* (2013.01); *C07K 16/28* (2013.01); *C07K 16/2866* (2013.01); *C07K 16/303* (2013.01); *A61K 9/0019* (2013.01); *A61K 2039/505* (2013.01); *C07K 2317/52* (2013.01); *C07K 2317/524* (2013.01); *C07K 2317/53* (2013.01); *C07K 2317/71* (2013.01); *C07K 2317/72* (2013.01); *C07K 2317/92* (2013.01); *C07K 2317/94* (2013.01); *C07K 2319/30* (2013.01); *Y02A 50/412* (2018.01)

(58) Field of Classification Search
None
See application file for complete search history.

(56) References Cited

U.S. PATENT DOCUMENTS

| | | |
|---|---|---|
| 5,827,733 A | 10/1998 | Lee et al. |
| 5,994,524 A | 11/1999 | Matsushima et al. |
| 6,024,956 A | 2/2000 | Matsushima et al. |
| 6,074,642 A | 6/2000 | Wang et al. |
| 6,096,506 A | 8/2000 | Lee et al. |
| 6,165,745 A | 12/2000 | Ward et al. |
| 6,245,894 B1 | 6/2001 | Matsushima et al. |
| 6,737,056 B1 | 5/2004 | Presta |
| 6,821,505 B2 | 11/2004 | Ward |
| 7,247,302 B1 | 7/2007 | Rosok et al. |
| 7,261,893 B2 | 8/2007 | Geertruida et al. |
| 7,282,568 B2 | 10/2007 | Teeling et al. |
| 7,317,091 B2 | 1/2008 | Lazar et al. |
| 7,320,789 B2 | 1/2008 | Aghajanian et al. |
| 7,371,826 B2 | 5/2008 | Presta |
| 7,632,499 B2 | 12/2009 | Davies et al. |
| 7,662,925 B2 | 2/2010 | Lazar et al. |
| 7,670,600 B2 | 3/2010 | Dell Acqua et al. |

(Continued)

FOREIGN PATENT DOCUMENTS

| | | |
|---|---|---|
| AU | 2011/244851 | 11/2011 |
| AU | 2012/222252 | 8/2012 |

(Continued)

OTHER PUBLICATIONS

U.S. Appl. No. 14/404,051, filed Nov. 26, 2014, Igawa et al.
Malbec et al., "Antibodies against growth factor receptors can inhibit the proliferation of transformed cells via a cis-interaction with inhibitory FcR," *Immunol Lett.*, Mar. 30, 2012;143(1):28-33.

(Continued)

*Primary Examiner* — Chun W Dahle
(74) *Attorney, Agent, or Firm* — Fish & Richardson P.C.

(57) ABSTRACT

An objective of the present invention is to provide an Fc region variant with enhanced FcγRIIb-binding activity, and/or enhanced binding selectivity to FcγRIIb compared to FcγRIIa (type R), as compared to those of a polypeptide containing an Fc region to which an amino acid alteration(s) has not been introduced; a polypeptide which includes the Fc region variant; a pharmaceutical composition containing the polypeptide; preventing therapeutic or preventive agent for immunological inflammatory diseases that includes the pharmaceutical composition; a production method thereof; and a method of enhancing FcγRIIb-binding activity and also enhancing binding selectivity to FcγRIIb compared to FcγRIIa (type R).

It was found that a polypeptide containing an antibody Fc region variant that contains an amino acid sequence in which an amino-acid alteration at position 238 (EU numbering) is combined with other specific amino-acid alterations enhances FcγRIIb-binding activity, and/or enhances binding selectivity to FcγRIIb compared to FcγRIIa (type R).

8 Claims, 37 Drawing Sheets

Specification includes a Sequence Listing.

(56) References Cited

U.S. PATENT DOCUMENTS

| | | |
|---|---|---|
| 7,785,791 B2 | 8/2010 | Presta |
| 7,807,159 B2 | 10/2010 | Chin et al. |
| 7,888,486 B2 | 2/2011 | Walsh et al. |
| 7,951,917 B1 | 5/2011 | Arathoon et al. |
| 7,960,512 B2 | 6/2011 | Stavenhagen et al. |
| 8,147,829 B2 | 4/2012 | Hariharan et al. |
| 8,188,231 B2 | 5/2012 | Lazar et al. |
| 8,323,962 B2 | 12/2012 | Dell Acqua et al. |
| 8,329,867 B2 | 12/2012 | Lazar et al. |
| 8,367,805 B2 | 2/2013 | Chamberlain et al. |
| 8,415,459 B2 | 4/2013 | La Vallie et al. |
| 8,524,867 B2 | 9/2013 | Bernett et al. |
| 8,551,485 B2 | 10/2013 | Bernett et al. |
| 8,562,991 B2 | 10/2013 | Igawa et al. |
| 8,568,726 B2 | 10/2013 | Beaumont et al. |
| 8,592,562 B2 | 11/2013 | Kannan et al. |
| 8,604,174 B2 | 12/2013 | Babcook et al. |
| 8,637,641 B2 | 1/2014 | Dahiyat et al. |
| 8,685,725 B2 | 4/2014 | Beliard et al. |
| 8,735,545 B2 | 5/2014 | Lazar et al. |
| 8,753,629 B2 | 6/2014 | Lazar et al. |
| 8,802,823 B2 | 8/2014 | Lazar et al. |
| 8,999,343 B2 | 4/2015 | Han et al. |
| 9,029,515 B2 | 5/2015 | Pons et al. |
| 9,051,373 B2 | 6/2015 | Lazar et al. |
| 9,079,949 B1 | 7/2015 | Andrien et al. |
| 9,107,861 B1 | 8/2015 | Andrien, Jr. et al. |
| 9,200,060 B2 | 12/2015 | Kannan et al. |
| 9,605,061 B2 | 3/2017 | Lazar et al. |
| 9,765,135 B2 | 9/2017 | Ruike |
| 9,890,218 B2 | 2/2018 | Mimoto et al. |
| 9,969,800 B2 | 5/2018 | Igawa et al. |
| 10,000,560 B2 | 6/2018 | Ruike et al. |
| 10,024,867 B2 | 7/2018 | Igawa |
| 10,253,100 B2 | 4/2019 | Igawa et al. |
| 10,519,229 B2 | 12/2019 | Igawa et al. |
| 2002/0082396 A1 | 6/2002 | Matsushima et al. |
| 2004/0001822 A1 | 1/2004 | Levanon et al. |
| 2004/0001839 A1 | 1/2004 | Levanon et al. |
| 2004/0002450 A1 | 1/2004 | Lazarovits et al. |
| 2004/0110226 A1* | 6/2004 | Lazar |
| 2005/0260213 A1 | 11/2005 | Koenig et al. |
| 2006/0134709 A1 | 6/2006 | Stavenhagen et al. |
| 2006/0275283 A1 | 12/2006 | Van Vlijmen et al. |
| 2007/0009523 A1 | 1/2007 | Presta et al. |
| 2007/0148164 A1 | 6/2007 | Farrington et al. |
| 2007/0190056 A1 | 8/2007 | Kambadur et al. |
| 2007/0224188 A1 | 9/2007 | Allan et al. |
| 2007/0231329 A1* | 10/2007 | Lazar ............... C07K 16/2863 424/144.1 |
| 2007/0237767 A1 | 10/2007 | Lazar et al. |
| 2007/0248602 A1 | 10/2007 | Lazar et al. |
| 2007/0253951 A1 | 11/2007 | Ng et al. |
| 2008/0044417 A1 | 2/2008 | Johnson et al. |
| 2008/0051563 A1 | 2/2008 | Lazar et al. |
| 2008/0089892 A1 | 4/2008 | Allan et al. |
| 2008/0138349 A1 | 6/2008 | Stavenhagen et al. |
| 2008/0181890 A1 | 7/2008 | Lazar et al. |
| 2008/0199471 A1 | 8/2008 | Bernett et al. |
| 2008/0292637 A1 | 11/2008 | Fishman |
| 2009/0035836 A1 | 2/2009 | Datta et al. |
| 2009/0041770 A1 | 2/2009 | Chamberlain et al. |
| 2009/0053240 A1 | 2/2009 | Lazar et al. |
| 2009/0076251 A1 | 3/2009 | Koenig et al. |
| 2009/0136485 A1 | 5/2009 | Chu et al. |
| 2009/0142340 A1 | 6/2009 | Lazar |
| 2009/0324589 A1 | 12/2009 | Igawa et al. |
| 2010/0098730 A1 | 4/2010 | Lowman et al. |
| 2010/0099147 A1 | 4/2010 | Hariharan et al. |
| 2010/0129365 A1 | 5/2010 | Kim et al. |
| 2010/0184959 A1 | 7/2010 | Guler-Gane et al. |
| 2010/0249482 A1 | 9/2010 | Chung et al. |
| 2010/0331527 A1 | 12/2010 | Davis et al. |
| 2011/0021755 A1 | 1/2011 | Lazar et al. |
| 2011/0059093 A1 | 3/2011 | Bohrmann et al. |
| 2011/0105724 A1 | 5/2011 | Clegg et al. |
| 2011/0111406 A1 | 5/2011 | Igawa et al. |
| 2011/0135662 A1 | 6/2011 | Finney et al. |
| 2011/0223658 A1 | 9/2011 | Beliard et al. |
| 2011/0229489 A1 | 9/2011 | Pons et al. |
| 2012/0009188 A1 | 1/2012 | Behrens |
| 2012/0093818 A1 | 4/2012 | Jackson et al. |
| 2012/0149876 A1 | 6/2012 | Kreudenstein et al. |
| 2012/0189639 A1 | 7/2012 | Schebye et al. |
| 2012/0244578 A1 | 9/2012 | Kannan et al. |
| 2012/0301488 A1 | 11/2012 | Zhang et al. |
| 2012/0321620 A1 | 12/2012 | Chu et al. |
| 2013/0011866 A1 | 1/2013 | Igawa et al. |
| 2013/0085074 A1 | 4/2013 | Walker et al. |
| 2013/0085265 A1 | 4/2013 | Jackson et al. |
| 2013/0131319 A1 | 5/2013 | Igawa et al. |
| 2013/0209489 A1 | 8/2013 | Han et al. |
| 2013/0247234 A1 | 9/2013 | McWhirter et al. |
| 2013/0259876 A1 | 10/2013 | Murphy et al. |
| 2013/0302399 A1 | 11/2013 | Feldhaus et al. |
| 2013/0303396 A1 | 11/2013 | Igawa et al. |
| 2013/0336963 A1 | 12/2013 | Igawa et al. |
| 2014/0044730 A1 | 2/2014 | Yancopoulos et al. |
| 2014/0082760 A1 | 3/2014 | McWhirter et al. |
| 2014/0086916 A1 | 3/2014 | Zha |
| 2014/0093496 A1 | 4/2014 | Mimoto et al. |
| 2014/0105889 A1 | 4/2014 | Igawa et al. |
| 2014/0112926 A1 | 4/2014 | Liu |
| 2014/0127209 A1 | 5/2014 | Grabstein et al. |
| 2014/0199294 A1 | 7/2014 | Mimoto et al. |
| 2014/0227292 A1 | 8/2014 | Flanagan et al. |
| 2014/0234340 A1 | 8/2014 | Igawa et al. |
| 2014/0255398 A1 | 9/2014 | Igawa et al. |
| 2014/0271459 A1 | 9/2014 | Dutzar et al. |
| 2014/0294833 A1 | 10/2014 | Desjarlais et al. |
| 2014/0335089 A1 | 11/2014 | Igawa et al. |
| 2014/0356371 A1 | 12/2014 | Swergold et al. |
| 2014/0363426 A1 | 12/2014 | Moore et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0079088 A1 | 3/2015 | Lowman et al. |
| 2015/0166636 A1 | 6/2015 | Igawa et al. |
| 2015/0166654 A1 | 6/2015 | Igawa et al. |
| 2015/0203577 A1 | 7/2015 | Igawa et al. |
| 2015/0210763 A1 | 7/2015 | Kuramochi et al. |
| 2015/0252107 A1 | 9/2015 | Stevis et al. |
| 2015/0299313 A1 | 10/2015 | Igawa et al. |
| 2015/0344570 A1 | 12/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0200807 A1 | 7/2016 | Ruike et al. |
| 2016/0229908 A1 | 8/2016 | Igawa et al. |
| 2016/0229915 A1 | 8/2016 | Igawa et al. |
| 2016/0244526 A1 | 8/2016 | Igawa et al. |
| 2017/0022270 A1 | 1/2017 | Igawa et al. |
| 2017/0181987 A1 | 6/2017 | Camilla et al. |
| 2018/0155451 A1 | 6/2018 | Mimoto et al. |
| 2019/0112393 A1 | 4/2019 | Igawa et al. |
| 2019/0185557 A1 | 6/2019 | Igawa et al. |
| 2019/0218309 A1 | 7/2019 | Igawa et al. |
| 2019/0233525 A1 | 8/2019 | Igawa et al. |

FOREIGN PATENT DOCUMENTS

| | | |
|---|---|---|
| AU | 2015/227424 | 10/2015 |
| CA | 2 721 052 | 10/2009 |
| CA | 2 794 860 | 10/2011 |
| CA | 2 815 266 | 5/2012 |
| CA | 2 827 923 | 8/2012 |
| CA | 2 831 770 | 10/2012 |
| CN | 1291198 | 4/2001 |
| CN | 1763097 | 4/2006 |
| CN | 101001873 | 7/2007 |
| CN | 101014619 | 8/2007 |
| CN | 101098890 | 1/2008 |
| CN | 101277976 | 10/2008 |
| CN | 101282992 | 10/2008 |

(56) References Cited

FOREIGN PATENT DOCUMENTS

| | | |
|---|---|---|
| CN | 102056946 | 5/2011 |
| CN | 103492565 | 1/2014 |
| CN | 103827300 | 5/2014 |
| CN | 102633880 | 2/2015 |
| CO | 07124506 | 11/2007 |
| CO | 11080753 | 6/2011 |
| CO | 13047993 | 3/2013 |
| CO | 15075851 | 4/2015 |
| EA | 2008/01027 | 10/2008 |
| EP | 1 509 770 | 3/2005 |
| EP | 0 770 628 | 9/2006 |
| EP | 1 787 998 | 5/2007 |
| EP | 2 006 381 | 12/2008 |
| EP | 2 189 526 | 5/2010 |
| EP | 2 196 541 | 6/2010 |
| EP | 2 202 245 | 6/2010 |
| EP | 2 275 443 | 1/2011 |
| EP | 2 314 618 | 4/2011 |
| EP | 2 366 713 | 9/2011 |
| EP | 2 368 911 | 9/2011 |
| EP | 2 431 393 | 3/2012 |
| EP | 2 471 813 | 7/2012 |
| EP | 2 543 730 | 1/2013 |
| EP | 2 647 706 | 10/2013 |
| EP | 2 679 681 | 1/2014 |
| EP | 2 698 431 | 2/2014 |
| EP | 2 728 002 | 5/2014 |
| EP | 2 762 166 | 8/2014 |
| EP | 2 762 564 | 8/2014 |
| EP | 2 818 183 | 12/2014 |
| EP | 2 853 898 | 4/2015 |
| EP | 2 889 377 | 7/2015 |
| EP | 2 940 043 | 11/2015 |
| EP | 2 940 135 | 11/2015 |
| EP | 3 240 804 | 11/2017 |
| JP | H01-144991 | 6/1989 |
| JP | H02-501112 | 4/1990 |
| JP | H02-163085 | 6/1990 |
| JP | H08-217799 | 8/1996 |
| JP | 2003-512019 | 4/2003 |
| JP | 2006-512407 | 4/2006 |
| JP | 2006-517525 | 7/2006 |
| JP | 2006-519583 | 8/2006 |
| JP | 2006-524039 | 10/2006 |
| JP | 3865418 | 1/2007 |
| JP | 2007-532139 | 11/2007 |
| JP | 2008-505174 | 2/2008 |
| JP | 2008-510466 | 4/2008 |
| JP | 2008-511292 | 4/2008 |
| JP | 2009-511067 | 3/2009 |
| JP | 2009-541352 | 11/2009 |
| JP | 2010-079667 | 3/2010 |
| JP | 2010-514460 | 5/2010 |
| JP | 2010-250830 | 11/2010 |
| JP | 2011-504096 | 2/2011 |
| JP | 2011-184418 | 9/2011 |
| JP | 2012-505833 | 3/2012 |
| JP | 2012-512641 | 6/2012 |
| JP | 2013-518606 | 5/2013 |
| JP | 2013-531486 | 8/2013 |
| JP | 2013-537425 | 10/2013 |
| JP | 2014-055145 | 3/2014 |
| JP | 2014-528906 | 10/2014 |
| JP | 5756291 | 7/2015 |
| JP | 2016-026190 | 2/2016 |
| JP | 6433297 | 12/2018 |
| KR | 2011/0004435 | 1/2011 |
| KR | 2012-0035192 | 4/2012 |
| KR | 2014/0005864 | 1/2014 |
| RU | 2236222 | 9/2004 |
| RU | 2005/112742 | 1/2006 |
| RU | 2325186 | 5/2008 |
| RU | 2006/142852 | 6/2008 |
| RU | 2337107 | 10/2008 |
| RU | 2007/121679 | 12/2008 |
| RU | 2367667 | 9/2009 |
| RU | 2390527 | 5/2010 |
| RU | 2398777 | 9/2010 |
| RU | 2009/112723 | 10/2010 |
| RU | 2010/150931 | 6/2012 |
| SG | 183867 | 10/2012 |
| SG | 192945 | 9/2013 |
| TW | 416960 | 1/2001 |
| TW | 2010/00127 | 1/2010 |
| TW | 2011/16625 | 5/2011 |
| TW | 2012/02419 | 1/2012 |
| TW | 2016/43190 | 12/2016 |
| TW | 2017/12032 | 4/2017 |
| WO | WO 88/004692 | 6/1988 |
| WO | WO 91/13631 | 9/1991 |
| WO | WO 94/21681 | 9/1994 |
| WO | WO 95/002187 | 1/1995 |
| WO | WO 95/29697 | 11/1995 |
| WO | WO 96/02576 | 2/1996 |
| WO | WO 97/34631 | 9/1997 |
| WO | WO 98/05787 | 2/1998 |
| WO | WO 99/40117 | 8/1999 |
| WO | WO 99/51642 | 10/1999 |
| WO | WO 99/58572 | 11/1999 |
| WO | WO 00/15214 | 3/2000 |
| WO | WO 00/42072 | 7/2000 |
| WO | WO 02/09641 | 2/2002 |
| WO | WO 02/060919 | 8/2002 |
| WO | WO 03/027248 | 4/2003 |
| WO | WO 2003/057881 | 7/2003 |
| WO | WO 03/074679 | 9/2003 |
| WO | WO 2003/105757 | 12/2003 |
| WO | WO 2004/007553 | 1/2004 |
| WO | WO 2004/024890 | 3/2004 |
| WO | WO 2004/029207 | 4/2004 |
| WO | WO 2004/035752 | 4/2004 |
| WO | WO 2004/037861 | 5/2004 |
| WO | WO 2004/058797 | 7/2004 |
| WO | WO 2004/063351 | 7/2004 |
| WO | WO 2004/092219 | 10/2004 |
| WO | WO 2004/099249 | 11/2004 |
| WO | WO 2004/108157 | 12/2004 |
| WO | WO 2005/023193 | 3/2005 |
| WO | WO 2005/037867 | 4/2005 |
| WO | WO 2005/047307 | 5/2005 |
| WO | WO 2005/047327 | 5/2005 |
| WO | WO 2005/056759 | 6/2005 |
| WO | WO 2005/059106 | 6/2005 |
| WO | WO 2005/070963 | 8/2005 |
| WO | WO 2005/077981 | 8/2005 |
| WO | WO 2005/092925 | 10/2005 |
| WO | WO 2005/094446 | 10/2005 |
| WO | WO 2005/115452 | 12/2005 |
| WO | WO 2005/123780 | 12/2005 |
| WO | WO 2006/004663 | 1/2006 |
| WO | WO 2006/015371 | 2/2006 |
| WO | WO 2006/016644 | 2/2006 |
| WO | WO 2006/019447 | 2/2006 |
| WO | WO 2006/020114 | 2/2006 |
| WO | WO 2006/023403 | 3/2006 |
| WO | WO 2006/031370 | 3/2006 |
| WO | WO 2006/036291 | 4/2006 |
| WO | WO 2006/047350 | 5/2006 |
| WO | WO 2006/050166 | 5/2006 |
| WO | WO 2006/053301 | 5/2006 |
| WO | WO 2006/071877 | 7/2006 |
| WO | WO 2006/076594 | 7/2006 |
| WO | WO 2006/083182 | 8/2006 |
| WO | WO 2006/083183 | 8/2006 |
| WO | WO 2006/085938 | 8/2006 |
| WO | WO 2006/085967 | 8/2006 |
| WO | WO 2006/088494 | 8/2006 |
| WO | WO 2006/102095 | 9/2006 |
| WO | WO 2006/105338 | 10/2006 |
| WO | WO 2006/106905 | 10/2006 |
| WO | WO 2006/113643 | 10/2006 |
| WO | WO 2006/116260 | 11/2006 |
| WO | WO 2006/116269 | 11/2006 |
| WO | WO 2006/130834 | 12/2006 |

(56) References Cited

FOREIGN PATENT DOCUMENTS

| | | |
|---|---|---|
| WO | WO 2006/133486 | 12/2006 |
| WO | WO 2007/001422 | 1/2007 |
| WO | WO 2007/008943 | 1/2007 |
| WO | WO 2007/021841 | 2/2007 |
| WO | WO 2007/024249 | 3/2007 |
| WO | WO 2007/024535 | 3/2007 |
| WO | WO 2007/041635 | 4/2007 |
| WO | WO 2007/044411 | 4/2007 |
| WO | WO 2007/044616 | 4/2007 |
| WO | WO 2007/047112 | 4/2007 |
| WO | WO 2007/047578 | 4/2007 |
| WO | WO 2007/084253 | 7/2007 |
| WO | WO 2007/092772 | 8/2007 |
| WO | WO 2007/114319 | 10/2007 |
| WO | WO 2007/114325 | 10/2007 |
| WO | WO 2007/150015 | 12/2007 |
| WO | WO 2007/150016 | 12/2007 |
| WO | WO 2008/002933 | 1/2008 |
| WO | WO 2008/022152 | 2/2008 |
| WO | WO 2008/030706 | 3/2008 |
| WO | WO 2008/031056 | 3/2008 |
| WO | WO 2008/036688 | 3/2008 |
| WO | JP 2008-519860 | 6/2008 |
| WO | WO 2008/091798 | 7/2008 |
| WO | WO 2008/091954 | 7/2008 |
| WO | WO 2008/092117 | 7/2008 |
| WO | WO 2008/098115 | 8/2008 |
| WO | WO 2008/121160 | 10/2008 |
| WO | WO 2008/130969 | 10/2008 |
| WO | WO 2008/143954 | 11/2008 |
| WO | WO 2008/150494 | 12/2008 |
| WO | WO 2009/000098 | 12/2008 |
| WO | WO 2009/000099 | 12/2008 |
| WO | WO 2009/008529 | 1/2009 |
| WO | WO 2009/026117 | 2/2009 |
| WO | WO 2009/032145 | 3/2009 |
| WO | WO 2009/032782 | 3/2009 |
| WO | WO 2009/041062 | 4/2009 |
| WO | WO 2009/041643 | 4/2009 |
| WO | WO 2009/053358 | 4/2009 |
| WO | WO 2009/058346 | 5/2009 |
| WO | WO 2009/058492 | 5/2009 |
| WO | WO 2009/062083 | 5/2009 |
| WO | WO 2009/086320 | 7/2009 |
| WO | WO 2009/089846 | 7/2009 |
| WO | WO 2009/095235 | 8/2009 |
| WO | WO 2009/125825 | 10/2009 |
| WO | WO 2009/137880 | 11/2009 |
| WO | WO 2009/139822 | 11/2009 |
| WO | WO 2009/155513 | 12/2009 |
| WO | WO 2010/015608 | 2/2010 |
| WO | WO 2010/033736 | 3/2010 |
| WO | WO 2010/045193 | 4/2010 |
| WO | WO 2010/058860 | 5/2010 |
| WO | WO 2010/070094 | 6/2010 |
| WO | WO 2010/077854 | 7/2010 |
| WO | WO 2010/081173 | 7/2010 |
| WO | WO 2010/085682 | 7/2010 |
| WO | WO 2010/106180 | 9/2010 |
| WO | WO 2010/107109 | 9/2010 |
| WO | WO 2010/151338 | 12/2010 |
| WO | WO 2011/021009 | 2/2011 |
| WO | WO 2011/043643 | 4/2011 |
| WO | WO 2011/044368 | 4/2011 |
| WO | WO 2011/091078 | 7/2011 |
| WO | WO 2011/100271 | 8/2011 |
| WO | WO 2011/107989 | 9/2011 |
| WO | WO 2011/108714 | 9/2011 |
| WO | WO 2011/111007 | 9/2011 |
| WO | WO 2011/122011 | 10/2011 |
| WO | WO 2011/150008 | 12/2011 |
| WO | WO 2011/151432 | 12/2011 |
| WO | WO 2012/016227 | 2/2012 |
| WO | WO 2012/024242 | 2/2012 |
| WO | WO 2012/033953 | 3/2012 |
| WO | WO 2012/044831 | 4/2012 |
| WO | WO 2012/058768 | 5/2012 |
| WO | WO 2012/073992 | 6/2012 |
| WO | WO 2012/093704 | 7/2012 |
| WO | WO 2012/115241 | 8/2012 |
| WO | WO 2012/125850 | 9/2012 |
| WO | WO 2012/132067 | 10/2012 |
| WO | WO 2012/133782 | 10/2012 |
| WO | WO 2013/002362 | 1/2013 |
| WO | WO 2013/004842 | 1/2013 |
| WO | WO 2013/012733 | 1/2013 |
| WO | WO 2013/046704 | 4/2013 |
| WO | WO 2013/046722 | 4/2013 |
| WO | WO 2013/047729 | 4/2013 |
| WO | WO 2013/047748 | 4/2013 |
| WO | WO 2013/047752 | 4/2013 |
| WO | WO 2013/063702 | 5/2013 |
| WO | WO 2013/081143 | 6/2013 |
| WO | WO 2013/125667 | 8/2013 |
| WO | WO 2013/138680 | 9/2013 |
| WO | WO 2013/138681 | 9/2013 |
| WO | WO 2013/152001 | 10/2013 |
| WO | WO 2013/166099 | 11/2013 |
| WO | WO 2013/180200 | 12/2013 |
| WO | WO 2013/180201 | 12/2013 |
| WO | WO 2013/186719 | 12/2013 |
| WO | WO 2014/006217 | 1/2014 |
| WO | WO 2014/028354 | 2/2014 |
| WO | WO 2014/030728 | 2/2014 |
| WO | WO 2014/043344 | 3/2014 |
| WO | WO 2014/074532 | 5/2014 |
| WO | WO 2014/100689 | 6/2014 |
| WO | WO 2014/104165 | 7/2014 |
| WO | WO 2014/114651 | 7/2014 |
| WO | WO 2014/140366 | 9/2014 |
| WO | WO 2014/144080 | 9/2014 |
| WO | WO 2014/144577 | 9/2014 |
| WO | WO 2014/144903 | 9/2014 |
| WO | WO 2014/145159 | 9/2014 |
| WO | WO 2014/145806 | 9/2014 |
| WO | WO 2014/150983 | 9/2014 |
| WO | WO 2014/163101 | 10/2014 |
| WO | WO 2014/164959 | 10/2014 |
| WO | WO 2014/182676 | 11/2014 |
| WO | WO 2014/184384 | 11/2014 |
| WO | WO 2014/190441 | 12/2014 |
| WO | WO 2015/022658 | 2/2015 |
| WO | WO 2015/042250 | 3/2015 |
| WO | WO 2015/077491 | 5/2015 |
| WO | WO 2015/111008 | 7/2015 |
| WO | WO 2015/134894 | 9/2015 |
| WO | WO 2015/162590 | 10/2015 |
| WO | WO 2016/000813 | 1/2016 |
| WO | WO 2016/073853 | 5/2016 |
| WO | WO 2016/073879 | 5/2016 |
| WO | WO 2016/073906 | 5/2016 |
| WO | WO 2016/092439 | 6/2016 |
| WO | WO 2016/098356 | 6/2016 |
| WO | WO 2016/098357 | 6/2016 |
| WO | WO 2016/125495 | 8/2016 |
| WO | WO 2016/168613 | 10/2016 |
| WO | WO 2017/046994 | 3/2017 |
| WO | WO 2017/049011 | 3/2017 |
| WO | WO 2017/104783 | 6/2017 |
| WO | WO 2017/110981 | 6/2017 |
| WO | WO 2017/120523 | 7/2017 |
| WO | WO 2017/217525 | 12/2017 |
| WO | WO 2018/025982 | 2/2018 |
| WO | WO 2018/169993 | 9/2018 |

OTHER PUBLICATIONS

Wenink et al., "The inhibitory Fc gamma IIb receptor dampens TLR4-mediated immune responses and is selectively up-regulated on dendritic cells from rheumatoid arthritis patients with quiescent disease," *J Immunol.*, Oct. 1, 2009;183(7):4509-20. doi: 10.4049/jimmunol.0900153. Epub Sep. 4, 2009.

(56) References Cited

OTHER PUBLICATIONS

Zhang et al., "Immune complex/Ig negatively regulate TLR4-triggered inflammatory response in macrophages through Fc gamma RIIb-dependent PGE2 production," *J Immunol.*, Jan. 1, 2009;182(1):554-62.

Beringhelli et al., "pH and ionic strength dependence of protein (un)folding and ligand binding to bovine beta-lactoglobulins A and B," *Biochemistry*, Dec. 24, 2002;41(51):15415-22.

Epstein, "Non-randomness of amino-acid changes in the evolution of homologous proteins," *Nature*, Jul. 22, 1967;215(5099):355-9.

Idusogie et al., "Engineered antibodies with increased activity to recruit complement," *J Immunol.*, Feb. 15, 2001;166(4):2571-5.

Information Meeting on Antibody Engineering Technologies, Copyright © Chugai Pharmaceutical Co., Ltd., Dec. 18, 2012.

Liu et al., "Asymmetrical Fc engineering greatly enhances antibody-dependent cellular cytotoxicity (ADCC) effector function and stability of the modified antibodies," *J Biol Chem.*, Feb. 7, 2014;289(6):3571-90. doi: 10.1074/jbc.M113.513366. Epub Dec. 5, 2013.

Luttrell et al., "Reaction coupling of chelation and antigen binding in the calcium ion-dependent antibody binding of cyclic AMP," *J Biol Chem.*, Nov. 15, 1991;266(32):21626-30.

Mimoto et al., "Novel asymmetrically engineered antibody Fc variant with superior FcγR binding affinity and specificity compared with afucosylated Fc variant," *MAbs.*, Mar.-Apr. 2013;5(2):229-36. doi: 10.4161/mabs.23452. Epub Feb. 13, 2013.

Moore et al., "Engineered Fc variant antibodies with enhanced ability to recruit complement and mediate effector functions," *MAbs.*, Mar.-Apr. 2010;2(2):181-9.

Okabe, "Proprietary Innovative Antibody Engineering Technologies in Chugai Pharmaceutical," Information meeting on Antibody Engineering Technologies, Dec. 18, 2012, 78 pages.

Mimoto et al., "Engineered antibody Fc variant with selectively enhanced FcγRIIb binding over both FcγRIIa(R131) and FcγRIIa(H131)," *Protein Eng Des Sel.*, Oct. 2013;26(10):589-98. doi: 10.1093/protein/gzt022. Epub Jun. 5, 2013.

U.S. Appl. No. 14/001,218, filed Aug. 23, 2013, Mimoto et al.
U.S. Appl. No. 14/127,576, filed Dec. 19, 2013, Mimoto et al.
U.S. Appl. No. 14/347,034, filed Mar. 25, 2014, Igawa et al.
U.S. Appl. No. 14/347,187, filed Mar. 25, 2014, Igawa et al.
U.S. Appl. No. 14/347,321, filed Mar. 26, 2014, Igawa et al.
U.S. Appl. No. 14/361,013, filed May 28, 2014, Igawa et al.
U.S. Appl. No. 14/379,825, filed Aug. 20, 2014, Igawa et al.

Amigorena et al., "Fc gamma RII expression in resting and activated B lymphocytes," *Eur J Immunol.*, 19(8):1379-85 (1989).

Amigorena et al., "Cytoplasmic domain heterogeneity and functions of IgG Fc receptors in B lymphocytes," *Science*, 256(5065):1808-12 (1992).

Armour et al., "Differential binding to human FcgammaRIIa and FcgammaRIIb receptors by human IgG wildtype and mutant antibodies," *Mol Immunol.*, 40(9):585-93 (2003).

Blank et al., Decreased transcription of the human FCGR2B gene mediated by the −343 G/C promoter polymorphism and association with systemic lupus erythematosus. *Hum Genet.*, 117(2-3):220-7 (2005).

Boruchov et al., "Activating and inhibitory IgG Fc receptors on human DCs mediate opposing functions," *J Clin Invest.*, Oct. 2005;115(10):2914-23. Epub Sep. 15, 2005.

Boumpas et al., "A short course of BG9588 (anti-CD40 ligand antibody) improves serologic activity and decreases hematuria in patients with proliferative lupus glomerulonephritis," *Arthritis Rheum.*, 48(3):719-27 (2003).

Bruhns et al., Specificity and affinity of human Fcgamma receptors and their polymorphic variants for human IgG subclasses, *Blood*, Apr. 16, 2009;113(16):3716-25. doi: 10.1182/blood-2008-09-179754. Epub Nov. 18, 2008.

Cartron et al., "Therapeutic activity of humanized anti-CD20 monoclonal antibody and polymorphism in IgG Fc receptor FcgammaRIIIa gene," *Blood*, 99(3):754-8 (2002).

Cemerski et al., "Suppression of mast cell degranulation through a dual-targeting tandem IgE-IgG Fc domain biologic engineered to bind with high affinity to FcγRIIb," *Immunol Lett.*, Mar. 30, 2012;143(1):34-43. doi: 10.1016/j.imlet.2012.01.008. Epub Jan. 25, 2012.

Chen et al., "Association of a transmembrane polymorphism of Fcgamma receptor IIb (FCGR2B) with systemic lupus erythematosus in Taiwanese patients," *Arthritis Rheum.*, 54(12):3908-17 (2006).

Chu et al., "Inhibition of B cell receptor-mediated activation of primary human B cells by coengagement of CD19 and FcgammaRIIb with Fc-engineered antibodies," *Mol Immunol.*, Sep. 2008;45(15):3926-33. doi: 10.1016/j.molimm.2008.06.027. Epub Aug. 8, 2008.

Chu et al., "Reduction of total IgE by targeted coengagement of IgE B-cell receptor and FcγRIIb with Fc-engineered antibody," *J Allergy Clin Immunol.*, Apr. 2012;129(4):1102-15. doi: 10.1016/j.jaci.2011.11.029. Epub Jan. 16, 2012.

Chuntharapai et al., "Isotype-dependent inhibition of tumor growth in vivo by monoclonal antibodies to death receptor 4," *J Immunol.*, 166(8):4891-8 (2001).

Clark, "IgG effector mechanisms," *Chem Immunol.*, 65:88-110 (1997).

Clark, "An alignment of IgG sequences from Human, Mouse and Rat," Part II Immunoglobulin lectures (v4), pp. 5(i)-(ii) [retrieved on Jul. 25, 2014]. Retrieved from the Internet: http://www.path.cam.ac.uk/~mrc7/lecturenotes/handout1a.pdf.

Clarkson et al., "Blockade of clearance of immune complexes by an anti-Fc gamma receptor monoclonal antibody," *J Exp Med.*, Aug. 1, 1986;164(2):474-89.

Clynes et al., "Fc receptors are required in passive and active immunity to melanoma," *Proc Natl Acad Sci USA*, 95(2):652-6 (1998).

Clynes et al., "Inhibitory Fc receptors modulate in vivo cytotoxicity against tumor targets," *Nat Med.*, 6(4):443-6 (2000).

Dall'Acqua et al., "Increasing the affinity of a human IgG1 for the neonatal Fc receptor: biological consequences," *J. Immunol.*, 169(9):5171-80 (2002).

Datta-Mannan et al., "Monoclonal antibody clearance. Impact of modulating the interaction of IgG with the neonatal Fc receptor," *J Biol Chem.*, Jan. 19, 2007;282(3):1709-17. Epub Nov. 29, 2006.

Desai et al., "Fc gamma receptor IIB on dendritic cells enforces peripheral tolerance by inhibiting effector T cell responses," *J Immunol.*, 178(10):6217-26 (2007).

Dhodapkar et al., "Selective blockade of inhibitory Fcgamma receptor enables human dendritic cell maturation with IL-12p70 production and immunity to antibody-coated tumor cells," *Proc Natl Acad Sci USA*, Feb. 22, 2005;102(8):2910-5. Epub Feb. 9, 2005.

Duffau et al., "Platelet CD154 potentiates interferon-alpha secretion by plasmacytoid dendritic cells in systemic lupus erythematosus," *Sci Transl Med.*, Sep. 1, 2010;2(47):47ra63. doi: 10.1126/scitranslmed.3001001.

Floto et al., "Loss of function of a lupus-associated FcgammaRIIb polymorphism through exclusion from lipid rafts," *Nat Med.*, Oct. 2005;11(10):1056-8. Epub Sep. 18, 2005.

Fournier et al., "Activation of human peripheral IgM+ B cells is transiently inhibited by BCR-independent aggregation of Fc gammaRIIB," *J Immunol.*, 181(8):5350-9 (2008).

Ghetie et al., "Increasing the serum persistence of an IgG fragment by random mutagenesis," *Nat. Biotechnol.*, 15(7):637-40 (1997).

Greenwood et al., "Structural motifs involved in human IgG antibody effector functions," *Eur J Immunol.*, 23(5):1098-104 (1993).

Gunasekaran et al., "Enhancing antibody Fc heterodimer formation through electrostatic steering effects: applications to bispecific molecules and monovalent IgG," *J Biol Chem.*, 285(25):19637-46 (2010).

Haakenstad et al., "The disappearance kinetics and glomerular deposition of small-latticed soluble immune complexes," *Immunology*, Nov. 1982;47(3):407-14.

Hamilton, "Molecular engineering: applications to the clinical laboratory," *Clin Chem.*, Sep. 1993;39(9):1988-97.

Hanson et al., "Catalytic antibodies and their applications," *Curr. Opin. Biotechnol.*, Dec. 2005;16(6):631-6. Epub Oct. 21, 2005.

(56) References Cited

OTHER PUBLICATIONS

Heyman, "Feedback regulation by IgG antibodies," Immunol Lett., 88(2):157-61 (2003).
Hinton et al., "An engineered human IgG1 antibody with longer serum half-life," J. Immunol., 176(1):346-56 (2006).
Horton et al., "Potent in vitro and in vivo activity of an Fc-engineered anti-CD19 monoclonal antibody against lymphoma and leukemia," Cancer Res., 68(19):8049-57 (2008).
Igawa et al., "Antibody recycling by engineered pH-dependent antigen binding improves the duration of antigen neutralization," Nat Biotechnol., Nov. 2010;28(11):1203-7. doi: 10.1038/nbt.1691. Epub Oct. 17, 2010.
Igawa et al., "Antibody Optimization Technologies for Developing Next Generation Antibody Therapeutics," Bio Industry, 28(7):15-21 (2011) (with English translation).
Jefferis et al., "Interaction sites on human IgG-Fc for Fc gamma R: current models," Immunol Lett., 82(1-2):57-65 (2002).
Kim et al., "Antibody Engineering for the Development of Therapeutic Antibodies," Mol. Cells, 20(1):17-29 (2005).
Kohrt et al., "Stimulation of natural killer cells with a CD137-specific antibody enhances trastuzumab efficacy in xenotransplant models of breast cancer," J Clin Invest., Mar. 1, 2012;122(3):1066-75. doi: 10.1172/JCI61226. Epub Feb. 13, 2012.
Lazar et al., "Engineered antibody Fc variants with enhanced effector function," Proc Natl Acad Sci USA, 103(11):4005-10 (2006).
Li et al., "CD72 down-modulates BCR-induced signal transduction and diminishes survival in primary mature B lymphocytes," J Immunol., 176(9):5321-8 (2006).
Li et al., "Inhibitory Fcγ receptor engagement drives adjuvant and anti-tumor activities of agonistic CD40 antibodies," Science, Aug. 19, 2011;333(6045):1030-4. doi: 10.1126/science.1206954.
Li et al., "Apoptotic and antitumor activity of death receptor antibodies require inhibitory Fcγ receptor engagement," Proc Natl Acad Sci U S A., Jul. 3, 2012;109(27):10966-71. doi: 10.1073/pnas.1208698109. Epub Jun. 20, 2012.
MacKay et al., "Selective dysregulation of the FcgammaIIB receptor on memory B cells in SLE," J Exp Med., Sep. 4, 2006;203(9):2157-64. Epub Aug. 21, 2006.
Manger et al., "Fcgamma receptor IIa polymorphism in Caucasian patients with systemic lupus erythematosus: association with clinical symptoms," Arthritis Rheum., 41(7):1181-9 (1998).
Meyer et al., "Bevacizumab immune complexes activate platelets and induce thrombosis in FCGR2A transgenic mice," J Thromb Haemost., Jan. 2009;7(1):171-81. doi: 10.1111/j.1538-7836.2008.03212.x. Epub Oct. 30, 2008.
Mi et al., "Targeting the neonatal fc receptor for antigen delivery using engineered fc fragments," J Immunol., Dec. 1, 2008;181(11):7550-61.
Morgan et al., "The N-terminal end of the CH2 domain of chimeric human IgG1 anti-HLA-DR is necessary for C1q, Fc gamma RI and Fc gamma RIII binding," Immunology, 86(2):319-24 (1995).
Muta et al., "A 13-amino-acid motif in the cytoplasmic domain of Fc gamma RIIB modulates B-cell receptor signaling," Nature, 368(6466):70-3 (1994).
Nakamura et al., "Fcgamma receptor IIB-deficient mice develop Goodpasture's syndrome upon immunization with type IV collagen: a novel murine model for autoimmune glomerular basement membrane disease," J Exp Med., 191(5):899-906 (2000).
Nicholas et al., "Regulation of the immune response. I. Reduction in ability of specific antibody to inhibit long-lasting IgG immunological priming after removal of the Fc fragment," J Exp Med., 129(6):1183-201 (1969).
Nimmerjahn et al., "Fcgamma receptors as regulators of immune responses," Nat Rev Immunol., 8(1):34-47 (2008).
Nimmerjahn et al., "Divergent immunoglobulin g subclass activity through selective Fc receptor binding," Science, 310(5753):1510-2 (2005).
Olferiev et al., "The role of activating protein 1 in the transcriptional regulation of the human FCGR2B promoter mediated by the −343 G->C polymorphism associated with systemic lupus erythematosus," J Biol Chem., 282(3):1738-46 (2007).
Pavlou et al., "The therapeutic antibodies market to 2008," Eur J Pharm Biopharm., 59(3):389-96 (2005).
Prickett et al., "A calcium-dependent antibody for identification and purification of recombinant proteins," Biotechniques, Jun. 1989;7(6):580-9.
Radaev et al., "The role of Fc glycosylation and the binding of peptide inhibitors," J Biol Chem., May 11, 2001;276(19):16478-83. Epub Jan. 31, 2001.
Rajpal et al., A general method for greatly improving the affinity of antibodies by using combinatorial libraries, Proc. Natl. Acad. Sci. USA, Jun. 14, 2005;102(24):8466-71. Epub Jun. 6, 2005.
Rathanaswami et al., "Demonstration of an in vivo generated sub-picomolar affinity fully human monoclonal antibody to interleukin-8," Biochem. Biophys. Res. Commun., 334(4):1004-13 (2005).
Ravetch et al., "Immune inhibitory receptors," Science, 290(5489):84-9 (2000).
Reichert et al., "Monoclonal antibody successes in the clinic," Nat Biotechnol., 23(9):1073-8 (2005).
Richards et al., "Optimization of antibody binding to FcgammaRIIa enhances macrophage phagocytosis of tumor cells," Mol Cancer Ther., Aug. 2008;7(8):2517-27. doi: 10.1158/1535-7163.MCT-08-0201.
Robles-Carrillo et al., "Anti-CD40L immune complexes potently activate platelets in vitro and cause thrombosis in FCGR2A transgenic mice," J Immunol., Aug. 1, 2010;185(3):1577-83. doi: 10.4049/jimmunol.0903888. Epub Jun. 28, 2010.
Salmon et al., "Fc gamma RIIA alleles are heritable risk factors for lupus nephritis in African Americans," J Clin Invest., 97(5):1348-54 (1996).
Samuelsson et al., "Anti-inflammatory activity of IVIG mediated through the inhibitory Fc receptor," Science, 291(5503):484-6 (2001).
Scappaticci et al., "Arterial thromboembolic events in patients with metastatic carcinoma treated with chemotherapy and bevacizumab," J Natl Cancer Inst., Aug. 15, 2007;99(16):1232-9. Epub Aug. 8, 2007.
Schulke et al., "The homodimer of prostate-specific membrane antigen is a functional target for cancer therapy," *Proc Natl Acad Sci U S A.*, Oct. 28, 2003;100(22):12590-5.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., Mar. 2, 2001;276(9):6591-604. Epub Nov. 28, 2000.
Shinkawa et al., "The absence of fucose but not the presence of galactose or bisecting N-acetylglucosamine of human IgG1 complex type oligosaccharides shows the critical role of enhancing antibody-dependent cellular cytotoxicity," J Biol Chem., 278(5):3466-73 (2003).
Siberil et al., "Molecular aspects of human FcgammaR interactions with IgG: functional and therapeutic consequences," Immunol Lett., Aug. 15, 2006;106(2):111-8. Epub Jun. 12, 2006.
Smith et al., "FcgammaRIIB in autoimmunity and infection: evolutionary and therapeutic implications," Nat Rev Immunol., May 2010;10(5):328-43. doi: 10.1038/nri2762.
Su et al., Expression profile of FcgammaRIIb on leukocytes and its dysregulation in systemic lupus erythematosus, J Immunol., 178(5):3272-80 (2007).
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J Immunol., Feb. 15, 2010;184(4):1968-76. doi: 10.4049/jimmunol.0903296. Epub Jan. 18, 2010.
Veri et al., "Monoclonal antibodies capable of discriminating the human inhibitory Fcgamma-receptor IIB (CD32B) from the activating Fcgamma-receptor IIA (CD32A): biochemical, biological and functional characterization," Immunology, 121(3):392-404 (2007).
Veri et al., "Therapeutic control of B cell activation via recruitment of Fcgamma receptor IIB (CD32B) inhibitory function with a novel bispecific antibody scaffold," Arthritis Rheum., Jul. 2010;62(7):1933-43. doi: 10.1002/art.27477.

(56) References Cited

OTHER PUBLICATIONS

Warmerdam et al., Molecular basis for a polymorphism of human Fc gamma receptor II (CD32), J Exp Med., 172(1):19-25 (1990).
Wernersson et al., "IgG-mediated enhancement of antibody responses is low in Fc receptor gamma chain-deficient mice and increased in Fc gamma RII-deficient mice," J Immunol., 163(2):618-22 (1999).
Wilson et al., "An Fcγ receptor-dependent mechanism drives antibody-mediated target-receptor signaling in cancer cells," Cancer Cell, Jan. 18, 2011;19(1):101-13. doi: 10.1016/j.ccr.2010.11.012.
Wu et al., "Development of motavizumab, an ultra-potent antibody for the prevention of respiratory syncytial virus infection in the upper and lower respiratory tract," J. Mol. Biol., May 4, 2007;368(3):652-65. Epub Feb. 20, 2007.
Xu et al., "Fc gamma Rs modulate cytotoxicity of anti-Fas antibodies: implications for agonistic antibody-based therapeutics," J Immunol., 171(2):562-8 (2003).
Yarmush et al., "Immunoadsorption: strategies for antigen elution and production of reusable adsorbents," Biotechnol Prog., May-Jun. 1992;8(3):168-78.
Yeung et al., "Engineering human IgG1 affinity to human neonatal Fc receptor: impact of affinity improvement on pharmacokinetics in primates," J. Immunol., Jun. 15, 2009;182(12):7663-71. doi: 10.4049/jimmunol.0804182.
Yuasa et al., "Deletion of fcgamma receptor IIB renders H-2(b) mice susceptible to collagen-induced arthritis," J Exp Med., 189(1):187-94 (1999).
Zalevsky et al., "The impact of Fc engineering on an anti-CD19 antibody: increased Fcgamma receptor affinity enhances B-cell clearing in nonhuman primates," Blood, 113(16):3735-43 (2009). Epub Dec. 24, 2008.
Zalevsky et al., "Enhanced antibody half-life improves in vivo activity," Nat Biotechnol., Feb. 2010;28(2):157-9. doi: 10.1038/nbt.1601. Epub Jan. 17, 2010.
Zhang et al., "Effective therapy for a murine model of human anaplastic large-cell lymphoma with the anti-CD30 monoclonal antibody, HeFi-1, does not require activating Fc receptors," Blood, Jul. 15, 2006;108(2):705-10. Epub Mar. 21, 2006.
International Search Report and Written Opinion for App. Ser. No. PCT/JP2012/054624, dated Apr. 3, 2013, 7 pages.
International Preliminary Report on Patentability for App. Ser. No. PCT/JP2012/054624, dated Aug. 27, 2013, 7 pages.
International Search Report for App. Ser. No. PCT/JP2012/075092, dated Dec. 25, 2012, 4 pages.
International Preliminary Report on Patentability for App. Ser. No. PCT/JP2012/075092, dated Apr. 1, 2014, 10 pages.
International Search Report for App. Ser. No. PCT/JP2013/054461, dated May 7, 2013, 7 pages.
International Preliminary Report on Patentability for App. Ser. No. PCT/JP2013/054461, dated Aug. 26, 2014, 6 pages.
International Preliminary Report on Patentability for App. Ser. No. PCT/JP2012/066665, dated Jan. 16, 2014, 10 pages.
International Search Report and Written Opinion for App. Ser. No. PCT/JP2012/066665, dated Sep. 25, 2012, 10 pages.
Dall'Acqua et al., "Properties of human IgG1s engineered for enhanced binding to the neonatal Fc receptor (FcRn),"*J Biol Chem.*, Aug. 18, 2006;281(33):23514-24. Epub Jun. 21, 2006.
Davis et al., "SEEDbodies: fusion proteins based on strand-exchange engineered domain (SEED) CH3 heterodimers in an Fc analogue platform for asymmetric binders or immunofusions and bispecific antibodies," *Protein Eng Des Sel.*, Apr. 2010;23(4):195-202. doi: 10.1093/protein/gzp094. Epub Feb. 4, 2010.
Deng et al., "Pharmacokinetics of humanized monoclonal anti-tumor necrosis factor-{alpha} antibody and its neonatal Fc receptor variants in mice and cynomolgus monkeys," *Drug Metab Dispos.*, Apr. 2010;38(4):600-5. doi: 10.1124/dmd.109.031310. Epub Jan. 13, 2010.
Marvin et al., "Recombinant approaches to IgG-like bispecific antibodies," *Acta Pharmacol Sin.*, Jun. 2005;26(6):649-58.
International Search Report for App. Ser. No. PCT/JP2013/072507, dated Oct. 29, 2013, 4 pages.

International Preliminary Report on Patentability for App. Ser. No. PCT/JP2013/072507, dated Feb. 24, 2015, 6 pages.
U.S. Appl. No. 15/210,360, filed Jul. 14, 2016, Igawa et al.
U.S. Appl. No. 15/210,353, filed Jul. 14, 2016, Igawa et al.
Bogdanovich et al., "Functional improvement of dystrophic muscle by myostatin blockade," *Nature*, Nov. 28, 2002;420(6914):418-21.
Fillipovich, Biochemical basis of human life, VLADOS, 2005:49-50 (with English translation).
Hoodless et al., "Mechanism and function of signaling by the TGF beta superfamily," *Curr Top Microbiol Immunol.*, 1998;228:235-72.
Kingsley et al., "The TGF-beta superfamily: new members, new receptors, and new genetic tests of function in different organisms," *Genes Dev.*, Jan. 1994;8(2):133-46.
Lee et al., "Genetic analysis of the role of proteolysis in the activation of latent myostatin," *PLoS One*, Feb. 20, 2008;3(2):e1628.
Lee et al., "Regulation of myostatin activity and muscle growth," *Proc Natl Acad Sci U S A.*, Jul. 31, 2001;98(16):9306-11.
Matsumiya et al., "Structural comparison of fucosylated and nonfucosylated Fc fragments of human immunoglobulin G1," *J Mol Biol.*, May 4, 2007;368(3):767-79. Epub Feb. 22, 2007.
McCroskery et al., "Improved muscle healing through enhanced regeneration and reduced fibrosis in myostatin-null mice," *J Cell Sci.*, Aug. 1, 2005;118(Pt 15):3531-41.
McPherron et al., "Regulation of skeletal muscle mass in mice by a new TGF-beta superfamily member," *Nature*, May 1, 1997;387(6628):83-90.
McPherron et al., "Double muscling in cattle due to mutations in the myostatin gene," *Proc Natl Acad Sci U S A.*, Nov. 11, 1997;94(23):12457-61.
Szlama et al., "Latent myostatin has significant activity and this activity is controlled more efficiently by WFIKKN1 than by WFIKKN2," *FEBS J.*, Aug. 2013;280(16):3822-39. doi: 10.1111/febs.12377. Epub Jul. 5, 2013.
Wagner et al., "Loss of myostatin attenuates severity of muscular dystrophy in mdx mice," *Ann Neurol.*, Dec. 2002;52(6):832-6.
Whittemore et al., "Inhibition of myostatin in adult mice increases skeletal muscle mass and strength," *Biochem Biophys Res Commun.*, Jan. 24, 2003;300(4):965-71.
Zimmers et al., "Induction of cachexia in mice by systemically administered myostatin," *Science*, May 24, 2002;296(5572):1486-8.
Radaev et al., "The structure of a human type III Fcgamma receptor in complex with Fc," *J Biol Chem.*, May 11, 2001;276(19):16469-77. Epub Jan. 31, 2001.
Reverberi et al., "Factors affecting the antigen-antibody reaction," *Blood Transfus.*, Nov. 2007;5(4):227-40. doi: 10.2450/2007.0047-07.
Ito et al., "The His-probe method: effects of histidine residues introduced into the complementarity-determining regions of antibodies on antigen-antibody interactions at different pH values," *FEBS Lett.*, 309:85-88 (1992).
Janeway et al., Immunobiology, The Immune System in Health and Disease, 3rd Edition, 1997 Garland Publishing Inc., pp. 3:1-3:11.
Patton et al., "An acid dissociation bridging ELISA for detection of antibodies directed against therapeutic proteins in the presence of antigen," *J Immunol Methods*, Sep. 2005;304(1-2):189-95.
Rudikoff et al., "Single amino acid substitution altering antigen-binding specificity," *Proc Natl Acad Sci U S A.*, Mar. 1982;79(6):1979-83.
Horn et al., "Analysis of the binding of pro-urokinase and urokinase-plasminogen activator inhibitor-1 complex to the low density lipoprotein receptor-related protein using a Fab fragment selected from a phage-displayed Fab library," *J Biol Chem.*, May 19, 1995;270(20):11770-5.
Ward et al., "A calcium-binding monoclonal antibody that recognizes a non-calcium-binding epitope in the short consensus repeat units (SCRs) of complement C1r," *Mol Immunol.*, Jan. 1992;29(1):83-93.
International Search Report for App. Ser. No. PCT/JP2013/084809, dated Apr. 1, 2014, 4 pages.
International Preliminary Report on Patentability for App. Ser. No. PCT/JP2013/084809, dated Jun. 30, 2015, 7 pages.
U.S. Appl. No. 14/974,488, Ruike et al., filed Dec. 18, 2015.
U.S. Appl. No. 15/015,287, Igawa et al., filed Feb. 4, 2016.

(56) References Cited

OTHER PUBLICATIONS

U.S. Appl. No. 14/001,218, Mimoto et al., filed Aug. 23, 2013.
U.S. Appl. No. 14/007,947, Igawa et al., filed Sep. 26, 2013.
U.S. Appl. No. 14/127,576, Mimoto et al., filed Dec. 19, 2013.
U.S. Appl. No. 14/347,034, Igawa et al., filed Mar. 25, 2014.
U.S. Appl. No. 15/230,904, Igawa et al., filed Aug. 8, 2016.
U.S. Appl. No. 14/347,321, Igawa et al., filed Mar. 26, 2014.
U.S. Appl. No. 14/347,187, Igawa et al., filed Mar. 25, 2014.
U.S. Appl. No. 14/361,013, Igawa et al., filed May 28, 2014.
Bruhns, "Properties of mouse and human IgG receptors and their contribution to disease models," Blood, Jun. 14, 2012;119(24):5640-9. doi: 10.1182/blood-2012-01-380121. Epub Apr. 25, 2012.
Hjelm et al., "Antibody-mediated regulation of the immune response," Scand J Immunol., Sep. 2006;64(3):177-84.
Idusogie et al., "Mapping of the C1q binding site on rituxan, a chimeric antibody with a human IgG1 Fc," J Immunol., Apr. 15, 2000;164(8):4178-84.
Kamei et al., "Quantitative methods for developing Fc mutants with extended half-lives," Biotechnol Bioeng., Dec. 20, 2005;92(6):748-60.
Biasini et al., "Immunopurification of pathological prion protein aggregates," PLoS One, Nov. 12, 2009;4(11):e7816. doi: 10.1371/journal.pone.0007816.
Pakula et al., "Genetic Analysis of Protein Stability and Function," Annu Rev Genet., 1989;23:289-310.
Wang et al., "Monoclonal Antibodies with Identical Fc Sequences Can Bind to FcRn Differentially with Pharmacokinetic Consequences," Drug Metabolism and Disposition, Sep. 2011; 39(9):1469-77.
Burmeister et al., "Crystal structure of the complex of rat neonatal Fc receptor with Fc," Nature, Nov. 24, 1994;372(6504):379-83.
Sondermann et al., "The 3.2-A crystal structure of the human IgG1 Fc fragment-Fc gammaRIII complex," Nature, Jul. 20, 2000;406(6793):267-73.
International Search Report for App. Ser. No. PCT/JP2014/059706, dated Jul. 15, 2014, 4 pages.
International Preliminary Report on Patentability for App. Ser. No. PCT/JP2014/059706, dated Oct. 6, 2015, 10 pages.
U.S. Appl. No. 15/495,026, filed Apr. 24, 2017, Igawa et al.
Alley et al., "Antibody-drug conjugates: targeted drug delivery for cancer," Curr Opin Chem Biol., 14(4):529-37 (2010), 8 pages. doi: 10.1016/j.cbpa.2010.06.170. Epub Jul. 17, 2010.
Araujo et al., "Increased rheumatoid factor interference observed during immunogenicity assessment of an Fc-engineered therapeutic antibody," J Pharm Biomed Anal., Jul. 15, 2011;55(5):1041-9. doi: 10.1016/j.jpba.2011.03.008. Epub Mar. 11, 2011.
Baeuerle et al., "BiTE: Teaching antibodies to engage T-cells for cancer therapy," Curr Opin Mol Ther., Feb. 2009;11(1):22-30.
Bjellqvist et al., "The focusing positions of polypeptides in immobilized pH gradients can be predicted from their amino acid sequences," Electrophoresis. Oct. 1993;14(10):1023-31.
Borrok et al., "pH-dependent Binding Engineering Reveals an FcRn Affinity Threshold That Governs IgG Recycling," J Biol Chem. Feb. 13, 2015;290(7):4282-90. doi: 10. 1074/ jbc. M114.603712. Epub Dec. 23, 2014.
Brown et al., "Tolerance to Single, but Not Multiple, Amino Acid Replacements in Antibody VHCDR2," J Immunol. May 1, 1996; 156(9):3285-91.
Cooper et al., "Variable domain-identical antibodies exhibit IgG subclass-related differences in affinity and kinetic constants as determined by surface plasmon resonance," Mol Immunol. Jun. 1994; 31(8): 577-84.
Davda et al., "Properties of a general PK/PD model of antibody-ligand interactions for therapeutic antibodies that bind to soluble endogenous targets," Mabs. 2(5):576-88 (2010), 13 pages. doi: 10.4161/mabs.2.5.12833. Epub Sep. 1, 2010.
De Bono et al., "ING-1, a monoclonal antibody targeting Ep-CAM in patients with advanced adenocarcinomas," Clin Cancer Res., Nov. 15, 2004;10(22):7555-65.
De Groot et al., "Reducing risk, improving outcomes: bioengineering less immunogenic protein therapeutics," Clin Immunol., May 2009;131(2):189-201. doi: 10.1016/j.clim.2009.01.009. Epub Mar. 6, 2009.
Desjarlais et al., "Optimizing engagement of the immune system by anti-tumor antibodies: an engineer's perspective," Drug Discovery Today, 12(21-22):898-910 (2007), 13 pages. Epub Oct. 22, 2007.
Dufner et al., "Harnessing phage and ribosome display for antibody optimization," Trends Biotechnol., Nov. 2006;24(11):523-9. Epub Sep. 26, 2006.
Haringman et al., "A randomized controlled trial with an anti-CCL2 (anti-monocyte chemotactic protein 1) monoclonal antibody in patients with rheumatoid arthritis," Arthritis Rheum., Aug. 2006;54(8):2387-92.
Hebert, "The clearance of immune complexes from the circulation of man and other primates," Am J. Dis., Mar. 1991;17(3):352-61.
Hinton et al., "Engineered human IgG antibodies with longer serum half-lives in primates," J Biol Chem., Feb. 20, 2004;279(8):6213-6. Epub Dec. 29, 2003.
Holash et al., "VEGF-Trap: a VEGF blocker with potent antitumor effects," Proc Natl Acad Sci U S A., Aug. 20, 2002;99(17):11393-8. Epub Aug. 12, 2002.
Igawa et al., "Reduced elimination of IgG antibodies by engineering the variable region," Protein Eng Des Sel., May 2010;23(5):385-92. Epub Feb. 15, 2010.
Ishii et al., "FcRn, a critical regulator of antibody pharmacokinetics," Folia Pharmacol Jpn., Jun. 2010;136(5):280-4.
Iwabe et al., "Pathogenetic significance of increased levels• of interleukin-a in the peritoneal fluid of patients with endometriosis," Fertil Steril. May 1998:69(5):924-30.
Juszczak et al., "Ipilimumab: a novel immunomodulating therapy causing autoimmune hypophysitis: a case report and review," Eur J Endocrinol 167(1):1-5 (2012), 5 pages. doi: 10.1530/EJE-12-0167. Epub Apr. 10, 2012.
Lewis et al., "Differential responses of human tumor cell lines to anti-p185HER2 monoclonal antibodies," Cancer Immunol Immunother., Sep. 1993;37(4):255-63.
Liang et al., "Immunity against a therapeutic xenoprotein/Fc construct delivered by gene transfer is reduced through binding to the inhibitory receptor FcγRIIb," J Gene Med., Sep. 2011;13(9):470-7.
Lutterbuese et al., "T cell-engaging BiTE antibodies specific for EGFR potently eliminate KRAS- and BRAF-mutated colorectal cancer cells," Proc Natl Acad Sci U.S.A., 107(28):12605-10 (2010), 6 pages. doi: 10.1073/pnas.1000976107. Epub Jun. 28, 2010.
Martin et al., "Reviews Preclinical Safety and Immune-Modulating Effects of Therapeutic Monoclonal Antibodies to Interleukin-6 and Tumor Necrosis Factor-alpha in Cynomolgus Macaques," J. Immunotoxicol., 1(3):131-9 (2004), 9 pages. Doi: 10.1080/15476910490894904.
Matsunaga et al., "A pH-dependent conformational transition of Abeta peptide and physicochemical properties of the conformers in the glial cell," Biochem J., Feb. 1, 2002;361(Pt 3):547-56.
Maurer et al., "Antigenicity of polypeptides (poly alpha amino acids): calcium-dependent and independent antibodies," J Immunol., Sep. 1970;105(3):567-73.
Mazda et al., "Regulation of Muscle Homeostasis and Metabolism by the TGF-β Superfamily Cytokine, Myostatin/growth Differentiation Factor 8 (GDF8)," Journal of Kyoto Prefectural University of Medicine, 2013;122(3):133-41.
Meulenbroek et al., "Properties of human IgG subclasses," Chapter 2.3 of Human IgG Subclasses: Useful Diagnostic Markers for Immunocompetence, published online by Sanquin, Amsterdam, The Netherlands. Retrieved from the Internet on Mar. 23 and 24, 2017: <http://ednieuw.home.xs4a11.nl/IgGsubclasses/subk123.htm>, 8 pages.
Montero-Julian et al., "Pharmacokinetic study of anti-interleukin-6 (IL-6) therapy with monoclonal antibodies: enhancement of IL-6 clearance by cocktails of anti-IL-6 antibodies," Blood, Feb. 15, 1995; 85(4):917-24.
Nam et al., "Current evidence for the management of rheumatoid arthritis with biological disease-modifying antirheumatic drugs: a systematic literature review informing the EULAR recommendations for the management of RA," Ann Rheum Dis., 69(6):976-86 (2010). doi: 10.1136/ard.2009.126573. Epub May 6, 2010.

(56) References Cited

OTHER PUBLICATIONS

Niebecker et al., "Safety of therapeutic monoclonal antibodies," Curr Drug Saf., Oct. 2010;5(4):275-86.
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease" Blood. ,112(10):3959-64 (2008), 8 pages. doi: 10.1182/blood-2008-05-155846. Epub Sep. 10, 2008.
Petkova et al., "Enhanced half-life of genetically engineered human IgG1 antibodies in a humanized FcRn mouse model: potential application in humorally mediated autoimmune disease," Int Immunol., 18(12):1759-69 (2006), 11 pages. Epub Oct. 31, 2006.
Qiao et al., "Dependence of antibody-mediated presentation of antigen on FcRn," Proc Natl Acad Sci U S A., Jul. 8, 2008;105(27):9337-42. Epub Jul. 1, 2008.
Ramos et al., "Evaluation of CA-125 and soluble CD-23 in patients with pelvic endometriosis: a case-control study," Rev. Assoc. Med. Bras. (1992). Jan.-Feb. 2012; 58(1):26-32).
Riechelmann et al., "Phase I trial with the CD44v6-targeting immunoconjugate bivatuzumab mertansine in head and neck squamous cell carcinoma," Oral Oncol., Sep. 2008;44(9):823-9. doi: 10.1016/j.oraloncology.2007.10.009. Epub Jan. 18, 2008.
Roopenian et al., "FcRn: the neonatal Fc receptor comes of age," Nat Rev Immunol., 7(9):715-25 (2007), 8 pages. Epub Aug. 17, 2007.
Rudge et al., "VEGF Trap complex formation measures production rates of VEGF, providing a biomarker for predicting efficacious angiogenic blockade," 104(47):18363-70 (2007), 8 pages. Epub Nov. 13, 2007.
Russo et al., "The CXCL8/IL-8 chemokine family and its receptors in inflammatory diseases," Expert Rev Clin Immunol., May 2014;10(5):593-619. doi: 10.1586/1744666X.2014.894886. Epub Mar. 29, 2014.
Satoh et al., "Non-fucosylated therapeutic antibodies as next-generation therapeutic antibodies," Expert Opin Biol Ther., Nov. 2006;6(11):1161-73.
Schuster et al., "Signaling of human ciliary neurotrophic factor (CNTF) revisited. The interleukin-6 receptor can serve as an alpha-receptor for CTNF," J Biol Chem, Mar. 14, 2003;278(11):9528-35.
Seda et al., "B-cell receptor signaling and its crosstalk with other pathways in normal and malignant cells," Eur. J. Haematol., 1-13 (2014), 13 pages. doi:10.1111/ejh.12427.
Sims et al., "HMGB1 and RAGE in inflammation and cancer," Annu rev Immunol., 28:367-88 (2010), 24 pages.
Strohl, "Optimization of Fc-mediated effector functions of monoclonal antibodies," Curr Opin Biotechnol. Dec. 2009;20(6):685-91.
Takeuchi et al., "The Japanese experience with biologic therapies for rheumatoid arthritis," Nat Rev Rheumatol., 6(11):644-52 (2010). doi: 10.1038/nrrheum.2010.154. Epub Sep. 28, 2010.
Trinh et al., "Ipilimumab in the treatment of melanoma," Expert Opin Biol Ther., Jun. 2012;12(6):773-82. doi: 10.1517/14712598. 2012.675325. Epub Apr. 14, 2012.
Vajdos et al., "Comprehensive Functional Maps of the Antigen binding Site of an Anti-ErbB2 Antibody Obtained with Shotgun Scanning Mutagenesis," J Mol Biol. Jul. 5, 2002; 320(2):415-28.
Vidarsson et al., "IgG subclasses and allotypes: from structure to effector functions," Front Immunol. Oct. 20, 2014;5:520. doi:10. 3389/ fimmu.2014.00520. eCollection 2014.
Wang et al., "HMG-1 as a late mediator of endotoxin lethality in mice," Science, 285(5425):248-51 (1999).
Warncke et al., "Different adaptations of IgG effector function in human and nonhuman primates and implications for therapeutic antibody treatment," J Immunol. May 1, 2012 :188(9) :4405-11. doi: 10.4049/jimmunol. 1200090. Epub Mar. 28, 2012.
Weiner et al., "Monoclonal antibodies: versatile platforms for cancer immunotherapy," Nat Rev Immunol., 10(5):317-27 (2010), 26 pages. doi: 10.1038/nri2744.
Wu et al., "Humanization of a murine monoclonal antibody by simultaneous optimization of framework and CDR residues," J Mol Biol., Nov. 19, 1999;294(1):151-62.
Wu et al., "Structure-based engineering of a monoclonal antibody for improved solubility," Protein Eng Des Sel., Aug. 2010;23(8):643-51. doi:10.1093/protein/gzq037. Epub Jun. 11, 2010.
Xiao et al., "Pharmacokinetics of anti-hepcidin monoclonal antibody Ab 12B9m and hepcidin in cynomolgus monkeys" AAPS J. 12(4):646-57 (2010), 12 pages. doi: 10.1208/s12248-010-9222-0. Epub Aug. 25, 2010.
Xolair (omalizumab) Prescribing Information, https://www.gene.com/download/pdf/xolair_prescribing.pdf, Jul. 2016, 27 pages.
Zheng et al., "Translational pharmacokinetics and pharmacodynamics of an FcRn-variant anti-CD4 monoclonal antibody from preclinical model to phase I study." Clin Pharmacol Ther., 89(2):283-90 (2011). doi: 10.1038/clpt.2010.311. Epub Dec. 29, 2010.
International Search Report for App. Ser. No. PCT/JP2016/003616, dated Nov. 25, 2016, 4 pages.
Singer et al., "Genes & Genomes," Moscow, "Mir," 1998;1:63-4.
Vaccaro et al., "Engineering the Fc region of immunoglobulin G to modulate in vivo antibody levels," *Nat Biotechnol.*, Oct. 2005;23(10):1283-8. Epub Sep. 25, 2005.
U.S. Appl. No. 15/860,163, filed Jan. 2, 2018, Mimoto et al.
U.S. Appl. No. 15/963,449, filed Apr. 26, 2018, Ruike et al.
U.S. Appl. No. 15/963,455, filed Apr. 26, 2018, Ruike et al.
U.S. Appl. No. 15/976,288, filed May 10, 2018, Igawa et al.
U.S. Appl. No. 15/977,757, filed May 11, 2018, Igawa et al.
U.S. Appl. No. 61/313,102, filed Mar. 11, 2010, Pons.
Alignment of constant region sequences from WO 2009/125825 (document submitted in EP opposition and posted by EPO on Feb. 2, 2018); 1 page.
Alignment of the amino acid sequences of the Fc regions of antibodies exemplified in EP 2275443 (document submitted in EP opposition and posted by EPO on Feb. 2, 2018); 1 page.
Alignment of variable heavy and light chain amino acid sequences from WO 2009/125825 (document submitted in EP opposition and posted by EPO on Feb. 2, 2018); 2 pages.
Akbarzadeh-Sharbaf et al., "In silico design, construction and cloning of Trastuzumab humanized monoclonal antibody: A possible biosimilar for Herceptin," Adv Biomed Res 2012 :1: 21. doi: 10. 4103/ 2277-9175. 98122. Epub Jul. 6, 2012.
Atherton et al., "Acid-base balance: maintenance of plasma pH," Anaesthesia & Intensive Care Medicine. 2009:10(11 ):557-61 (abstract).
Breitbart et al., "Highly Specific Detection of Myostatin Prodomain by an Immunoradiometric Sandwich Assay in Serum of Healthy Individuals and Patients," PLoS One. Nov. 15, 2013;8(11):e80454. doi: 10.1371/journal.pone.0080454. eCollection 2013.
Claims as granted for EP 2275443 (document submitted in EP opposition); 6 pages.
Datta-Mannan et al., "Humanized IgG1 Variants with Differential Binding Properties to the Neonatal Fc Receptor: Relationship to Pharmacokinetics in Mice and Primates," Drug Metab Dispos. Jan. 2007 :35 (1) :86-94. Epub Oct. 18, 2006.
Davydov, "Omalizuman (Xolair) for Treatment of Asthma," Am Fam Physician. Jan. 15, 2005;71(2):341-2.
De Felice et al., "Formation of amyloid aggregates from human lysozyme and its disease-associated variants using hydrostatic pressure," FASEB J., Jul. 2004, 18(10):1099-101. (dol:10.1096/fj.03-1072fje; PMID 15155566).
Declaration of Nimish Gera, Ph.D., CV and Exhibits, Sep. 1, 2016 (submitted in the matter of EP 2275443, Opposition thereto by Alexion Pharmaceuticals, Inc.); 24 pages.
"EMA product information: Annexes to file of the tocilizumab preparation RoActemra (WC500054890)", published by EMA on Jan. 8, 2010.
Experimental data characterizing the binding of rituximab to its antigen CD20 and to human FcRn (document submitted in EP opposition and posted by EPO on Feb. 5, 2018); 6 pages.
Expert Declaration by Dr. Madhusudan Natarajan, submitted in EP opposition regarding EP 2552955 and posted by EPO on Feb. 5, 2018; 4 pages.
Fillipovic, Biochemical basis of human life, VLADOS, 2005:38-43 (with English translation).

(56) References Cited

OTHER PUBLICATIONS

Gurbaxani et al., "Analysis of a family of antibodies with different half-lives in mice fails to find a correlation between affinity for FcRn and serum half-life," Mol Immunol Mar. 2006:43(9):1462-73. Epub Sep. 1, 2005.

Goebl et al., ""Neonatal Fc Receptor Mediates Internalization of Fc Transfected Human Endothelial Cells,"" Molecular Biology of the Cell, Dec. 2008 :19 (12) :5490-5505.

Hu et al., "Combinatorial libraries against libraries for selecting neoepitope activation-specific antibodies," Proc Natl Acad Sci USA, Apr. 2010, 107(14):6252-57.

Irani et al., "Molecular properties of human IgG subclasses and their implications for designing therapeutic monoclonal antibodies against infectious diseases," Mol Immunol, Oct. 2015 :67 (2 Pt A) :171-82. doi : 10. 1016/ j. molimm 2015. 03. 255. Epub Apr. 18, 2015.

Kabat et al., "Sequences of proteins of immunological interest", U.S. Department of Health and Human Services, National Institutes of Health, NIH Publication No. 91-3242, 5th ed., 1991, vol. 1, pp. 679-687.

Kim et al., "Production of a Polyclonal Anti-Myostatin Antibody and the Effects of In Ovo Administration of the Antibody on Posthatch Broiler Growth and Muscle Mass," Poult Sci. Jun. 2007; 86(6):1196-205.

King et al., Applications and Engineering of Monoclonal Antibodies. 1998:68-71.

Maxfield et al., "Endocytic Recycling," Nat Rev Mol Cell Biol. Feb. 2004;5(2):121-32.

Maxwell et al., "Crystal structure of the human leukocyte Fc receptor, FcγRIIa," Nat Struct Biol. May 1999;6(5):437-42.

Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res. Jun. 15, 2001;61(12):4744-9.

O'Donovan et al., "EGFR and HER-2 Antagonists in Breast Cancer," Anticancer Res. May-Jun. 2007 :27 (3A) :1285-94.

Experimental information regarding off-rate of Xolair Fab for binding to human IgE at pH7.4 and pH5.5 (document submitted in EP opposition and posted by EPO on Feb. 2, 2018); 3 pages.

Official Action dated Oct. 13, 2016, issued for EP Application No. 11714860.1 and submitted as evidence during EP opposition; 3 pages.

Papista et al., "Dysfunctions of the IgA system: a common link between intestinal and renal diseases," Cell Mol Immunol. Mar. 2011;8(2):126-34. doi: 10.1038/cmi.2010.69. Epub Jan. 31, 2011.

Presta, "Molecular engineering and design of therapeutic antibodies," Curr Opin Immunol . Aug. 2008 :20 (4) :460-70. doi : 10.1016/j.coi.2008. 06.012.

Presta at el., "Humanization of an Anti-Vascular Endothelial Growth Factor Monoclonal Antibody for the Therapy of Solid Tumors and Other Disorders," Cancer Res. Oct. 15, 1997 :57 (20): 4593-9.

Product labelling information for Rituxan (Rituximab), dated Nov. 1997.

Raghavan et al, "Analysis of the pH Dependence of the Neonatal Fc Receptor/immunoglobulin G Interaction Using Antibody and Receptor Variants," Biochemistry, Nov. 14, 1995;34(45):14649-57.

Sondermann et al., "Molecular Basis for Immune Complex Recognition: A Comparison of Fc-Receptor Structures," J Mol Biol. Jun. 8, 2001;309(3):737-49.

Sondermann et al., "Crystal structure of the soluble form of the human Fcγ-receptor IIb: a new member of the immunoglobulin superfamily at 1.7 A resolution," EMBO J. Mar. 1, 1999;18(5):1095-103.

Supplementary data provided by opponent for EP Application No. 11714860.1 (document submitted in EP opposition and posted by EPO on Feb. 20, 2018); 3 pages.

Tanabe et al., "Characterization of the Monoclonal Antibodies Against Human Protein C Specific For Calcium Ion-induced Conformers," Japanese Journal of Thrombosis and Hemostasis, 1992;3(1):29-35.

Tanzi et al., "Twenty years of the Alzheimer's disease amyloid hypothesis: a genetic perspective," Cell, Feb. 2005, 120(4):545-55 (doi:10.1016/j.cell.2005.02.008; PMID 15734686).

Vaccaro et al., "Divergent activities of an engineered antibody in murine and human systems have implications for therapeutic antibodies," Proc Natl Acad Sci USA. Dec. 5, 2006;103(49):18709-14. Epub Nov. 20, 2006.

Waelbroeck et al., "The pH Dependence of Insulin Binding," J Biol Chem. Jul. 25, 1982 :257 (14) :8284-91.

Ward et al., "Evidence to support the cellular mechanism involved in serum IgG homeostasis in humans," Int Immunol Feb. 2003 :15(2):187-95.

Welch et al., "Adalimumab (Humira) for the Treatment of Rheumatoid Arthritis" Am Fam Physician. Dec. 15, 2008 :78 (12) :1406-1408.

Yang et al., "Dataset of the binding kinetic rate constants of anti-PCSK9 antibodies obtained using the Biacore T100, Protean XPR36, Octet RED384, and IBIS MX96 biosensor platforms," Data Brief. Jul. 27, 2016 :8:1173-83. doi : 10. 1016/ J. dib. 2016.07.044. eCollection Sep. 2016.

Yang et al., "Maximizing in vivo target clearance by design of pH-dependent target binding antibodies with altered affinity to FcRn," MAbs. Oct. 2017 :9(7) :1105-1117. doi : 10. 1080/19420862. 2017. 1359455. Epub Aug. 8, 2017.

Yarilin, Fundamentals of Immunology. M: Medicina, 1999, p. 169-72, 354-8 (with English translation).

Yeung et al., "A Therapeutic Anti-VEGF Antibody with Increased Potency Independent of Pharmacokinetic Half-life," Cancer Res. Apr. 15, 2010;70(8):3269-77. doi: 10.1158/0008-5472.CAN-09-4580 Eoub Mar. 30, 2010.

Ying et al., "Large Yellow Croaker MSTN-1 Prodomain Prokaryotic Expression, Polyclonal Antibody Preparation and Antibody Function Identification," Chinese Journal of Cell Biology. Oct. 2014;36(10):1344-1349 (in Japanese, with English abstract).

USPTO Restriction Requirement in U.S. Appl. No. 14/379,825, dated Dec. 22, 2016, 8 pages.

USPTO Non-Final Office Action in U.S. Appl. No. 14/379,825, dated Jul. 20, 2017, 18 pages.

USPTO Final Office Action in U.S. Appl. No. 14/379,825, dated Apr. 2, 2018, 20 pages.

USPTO Final Office Action in U.S. Appl. No. 14/001,218, dated Jan. 29, 2018, 11 pages.

USPTO Restriction Requirement in U.S. Appl. No. 14/404,051, dated Apr. 4, 2016, 13 pages.

USPTO Non-Final Office Action in U.S. Appl. No. 14/404,051, dated Dec. 6, 2016, 22 pages.

USPTO Final Office Action in U.S. Appl. No. 14/404,051, dated Oct. 18, 2017, 15 pages.

USPTO Restriction Requirement in U.S. Appl. No. 14/781,069, dated Dec. 7, 2017, 7 pages.

USPTO Advisory Action in U.S. Appl. No. 14/402,574, dated Feb. 16, 2017, 3 pages.

USPTO Final Office Action in U.S. Appl. No. 14/402,574, dated Oct. 31, 2016, 16 pages.

USPTO Non-Final Office Action in U.S. Appl. No. 14/402,574, dated May 6, 2016, 31 pages.

USPTO Restriction Requirement in U.S. Appl. No. 14/402,574, dated Feb. 11, 2016, 10 pages.

USPTO Office Action in U.S. Appl. No. 14/402,574, dated Jan. 16, 2018, 24 pages.

USPTO Interview Summary in U.S. Appl. No. 14/402,574, dated May 4, 2018, 27 pages.

USPTO Non-Final Office Action in U.S. Appl. No. 14/422,207, dated Feb. 7, 2017.

USPTO Non-Final Office Action in U.S. Appl. No. 14/422,207, dated Feb. 11, 2016.

USPTO Restriction Requirement in U.S. Appl. No. 14/422,207, dated Nov. 20, 2015.

USPTO Final Office Action in U.S. Appl. No. 14/422,207, dated Nov. 16, 2017, 30 pages.

USPTO Restriction Requirement in U.S. Appl. No. 14/654,895, dated Sep. 21, 2017, 7 pages.

(56) References Cited

OTHER PUBLICATIONS

USPTO Non-final Office Action in U.S. Appl. No. 14/654,895, dated Feb. 7, 2018, 39 pages.
USPTO Non-final Office Action in U.S. Appl. No. 15/024,063, dated Feb. 7, 2018, 91 pages.
U.S. Appl. No. 15/976,288, Igawa et al., filed May 10, 2018.
U.S. Appl. No. 14/001,218, filed Dec. 2, 2013, Mimoto et al.
U.S. Appl. No. 15/952,945, filed Apr. 13, 2018, Igawa et al.
U.S. Appl. No. 16/028,140, filed Jul. 5, 2018, Igawa et al.
U.S. Appl. No. 16/065,192, filed Jun. 22, 2018, Ruike et al.
U.S. Appl. No. 16/108,897, filed Aug. 22, 2018, Igawa et al.
U.S. Appl. No. 16/264,735, filed Feb. 1, 2019, Igawa et al.
U.S. Appl. No. 16/323,142, filed Feb. 4, 2019, Kakiuchi et al.
[Anonymous] "Rabbit Antibody to Human pro-Myostatin (amino acids 79-92)," Meridian Life Science Inc, Nov. 13, 2015 (Nov. 13, 2015), XP055478289, Retrieved from the Internet: URL:https://meridianlifescience.com/biospecs/K24340R.pdf [retrieved on May 24, 2018].
[Anonymous] "Blog entry," Jun. 1, 2014 (Jun. 1, 2014), Retrieved from the Internet: URL:https://www.thundersplace.org/male-supplements/the-chemical-pe thread-7.html92 [retrieved on May 23, 2018].
[Anonymous] "polyclonal human pro-Myostatin (aa 79-92) antibody," Immun Diagnostik Antibodies Catalogue, Jun. 30, 2016 (Jun. 30, 2016), Retrieved from the Internet: URL:https://www.immundiagnostik.com/fileadmin/pdf/AK3004.pdf [retrieved on May 24, 2018].
[Anonymous] "Mouse GDF-8/Myostatin Propeptide Antibody," R&D Catalogue AF 1539, Feb. 6, 2018 (Feb. 6, 2018), XP055478493, Retrieved from the Internet: URL:https://resources.rndsystems.com/pdfs/datasheets/af1539.pdf [retrieved on May 24, 2018].
Antibodies from www.bioinf.org.uk: Dr. Andrew C.R. Martin's Group, downloaded Jul. 11, 2018, 9 pages.
Becker et al., "Prevention of postoperative abdominal adhesions by a sodium hyaluronate-based bioresorbable membrane: a prospective, randomized, double-blind multicenter study," J Am Coll Surg, Oct. 1996, 183(4):297-306.
Bonvin et al., "De novo isolation of antibodies with pH-dependent binding properties," mAbs, Mar./Apr. 2015, 7(2):294-302.
Bulun, "Endometriosis," New Eng J Med, Jan. 2009, 360(3):268-279.
Chaparro-Riggers et al., "Increasing serum half-life and extending cholesterol lowering in vivo by engineering antibody with pH-sensitive binding to PCSK9," J Biol Chem, Mar. 2012, 287(14):11090-11097. doi: 10.1074/jbc.M111.319764. Epub Jan. 31, 2012.
Devanaboyina et al., "The effect of pH dependence of antibody-antigen interactions on subcellular trafficking dynamics," mAbs, Nov. 2013, 5(6):851-859.
Donnez et al., "Current thinking on the pathogenesis of endometriosis," Gynecol Obstet Invest, Dec. 2002, 54(Suppl 1):52-58; post presentation discussion 59-62.
Examination Report No. 1 for AU 2013306700 (IP Australia) dated Jun. 7, 2018, 3 pages.
Fan et al., "Self-association of human PCSK9 correlates with its LDLR-degrading activity," Biochemistry, Feb. 2008, 47(6):1631-16399. doi: 10.1021/bi7016359. Epub Jan. 16, 2008.
Giudice et al., "Endometriosis," Lancet, Nov. 2004, 364(9447):1789-1799.
Guo, "Recurrence of endometriosis and its control," Hum Reprod Update, Jul.-Aug. 2009 (Epub Mar. 2009), 15(4):441-461.
Han et al., "Targeting the myostatin signaling pathway to treat muscle wasting diseases," Curr Opin Support Palliat Care, Dec. 2011, 5(4):334-341. doi: 10.1097/SPC.0b013e32834bddf9.
Harvey et al., Lippincott's Illustrated Reviews: Immunology, Second Edition, Chapter 2 "Antigens and Receptors" pp. 11-23 and Chapter 11 "Lymphocyte Effector Functions," pp. 141-157 (2008).
Hill et al., "The myostatin propeptide and the follistatin-related gene are inhibitory binding proteins of myostatin in normal serum," J Biol Chem, Oct. 2002, 277(43):40735-40741. Epub Aug. 22, 2002.
Hirose, "Visualization of intracellular calcium signalling," Folia Pharmacol Jpn, May 2006, 127(5):362-367 (with English translation).
Igawa et al., "Engineering the variable region of therapeutic IgG antibodies," mAbs, May-Jun. 2011, 3(3):243-252. Epub May 1, 2011.
Jaeger, Clinical Immunology and Allergology, 2nd edition, M.: Medicina, 1990, 2:484-485 (with English translation).
Kamata et al., "Comparison of pH and ionic strength dependence of interactions between monoclonal antibodies and bovine β-lactoglobulin," Biosci Biotechnol Biochem, Jan. 1996, 60(1):25-29.
Kim et al., "Production of a monoclonal anti-myostatin antibody and the effects of in ovo administration of the antibody on posthatch broiler growth and muscle mass," Poult Sci, Jun. 2006, 85(6):1062-1071.
MacCallum et al., "Antibody-antigen interactions: contact analysis and binding site topography," J Mol Biol, Oct. 1996, 262:732-745.
Male et al., Immunology, 7th edition, 2006, Chapter 3 "Antibodies," pp. 77-78.
Murtaugh et al., "A combinatorial histidine scanning library approach to engineer highly pH-dependent protein switches," Protein Sci, Sep. 2011, 20(9):1619-1631. doi: 10.1002/pro.696. Epub Aug. 3, 2011.
OriGene Technologies, Inc., AP02123SU-N, Polyclonal Antibody to Myostatin (79-92)—Serum, Mar. 19, 2013, https://m1.acris-antibodies.com/pdf/AP02123SU-N.pdf.
Popov et al., "The stoichiometry and affinity of the interaction of murine Fc fragments with the MHC class I-related receptor, FcRn," Mol Immunol, Apr. 1996, 33(6):521-530.
Roitt et al., Immunology, Moscow: Mir, 2000, pp. 97-113 (including what are believed to be corresponding pages from an English language edition of Immunology).
Roitt et al., Immunology, Moscow: Mir, 2000, pp. 111-112 (including what are believed to be corresponding pages from an English language edition of Immunology).
Roitt et al., Immunology, Moscow: Mir, 2000, pp. 373-374 (with English translation).
Sazinsky et al., "Aglycosylated immunoglobulin $G_1$ variants productively engage activating Fc receptors," Proc Natl Acad Sci USA, Dec. 2008, 105(51):20167-20172. doi: 10/1073/pnas.0809257105. Epub Dec. 12, 2008.
Schroter et al., "A generic approach to engineer antibody pH-switches using combinatorial histidine scanning libraries and yeast display," mAbs, Jan./Feb. 2015, 7(1):138-51. doi: 10.416119420862. 2014.985993.
Stepanov, Molecular Biology, Structure and Functions of Proteins, M.: NAUKA, 2005, pp. 61-62 (with English translation).
Travis et al., "Isolation of albumin from whole human plasma and fractionation of albumin-depleted plasma," Biochem J, Aug. 1976, 157(2):301-306.
Vercellini et al., "Postoperative oral contraceptive exposure and risk of endometrioma recurrence," Am J Obstet Gynecol, May 2008, 198(5):504.e1-5. doi: 10.1016/j.ajog.2007.11.010 Feb. 1, 2008.
Weiss et al., "Rapid mapping of protein functional epitopes by combinatorial alanine scanning," Proc Natl Acad Sci USA, Aug. 2000, 97(16):8950-8954.
Yada et al., Lippincott's Illustrated Reviews: Immunology, Second Edition, Mar. 30, 2013, Chapter 2, pp. 11-23, and Chapter 11, pp. 149-165 (with English translation).
Yarilin, Fundamentals of Immunology, M: Medicina, 1999, pp. 175, 182 (with English translation).
Yarilin, Fundamentals of Immunology, M: Medicina, 1999, pp. 172-174 (with English translation).
Yarilin, Fundamentals of Immunology, M: Medicina, 1999, pp. 181-184 (with English translation).
USPTO Non-Final Office Action in U.S. Appl. No. 14/379,825, dated Nov. 1, 2018, 27 pages.
USPTO Final Office Action in U.S. Appl. No. 14/379,825, dated Jun. 14, 2019, 30 pages.
USPTO Advisory Action Before the Filing of an Appeal Brief and Notice of Non-Compliant Amendment (37 CFR 1.121) in U.S. Appl. No. 14/404,051, dated Jun. 28, 2018, 4 pages.

(56) References Cited

OTHER PUBLICATIONS

USPTO Advisory Action Before the Filing of an Appeal Brief in U.S. App. No. 14/404,051, dated Aug. 30, 2018, 3 pages.
USPTO Non-Final Office Action in U.S. Appl. No. 14/781,069, dated Aug. 27, 2018, 59 pages.
USPTO Applicant-Initiated Interview Summary in U.S. Appl. No. 14/781,069, dated Feb. 26, 2019, 3 pages.
USPTO Final Office Action in U.S. Appl. No. 14/781,069, dated May 20, 2019, 29 pages.
USPTO Final Office Action in U.S. Appl. No. 14/402,574, dated Jul. 16, 2018, 10 pages.
USPTO Non-Final Office Action in U.S. Appl. No. 14/422,207, dated Jun. 18, 2019, 43 pages.
Roitt et al., "Introduction to the Immune System," Immunology, M., Mir, 2000, p. 9 (with English translation).
U.S. Appl. No. 16/697,310, Igawa et al., filed Nov. 27, 2019.
U.S. Appl. No. 16/323,142, Kakiuchi et al., filed Feb. 4, 2019.
U.S. Appl. No. 16/065,192, Ruike et al., filed Jun. 22, 2018.
U.S. Appl. No. 15/963,449, Ruike et al., filed Apr. 26, 2018.
U.S. Appl. No. 15/963,455, Ruike et al., filed Apr. 26, 2018.
U.S. Pat. No. 10,519,229, Igawa et al., issued Dec. 31, 2019.
U.S. Appl. No. 13/637,415, Igawa et al., filed Feb. 4, 2013.
U.S. Pat. No. 10,000,560, Ruike et al., issued Jun. 19, 2018.
U.S. Pat. No. 9,969,800, Igawa et al., issued May 15, 2018.
U.S. Appl. No. 15/050,145, Igawa et al., filed Feb. 22, 2016.
U.S. Appl. No. 15/210,353, Igawa et al., filed Jul. 14, 2016.
U.S. Appl. No. 15/210,360, Igawa et al., filed Jul. 14, 2016.
U.S. Appl. No. 15/495,026, Igawa et al., filed Apr. 24, 2017.
U.S. Appl. No. 14/001,218, Mimoto et al., filed Dec. 2, 2013.
U.S. Appl. No. 14/007,947, Igawa et al., filed Dec. 30, 2013.
U.S. Appl. No. 16/806,027, Igawa et al., filed Mar. 2, 2020.
U.S. Pat. No. 9,890,218, Mimoto et al., issued Feb. 13, 2018.
U.S. Appl. No. 15/860,163, Mimoto et al., filed Jan. 2, 2018.
U.S. Appl. No. 14/347,034, Igawa et al., filed Mar. 25, 2014 (abandoned).
U.S. Appl. No. 15/230,904, Igawa et al., filed Aug. 8, 2016 (abandoned).
U.S. Appl. No. 16/028,140, Igawa et al., filed Jul. 5, 2018.
U.S. Appl. No. 14/347,321, Igawa et al., filed Mar. 26, 2014 (abandoned).
U.S. Appl. No. 15/977,757, Igawa et al., filed May 11, 2018.
U.S. Pat. No. 10/253,100, Igawa et al., issued Apr. 9, 2019.
U.S. Appl. No. 16/264,735, Igawa et al., filed Feb. 1, 2019.
U.S. Appl. No. 14/361,013, Igawa et al., filed May 28, 2014 (abandoned).
U.S. Appl. No. 16/108,897, Igawa et al., filed Aug. 22, 2018.
U.S. Appl. No. 14/404,051, Igawa et al., filed Nov. 26, 2014.
U.S. Appl. No. 14/379,825, Igawa et al., filed Aug. 20, 2014.
U.S. Appl. No. 14/654,895, Igawa et al., filed Jun. 23, 2015.
U.S. Appl. No. 14/781,069, Mimoto et al., filed Sep. 29, 2015.
U.S. Appl. No. 16/697,310, filed Nov. 27, 2019, Igawa et al.
U.S. Appl. No. 16/806,027, filed Mar. 2, 2020, Igawa et al.
Annotated amino acid sequence of the variable heavy (VH) and variable light (VL) domains of the monoclonal antibodies bevacizumab/Avastin, adalimumab/Humira, omalizumab/Xolair, and rituximab/Mabthera, 10 pages (submitted to the EPO with the written submission to attend oral proceedings on Sep. 6, 2019 by Opponent 1 in EP 11714860.1).
Arici, "Local Cytokines in Endometrial Tissue: The Role of Interleukin-8 in the Pathogenesis of Endometriosis," Ann NY Acad Sci, Mar. 2002, 955:101-9, discussion 118, pp. 396-406.
Buckler, Section 2.4 "Library Selection," Antibody Drug Discovery, edited by Clive R. Wood, Imperial College Press, 2012, vol. 4—Molecular Medicine and Medicinal Chemistry, pp. 49-57.
Chen et al., "Enhancement and destruction of antibody function by somatic mutation: unequal occurrence is controlled by V gene combinatorial associations," EMBO J, Jun. 15, 1995, 14(12):2784-2794.
Cunningham et al., "The Covalent Structure of a Human γG-Immunoglobulin. VII. Amino Acid Sequence of Heavy-Chain Cyanogen Bromide Fragments $H_1$-$H_4$," Biochemistry, Aug. 4, 1970, 9(16):3161-3170.
Diamond et al., "Somatic mutation of the T15 heavy chain gives rise to an antibody with autoantibody specificity," Proc Natl Acad Sci USA, Sep. 1984, 81(18):5841-5844.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-118.
Evidence for the publication date of Zalevsky et al., Nat Biotechnol, Feb. 2010, 28(2):157-159, 1 page (submitted to the EPO with the written submission to attend oral proceedings on Sep. 6, 2019 by Opponent 1 in EP 11714860.1).
Expert Declaration of J. Boucneau, dated Sep. 6, 2019, 13 pages (submitted to the EPO with the written submission to attend oral proceedings on Sep. 6, 2019 by Opponent 1 in EP 11714860.1).
Ghetie et al., "Multiple Roles for the Major Histocompatibility Complex Class I—Related Receptor FcRn," Annu Rev Immunol, Apr. 2000, 18:739-766.
Goel et al., "Plasticity within the Antigen-Combining Site May Manifest as Molecular Mimicry in the Humoral Immune Response," J Immunol, Dec. 15, 2004, 173(12):7358-7367.
Gonzalez et al., "BMP-1/Tolloid-like Metalloproteases Process Endorepellin, the Angiostatic C-terminal Fragment of Perlecan," J Biol Chem, Feb. 25, 2005, 280(8):7080-7087. Epub Dec. 9, 2004.
Hasemann et al., "Mutational Analysis of Arsonate Binding by a $CRI_{A+}$ Antibody—$V_H$ and $V_L$ Junctional Diversity are Essential for Binding Activity," J Biol Chem, Apr. 25, 1991, 266(12):7626-7632.
Hoogenboom, "Selecting and screening recombinant antibody libraries," Nat Biotechnol, Sep. 2005, 23(9):1105-1116.
Igawa et al., "Engineered Monoclonal Antibody with Novel Antigen-Sweeping Activity In Vivo," PLoS One, May 7, 2013, 8(5):e63236, 10 pages. doi: 10.1371/journal.pone.0063236. Print 2013.
Igawa et al., "pH-dependent antigen-binding antibodies as a novel therapeutic modality," Biochim Biophys Acta, Nov. 2014, 1844(11):1943-1950. doi: 10.1016/j.bbapap.2014.08.003. Epub Aug. 12, 2014.
Ito et al., "Molecular Designs of Antibodies and Peptides by Phage Display," Seibutsubutsuri, 2008, 48(5) : 294-298 (with English translation).
Kanyavuz et al., "Breaking the law: unconventional strategies for antibody diversification," Nat Rev Immunol, Jun. 2019, 19(6):355-368. doi: 10.1038/s41577-019-0126-7.
King, "Preparation, structure and function of monoclonal antibodies," Applications and Engineering of Monoclonal Antibodies, CRC Press, 1998, pp. 2, 13-14.
Kipriyanov et al., "Review—Generation of Recombinant Antibodies," Mol Biotechnol, Sep. 1999, 12(2):173-201.
Kurki et al., "Desmin antibodies in acute infectious myopericarditis," APMIS, Jun. 1989, 97(6):527-532.
Lloyd et al., "Modelling the human immune response: performance of a $10^{11}$ human antibody repertoire against a broad panel of therapeutically relevant antigens," Protein Eng Des Sel, Mar. 2009, 22(3):159-168. doi: 10.1093/protein/gzn058. Epub Oct. 29, 2008.
Medesan et al., "Comparative studies of rat IgG to further delineate the Fc:FcRn interaction site," Eur J Immunol, Jul. 1998, 28(7):2092-2100.
Ohno et al., "Antigen-binding specificities of antibodies are primarily determined by seven residues of $V_H$," Proc Natl Acad Sci USA, May 1985, 82(9):2945-2949.
Perng et al., "Desmin Aggregate Formation by R120G αB-Crystallin Is Caused by Altered Filament Interactions and Is Dependent upon Network Status in Cells," Mol Biol Cell, May 2004, 15(5):2335-2346.
Pirruccello-Straub, "Blocking extracellular activation of myostatin as a strategy for treating muscle wasting," Scientific Reports, Feb. 2, 2018, 8:2292, 15 pages.
Proprietor's (Chugai Seiyaku Kabushiki Kaisha) Submission dated Sep. 19, 2016 in EP11714860.1, 3 pages (submitted to the EPO with the written submission to attend oral proceedings on Sep. 6, 2019 by Opponent 1 in EP 11714860.1).

(56) References Cited

OTHER PUBLICATIONS

Proprietor's (Chugai Seiyaku Kabushiki Kaisha) Submission dated Sep. 5, 2016 in EP11714860.1, 6 pages (submitted to the EPO with the written submission to attend oral proceedings on Sep. 6, 2019 by Opponent 1 in EP 11714860.1).

Proprietor's (Chugai Seiyaku) Submission dated Feb. 20, 2017 in EP 2 275 443, 35 pages (submitted to the EPO with the written submission to attend oral proceedings on Sep. 6, 2019 by Opponent 5 in EP 11714860.1).

Rich et al., "A global study using affinity-based biosensors," Anal Biochem, Mar. 15, 2009, 386(2):194-216. doi: 10.1016/j.ab.2008.11.021. Epub Nov. 27, 2008.

Schlothauer et al., "Novel human IgG1 and IgG4 Fc-engineered antibodies with completely abolished immune effector functions," Protein Eng Des Sel, Oct. 2016, 29(10):457-466. doi: 10.1093/protein/gzw040. Epub Aug. 29, 2016.

Sigma product information for ACES buffer, 1 page (submitted to the EPO with the written submission to attend oral proceedings on Sep. 6, 2019 by Opponent 1 in EP 11714860.1).

Table summarizing alleged lack of novelty over WO 2009/086320A, Jul. 9, 2009, 4 pages (submitted to the EPO with the written submission to attend oral proceedings on Sep. 6, 2019 by Opponent 1 in EP 11714860.1).

Tarantul, "Antibodies," Explanatory Biotechnological Dictionary—Russian-English, Moscow, Languages of Slavic Cultures, 2009, p. 72 (with English translation).

Wolfman et al., "Activation of latent myostatin by the BMP-1/tolloid family of metalloproteinases," Proc Natl Acad Sci USA, Dec. 23, 2003, 100(26):15842-15846. Epub Dec. 11, 2003.

Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.

USPTO Non-Final Office Action in U.S. Appl. No. 14/404,051, dated Oct. 11, 2019, 20 pages.

USPTO Non-Final Office Action in U.S. Appl. No. 14/781,069, dated Mar. 13, 2020, 12 pages.

USPTO Final Office Action in U.S. Appl. No. 14/422,207, dated Mar. 27, 2020, 15 pages.

* cited by examiner

THIN LINE: X-RAY CRYSTAL STRUCTURE OF Fc(P238D)/FcγRIIb
EXTRACELLULAR REGION COMPLEX
HEAVY LINE: X-RAY CRYSTAL STRUCTURE OF Fc(P208)/FcγRIIb
EXTRACELLULAR REGION COMPLEX

BLACK: X-RAY CRYSTAL STRUCTURE OF Fc(P208)/FcγRIIaR
EXTRACELLULAR REGION COMPLEX
GRAY: X-RAY CRYSTAL STRUCTURE OF Fc(P208)/FcγRIIb
EXTRACELLULAR REGION COMPLEX

THIN LINE: Fc(P208)
HEAVY LINE: FcγRIIaR or FcγRIIb EXTRACELLULAR REGION
LEFT: X-RAY CRYSTAL STRUCTURE OF Fc(P208)/FcγRIIaR EXTRACELLULAR REGION COMPLEX
RIGHT: X-RAY CRYSTAL STRUCTURE OF Fc(P208)/FcγRIIb EXTRACELLULAR REGION COMPLEX

THIN LINE: Fc(P208)
HEAVY LINE: FcγRIIaR or FcγRIIb EXTRACELLULAR REGION
LEFT: X-RAY CRYSTAL STRUCTURE OF Fc(P208)/FcγRIIaR EXTRACELLULAR REGION COMPLEX
RIGHT: X-RAY CRYSTAL STRUCTURE OF Fc(P208)/FcγRIIb EXTRACELLULAR REGION COMPLEX

```
G1d  118 ASTKGPSVFPLAPSSKSTSGGTAALGCLVKDYFPEPVTVSWNSGALTSGVHTFPAVLQSSGLYSLSSVVTVPSSSLGTQTYICNVNHKPS
G4d  118 ASTKGPSVFPLAPCSRSTSESTAALGCLVKDYFPEPVTVSWNSGALTSGVHTFPAVLQSSGLYSLSSVVTVPSSSLGTKTYTCNVDHKPS

G1d  208 NTKVDKKVEPKSCDKTHTCPPCPAPELLGGPSVFLFPPKPKDTLMISRTPEVTCVVVDVSHEDPEVKFNWYVDGVEVHNAKTKPREEQYN
G4d  208 NTKVDKRVESK---YGPPCPPCPAPEFLGGPSVFLFPPKPKDTLMISRTPEVTCVVVDVSQEDPEVQFNWYVDGVEVHNAKTKPREEQFN

G1d  298 STYRVVSVLTVLHQDWLNGKEYKCKVSNKALPAPIEKTISKAKGQPREPQVYTLPPSRDELTKNQVSLTCLVKGFYPSDIAVEWESNGQP
G4d  298 STYRVVSVLTVLHQDWLNGKEYKCKVSNKGLPSSIEKTISKAKGQPREPQVYTLPPSQEEMTKNQVSLTCLVKGFYPSDIAVEWESNGQP

G1d  388 ENNYKTTPPVLDSDGSFFLYSKLTVDKSRWQQGNVFSCSVMHEALHNHYTQKSLSLSP
G4d  388 ENNYKTTPPVLDSDGSFFLYSRLTVDKSRWQEGNVFSCSVMHEALHNHYTQKSLSLSL
```

FIG. 14

SEQUENCE LISTING

<160> NUMBER OF SEQ ID NOS: 81

<210> SEQ ID NO 1
<211> LENGTH: 1125
<212> TYPE: DNA
<213> ORGANISM: Homo sapiens

<400> SEQUENCE: 1

```
atgtggttct tgacaactct gctcctttgg gttccagttg atgggcaagt ggacaccaca       60
aaggcagtga tcactttgca gcctccatgg gtcagcgtgt tccaagagga aaccgtaacc      120
ttgcactgtg aggtgctcca tctgcctggg agcagctcta cacagtggtt tctcaatggc      180
acagccactc agacctcgac ccccagctac agaatcacct ctgccagtgt caatgacagt      240
ggtgaataca ggtgccagag aggtctctca gggcgaagtg accccataca gctggaaatc      300
cacagaggct ggctactact gcaggtctcc agcagagtct tcacggaagg agaacctctg      360 gcctgagt gtcatgcgtg gaaggataag ctggtgtaca atgtgcttta ctatcgaaat      420
ggcaaagcct ttaagttttt ccactggaat tctaacctca ccattctgaa aaccaacata      480
```

```
agtcacaatg gcacctacca ttgctcaggc atgggaaagc atcgctacac atcagcagga        540
atatctgtca ctgtgaaaga gctatttcca gctccagtgc tgaatgcatc tgtgacatcc        600
ccactcctgg aggggaatct ggtcaccctg agctgtgaaa caaagttgct cttgcagagg        660 cctggttttgc agctttactt ctccttctac atgggcagca agaccctgcg aggcaggaac       720
acatcctctg aataccaaat actaactgct agaagagaag actctgggtt atactggtgc        780
gaggctgcca cagaggatgg aaatgtcctt aagcgcagcc tgagttgga gcttcaagtg         840 cttggcctcc agttaccaac tcctgtctgg tttcatgtcc ttttctatct ggcagtggga        900
ataatgtttt tagtgaacac tgttctctgg gtgacaatac gtaaagaact gaaaagaaag        960
aaaaagtggg atttagaaat ctctttggat tctggtcatg agaagaaggt aatttccagc       1020
cttcaagaag acagacattt agaagaagag ctgaaatgtc aggaacaaaa agaagaacag       1080
ctgcaggaag gggtgcaccg gaaggagccc caggggccca cgtag                      1125
```

<210> SEQ ID NO 2
<211> LENGTH: 374
<212> TYPE: PRT
<213> ORGANISM: Homo sapiens

<400> SEQUENCE: 2

```
Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Thr Gln Trp Phe Leu Asn Gly Thr Ala Thr Gln
    50                  55                  60

Thr Ser Thr Pro Ser Tyr Arg Ile Thr Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255
```

Leu Tyr Trp Cys Glu Ala Ala Thr Glu Asp Gly Asn Val Leu Lys Arg
                260                 265                 270

Ser Pro Glu Leu Glu Leu Gln Val Leu Gly Leu Gln Leu Pro Thr Pro
            275                 280                 285

Val Trp Phe His Val Leu Phe Tyr Leu Ala Val Gly Ile Met Phe Leu
        290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Leu Lys
                340                 345                 350

Cys Gln Glu Gln Lys Glu Glu Gln Leu Gln Glu Gly Val His Arg Lys
            355                 360                 365

Glu Pro Gln Gly Ala Thr
        370

<210> SEQ ID NO 3
<211> LENGTH: 951
<212> TYPE: DNA
<213> ORGANISM: Homo sapiens

<400> SEQUENCE: 3

| | |
|---|---|
| atgactatgg agacccaaat gtctcagaat gtatgtccca gaaacctgtg gctgcttcaa | 60 |
| ccattgacag ttttgctgct gctggcttct gcagacagtc aagctgctcc cccaaaggct | 120 |
| gtgctgaaac ttgagccccc gtggatcaac gtgctccagg aggactctgt gactctgaca | 180 |
| tgccaggggg ctcgcagccc tgagagcgac tccattcagt ggttccacaa tgggaatctc | 240 |
| attcccaccc acacgcagcc cagctacagg ttcaaggcca caacaatga cagcggggag | 300 |
| tacacgtgcc agactggcca gaccagcctc agcgaccctg tgcatctgac tgtgctttcc | 360 |
| gaatggctgg tgctccagac ccctcacctg gagttccagg agggagaaac catcatgctg | 420 |
| aggtgccaca gctggaagga caagcctctg gtcaaggtca cattcttcca gaatggaaaa | 480 |
| tcccagaaat ctcccatttt ggatcccacc ttctccatcc acaagcaaaa ccacagtcac | 540 |
| agtggtgatt accactgcac aggaaacata ggctacacgc tgttctcatc caagcctgtg | 600 |
| accatcactg tccaagtgcc agcatgggc agctcttcac caatgggggt cattgtggct | 660 |
| gtggtcattg cgactgctgt agcagccatt gttgctgctg tagtggcctt gatctactgc | 720 |
| aggaaaaagc ggatttcagc caattccact gatcctgtga aggctgccca atttgagcca | 780 |
| cctgacgtc aaatgattgc catcagaaag agacaacttg aagaaccaa caatgactat | 840 |
| gaaacagctg acggcggcta catgactctg aaccccaggg cacctactga cgatgataaa | 900 |
| aacatctacc tgactcttcc tcccaacgac catgtcaaca gtaataacta a | 951 |

<210> SEQ ID NO 4
<211> LENGTH: 316
<212> TYPE: PRT
<213> ORGANISM: Homo sapiens

<400> SEQUENCE: 4

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp

```
         35                  40                  45
Ile Asn Val Leu Gln Glu Asp Ser Val Thr Leu Thr Cys Gln Gly Ala
 50                  55                  60
Arg Ser Pro Glu Ser Asp Ser Ile Gln Trp Phe His Asn Gly Asn Leu
 65                  70                  75                  80
Ile Pro Thr His Thr Gln Pro Ser Tyr Arg Phe Lys Ala Asn Asn Asn
                 85                  90                  95
Asp Ser Gly Glu Tyr Thr Cys Gln Thr Gly Gln Thr Ser Leu Ser Asp
            100                 105                 110
Pro Val His Leu Thr Val Leu Ser Glu Trp Leu Val Leu Gln Thr Pro
        115                 120                 125
His Leu Glu Phe Gln Glu Gly Glu Thr Ile Met Leu Arg Cys His Ser
    130                 135                 140
Trp Lys Asp Lys Pro Leu Val Lys Val Thr Phe Phe Gln Asn Gly Lys
145                 150                 155                 160
Ser Gln Lys Phe Ser His Leu Asp Pro Thr Phe Ser Ile Pro Gln Ala
                165                 170                 175
Asn His Ser His Ser Gly Asp Tyr His Cys Thr Gly Asn Ile Gly Tyr
            180                 185                 190
Thr Leu Phe Ser Ser Lys Pro Val Thr Ile Thr Val Gln Val Pro Ser
        195                 200                 205
Met Gly Ser Ser Pro Met Gly Val Ile Val Ala Val Val Ile Ala
    210                 215                 220
Thr Ala Val Ala Ala Ile Val Ala Ala Val Val Ala Leu Ile Tyr Cys
225                 230                 235                 240
Arg Lys Lys Arg Ile Ser Ala Asn Ser Thr Asp Pro Val Lys Ala Ala
                245                 250                 255
Gln Phe Glu Pro Pro Gly Arg Gln Met Ile Ala Ile Arg Lys Arg Gln
            260                 265                 270
Leu Glu Glu Thr Asn Asn Asp Tyr Glu Thr Ala Asp Gly Gly Tyr Met
        275                 280                 285
Thr Leu Asn Pro Arg Ala Pro Thr Asp Asp Lys Asn Ile Tyr Leu
    290                 295                 300
Thr Leu Pro Pro Asn Asp His Val Asn Ser Asn Asn
305                 310                 315

<210> SEQ ID NO 5
<211> LENGTH: 876
<212> TYPE: DNA
<213> ORGANISM: Homo sapiens

<400> SEQUENCE: 5
atgggaatcc tgtcattctt acctgtcctt gccactgaga gtgactgggc tgactgcaag      60
tccccccagc cttggggtca tatgcttctg tggacagctg tgctattcct ggctcctgtt     120
gctgggacac ctgcagctcc cccaaaggct gtgctgaaac tcgagcccca gtggatcaac     180
gtgctccagg aggactctgt gactctgaca tgccggggga ctcacagccc tgagagcgac     240
tccattcagt ggttccacaa tgggaatctc attcccaccc acacgcagcc cagctacagg     300
ttcaaggcca acaacaatga cagcggggag tacacgtgcc agactggcca gaccagcctc     360
agcgaccctg tgcatctgac tgtgctttct gagtggctgg tgctccagac ccctcacctg     420
gagttccagg agggagaaac catcgtgctg aggtgccaca gctggaagga caagcctctg     480
gtcaaggtca cattcttcca gaatggaaaa tccaagaaat ttcccgttc ggatcccaac     540
```

```
ttctccatcc cacaagcaaa ccacagtcac agtggtgatt accactgcac aggaaacata    600
ggctacacgc tgtactcatc caagcctgtg accatcactg tccaagctcc cagctcttca    660
ccgatgggga tcattgtggc tgtggtcact gggattgctg tagcggccat tgttgctgct    720
gtagtggcct tgatctactg caggaaaaag cggatttcag ccaatcccac taatcctgat    780
gaggctgaca agttggggc tgagaacaca atcacctatt cacttctcat gcacccggat    840
gctctggaag agcctgatga ccagaaccgt atttag                             876
```

<210> SEQ ID NO 6
<211> LENGTH: 291
<212> TYPE: PRT
<213> ORGANISM: Homo sapiens
<400> SEQUENCE: 6

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290
```

<210> SEQ ID NO 7

```
<211> LENGTH: 765
<212> TYPE: DNA
<213> ORGANISM: Homo sapiens

<400> SEQUENCE: 7
atgtggcagc tgctcctccc aactgctctg ctacttctag tttcagctgg catgcggact      60
gaagatctcc caaaggctgt ggtgttcctg gagcctcaat ggtacagggt gctcgagaag     120
gacagtgtga ctctgaagtg ccagggagcc tactcccctg aggacaattc acacagtgg     180 tttcacaatg agagcctcat ctcaagccag gcctcgagct acttcattga cgctgccaca     240
gttgacgaca gtggagagta caggtgccag acaaacctct ccaccctcag tgacccggtg     300
cagctagaag tccatatcgg ctggctgttg ctccaggccc ctcggtgggt gttcaaggag     360
gaagacccta ttcacctgag gtgtcacagc tggaagaaca ctgctctgca taaggtcaca     420
tatttacaga atggcaaagg caggaagtat tttcatcata attctgactt ctacattcca     480
aaagccacac tcaaagacag cggctcctac ttctgcaggg ggcttgttgg gagtaaaaat     540
gtgtcttcag agactgtgaa catcaccatc actcaaggtt tgtcagtgtc aaccatctca     600
tcattctttc cacctgggta ccaagtctct ttctgcttgg tgatggtact ccttttttgca    660 gtggacacag gactatattt ctctgtgaag acaaacattc gaagctcaac aagagactgg     720
aaggaccata atttaaatg gagaaaggac cctcaagaca aatga                     765

<210> SEQ ID NO 8
<211> LENGTH: 254
<212> TYPE: PRT
<213> ORGANISM: Homo sapiens

<400> SEQUENCE: 8

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205
```

```
Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 9
<211> LENGTH: 702
<212> TYPE: DNA
<213> ORGANISM: Homo sapiens

<400> SEQUENCE: 9

```
atgtggcagc tgctcctccc aactgctctg ctacttctag tttcagctgg catgcggact      60
gaagatctcc caaaggctgt ggtgttcctg gagcctcaat ggtacagcgt gcttgagaag     120
gacagtgtga ctctgaagtg ccagggagcc tactcccctg aggacaattc cacacagtgg     180
tttcacaatg agagcctcat ctcaagccag gcctcgagct acttcattga cgctgccaca     240
gtcaacgaca gtggagagta caggtgccag acaaacctct ccaccctcag tgacccggtg     300
cagctagaag tccatatcgg ctggctgttg ctccaggccc ctcggtgggt gttcaaggag     360
gaagaccctaT ttcacctgag gtgtcacagc tggaagaaca ctgctctgca taaggtcaca     420
tatttacaga atggcaaaga caggaagtat tttcatcata attctgactt ccacattcca     480
aaagccacac tcaaagatag cggctcctac ttctgcaggg ggcttgttgg gagtaaaaat     540
gtgtcttcag agactgtgaa catcaccatc actcaaggtt tggcagtgtc aaccatctca     600
tcattctctc cacctgggta ccaagtctct ttctgcttgg tgatggtact ccttttttgca     660
gtggacacag gactatattt ctctgtgaag acaaacattt ga                         702
```

<210> SEQ ID NO 10
<211> LENGTH: 233
<212> TYPE: PRT
<213> ORGANISM: Homo sapiens

<400> SEQUENCE: 10

```
Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Asp Arg Lys Tyr Phe His His Asn Ser Asp Phe His Ile Pro
145                 150                 155                 160
```

```
Lys Ala Thr Leu Lys Asp Ser Gly Ser Tyr Phe Cys Arg Gly Leu Val
            165                 170                 175

Gly Ser Lys Asn Val Ser Ser Glu Thr Val Asn Ile Thr Ile Thr Gln
        180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```

<210> SEQ ID NO 11
<211> LENGTH: 330
<212> TYPE: PRT
<213> ORGANISM: artificial
<220> FEATURE:
<223> OTHER INFORMATION: An artificially generated sequence

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 326
<212> TYPE: PRT
<213> ORGANISM: artificial
<220> FEATURE:
<223> OTHER INFORMATION: An artificially generated sequence

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

```
Ser Leu Ser Pro Gly Lys
            325
```

```
<210> SEQ ID NO 13
<211> LENGTH: 377
<212> TYPE: PRT
<213> ORGANISM: artificial
<220> FEATURE:
<223> OTHER INFORMATION: An artificially generated sequence

<400> SEQUENCE: 13

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

Phe Ser Cys Ser Val Met His Glu Ala Leu His Asn Arg Phe Thr Gln
            355                 360                 365

Lys Ser Leu Ser Leu Ser Pro Gly Lys
    370                 375

<210> SEQ ID NO 14
<211> LENGTH: 327
<212> TYPE: PRT
<213> ORGANISM: artificial
<220> FEATURE:
<223> OTHER INFORMATION: An artificially generated sequence

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

```
<210> SEQ ID NO 15
<211> LENGTH: 115
<212> TYPE: PRT
<213> ORGANISM: Artificial
<220> FEATURE:
<223> OTHER INFORMATION: An artificially generated sequence

<400> SEQUENCE: 15

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
                20                  25                  30

Glu Met His Trp Ile Arg Gln Pro Pro Gly Glu Gly Leu Glu Trp Ile
            35                  40                  45

Gly Ala Ile Asp Pro Lys Thr Gly Asp Thr Ala Tyr Ser Glu Ser Phe
        50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 16
<211> LENGTH: 219
<212> TYPE: PRT
<213> ORGANISM: Artificial
<220> FEATURE:
<223> OTHER INFORMATION: An artificially generated sequence

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
                20                  25                  30

Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190
```

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 17
<211> LENGTH: 443
<212> TYPE: PRT
<213> ORGANISM: Artificial
<220> FEATURE:
<223> OTHER INFORMATION: An artificially generated sequence

<400> SEQUENCE: 17

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

```
Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
        435                 440

<210> SEQ ID NO 18
<211> LENGTH: 119
<212> TYPE: PRT
<213> ORGANISM: Artificial
<220> FEATURE:
<223> OTHER INFORMATION: An artificially generated sequence

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 19
<211> LENGTH: 447
<212> TYPE: PRT
<213> ORGANISM: Artificial
<220> FEATURE:
<223> OTHER INFORMATION: An artificially generated sequence

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
```

```
              65                  70                  75                  80
Leu Gln Met Asn Ser Leu Arg Ala Glu Asp Thr Ala Val Tyr Tyr Cys
                    85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 20
<211> LENGTH: 447
<212> TYPE: PRT
<213> ORGANISM: Artificial
<220> FEATURE:
<223> OTHER INFORMATION: An artificially generated sequence
```

```
<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 21
<211> LENGTH: 214
<212> TYPE: PRT
<213> ORGANISM: Artificial
<220> FEATURE:
<223> OTHER INFORMATION: An artificially generated sequence

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 447
<212> TYPE: PRT
<213> ORGANISM: Artificial
<220> FEATURE:
<223> OTHER INFORMATION: An artificially generated sequence

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
```

```
                50                  55                  60
Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
               100                 105                 110

Thr Leu Val Thr Val Ser Ser Ala Ser Thr Lys Gly Pro Ser Val Phe
               115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
               165                 170                 175

Gln Ser Ser Gly Leu Tyr Ser Leu Ser Ser Val Val Thr Val Pro Ser
               180                 185                 190

Ser Ser Leu Gly Thr Gln Thr Tyr Ile Cys Asn Val Asn His Lys Pro
               195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
               245                 250                 255

Arg Thr Pro Glu Val Thr Cys Val Val Val Asp Val Ser His Glu Asp
               260                 265                 270

Pro Glu Val Lys Phe Asn Trp Tyr Val Asp Gly Val Glu Val His Asn
               275                 280                 285

Ala Lys Thr Lys Pro Arg Glu Glu Gln Tyr Asn Ser Thr Tyr Arg Val
               290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
               325                 330                 335

Thr Ile Ser Lys Ala Lys Gly Gln Pro Arg Glu Pro Gln Val Tyr Thr
               340                 345                 350

Leu Pro Pro Ser Arg Asp Glu Leu Thr Lys Asn Gln Val Ser Leu Thr
               355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
               405                 410                 415

Ser Arg Trp Gln Gln Gly Asn Val Phe Ser Cys Ser Val Met His Glu
               420                 425                 430

Ala Leu His Tyr His Tyr Thr Gln Lys Ser Leu Ser Leu Ser Pro
               435                 440                 445

<210> SEQ ID NO 23
<211> LENGTH: 447
<212> TYPE: PRT
<213> ORGANISM: Artificial
```

<220> FEATURE:
<223> OTHER INFORMATION: An artificially generated sequence

<400> SEQUENCE: 23

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

<210> SEQ ID NO 24
<211> LENGTH: 447
<212> TYPE: PRT
<213> ORGANISM: Artificial
<220> FEATURE:
<223> OTHER INFORMATION: An artificially generated sequence

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 25
<211> LENGTH: 449
<212> TYPE: PRT
<213> ORGANISM: Artificial
<220> FEATURE:
<223> OTHER INFORMATION: An artificially generated sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 26
<211> LENGTH: 218
<212> TYPE: PRT
<213> ORGANISM: Artificial
<220> FEATURE:
<223> OTHER INFORMATION: An artificially generated sequence

<400> SEQUENCE: 26

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 27
<211> LENGTH: 447
<212> TYPE: PRT
<213> ORGANISM: Artificial
<220> FEATURE:
<223> OTHER INFORMATION: An artificially generated sequence

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285
```

```
Ala Lys Thr Lys Pro Arg Glu Glu Gln Asp Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

<210> SEQ ID NO 28
<211> LENGTH: 447
<212> TYPE: PRT
<213> ORGANISM: Artificial
<220> FEATURE:
<223> OTHER INFORMATION: An artificially generated sequence

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Glu Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 29
<211> LENGTH: 447
<212> TYPE: PRT
<213> ORGANISM: Artificial
<220> FEATURE:
<223> OTHER INFORMATION: An artificially generated sequence

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser Glu Glu Asp
                260                 265                 270

Gly Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 30
<211> LENGTH: 444
<212> TYPE: PRT
<213> ORGANISM: Artificial
<220> FEATURE:
<223> OTHER INFORMATION: An artificially generated sequence

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
                35                  40                  45
```

```
Ile Gly Phe Ile Ser Tyr Ser Gly Ile Thr Asn Tyr Asn Pro Ser Leu
     50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
        435                 440

<210> SEQ ID NO 31
<211> LENGTH: 444
<212> TYPE: PRT
```

<213> ORGANISM: Artificial
<220> FEATURE:
<223> OTHER INFORMATION: An artificially generated sequence

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Asp Leu Leu Gly Asp Asp Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Asp Gly Glu Val
            260                 265                 270

Lys Phe Asn Trp Tyr Val Asp Gly Val Glu Val His Asn Ala Lys Thr
        275                 280                 285

Lys Pro Arg Glu Glu Gln Asp Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Arg Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp

```
                385                 390                 395                 400
Gly Ser Phe Phe Leu Tyr Ser Lys Leu Thr Val Asp Lys Ser Arg Trp
                    405                 410                 415

Gln Gln Gly Asn Val Phe Ser Cys Ser Val Met His Glu Ala Leu His
                420                 425                 430

Asn His Tyr Thr Gln Glu Ser Leu Ser Leu Ser Pro
                435                 440

<210> SEQ ID NO 32
<211> LENGTH: 447
<212> TYPE: PRT
<213> ORGANISM: Artificial
<220> FEATURE:
<223> OTHER INFORMATION: An artificially generated sequence

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
                305                 310                 315                 320
Tyr Lys Cys Lys Val Ser Asn Lys Ala Phe Pro Ala Pro Ile Glu Lys
                    325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Glu Ser Leu Ser Leu Ser Pro
            435                 440                 445

<210> SEQ ID NO 33
<211> LENGTH: 447
<212> TYPE: PRT
<213> ORGANISM: Artificial
<220> FEATURE:
<223> OTHER INFORMATION: An artificially generated sequence

<400> SEQUENCE: 33

Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
                20                  25                  30
His Ala Trp Ser Trp Val Arg Gln Pro Pro Gly Glu Gly Leu Glu Trp
            35                  40                  45
Ile Gly Phe Ile Ser Tyr Ser Gly Ile Thr Asn Tyr Asn Pro Ser Leu
        50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
                    100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Asp Leu Leu Gly Asp Asp
```

```
                225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ala Glu Glu Asp
                260                 265                 270

Gly Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 34
<211> LENGTH: 443
<212> TYPE: PRT
<213> ORGANISM: Artificial
<220> FEATURE:
<223> OTHER INFORMATION: An artificially generated sequence

<400> SEQUENCE: 34

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
                20                  25                  30

Glu Met His Trp Ile Arg Gln Pro Pro Gly Glu Gly Leu Glu Trp Ile
            35                  40                  45

Gly Ala Ile Asp Pro Lys Thr Gly Asp Thr Ala Tyr Ser Glu Ser Phe
        50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
```

```
                145                 150                 155                 160
        Leu Thr Ser Gly Val His Thr Phe Pro Ala Val Leu Gln Ser Ser Gly
                        165                 170                 175

Leu Tyr Ser Leu Ser Ser Val Val Thr Val Pro Ser Ser Ser Leu Gly
                        180                 185                 190

Thr Gln Thr Tyr Ile Cys Asn Val Asn His Lys Pro Ser Asn Thr Lys
                        195                 200                 205

Val Asp Lys Lys Val Glu Pro Lys Ser Cys Asp Lys Thr His Thr Cys
                210                 215                 220

Pro Pro Cys Pro Ala Pro Glu Leu Leu Gly Gly Pro Ser Val Phe Leu
        225                 230                 235                 240

Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Lys
                        260                 265                 270

Phe Asn Trp Tyr Val Asp Gly Val Glu Val His Asn Ala Lys Thr Lys
                        275                 280                 285

Pro Arg Glu Glu Gln Tyr Asn Ser Thr Tyr Arg Val Val Ser Val Leu
                290                 295                 300

Thr Val Leu His Gln Asp Trp Leu Asn Gly Lys Glu Tyr Lys Cys Lys
        305                 310                 315                 320

Val Ser Asn Lys Ala Leu Pro Ala Pro Ile Glu Lys Thr Ile Ser Lys
                        325                 330                 335

Ala Lys Gly Gln Pro Arg Glu Pro Gln Val Tyr Thr Leu Pro Pro Ser
                        340                 345                 350

Arg Asp Glu Leu Thr Lys Asn Gln Val Ser Leu Thr Cys Leu Val Lys
                        355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro
                        435                 440

<210> SEQ ID NO 35
<211> LENGTH: 443
<212> TYPE: PRT
<213> ORGANISM: Artificial
<220> FEATURE:
<223> OTHER INFORMATION: An artificially generated sequence

<400> SEQUENCE: 35

Gln Val Gln Leu Val Gln Ser Gly Ala Glu Val Lys Lys Pro Gly Ala
        1               5                   10                  15

Ser Val Thr Val Ser Cys Lys Ala Ser Gly Tyr Thr Phe Thr Asp Tyr
                        20                  25                  30

Glu Met His Trp Ile Arg Gln Pro Pro Gly Glu Gly Leu Glu Trp Ile
                        35                  40                  45

Gly Ala Ile Asp Pro Lys Thr Gly Asp Thr Ala Tyr Ser Glu Ser Phe
                50                  55                  60

Gln Asp Arg Val Thr Leu Thr Ala Asp Lys Ser Thr Ser Thr Ala Tyr
```

Met Glu Leu Ser Ser Leu Thr Ser Glu Asp Thr Ala Val Tyr Tyr Cys
 65                  70                  75                  80

Thr Arg Phe Tyr Ser Tyr Thr Tyr Trp Gly Gln Gly Thr Leu Val Thr
             85                  90                  95

Val Ser Ser Ala Ser Thr Lys Gly Pro Ser Val Phe Pro Leu Ala Pro
            100                 105                 110

Ser Ser Lys Ser Thr Ser Gly Gly Thr Ala Ala Leu Gly Cys Leu Val
        115                 120                 125

Lys Asp Tyr Phe Pro Glu Pro Val Thr Val Ser Trp Asn Ser Gly Ala
130                 135                 140

Leu Thr Ser Gly Val His Thr Phe Pro Ala Val Leu Gln Ser Ser Gly
145                 150                 155                 160

Leu Tyr Ser Leu Ser Ser Val Val Thr Val Pro Ser Ser Leu Gly
            165                 170                 175

Thr Gln Thr Tyr Ile Cys Asn Val Asn His Lys Pro Ser Asn Thr Lys
        180                 185                 190

Val Asp Lys Lys Val Glu Pro Lys Ser Cys Asp Lys Thr His Thr Cys
    195                 200                 205

Pro Pro Cys Pro Ala Pro Glu Leu Leu Gly Gly Pro Ser Val Phe Leu
210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Lys
            245                 250                 255

Phe Asn Trp Tyr Val Asp Gly Val Glu Val His Asn Ala Lys Thr Lys
        260                 265                 270

Pro Arg Glu Glu Gln Tyr Asn Ser Thr Tyr Arg Val Val Ser Val Leu
    275                 280                 285

Thr Val Leu His Gln Asp Trp Leu Asn Gly Lys Glu Tyr Lys Cys Lys
290                 295                 300

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
            325                 330                 335

Arg Lys Glu Leu Thr Lys Asn Gln Val Ser Leu Thr Cys Leu Val Lys
        340                 345                 350

Gly Phe Tyr Pro Ser Asp Ile Ala Val Glu Trp Glu Ser Asn Gly Gln
    355                 360                 365

Pro Glu Asn Asn Tyr Lys Thr Thr Pro Pro Val Leu Asp Ser Asp Gly
370                 375                 380

Ser Phe Phe Leu Tyr Ser Lys Leu Thr Val Asp Lys Ser Arg Trp Gln
385                 390                 395                 400

Gln Gly Asn Val Phe Ser Cys Ser Val Met His Glu Ala Leu His Asn
            405                 410                 415

Arg Tyr Thr Gln Lys Ser Leu Ser Leu Ser Pro
        420                 425                 430

<210> SEQ ID NO 36
<211> LENGTH: 447
<212> TYPE: PRT
<213> ORGANISM: Artificial
<220> FEATURE:
<223> OTHER INFORMATION: An artificially generated sequence

<400> SEQUENCE: 36

```
Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
            20                  25                  30
His Ala Trp Ser Trp Val Arg Gln Pro Pro Gly Glu Gly Leu Glu Trp
        35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Asp Tyr Leu Gly Asp Asp
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Glu Glu Asp
            260                 265                 270
Gly Glu Val Lys Phe Asn Trp Tyr Val Asp Gly Val Glu Val His Asn
        275                 280                 285
Ala Lys Thr Lys Pro Arg Glu Glu Gln Asp Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Arg Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 37
<211> LENGTH: 447
<212> TYPE: PRT
<213> ORGANISM: Artificial
<220> FEATURE:
<223> OTHER INFORMATION: An artificially generated sequence

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Asp Leu Gln Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Glu Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

```
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 38
<211> LENGTH: 447
<212> TYPE: PRT
<213> ORGANISM: Artificial
<220> FEATURE:
<223> OTHER INFORMATION: An artificially generated sequence

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Phe Gly Asp Asp
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser Glu Glu Asp
            260                 265                 270

Gly Glu Val Lys Phe Asn Trp Tyr Val Asp Gly Val Glu Val His Asn
            275                 280                 285

Ala Lys Thr Lys Pro Arg Glu Glu Gln Asp Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Glu Ser Leu Ser Leu Ser Pro
            435                 440                 445

<210> SEQ ID NO 39
<211> LENGTH: 447
<212> TYPE: PRT
<213> ORGANISM: Artificial
<220> FEATURE:
<223> OTHER INFORMATION: An artificially generated sequence

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

-continued

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Asp Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Glu Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 40
<211> LENGTH: 447
<212> TYPE: PRT
<213> ORGANISM: Artificial
<220> FEATURE:
<223> OTHER INFORMATION: An artificially generated sequence

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Glu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Glu Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 41
<211> LENGTH: 447
<212> TYPE: PRT
<213> ORGANISM: Artificial
<220> FEATURE:
<223> OTHER INFORMATION: An artificially generated sequence

<400> SEQUENCE: 41

Gln Val Gln Leu Gln Glu Ser Gly Pro Gly Leu Val Lys Pro Ser Glu
1               5                   10                  15

```
Thr Leu Ser Leu Thr Cys Ala Val Ser Gly His Ser Ile Ser His Asp
             20                  25                  30

His Ala Trp Ser Trp Val Arg Gln Pro Gly Glu Gly Leu Glu Trp
         35                  40                  45

Ile Gly Phe Ile Ser Tyr Ser Gly Ile Thr Asn Tyr Asn Pro Ser Leu
     50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Asp Leu Thr Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Glu Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Glu Ser Leu Ser Leu Ser Pro
            435                 440                 445

<210> SEQ ID NO 42
<211> LENGTH: 447
<212> TYPE: PRT
<213> ORGANISM: Artificial
<220> FEATURE:
<223> OTHER INFORMATION: An artificially generated sequence

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Glu Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Lys Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Tyr Thr Gln Lys Ser Leu Ser Leu Ser Pro
        435                 440                 445

<210> SEQ ID NO 43
<211> LENGTH: 328
<212> TYPE: PRT
<213> ORGANISM: Artificial
<220> FEATURE:
<223> OTHER INFORMATION: An artificially generated sequence

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Asp Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 44
<211> LENGTH: 328
<212> TYPE: PRT
<213> ORGANISM: Artificial
<220> FEATURE:
<223> OTHER INFORMATION: An artificially generated sequence

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Asp Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 45
<211> LENGTH: 328
<212> TYPE: PRT
<213> ORGANISM: Artificial
<220> FEATURE:
<223> OTHER INFORMATION: An artificially generated sequence

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Glu Ser Leu Ser Leu Ser Pro
                325

-continued

```
<210> SEQ ID NO 46
<211> LENGTH: 328
<212> TYPE: PRT
<213> ORGANISM: Artificial
<220> FEATURE:
<223> OTHER INFORMATION: An artificially generated sequence

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Asp Glu Asp Gly Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Thr Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 47
<211> LENGTH: 328
<212> TYPE: PRT
<213> ORGANISM: Artificial
<220> FEATURE:
```

<223> OTHER INFORMATION: An artificially generated sequence

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Ile Asp Val Gly Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 48
<211> LENGTH: 328
<212> TYPE: PRT
<213> ORGANISM: Artificial
<220> FEATURE:
<223> OTHER INFORMATION: An artificially generated sequence

<400> SEQUENCE: 48

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Thr Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325
```

<210> SEQ ID NO 49
<211> LENGTH: 328
<212> TYPE: PRT
<213> ORGANISM: Artificial
<220> FEATURE:
<223> OTHER INFORMATION: An artificially generated sequence

<400> SEQUENCE: 49

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Arg Pro Thr Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 50
<211> LENGTH: 328
<212> TYPE: PRT
<213> ORGANISM: Artificial
<220> FEATURE:
<223> OTHER INFORMATION: An artificially generated sequence

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 51
<211> LENGTH: 328
<212> TYPE: PRT
<213> ORGANISM: Artificial
<220> FEATURE:
<223> OTHER INFORMATION: An artificially generated sequence

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Asp Leu Leu Gly Asp Asp Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser Asp Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 52
<211> LENGTH: 325
<212> TYPE: PRT
<213> ORGANISM: Artificial
<220> FEATURE:
<223> OTHER INFORMATION: An artificially generated sequence

<400> SEQUENCE: 52

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Asp Leu Leu Gly Asp Asp Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

-continued

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Asp
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Arg Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Pro
                325

<210> SEQ ID NO 53
<211> LENGTH: 328
<212> TYPE: PRT
<213> ORGANISM: Artificial
<220> FEATURE:
<223> OTHER INFORMATION: An artificially generated sequence

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro
            325

<210> SEQ ID NO 54
<211> LENGTH: 328
<212> TYPE: PRT
<213> ORGANISM: Artificial
<220> FEATURE:
<223> OTHER INFORMATION: An artificially generated sequence

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Asp Leu Leu Gly Asp Ser Val Phe Leu Phe Pro Pro
    115                 120                 125

Lys Pro Lys Asp Thr Leu Met Ile Ser Arg Thr Pro Glu Val Thr Cys
            130                 135                 140

Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

```
Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Met Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325
```

<210> SEQ ID NO 55
<211> LENGTH: 328
<212> TYPE: PRT
<213> ORGANISM: Artificial
<220> FEATURE:
<223> OTHER INFORMATION: An artificially generated sequence

<400> SEQUENCE: 55

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Ile Asp Val Ala Glu Glu Asp Gly Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 56
<211> LENGTH: 328
<212> TYPE: PRT
<213> ORGANISM: Artificial
<220> FEATURE:
<223> OTHER INFORMATION: An artificially generated sequence

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Met Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 57
<211> LENGTH: 328
<212> TYPE: PRT
<213> ORGANISM: Artificial
<220> FEATURE:
<223> OTHER INFORMATION: An artificially generated sequence

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Glu Ser Leu Ser Leu Ser Pro
                325
```

<210> SEQ ID NO 58
<211> LENGTH: 328
<212> TYPE: PRT
<213> ORGANISM: Artificial
<220> FEATURE:
<223> OTHER INFORMATION: An artificially generated sequence

<400> SEQUENCE: 58

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Glu Ser Leu Ser Leu Ser Pro
                325
```

<210> SEQ ID NO 59
<211> LENGTH: 328
<212> TYPE: PRT
<213> ORGANISM: Artificial
<220> FEATURE:
<223> OTHER INFORMATION: An artificially generated sequence

<400> SEQUENCE: 59

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325
```

<210> SEQ ID NO 60
<211> LENGTH: 328
<212> TYPE: PRT
<213> ORGANISM: Artificial

<220> FEATURE:
<223> OTHER INFORMATION: An artificially generated sequence

<400> SEQUENCE: 60

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Asp Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Ile Asp Val Ala Glu Glu Asp Gly Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Asp Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Glu Ser Leu Ser Leu Ser Pro
                325
```

<210> SEQ ID NO 61
<211> LENGTH: 328
<212> TYPE: PRT
<213> ORGANISM: Artificial
<220> FEATURE:
<223> OTHER INFORMATION: An artificially generated sequence

<400> SEQUENCE: 61

Ala Ser Thr Lys Gly Pro Ser Val Phe Pro Leu Ala Pro Ser Ser Lys

```
            1               5                  10                 15
Ser Thr Ser Gly Gly Thr Ala Ala Leu Gly Cys Leu Val Lys Asp Tyr
            20                 25                 30

Phe Pro Glu Pro Val Thr Val Ser Trp Asn Ser Gly Ala Leu Thr Ser
            35                 40                 45

Gly Val His Thr Phe Pro Ala Val Leu Gln Ser Ser Gly Leu Tyr Ser
            50                 55                 60

Leu Ser Ser Val Val Thr Val Pro Ser Ser Leu Gly Thr Gln Thr
 65                 70                 75                 80

Tyr Ile Cys Asn Val Asn His Lys Pro Ser Asn Thr Lys Val Asp Lys
                    85                 90                 95

Lys Val Glu Pro Lys Ser Cys Asp Lys Thr His Thr Cys Pro Pro Cys
            100                105                110

Pro Ala Pro Glu Leu Leu Gly Asp Asp Ser Val Phe Leu Phe Pro Pro
            115                120                125

Lys Pro Lys Asp Thr Leu Met Ile Ser Arg Thr Pro Glu Val Thr Cys
 130                135                140

Val Val Val Asp Val Ala Glu Glu Asp Gly Glu Val Lys Phe Asn Trp
 145                150                155                160

Tyr Val Asp Gly Val Glu Val His Asn Ala Lys Thr Lys Pro Arg Glu
                    165                170                175

Glu Gln Asp Asn Ser Thr Tyr Arg Val Val Ser Val Leu Thr Val Leu
            180                185                190

His Gln Asp Trp Leu Asn Gly Lys Glu Tyr Lys Cys Lys Val Ser Asn
            195                200                205

Lys Ala Leu Pro Arg Pro Ile Glu Lys Thr Ile Ser Lys Ala Lys Gly
 210                215                220

Gln Pro Arg Glu Pro Gln Val Tyr Thr Leu Pro Pro Ser Arg Asp Glu
 225                230                235                240

Leu Thr Lys Asn Gln Val Ser Leu Thr Cys Leu Val Lys Gly Phe Tyr
                    245                250                255

Pro Ser Asp Ile Ala Val Glu Trp Glu Ser Asn Gly Gln Pro Glu Asn
            260                265                270

Asn Tyr Lys Thr Thr Pro Pro Val Leu Asp Ser Asp Gly Ser Phe Phe
            275                280                285

Leu Tyr Ser Lys Leu Thr Val Asp Lys Ser Arg Trp Gln Gln Gly Asn
 290                295                300

Val Phe Ser Cys Ser Val Met His Glu Ala Leu His Asn His Tyr Thr
 305                310                315                320

Gln Glu Ser Leu Ser Leu Ser Pro
                    325

<210> SEQ ID NO 62
<211> LENGTH: 328
<212> TYPE: PRT
<213> ORGANISM: Artificial
<220> FEATURE:
<223> OTHER INFORMATION: An artificially generated sequence

<400> SEQUENCE: 62

Ala Ser Thr Lys Gly Pro Ser Val Phe Pro Leu Ala Pro Ser Ser Lys
 1               5                 10                  15

Ser Thr Ser Gly Gly Thr Ala Ala Leu Gly Cys Leu Val Lys Asp Tyr
            20                 25                 30

Phe Pro Glu Pro Val Thr Val Ser Trp Asn Ser Gly Ala Leu Thr Ser
```

```
              35                  40                  45
Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Gly Glu Asp Gly Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 63
<211> LENGTH: 328
<212> TYPE: PRT
<213> ORGANISM: Artificial
<220> FEATURE:
<223> OTHER INFORMATION: An artificially generated sequence

<400> SEQUENCE: 63

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
```

-continued

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Asp Leu Leu Gly Asp Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Ile Asp Val Ala Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 64
<211> LENGTH: 328
<212> TYPE: PRT
<213> ORGANISM: Artificial
<220> FEATURE:
<223> OTHER INFORMATION: An artificially generated sequence

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
            100                 105                 110
Pro Ala Pro Asp Leu Leu Gly Asp Asp Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Ile Asp Val Ala Glu Glu Asp Gly Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Asp Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Arg Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Leu Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Glu Ser Leu Ser Leu Ser Pro
                325

<210> SEQ ID NO 65
<211> LENGTH: 328
<212> TYPE: PRT
<213> ORGANISM: Artificial
<220> FEATURE:
<223> OTHER INFORMATION: An artificially generated sequence

<400> SEQUENCE: 65

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Asp Leu Leu Gly Asp Asp Ser Val Phe Leu Phe Pro Pro
            115                 120                 125
Lys Pro Lys Asp Thr Leu Met Ile Ser Arg Thr Pro Glu Val Thr Cys
```

```
                130                 135                 140
Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Gly Leu Pro Arg Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Met Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Glu Ser Leu Ser Leu Ser Pro
                325
```

<210> SEQ ID NO 66
<211> LENGTH: 328
<212> TYPE: PRT
<213> ORGANISM: Artificial
<220> FEATURE:
<223> OTHER INFORMATION: An artificially generated sequence

<400> SEQUENCE: 66

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Asp Leu Leu Gly Asp Asp Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Ile Asp Val Ala Glu Glu Asp Gly Asp Val Lys Phe Asn Trp
145                 150                 155                 160

Tyr Val Asp Gly Val Glu Val His Asn Ala Lys Thr Lys Pro Arg Glu
```

```
                    165                 170                 175
Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 67
<211> LENGTH: 328
<212> TYPE: PRT
<213> ORGANISM: Artificial
<220> FEATURE:
<223> OTHER INFORMATION: An artificially generated sequence

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Ile Asp Val Ala Glu Glu Asp Gly Pro Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
              195                 200                 205
Lys Ala Leu Pro Arg Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 68
<211> LENGTH: 328
<212> TYPE: PRT
<213> ORGANISM: Artificial
<220> FEATURE:
<223> OTHER INFORMATION: An artificially generated sequence

<400> SEQUENCE: 68

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Ile Asp Val Ala Glu Glu Asp Gly Pro Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
             225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 69
<211> LENGTH: 447
<212> TYPE: PRT
<213> ORGANISM: Artificial
<220> FEATURE:
<223> OTHER INFORMATION: An artificially generated sequence

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                260                265                270
Pro Glu Val Lys Phe Asn Trp Tyr Val Asp Gly Val Glu Val His Asn
            275                280                285
Ala Lys Thr Lys Pro Arg Glu Glu Gln Tyr Asn Ser Thr Tyr Arg Val
            290                295                300
Val Ser Val Leu Thr Val Leu His Gln Asp Trp Leu Asn Gly Lys Glu
305                310                315                320
Tyr Lys Cys Lys Val Ser Asn Lys Ala Leu Pro Ala Pro Ile Glu Lys
                325                330                335
Thr Ile Ser Lys Ala Lys Gly Gln Pro Arg Glu Pro Gln Val Tyr Thr
            340                345                350
Leu Pro Pro Ser Arg Lys Glu Leu Thr Lys Asn Gln Val Ser Leu Thr
            355                360                365
Cys Leu Val Lys Gly Phe Tyr Pro Ser Asp Ile Ala Val Glu Trp Glu
        370                375                380
Ser Asn Gly Gln Pro Glu Asn Asn Tyr Lys Thr Thr Pro Pro Val Leu
385                390                395                400
Asp Ser Asp Gly Ser Phe Phe Leu Tyr Ser Lys Leu Thr Val Asp Lys
                405                410                415
Ser Arg Trp Gln Gln Gly Asn Val Phe Ser Cys Ser Val Met His Glu
            420                425                430
Ala Leu His Asn Arg Tyr Thr Gln Lys Ser Leu Ser Leu Ser Pro
            435                440                445

<210> SEQ ID NO 70
<211> LENGTH: 328
<212> TYPE: PRT
<213> ORGANISM: Artificial
<220> FEATURE:
<223> OTHER INFORMATION: An artificially generated sequence

<400> SEQUENCE: 70

Ala Ser Thr Lys Gly Pro Ser Val Phe Pro Leu Ala Pro Ser Ser Lys
1               5                  10                 15
Ser Thr Ser Gly Gly Thr Ala Ala Leu Gly Cys Leu Val Lys Asp Tyr
            20                 25                 30
Phe Pro Glu Pro Val Thr Val Ser Trp Asn Ser Gly Ala Leu Thr Ser
        35                 40                 45
Gly Val His Thr Phe Pro Ala Val Leu Gln Ser Ser Gly Leu Tyr Ser
    50                 55                 60
Leu Ser Ser Val Val Thr Val Pro Ser Ser Ser Leu Gly Thr Gln Thr
65                 70                 75                 80
Tyr Ile Cys Asn Val Asn His Lys Pro Ser Asn Thr Lys Val Asp Lys
                85                 90                 95
Lys Val Glu Pro Lys Ser Cys Asp Lys Thr His Thr Cys Pro Pro Cys
            100                105                110
Pro Ala Pro Asp Leu Leu Gly Gly Asp Ser Val Phe Leu Phe Pro Pro
        115                120                125
Lys Pro Lys Asp Thr Leu Met Ile Ser Arg Thr Pro Glu Val Thr Cys
    130                135                140
Val Val Ile Asp Val Ala Glu Glu Asp Gly Glu Val Lys Phe Asn Trp
145                150                155                160
Tyr Val Asp Gly Val Glu Val His Asn Ala Lys Thr Lys Pro Arg Glu
                165                170                175
Glu Gln Tyr Asn Ser Thr Tyr Arg Val Val Ser Val Leu Thr Val Leu
```

```
                180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 71
<211> LENGTH: 328
<212> TYPE: PRT
<213> ORGANISM: Artificial
<220> FEATURE:
<223> OTHER INFORMATION: An artificially generated sequence

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Ile Asp Val Ala Glu Glu Asp Gly Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
```

```
            210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 72
<211> LENGTH: 447
<212> TYPE: PRT
<213> ORGANISM: Artificial
<220> FEATURE:
<223> OTHER INFORMATION: An artificially generated sequence

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
```

```
                    245                 250                 255
Arg Thr Pro Glu Val Thr Cys Val Val Ile Asp Val Ala Glu Glu Asp
                260                 265                 270

Gly Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 73
<211> LENGTH: 447
<212> TYPE: PRT
<213> ORGANISM: Artificial
<220> FEATURE:
<223> OTHER INFORMATION: An artificially generated sequence

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
            165                 170                 175
Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Ile Asp Val Ala Glu Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Leu His Glu
            420                 425                 430

Ala Leu His Ser His Tyr Thr Gln Lys Ser Leu Ser Leu Ser Pro
        435                 440                 445

<210> SEQ ID NO 74
<211> LENGTH: 214
<212> TYPE: PRT
<213> ORGANISM: Artificial
<220> FEATURE:
<223> OTHER INFORMATION: An artificially generated sequence

<400> SEQUENCE: 74

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
```

```
              85                  90                  95
Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 75
<211> LENGTH: 328
<212> TYPE: PRT
<213> ORGANISM: Artificial
<220> FEATURE:
<223> OTHER INFORMATION: An artificially generated sequence

<400> SEQUENCE: 75

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Gly Asp Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
            225                 230                 235                 240
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 76
<211> LENGTH: 328
<212> TYPE: PRT
<213> ORGANISM: Artificial
<220> FEATURE:
<223> OTHER INFORMATION: An artificially generated sequence

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Asp Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Ile Asp Val Ala Glu Glu Asp Gly Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                         260                 265                 270
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 77
<211> LENGTH: 328
<212> TYPE: PRT
<213> ORGANISM: Artificial
<220> FEATURE:
<223> OTHER INFORMATION: An artificially generated sequence

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Gly Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Ile Asp Val Ala Glu Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Asp Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
            290                 295                 300
Val Phe Ser Cys Ser Val Met His Glu Ala Leu His Asn His Tyr Thr
305                 310                 315                 320

Gln Glu Ser Leu Ser Leu Ser Pro
                325
```

<210> SEQ ID NO 78
<211> LENGTH: 328
<212> TYPE: PRT
<213> ORGANISM: Artificial
<220> FEATURE:
<223> OTHER INFORMATION: An artificially generated sequence

<400> SEQUENCE: 78

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 79
<211> LENGTH: 328
<212> TYPE: PRT
<213> ORGANISM: Artificial
<220> FEATURE:
<223> OTHER INFORMATION: An artificially generated sequence

<400> SEQUENCE: 79

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 80
<211> LENGTH: 328
<212> TYPE: PRT

<213> ORGANISM: Artificial
<220> FEATURE:
<223> OTHER INFORMATION: An artificially generated sequence

<400> SEQUENCE: 80

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 81
<211> LENGTH: 328
<212> TYPE: PRT
<213> ORGANISM: Artificial
<220> FEATURE:
<223> OTHER INFORMATION: An artificially generated sequence

<400> SEQUENCE: 81

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

FCGAMMARIIB-SPECIFIC FC REGION VARIANT

CROSS-REFERENCE TO RELATED APPLICATIONS

This application is the National Stage of International Application Serial No. PCT/JP2013/072507, filed on Aug. 23, 2013, which claims the benefit of Japanese Application Serial No. 2012-185868, filed on Aug. 24, 2012.

TECHNICAL FIELD

The present invention relates to Fc region variants introduced with amino acid alteration(s) into an antibody Fc region, which have enhanced FcγRIIb-binding activity, and/or enhanced binding selectivity to FcγRIIb compared to FcγRIIa (type R), as compared to an Fc region to which an amino acid alteration(s) has not been introduced; polypeptides comprising the Fc region variants; and pharmaceutical compositions comprising the polypeptides.

BACKGROUND ART

Antibodies are drawing attention as pharmaceuticals since they are highly stable in blood and have few side effects (Non-patent Documents 1 and 2). Almost all therapeutic antibodies currently on the market are antibodies of the human IgG1 subclass. One of the known functions of IgG class antibodies is antibody-dependent cell-mediated cytotoxicity (hereinafter denoted as ADCC activity) (Non-patent Document 3). For an antibody to exhibit ADCC activity, the antibody Fc region must bind to an Fcγ receptor (hereinafter denoted as FcγR) which is an antibody-binding receptor present on the surface of effector cells such as killer cells, natural killer cells, and activated macrophages.

In humans, the FcγRIa (CD64A), FcγRIIa (CD32A), FcγRIIb (CD32B), FcγRIIIa (CD16A), and FcγRIIIb (CD16B) isoforms have been reported as the FcγR protein family, and the respective allotypes have also been reported (Non-patent Document 7). FcγRIa, FcγRIIa, and FcγRIIIa are called activating FcγR since they have immunologically active functions, and FcγRIIb is called inhibitory FcγR since it has immunosuppressive functions (Non-patent Document 8).

In the binding between the Fc region and FcγR, several amino acid residues in the antibody hinge region and CH2 domain, and a sugar chain attached to Asn at position 297 (EU numbering) bound to the CH2 domain have been shown to be important (Non-patent Documents 4, 5, and 6). Various variants having FcγR-binding properties, mainly antibodies with mutations introduced into these sites, have been studied so far; and Fc region variants having higher binding activities towards activating FcγR have been obtained (Patent Documents 1, 2, 3, and 4).

When activating FcγR is cross-linked with an immune complex, it phosphorylates immunoreceptor tyrosine-based activating motifs (ITAMs) contained in the intracellular domain or FcR common γ-chain (an interaction partner), activates a signal transducer SYK, and triggers inflammatory immune response by initiating an activation signal cascade (Non-patent Document 9).

FcγRIIb is the only FcγR expressed on B cells (Non-patent Document 10). Interaction of the antibody Fc region with FcγRIIb has been reported to suppress the primary immune response of B cells (Non-patent Document 11). Furthermore, it is reported that when FcγRIIb on B cells and a B cell receptor (BCR) are cross-linked via an immune complex in blood, B cell activation is suppressed, and antibody production by B cells is suppressed (Non-patent Document 12). In this immunosuppressive signal transduction mediated by BCR and FcγRIIb, the immunoreceptor tyrosine-based inhibitory motif (ITIM) contained in the intracellular domain of FcγRIIb is necessary (Non-patent Documents 13 and 14). When ITIM is phosphorylated upon signaling, SH2-containing inositol polyphosphate 5-phosphatase (SHIP) is recruited, transduction of other activating FcγR signal cascades is inhibited, and inflammatory immune response is suppressed (Non-patent Document 15). Furthermore, aggregation of FcγRIIb alone has been reported to transiently suppress calcium influx due to BCR cross-linking and B cell proliferation in a BCR-independent manner without inducing apoptosis of IgM-producing B cells (Non-patent Document 16).

Furthermore, FcγRIIb is also expressed on dendritic cells, macrophages, activated neutrophils, mast cells, and basophils. FcγRIIb inhibits the functions of activating FcγR such as phagocytosis and release of inflammatory cytokines in these cells, and suppresses inflammatory immune responses (Non-patent Document 8).

The importance of immunosuppressive functions of FcγRIIb has been elucidated so far through studies using FcγRIIb knockout mice. There are reports that in FcγRIIb knockout mice, humoral immunity is not appropriately regulated (Non-Patent Document 17), sensitivity towards collagen-induced arthritis (CIA) is increased (Non-patent Document 18), lupus-like symptoms are presented, and Goodpasture's syndrome-like symptoms are presented (Non-patent Document 19).

Furthermore, regulatory inadequacy of FcγRIIb has been reported to be related to human autoimmune diseases. For example, the relationship between genetic polymorphism in the transmembrane region and promoter region of FcγRIIb, and the frequency of development of systemic lupus erythematosus (SLE) (Non-patent Documents 20, 21, 22, 23, and 24), and decrease of FcγRIIb expression on the surface of B cells in SLE patients (Non-patent Document 25 and 26) have been reported.

From mouse models and clinical findings as such, FcγRIIb is considered to play the role of controlling autoimmune diseases and inflammatory diseases through involvement in particular with B cells, and it is a promising target molecule for controlling autoimmune diseases and inflammatory diseases.

IgG1, mainly used as a commercially available therapeutic antibody, is known to bind not only to FcγRIIb, but also strongly to activating FcγR (Non-patent Document 27). It may be possible to develop therapeutic antibodies having greater immunosuppressive properties compared with those of IgG1, by utilizing an Fc region with enhanced FcγRIIb binding, or improved FcγRIIb-binding selectivity compared with activating FcγR. For example, it has been suggested that the use of an antibody having a variable region that binds to BCR and an Fc with enhanced FcγRIIb binding may inhibit B cell activation (Non-patent Document 28). It has been reported that crosslinking FcγRIIb on B cells and IgE bound to a B-cell receptor suppresses differentiation of B cells into plasma cells, which as a result causes suppression of IgE production; and in human PBMC-transplanted mice, human IgG and IgM concentrations are maintained whereas the human IgE concentration is decreased (Non-patent Document 29). Besides IgE, it has been reported that when FcγRIIB and CD79b which is a constituent molecule of a B-cell receptor complex are cross-linked by an antibody, B cell proliferation is suppressed in vitro, and arthritis symptoms are alleviated in the collagen arthritis model (Non-patent Document 30).

Besides B cells, it has been reported that crosslinking of FcεRI and FcγRIIb on mast cells using molecules, in which the Fc portion of an IgG with enhanced FcγRIIb binding is fused to the Fc portion of IgE that binds to an IgE receptor FcεRI, causes FcγRIIb phosphorylation of FcγRIIb, thereby suppressing FcεSRI-dependent calcium influx. This suggests that inhibition of degranulation via FcγRIIb stimulation is possible by enhancing FcγRIIb binding (Non-patent Document 31).

Accordingly, an antibody having an Fc with improved FcγRIIb-binding activity is suggested to be promising as a therapeutic agent for inflammatory diseases such as autoimmune diseases.

Furthermore, it has been reported that activation of macrophages and dendritic cells via Toll-like receptor 4 due to LPS stimulation is suppressed in the presence of an antibody-antigen immune complex, and this effect is also suggested to be actions of the immune complex via FcγRIIb (Non-patent Documents 32 and 33). Therefore, use of antibodies with enhanced FcγRIIb binding is expected to enable enhancement of TLR-mediated activation signal-suppressing actions; thus such antibodies have been suggested as being promising as therapeutic agents for inflammatory diseases such as autoimmune diseases.

Furthermore, mutants with enhanced FcγRIIb binding have been suggested to be promising therapeutic agents for cancer, as well as therapeutic agents for inflammatory diseases such as autoimmune diseases. So far, FcγRIIb has been found to play an important role in the agonistic activity of agonist antibodies against the anti-TNF receptor superfamily. Specifically, it has been suggested that interaction with FcγRIIb is required for the agonistic activity of antibodies against CD40, DR4, DR5, CD30, and CD137, which are included in the TNF receptor family (Non-patent Documents 34, 35, 36, 37, 38, 39 and 40). Non-patent Document 34 shows that the use of antibodies with enhanced FcγRIIb binding enhances the anti-tumor effect of anti-CD40 antibodies. Accordingly, antibodies with enhanced FcγRIIb are expected to have an effect of enhancing agonistic activity of agonist antibodies including antibodies against the anti-TNF receptor superfamily.

In addition, it has been shown that cell proliferation is suppressed when using an antibody that recognizes Kit, a type of receptor tyrosine kinase (RTK), to crosslink FcγRIIb and Kit on Kit-expressing cells. Similar effects have been reported even in cases where this Kit is constitutively activated and has mutations that cause oncogenesis (Non-patent Document 41). Therefore, it is expected that use of antibodies with enhanced FcγRIIb binding may enhance inhibitory effects on cells expressing RTK having constitutively activated mutations.

Antibodies having an Fc with improved FcγRIIb-binding activity have been reported (Non-patent Document 28). In this Document, FcγRIIb-binding activity was improved by adding alterations such as S267E/L328F, G236D/S267E, and S239D/S267E to an antibody Fc region. Among them, the antibody introduced with the S267E/L328F mutation most strongly binds to FcγRIIb, and maintains the same level of binding to FcγRIa and FcγRIIa type H in which a residue at position 131 of FcγRIIa is His as that of a naturally-occurring IgG1. However, another report shows that this alteration enhances the binding to FcγRIIa type R in which a residue at position 131 of FcγRIIa is Arg several hundred times to the same level of FcγRIIb binding, which means the FcγRIIb-binding selectivity is not improved in comparison with type-R FcγRIIa (Patent Document 5).

Only the effect of enhancing FcγRIIa binding and not the enhancement of FcγRIIb binding is considered to have influence on cells such as platelets which express FcγRIIa but do not express FcγRIIb (Non-patent Document 8). For example, the group of patients who were administered bevacizumab, an antibody against VEGF, is known to have an increased risk for thromboembolism (Non-patent Document 42). Furthermore, thromboembolism has been observed in a similar manner in clinical development tests of antibodies against the CD40 ligand, and the clinical study was discontinued (Non-patent Document 43). In both cases of these antibodies, later studies using animal models and such have suggested that the administered antibodies aggregate platelets via FcγRIIa binding on the platelets, and form blood clots (Non-patent Documents 44 and 45). In systemic lupus erythematosus which is an autoimmune disease, platelets are activated via an FcγRIIa-dependent mechanism, and platelet activation has been reported to correlate with the severity of symptoms (Non-patent Document 46). Administering an antibody with enhanced FcγRIa binding to such patients who already have a high risk for developing thromboembolism will increase the risk for developing thromboembolism, thus is extremely dangerous.

Furthermore, antibodies with enhanced FcγRIIa binding have been reported to enhance macrophage-mediated antibody dependent cellular phagocytosis (ADCP) (Non-patent Document 47). When antigens to be bound by the antibodies are phagocytized by macrophages, antibodies themselves are considered to be also phagocytized at the same time. When antibodies are administered as pharmaceuticals, it is supposed that peptide fragments derived from the administered antibodies are likely to be also presented as an antigen, thereby increasing the risk of production of antibodies against therapeutic antibodies (anti-therapeutic antibodies). More specifically, enhancing FcγRIIa binding will increase the risk of production of antibodies against the therapeutic antibodies, and this will remarkably decrease their value as pharmaceuticals. Furthermore, FcγRIIb on dendritic cells have been suggested to contribute to peripheral tolerance by inhibiting dendritic cell activation caused by immune complexes formed between antigens and antibodies, or by suppressing antigen presentation to T cells via activating Fcγ receptors (Non-patent Document 48). Since FcγRIIa is also expressed on dendritic cells, when antibodies having an Fc with enhanced selective binding to FcγRIIb are used as pharmaceuticals, antigens are not readily presented by dendritic cells and such due to enhanced selective binding to FcγRIIb, and risk of anti-drug antibody production can be relatively decreased. Such antibodies may be useful in that regard as well.

More specifically, the value as pharmaceuticals will be considerably reduced when FcγRIIa binding is enhanced, which leads to increased risk of thrombus formation via platelet aggregation and increased risk of anti-therapeutic antibody production due to an increased immunogenicity.

From such a viewpoint, the aforementioned Fc variant with enhanced FcγRIIb binding shows remarkably enhanced type-R FcγRIIa binding compared with that of a naturally-occurring IgG. Therefore, its value as a pharmaceutical for patients carrying type-R FcγRIIa is considerably reduced. Types H and R of FcγRIIa are observed in Caucasians and African-Americans with approximately the same frequency (Non-patent Documents 49 and 50). Therefore, when this Fc variant was used for treatment of autoimmune diseases, the number of patients who can safely use it while enjoying its effects as a pharmaceutical will be limited.

Furthermore, in dendritic cells deficient in FcγRIIb or dendritic cells in which the interaction between FcγRIIb and the antibody Fc portion is inhibited by an anti-FcγRIIb antibody, dendritic cells have been reported to mature (Non-patent Documents 51 and 52). This report suggests that FcγRIIb is actively suppressing maturation of dendritic cells in a steady state where inflammation and such are not taking place and activation does not take place. FcγRIIa is expressed on the dendritic cell surface in addition to FcγRIIb; therefore, even if binding to inhibitory FcγRIIb is enhanced and if binding to activating FcγR such as FcγRIIa is also enhanced, maturation of dendritic cells may be promoted as a result. More specifically, improving not only the FcγRIIb-binding activity but also the ratio of FcγRIIb-binding activity relative to FcγRIIa-binding activity is considered to be important in providing antibodies with an immunosuppressive action.

Therefore, when considering generation of pharmaceuticals that utilize the FcγRIIb binding-mediated immunosuppressive action, there is a need for an Fc variant that not only has enhanced FcγRIIb-binding activity, but also has binding to both FcγRIIa, types H and R allotypes, which is maintained at a similar level or is weakened to a lower level than that of a naturally-occurring IgG1.

Meanwhile, cases where amino acid alterations were introduced into the Fc region to increase the FcγRIIb-binding selectivity have been reported so far (Non-patent Document 53). However, all variants said to have improved FcγRIIb selectivity as reported in this document showed decreased FcγRIIb binding compared with that of a naturally-occurring IgG1. Therefore, it is considered to be difficult for these variants to actually induce an FcγRIIb-mediated immunosuppressive reaction more strongly than IgG1.

Furthermore, since FcγRIIb plays an important role in the agonist antibodies mentioned above, enhancing their binding activity is expected to enhance the agonistic activity. However, when FcγRIIa binding is similarly enhanced, unintended activities such as ADCC activity and ADCP activity will be exhibited, and this may cause side effects. Also from such viewpoint, it is preferable to be able to selectively enhance FcγRIIb-binding activity.

From these results, in producing therapeutic antibodies to be used for treating autoimmune diseases and cancer utilizing FcγRIIb, it is important that compared with those of a naturally-occurring IgG, the activities of binding to both FcγRIIa allotypes are maintained or decreased, and FcγRIIb binding is enhanced. However, FcγRIIb shares 93% sequence identity in the extracellular region with that of FcγRIIa which is one of the activating FcγRs, and they are very similar structurally. There are allotypes of FcγRIIa, H type and R type, in which the amino acid at position 131 is His (type H) or Arg (type R), and yet each of them reacts differently with the antibodies (Non-patent Document 54). Therefore, the difficult problem may be producing an Fc region variant with enhanced selective FcγRIIb binding as compared to each allotype of FcγRIIa, which involves distinguishing highly homologous sequences between FcγRIIa and FcγRIIb. In fact, variants having sufficient binding activity and selectivity to FcγRIIb have not been obtained so far. Patent Document 5 reports variants with enhanced FcγRIIb-binding activity; however, the degree of enhancement is low, and there is a demand for development of variants having properties similar to those described above.

PRIOR ART DOCUMENTS

Patent Documents

[Patent Document 1] WO 2000/42072
[Patent Document 2] WO 2006/019447
[Patent Document 3] WO 2004/99249
[Patent Document 4] WO 2004/29207
[Patent Document 5] US2009/0136485

Non-Patent Documents

[Non-patent Document 1] Nat Biotechnol, 23, 1073-1078, 2005
[Non-patent Document 2] Eur J Pharm Biopharm, 59(3), 389-96. 2005
[Non-patent Document 3] Chem Immunol, 65, 88-110, 1997
[Non-patent Document 4] J Biol Chem, 276, 16478-16483, 2001
[Non-patent Document 5] Eur J Immunol 23, 1098-1104, 1993
[Non-patent Document 6] Immunology, 86, 319-324, 1995
[Non-patent Document 7] Immunol Lett, 82, 57-65, 2002
[Non-patent Document 8] Nat Rev Immunol, 10, 328-343, 2010
[Non-patent Document 9] Nat Rev Immunol, 8, 34-47, 2008
[Non-patent Document 10] Eur J Immunol 19, 1379-1385, 1989
[Non-patent Document 11] J Exp Med 129, 1183-1201, 1969
[Non-patent Document 12] Immunol Lett 88, 157-161, 2003
[Non-patent Document 13] Science, 256, 1808-1812, 1992
[Non-patent Document 14] Nature, 368, 70-73, 1994
[Non-patent Document 15] Science, 290, 84-89, 2000
[Non-patent Document 16] J Imunol, 181, 5350-5359, 2008
[Non-patent Document 17] J Immunol, 163, 618-622, 1999
[Non-patent Document 18] J Exp Med, 189, 187-194, 1999
[Non-patent Document 19] J Exp Med, 191, 899-906, 2000
[Non-patent Document 20] Hum, Genet, 117, 220-227, 2005
[Non-patent Document 21] J Biol Chem, 282, 1738-1746, 2007
[Non-patent Document 22] Arthritis Rheum, 54, 3908-3917, 2006
[Non-patent Document 23] Nat Med, 11, 1056-1058, 2005
[Non-patent Document 24] J Immunol, 176, 5321-5328, 2006
[Non-patent Document 25] J Exp Med, 203, 2157-2164, 2006
[Non-patent Document 26] J Immunol. 178, 3272-3280, 2007
[Non-patent Document 27] Blood, 113, 3716-3725, 2009
[Non-patent Document 28] Mol Immunol, 45, 3926-3933, 2008
[Non-patent Document 29] J Allergy Clin Immunol, 2012, 129: 1102-1115
[Non-patent Document 30] Arthritis Rheum, 62, 1933-1943, 2010
[Non-patent Document 31] Immunol let, doi: 10.1016/j.imlet.2012.01.008)
[Non-patent Document 32] J. Immunol, 2009, 183: 4509-4520
[Non-patent Document 33] J. Immunol, 2009, 182: 554-562
[Non-patent Document 34] Science, 333, 1030-1034, 2011
[Non-patent Document 35] Cancer Cell 19, 101-113, 2011
[Non-patent Document 36] J Clin Invest, 122 (3), 1066-1075, 2012
[Non-patent Document 37] J Immunol 171, 562-, 2003

[Non-patent Document 38] Blood, 108, 705-, 2006
[Non-patent Document 39] J Immunol 166, 4891, 2001
[Non-patent Document 40] doi: 10.1073/pnas.1208698109
[Non-patent Document 41] Immunol let, 2002, 143: 28-33
[Non-patent Document 42] J Natl Cancer Inst, 99, 1232-1239, 2007
[Non-patent Document 43] Arthritis Rheum, 48, 719-727, 2003
[Non-patent Document 44] J Thromb Haemost, 7, 171-181, 2008
[Non-patent Document 45] J Immunol, 185, 1577-1583, 2010
[Non-patent Document 46] Sci Transl Med, vol 2, issue 47, 47-63, 2010
[Non-patent Document 47] Mol Cancer Ther 7, 2517-2527, 2008
[Non-patent Document 48] J. Immunol, 2007, 178: 6217-6226
[Non-patent Document 49] J Clin Invest, 97, 1348-1354, 1996
[Non-patent Document 50] Arthritis Rheum, 41, 1181-1189, 1998
[Non-patent Document 51] J Clin Invest 115, 2914-2923, 2005
[Non-patent Document 52] Proc Natl Acad Sci USA, 102, 2910-2915, 2005
[Non-patent Document 53] Mol Immunol, 40, 585-593, 2003
[Non-patent Document 54] J Exp Med, 172, 19-25, 1990

SUMMARY OF THE INVENTION

Problems to be Solved by the Invention

The present invention was achieved in view of the above circumstances. An objective of the present invention is to provide an Fc region variant by introducing an amino acid alteration(s) into an antibody Fc region, which variant has enhanced FcγRIIb-binding activity, and/or enhanced binding selectivity to FcγRIIb compared to FcγRIIa (type R), as compared to when no amino acid alteration has been introduced into the Fc region; a polypeptide comprising the Fc region variant; and a pharmaceutical composition containing the polypeptide.

Means for Solving the Problems

The present inventors carried out dedicated research on: an Fc region variant with enhanced FcγRIIb-binding and enhanced binding selectivity to FcγRIIb compared to FcγRIIa (type R), as compared to when the Fc region is unaltered, by introducing amino acid alteration(s) into the Fc region; and a polypeptide comprising the Fc region variant. As a result, the present inventors found that FcγRIIb-binding activity is enhanced and/or binding selectivity to FcγRIIb compared to FcγRIIa (type R) is enhanced by combining an Fc region variant in which the amino acid at position 238 (EU numbering) in the Fc Region has been altered with other amino acid alteration(s).

More specifically, the present invention relates to the following:

[1] an Fc region variant in which amino acid at position 238 according to EU numbering and at least one amino acid selected from those at positions 233, 234, 235, 237, 264, 265, 266, 267, 268, 269, 271, 272, 274, 296, 326, 327, 330, 331, 332, 333, 334, 355, 356, 358, 396, 409, and 419 according to EU numbering are altered to other amino acids, wherein binding activity of the variant to Fcγ receptors [KD value for FcγRIIb of a polypeptide comprising an Fc region to which an amino acid alteration(s) has not been introduced]/[KD value for FcγRIIb of a polypeptide comprising the Fc region variant] has a value which is 15.0 or greater;

[2] the Fc region variant of [1], wherein the amino acids at positions 238, 268, and 271 according to EU numbering are altered to other amino acids, and in addition, at least one amino acid selected from amino acids at positions 233, 237, 264, 267, 272, 296, 327, 330, 332, and 396 according to EU numbering are altered to other amino acids;

[3] an Fc region variant whose amino acid at position 238 according to EU numbering is Asp, and which comprises at least one amino acid selected from the amino acid group consisting of Asp at amino acid position 233, Tyr at amino acid position 234, Phe at amino acid position 235, Asp at amino acid position 237, Ile at amino acid position 264, Glu at amino acid position 265, Phe, Leu, or Met at amino acid position 266, Ala, Glu, Gly, or Gln at amino acid position 267, Asp, Gln, or Glu at amino acid position 268, Asp at amino acid position 269, Gly at amino acid position 271, Asp, Phe, Ile, Met, Asn, Pro, or Gln at amino acid position 272, Gln at amino acid position 274, Asp or Phe at amino acid position 296, Ala or Asp at amino acid position 326, Gly at amino acid position 327, Lys, Arg, or Ser at amino acid position 330, Ser at amino acid position 331, Lys, Arg, Ser, or Thr at amino acid position 332, Lys, Arg, Ser, or Thr at amino acid position 333, Arg, Ser, or Thr at amino acid position 334, Ala or Gln at amino acid position 355, Glu at amino acid position 356, Met at amino acid position 358, Ala, Asp, Glu, Phe, Gly, His, Ile, Lys, Leu, Met, Asn, Gln, Arg, Ser, Thr, Val, Trp, or Tyr at amino acid position 396, Arg at amino acid position 409, and Glu at amino acid position 419, wherein binding activity of the variant to Fcγ receptors [KD value for FcγRIIb of a polypeptide comprising an Fc region to which an amino acid alteration(s) has not been introduced]/[KD value for FcγRIIb of a polypeptide comprising the Fc region variant] has a value which is 15.0 or greater;

[4] the Fc region variant of [3], wherein the amino acid at position 238 is Asp, the amino acid at position 268 is Asp or Glu, and the amino acid at position 271 is Gly, according to EU numbering, and wherein the Fc region variant further comprises at least one amino acid selected from the amino acid group consisting of Asp at amino acid position 233, Asp at amino acid position 237, Ile at amino acid position 264, Ala or Gly at amino acid position 267, Asp or Pro at amino acid position 272, Asp at amino acid position 296, Gly at amino acid position 327, Arg at amino acid position 330, Thr at amino acid position 332, and Leu or Met at amino acid position 396;

[5] the Fc region variant of any one of [1] to [4], wherein the value for [KD value for FcγRIIb of a polypeptide comprising an Fc region to which an amino acid alteration(s) has not been introduced]/[KD value for FcγRIIb of a polypeptide comprising an Fc region variant] is 50.0 or more;

[6] the Fc region variant of any one of [1] to [4], wherein the value for [KD value for FcγRIIb of a polypeptide comprising an Fc region to which an amino acid alteration(s) has not been introduced]/[KD value for FcγRIIb of a polypeptide comprising an Fc region variant] is 100.0 or more;

[7] the Fc region variant of any one of [1] to [6], wherein the value for [KD value for FcγRIIa (type R) of a polypeptide comprising an Fc region variant]/[KD value for FcγRIIb of a polypeptide comprising an Fc region variant] is 10.0 or greater;

[8] the Fc region variant of any one of [1] to [6], wherein the value for [KD value for FcγRIIa (type R) of a polypeptide comprising an Fc region variant]/[KD value for FcγRIIb of a polypeptide comprising an Fc region variant] is 20.0 or greater;
[9] The Fc region variant of any one of [1] to [8], wherein the Fc region variant comprises any one of the following set of amino acid alterations of (a) to (x):
(a) amino acid alterations at positions 238, 233, 237, 268, 271, 296, and 330 (EU numbering) of an Fc region;
(b) amino acid alterations at positions 238, 237, 268, 271, 296, and 330 (EU numbering) of an Fc region;
(c) amino acid alterations at positions 238, 233, 237, 268, 271, 296, 330, and 332 (EU numbering) of an Fc region;
(d) amino acid alterations at positions 238, 233, 237, 264, 267, 268, 271, and 330 (EU numbering) of an Fc region;
(e) amino acid alterations at positions 238, 233, 237, 267, 268, 271, 296, 330, and 332 (EU numbering) of an Fc region;
(f) amino acid alterations at positions 238, 237, 267, 268, 271, 296, 330, and 332 (EU numbering) of an Fc region;
(g) amino acid alterations at positions 238, 233, 237, 268, 271, 296, 327, and 330 (EU numbering) of an Fc region;
(h) amino acid alterations at positions 238, 233, 237, 264, 267, 268, and 271 (EU numbering) of an Fc region;
(i) amino acid alterations at positions 238, 233, 237, 264, 267, 268, 271, 296, and 330 (EU numbering) of an Fc region;
(j) amino acid alterations at positions 238, 233, 237, 264, 267, 268, 271, 296, 330, and 396 (EU numbering) of an Fc region;
(k) amino acid alterations at positions 238, 237, 264, 267, 268, 271, and 330 (EU numbering) of an Fc region;
(l) amino acid alterations at positions 238, 237, 264, 267, 268, 271, 296, and 330 (EU numbering) of an Fc region;
(m) amino acid alterations at positions 238, 264, 267, 268, and 271 (EU numbering) of an Fc region;
(n) amino acid alterations at positions 238, 264, 267, 268, 271, and 296 (EU numbering) of an Fc region;
(o) amino acid alterations at positions 238, 237, 267, 268, 271, 296, and 330 (EU numbering) of an Fc region;
(p) amino acid alterations at positions 238, 233, 237, 264, 267, 268, 271, 330, and 396 (EU numbering) of the Fc region;
(q) amino acid alterations at positions 238, 233, 237, 264, 267, 268, 271, 296, 327, 330, and 396 (EU numbering) of an Fc region;
(r) amino acid alterations at positions 238, 233, 237, 264, 267, 268, 271, 272, and 296 (EU numbering) of an Fc region;
(s) amino acid alterations at positions 238, 237, 264, 267, 268, 271, 272, and 330 (EU numbering) of an Fc region;
(t) amino acid alterations at positions 238, 237, 264, 267, 268, 271, 272, 296, and 330 (EU numbering) of an Fc region;
(u) amino acid alterations at positions 238, 233, 264, 267, 268, and 271 (EU numbering) of an Fc region;
(v) amino acid alterations at positions 238, 237, 267, 268, 271, 296, and 330 (EU numbering) of an Fc region;
(w) amino acid alterations at positions 238, 264, 267, 268, 271, 272, and 296 (EU numbering) of an Fc region; and
(x) amino acid alterations at positions 238, 233, 264, 267, 268, 271, and 296 (EU numbering) of an Fc region;
[10] the Fc region variant of any one of [1] to [8], wherein the Fc region variant comprises any one of the following amino acid sequences of (a) to (x):

(a) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, and the amino acid at position 330 is Arg, according to EU numbering, in an Fc region;
(b) an amino acid sequence in which the amino acid at position 238 is Asp, the amino acid at position 237 is Asp, the amino acid at position 268 is Asp or Glu, the amino acid at position 271 is Gly, the amino acid at position 296 is Asp, and the amino acid at position 330 is Arg, according to EU numbering, in an Fc region;
(c) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, the amino acid at position 330 is Arg, and the amino acid at position 332 is Thr, according to EU numbering, in an Fc region;
(d) an amino acid sequence in which the amino acid at position 238 is Asp, the amino acid at position 233 is Asp, the amino acid at position 237 is Asp, the amino acid at position 264 is Ile, the amino acid at position 267 is Gly or Ala, the amino acid at position 268 is Glu, the amino acid at position 271 is Gly, and the amino acid at position 330 is Arg, according to EU numbering, in an Fc region;
(e) an amino acid sequence in which the amino acid at position 238 is Asp, the amino acid at position 233 is Asp, the amino acid at position 237 is Asp, the amino acid at position 267 is Ala, the amino acid at position 268 is Glu, the amino acid at position 271 is Gly, the amino acid at position 296 is Asp, the amino acid at position 330 is Arg, and the amino acid at position 332 is Thr, according to EU numbering, in an Fc region;
(f) an amino acid sequence in which the amino acid at position 238 is Asp, the amino acid at position 237 is Asp, the amino acid at position 267 is Ala, the amino acid at position 268 is Glu, the amino acid at position 271 is Gly, the amino acid at position 296 is Asp, the amino acid at position 330 is Arg, and the amino acid at position 332 is Thr, according to EU numbering, in an Fc region;
(g) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, the amino acid at position 327 is Gly, and the amino acid at position 330 is Arg, according to EU numbering, in an Fc region;
(h) an amino acid sequence in which the amino acid at position 238 is Asp, the amino acid at position 233 is Asp, the amino acid at position 237 is Asp, the amino acid at position 264 is lie, the amino acid at position 267 is Ala, the amino acid at position 268 is Glu, and the amino acid at position 271 is Gly, according to EU numbering, in an Fc region;
(i) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, and the amino acid at position 330 is Arg, according to EU numbering, in an Fc region;
(j) an amino acid sequence in which the amino acid at position 238 is Asp, the amino acid at position 233 is Asp, the amino acid at position 237 is Asp, the amino acid at position 264 is lie, the amino acid at position 267 is Ala, the amino acid at position 268 is Glu, the amino acid at position 271 is Gly, the amino acid at position 296 is Asp, the amino acid at position 330 is Arg, and the amino acid at position 396 is Met or Leu, according to EU numbering, in an Fc region;

(k) an amino acid sequence in which the amino acid at position 238 is Asp, the amino acid at position 237 is Asp, the amino acid at position 264 is lie, the amino acid at position 267 is Ala, the amino acid at position 268 is Glu, the amino acid at position 271 is Gly, and the amino acid at position 330 is Arg, according to EU numbering, in an Fc region;

(l) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, and the amino acid at position 330 is Arg, according to EU numbering, in an Fc region;

(m) an amino acid sequence in which the amino acid at position 238 is Asp, the amino acid at position 264 is lie, the amino acid at position 267 is Ala, the amino acid at position 268 is Glu, and the amino acid at position 271 is Gly, according to EU numbering, in an Fc region;

(n) an amino acid sequence in which the amino acid at position 238 is Asp, the amino acid at position 264 is Ile, the amino acid at position 267 is Ala, the amino acid at position 268 is Glu, the amino acid at position 271 is Gly, and the amino acid at position 296 is Asp, according to EU numbering, in an Fc region;

(o) an amino acid sequence in which the amino acid at position 238 is Asp, the amino acid at position 237 is Asp, the amino acid at position 267 is Ala or Gly, the amino acid at position 268 is Glu, the amino acid at position 271 is Gly, the amino acid at position 296 is Asp, and the amino acid at position 330 is Arg, according to EU numbering, in an Fc region;

(p) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 330 is Arg, and the amino acid at position 396 is Met or Leu, according to EU numbering, in an Fc region;

(q) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, the amino acid at position 327 is Gly, the amino acid at position 330 is Arg, and the amino acid at position 396 is Met, according to EU numbering, in an Fc region;

(r) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Asp, and the amino acid at position 296 is Asp, according to EU numbering, in an Fc region;

(s) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Pro, and the amino acid at position 330 is Arg, according to EU numbering, in an Fc region;

(t) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Pro, the amino acid at position 296 is Asp, and the amino acid at position 330 is Arg, according to EU numbering, in an Fc region;

(u) an amino acid sequence in which the amino acid at position 238 is Asp, the amino acid at position 233 is Asp, the amino acid at position 264 is Ile, the amino acid at position 267 is Ala, the amino acid at position 268 is Glu, and the amino acid at position 271 is Gly, according to EU numbering, in an Fc region;

(v) an amino acid sequence in which the amino acid at position 238 is Asp, the amino acid at position 237 is Asp, the amino acid at position 267 is Gly, the amino acid at position 268 is Asp, the amino acid at position 271 is Gly, the amino acid at position 296 is Asp, and the amino acid at position 330 is Arg, according to EU numbering, in an Fc region;

(w) an amino acid sequence in which the amino acid at position 238 is Asp, the amino acid at position 264 is Ile, the amino acid at position 267 is Ala, the amino acid at position 268 is Glu, the amino acid at position 271 is Gly, the amino acid at position 272 is Asp, and the amino acid at position 296 is Asp, according to EU numbering, in an Fc region; and (x) an amino acid sequence in which the amino acid at position 238 is Asp, the amino acid at position 233 is Asp, the amino acid at position 264 is Ile, the amino acid at position 267 is Ala, the amino acid at position 268 is Glu, the amino acid at position 271 is Gly, and the amino acid at position 296 is Asp, according to EU numbering, in an Fc region;

[11] an Fc region variant consisting of any one amino acid sequence selected from among SEQ ID NOs: 43 to 68, SEQ ID NO: 70, SEQ ID NO: 71, and SEQ ID NOs: 75 to 77;

[12] a polypeptide comprising at least two Fc region variants of any one of [1] to [11], wherein the two Fc region variants are associated;

[13] the polypeptide of [12], wherein the amino acid sequences of the two associated Fc region variants in the polypeptide are the same;

[14] the polypeptide of [12], wherein the amino acid sequences of the two associated Fc region variants in the polypeptide are different;

[15] the polypeptide of [14], wherein the amino acid sequences of the two associated Fc region variants have different amino acid(s) at at least one amino acid position selected from positions 235, 236, 237, 238, and 239 according to EU numbering in the Fc region variant;

[16] the polypeptide of [15], wherein one of the amino acid sequences of the two associated Fc region variants is an amino acid sequence comprising at least one amino acid selected from Asp, Gin, Glu, or Thr at amino acid position 235, Asn at amino acid position 236, Phe or Trp at amino acid position 237, Glu, Gly, or Asn at amino acid position 238, and Asp or Glu at amino acid position 239 according to EU numbering;

[17] the polypeptide of any one of [12] to [16], wherein the polypeptide comprising the Fc region variant is an IgG antibody;

[18] the polypeptide of any one of [12] to [16], wherein the polypeptide comprising the Fc region variant is an Fc fusion protein molecule; and

[19] a pharmaceutical composition comprising the polypeptide of any one of [12] to [18].

Furthermore, the present invention relates to a method of enhancing FcγRIIb-binding activity of an Fc region and enhancing binding selectivity to FcγRIIb compared to FcγRIIa (type R), by introducing an amino acid alteration(s) into the Fc region of the present invention. The present invention also relates to a method of suppressing production of antibodies against a polypeptide containing an Fc region, by introducing an amino acid alteration(s) of the present invention into the Fc region.

The present invention also relates to a therapeutic or preventive agent for immune inflammatory diseases that comprises a polypeptide of the present invention. Furthermore, the present invention relates to a method for treating or preventing immune inflammatory diseases, which comprises the step of administering a polypeptide of the present invention to a subject. In addition, the present invention relates to a kit for use in the method of the present invention for treating or preventing immune inflammatory diseases, which comprises a polypeptide of the present invention. The present invention also relates to use of a polypeptide of the present invention in the production of a therapeutic or preventive agent for immune inflammatory diseases. Furthermore, the present invention relates to a polypeptide of the present invention for use in the method for treating or preventing immune inflammatory diseases of the present invention.

The present invention relates to an activation inhibitor for B cells, mast cells, dendritic cells, and/or basophils, which comprises a polypeptide of the present invention. Furthermore, the present invention relates to a method of inhibiting activation of B cells, mast cells, dendritic cells, and/or basophils, which comprises administering a polypeptide of the present invention to a subject. The present invention also relates to a kit for use in the method of inhibiting activation of B cells, mast cells, dendritic cells, and/or basophils, which comprises a polypeptide of the present invention. The present invention relates to a use of a polypeptide of the present invention in producing activation inhibitors for B cells, mast cells, dendritic cells, and/or basophils. The present invention also relates to a polypeptide of the present invention for use in the method of the present invention of inhibiting activation of B cells, mast cells, dendritic cells, and/or basophils.

Furthermore, the present invention relates to a therapeutic agent for diseases in which a protein necessary for an organism is deficient, wherein the agent comprises a polypeptide of the present invention. The present invention also relates to a method for treating diseases in which a protein necessary for an organism is deficient, which comprises administering a polypeptide of the present invention to a subject. Furthermore, the present invention relates to a kit for use in the method of the present invention for treating diseases in which a protein necessary for an organism is deficient, wherein the kit comprises a polypeptide of the present invention. The present invention relates to use of a polypeptide of the present invention in producing a therapeutic agent for diseases in which a protein necessary for an organism is deficient. The present invention also relates to a polypeptide of the present invention for use in the method of the present invention for treating diseases in which a protein necessary for an organism is deficient.

In addition, the present invention relates to an agent for suppressing virus proliferation, which comprises a polypeptide of the present invention. The present invention also relates to a method of suppressing virus proliferation, which comprises administering a polypeptide of the present invention to a subject. Furthermore, the present invention relates to a kit of the present invention for use in the method of suppressing virus proliferation, wherein the kit comprises a polypeptide of the present invention. The present invention relates to use of a polypeptide of the present invention in producing an agent for suppressing virus proliferation. The present invention also relates to a polypeptide of the present invention for use in the method of the present invention of suppressing virus proliferation.

Effects of the Invention

Fc region variants with enhanced FcγRIIb-binding activity and/or enhanced binding selectivity to FcγRIIb compared to FcγRIIa (type R), as compared to when the Fc region is unaltered, are provided by the present invention. By using the polypeptides containing the Fc region variants, it is possible to enhance inhibitory signals of inflammatory immune responses mediated by phosphorylation of ITIM of FcγRIIb. Also, by conferring an Fc region with the property of selective FcγRIIb binding, it may be possible to suppress anti-drug antibody production. Also, by using an Fc region variant of the present invention as a polypeptide having human FcRn-binding activity under an acidic pH range condition and comprising an antigen-binding domain in which an antigen-binding activity of an antigen-binding molecule changes depending on the ion concentration conditions, it is possible to promote elimination of antigens that bind to the polypeptide, which are present in plasma.

BRIEF DESCRIPTION OF THE DRAWINGS

FIG. 14 shows a comparison of the constant region sequences of G1d and G4d. In the figure, the boxed amino acids show portions where the amino acid residues are different between G1d and G4d.

MODE FOR CARRYING OUT THE INVENTION

The present invention provides an Fc region variant with enhanced FcγRIIb-binding activity, and/or enhanced binding selectivity to FcγRIIb compared to FcγRIIa (type R), as compared to an Fc region to which an amino acid alteration(s) has not been introduced; and a polypeptide comprising the Fc region variant.

More specifically, the invention provides an Fc region variant containing an amino acid sequence that has a combination of an amino acid alteration at position 238 (EU numbering) and other specific amino acid alteration(s); and a polypeptide comprising the Fc region variant. Furthermore, the present invention provides a method of enhancing FcγRIIb-binding activity, and/or enhancing binding selectivity to FcγRIIb, compared to FcγRIIa (type R) as compared to those of an Fc region to which an amino acid alteration(s) has not been introduced, by introducing amino acid alteration(s) into the Fc region. The present invention also provides a method of suppressing production of antibodies against an Fc region by introducing an amino acid alteration(s) into the Fc region when the Fc region variant is administered to an organism, as compared to when the Fc region without introduction of amino acid alteration(s) is administered.

"Polypeptides" of the present invention generally refers to peptides or proteins approximately ten amino acids or more in length. Furthermore, they are generally polypeptides derived from organisms, but are not particularly limited, and for example, they may be polypeptides comprising an artificially designed sequence. Furthermore, they may be any of naturally-occurring polypeptides, synthetic polypeptides, recombinant polypeptides, or such.

Preferred examples of the polypeptides of the present invention include antibodies. More preferred examples include naturally-occurring IgGs, particularly naturally-occurring human IgGs. "Naturally-occurring (native) IgGs" refers to polypeptides belonging to a class of antibodies practically encoded by immunoglobulin gamma genes and comprising an amino acid sequence identical to those of IgGs found in nature. For example, a naturally-occurring human IgG means a naturally-occurring human IgG1, naturally-occurring human IgG2, naturally-occurring human IgG3, naturally-occurring human IgG4, or such. Naturally-occurring IgGs also include mutants spontaneously produced from them.

Figure 21:
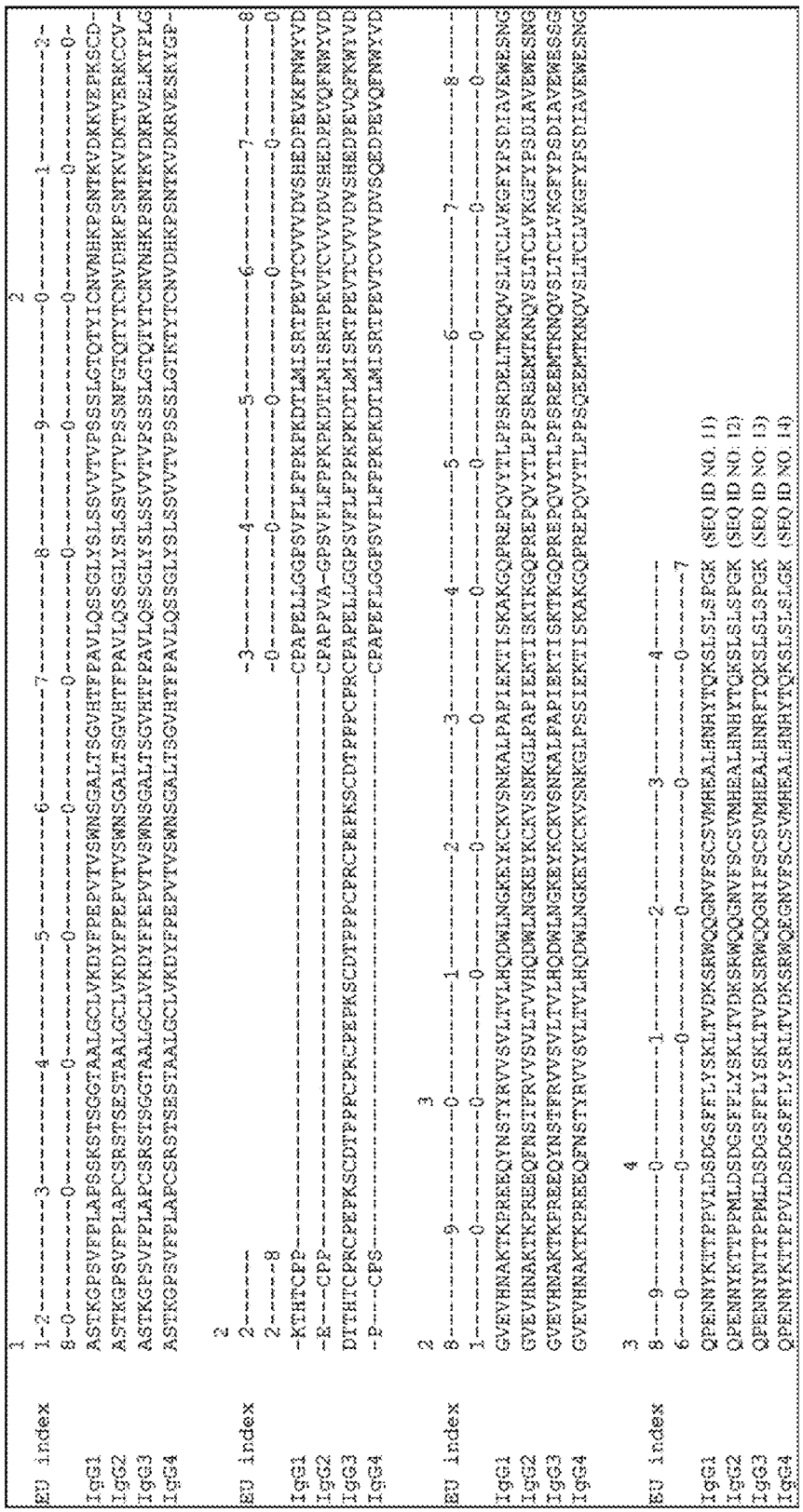
FIG. 21 shows the relationship between the amino acid residues constituting the constant regions of IgG1, IgG2, IgG3, and IgG4, and EU numbering (herein, also referred to as EU INDEX).

While an IgK (Kappa, κ chain), IgL1, IgL2, IgL3, IgL6, and IgL7 (Lambda, λ chain)-type constant region is present in the antibody light chain constant region, it may be any light chain constant region. For the human IgK (Kappa) constant region and human IgL7 (Lambda) constant region, a plurality of allotype sequences due to genetic polymorphism are described in "Sequences of proteins of immunological interest", NIH Publication No. 91-3242, and any of them may be used in the present invention. Furthermore, in the present invention, a light chain constant region may be a light chain constant region that has been altered with amino acid substitutions, additions, deletions, insertions, and/or modifications or such. For the antibody Fc region, for example, Fc regions of the IgA1, IgA2, IgD, IgE, IgG1, IgG2, IgG3, IgG4, and IgM types exist. For example, a human IgG antibody Fc region can be used as the antibody Fc region of the present invention, and human IgG1 antibody Fc regions are preferred. Fc regions that can be used as an Fc region of the present invention are, for example, those derived from naturally-occurring IgG constant regions, or specifically, a constant region derived from naturally-occurring human IgG1 (SEQ ID NO: 11), a constant region derived from naturally-occurring human IgG2 (SEQ ID NO: 12), a constant region derived from naturally-occurring human IgG3 (SEQ ID NO: 13), and a constant region derived from naturally-occurring human IgG4 (SEQ ID NO: 14). FIG. 21 shows the constant region sequences of the naturally-occurring IgG1, IgG2, IgG3, and IgG4. Constant regions of naturally-occurring IgGs also include mutants spontaneously produced from them. For the constant regions of human IgG1, human IgG2, human IgG3, and human IgG4 antibodies, a plurality of allotype sequences due to genetic polymorphism are described in "Sequences of proteins of immunological interest", NIH Publication No. 91-3242, and any of them may be used in the present invention. In particular, for the human IgG1 sequence, the amino acid sequence at positions 356 to 358 (EU numbering) may be either DEL or EEM.

"Fcγ receptors" (herein, referred to as Fcγ receptors, FcγR or FcgR) refers to receptors that may bind to the Fc region of IgG1, IgG2, IgG3, and IgG4 monoclonal antibodies, and practically means any member of the family of proteins encoded by the Fcγ receptor genes. In humans, this family includes FcγRI (CD64) including isoforms FcγRIa, FcγRIb, and FcγRIc; FcγRII (CD32) including isoforms FcγRIIa (including allotypes H131 (type H) and R131 (type R)), FcγRIIb (including FcγRIIb-1 and FcγRIIb-2), and FcγRIIc; and FcγRIII (CD16) including isoforms FcγRIIIa (including allotypes V158 and F158), and FcγRIIIb (including allotypes FcγRIIIb-NA1 and FcγRIIIb-NA2), and any human FcγRs, FcγR isoforms or allotypes yet to be discovered, but is not limited thereto. FcγRIIb1 and FcγRIIb2 have been reported as splicing variants of human FcγRIIb. In addition, a splicing variant named FcγRIIb3 has been reported (J. Exp. Med, 1989, 170: 1369). In addition to these splicing variants, human FcγRIIb includes all splicing variants registered in NCBI, which are NP_001002273.1, NP_001002274.1, NP_001002275.1, NP_001177757.1, and NP_003992.3. Furthermore, human FcγRIIb includes every previously-reported genetic polymorphism, as well as FcγRIIb (Arthritis Rheum, 2003, 48: 3242-52; Hum Mol Genet, 2005, 14: 2881-92; and Arthritis Rheum. 2002 May; 46(5): 1242-54), and every genetic polymorphism that will be reported in the future.

The FcγR includes human, mouse, rat, rabbit, and monkey-derived FcγRs but is not limited thereto, and may be derived from any organism. Mouse FcγRs include FcγRI (CD64), FcγRII (CD32), FcγRIII (CD16), and FcγRIII-2 (CD16-2), and any mouse FcγRs, or FcγR isoforms or allotypes yet to be discovered, but are not limited thereto. Favorable examples of such Fcγ receptors include human FcγRI (CD64), FcγRIIA (CD32), FcγRIIB (CD32), FcγRIIIA (CD16), and/or FcγRIIIB (CD16).

The polynucleotide sequence and amino acid sequence of FcγRI are set forth in SEQ ID NOs: 1 (NM_000566.3) and 2 (NP_000557.1), respectively;
the polynucleotide sequence and amino acid sequence of FcγRIIA are set forth in SEQ ID NOs: 3 (BC020823.1) and 4 (AAH20823.1), respectively;
the polynucleotide sequence and amino acid sequence of FcγRIIB are set forth in SEQ ID NOs: 5 (BC146678.1) and 6 (AA146679.1), respectively;
the polynucleotide sequence and amino acid sequence of FcγRIIIA are set forth in SEQ ID NOs: 7 (BC033678.1) and 8 (AAH33678.1), respectively; and
the polynucleotide sequence and amino acid sequence of FcγRIIIB are set forth in SEQ ID NOs 9 (BC128562.1) and 10 (AAI28563.1), respectively (the RefSeq Registration number is indicated inside the parentheses).

In FcγRIIa, there are two allotypes, one where the amino acid at position 131 of FcγRIIa is histidine (type H) and the other where this amino acid is substituted with arginine (type R) (J. Exp. Med, 172: 19-25, 1990).

Herein, an "Fc region to which an amino acid alteration(s) has not been introduced", or a similar expression, refers to an Fc region prior to introduction of amino acid alteration(s) of the present invention. In the present invention, this may be, for example, a native IgG Fc region, or an IgG Fc region produced by adding an alteration other than the amino acid alteration(s) of the present invention to a native IgG. Furthermore, in the present invention, "Fc region variant" means an Fc region in which at least one amino acid has been altered to another amino acid of the present invention in the Fc region without introduction of amino acid alteration(s) of the present invention. Herein, Fc region with "at least one amino acid has been altered to another amino acid" includes an Fc region introduced with this amino acid alteration, and an Fc region consisting of the same amino acid sequence.

"Naturally-occurring IgGs" refers to polypeptides belonging to a class of antibodies practically encoded by immunoglobulin gamma genes and comprising an amino acid sequence identical to those of IgGs found in nature. For example, a naturally-occurring human IgG means a native human IgG1, native human IgG2, native human IgG3, naturally-occurring human IgG4, or such. Naturally-occurring IgGs also include mutants spontaneously produced from them.

The Fc region of a native IgG means an Fc region comprising an amino acid sequence identical to that of the Fc region derived from an IgG found in nature. The heavy-chain constant region of a native IgG is shown in FIG. 21 (SEQ ID NOs: 11-14), and for example, it refers to, in FIG. 21, Fc regions in heavy-chain constant region derived from native human IgG1, Fc regions in heavy-chain constant region derived from native human IgG2, Fc regions in heavy-chain constant region derived from native human IgG3, and Fc regions in heavy-chain constant region derived from native human IgG4. The Fc regions of native IgGs also include mutants spontaneously produced from them.

In the present invention, whether or not the binding activity towards each type of FcγR is enhanced, or maintained or decreased in a polypeptide comprising an Fc region variant or an Fc region variant of the present invention can be determined, for example, by observing whether there is a decrease or an increase in the dissociation constant (KD) value obtained from the results of sensorgram analysis, where various FcγRs are subjected to interaction as an analyte with antibodies immobilized onto the sensor chips or captured onto the sensor chips using Protein A, Protein L, Protein A/G, Protein G, anti-lambda chain antibodies, anti-kappa chain antibodies, antigenic peptides, antigenic proteins, or such using a BIACORE™ system that is an interaction analyzer that utilizes the surface plasmon resonance (SPR) phenomena, as shown in the Examples. Alternatively, it can also be determined by observing whether there is an increase or a decrease in the value obtained by dividing the amount of change in the resonance unit (RU) value on the sensorgram before and after various types of FcγRs are subjected to interaction as an analyte with antibodies immobilized onto the sensor chips or captured onto the sensor chips using Protein A, Protein L, Protein A/G, Protein G, anti-lambda chain antibodies, anti-kappa chain antibodies, antigenic peptides, antigenic proteins, or such, by the amount of change of resonance units (RU) before and after antibodies are immobilized or captured onto the sensor chip. Furthermore, it can be determined by observing an increase or a decrease in the dissociation constant (KD) values obtained from sensorgram analysis, where a sample such as an antibody to be evaluated is subjected to interaction as an analyte using a sensor chip onto which FcγR is immobilized directly or via an anti-tag antibody. Alternatively, it can be determined by observing whether the amount of change in sensorgram values increases or decreases before and after a sample such as an antibody to be evaluated is subjected to interaction as an analyte with the sensor chip onto which FcγR is immobilized directly or via an anti-tag antibody.

Specifically, the binding activity of an Fc region variant towards an Fcγ receptor can be measured by the Amplified Luminescent Proximity Homogeneous Assay (ALPHA) screening, the BIACORE™ method which utilizes the surface plasmon resonance (SPR) phenomena, or such, in addition to ELISA or fluorescence activated cell sorting (FACS) (Proc. Natl. Acad. Sci. USA (2006) 103 (11): 4005-4010).

ALPHA screening is performed by ALPHA technology which uses two beads, a donor and an acceptor, based on the following principles. Luminescent signals are detected only when molecules bound to donor beads physically interact with molecules bound to the acceptor beads, and the two beads are in close proximity to each other. Laser-excited photosensitizer in the donor beads converts ambient oxygen to excited-state singlet oxygen. Singlet oxygen is dispersed around the donor beads, and when it reaches the adjacent acceptor beads, chemiluminescent reaction is induced in the beads, and light is ultimately emitted. When the molecules bound to the donor beads do not interact with the molecules bound to the acceptor beads, the chemiluminescent reaction does not take place because singlet oxygen produced by the donor beads does not reach the acceptor beads.

For example, a biotinylated polypeptide complex is bound to the donor beads, and Fcγ receptor tagged with glutathione S transferase (GST) is linked to the acceptor beads. In the absence of a competing polypeptide complex comprising an Fc region variant, the polypeptide complex comprising a wild-type Fc region interacts with the Fcγ receptor and produces 520-620 nm signals. The polypeptide complex comprising an untagged mutant Fc region competes with the polypeptide complex comprising a wild-type Fc region for interaction with the Fcγ receptor. Relative binding activities can be determined by quantifying the decrease in fluorescence observed as a result of the competition. Biotinylation of polypeptide complexes such as antibodies using Sulfo-NHS-biotin and such is well known. The method of expressing the Fcγ receptor and GST in a cell carrying a fusion gene produced by fusing a polynucleotide encoding the Fcγ receptor in frame with a polynucleotide encoding GST in an expressible vector, and performing purification using a glutathione column is appropriately adopted as a method for tagging an Fcγ receptor with GST. The obtained signals are preferably analyzed, for example, by fitting them to a one-site competition model which uses a non-linear regression analysis using software such as GRAPHPAD PRISM (GraphPad, San Diego).

One of the substances (the ligand) in observation of an interaction is immobilized onto a gold thin film on a sensor chip, and by shining light from the reverse side of the sensor chip so that total reflection takes place at the interface between the gold thin film and glass, a portion of reduced reflection intensity is formed in part of the reflected light (SPR signal). When the other one of the substances (the analyte) in observation of an interaction is made to flow on the sensor chip surface and the ligand binds to the analyte, the mass of the immobilized ligand molecule increases and the refractive index of the solvent on the sensor chip surface changes. The position of the SPR signal shifts as a result of this change in refractive index (on the other hand, the signal position returns when this binding dissociates). The Biacore™ system indicates the amount of shift mentioned above, or more specifically the time variable of mass by plotting the change in mass on the sensor chip surface on the ordinate as the measurement data (sensorgram). The amount of analyte bound to the ligand trapped on the sensor chip surface is determined from the sensorgram. Kinetic parameters such as association rate constants (ka) and dissociation rate constants (kd) are determined from the curves of the sensorgram, and the dissociation constants (KD) are determined from the ratio of these constants. In the BIACORE™ method, a method for measuring inhibition is preferably used. An example of the method for measuring inhibition is described in Proc. Natl. Acad. Sci USA (2006) 103 (11): 4005-4010.

An Fc region with decreased FcγR-binding activity or a polypeptide comprising this Fc region refers to an Fc region variant or a polypeptide comprising the Fc region variant which binds to FcγR with essentially weaker binding activity than a polypeptide comprising the parent Fc region when assays are performed by using substantially the same amount of a polypeptide comprising an Fc region to which an amino acid alteration(s) has not been introduced (also referred to as polypeptides comprising parent Fc regions or parent polypeptides) and a polypeptide comprising at least one amino acid alteration in the Fc region (also referred to as a polypeptide comprising an Fc region variant or an altered polypeptide).

Furthermore, an Fc region with enhanced FcγR-binding activity or a polypeptide comprising the Fc region refers to an Fc region variant or a polypeptide comprising the Fc region variant which binds to FcγR with essentially stronger binding activity than a polypeptide containing the parent Fc region when assays are performed by using substantially the same amount of a polypeptide comprising a parent Fc region and a polypeptide comprising an Fc region variant.

A polypeptide with maintained FcγR-binding activity refers to a polypeptide that binds to FcγR with binding activity equivalent to or essentially not different from that of the parent polypeptide when assays are performed by using substantially the same amount of a polypeptide comprising a parent Fc region and a polypeptide comprising the Fc region variant.

In the present invention, enhanced FcγRIIb-binding activity preferably means, for example, that the KD value ratio for [KD value of a polypeptide comprising a parent Fc region for FcγRIIb]/[KD value of a polypeptide comprising an Fc region variant for FcγRIIb] in the KD values measured by the above-mentioned measurement method preferably becomes 15.0 or greater, 20.0 or greater, 25.0 or greater, 30.0 or greater, 35.0 or greater, 40.0 or greater, 45.0 or greater, or even 50.0 or greater, 55.0 or greater, 60.0 or greater, 65.0 or greater, 70.0 or greater, 75.0 or greater, 80.0 or greater, 85.0 or greater, 90.0 or greater, 95.0 or greater, or 100.0 or greater.

Furthermore, "an Fc region variant of the present invention shows enhanced binding selectivity to FcγRIIb compared to FcγRIIa" means that:
(i) FcγRIIb-binding activity is enhanced, and FcγRIIa-binding activity is maintained or decreased;
(ii) FcγRIIb-binding activity is enhanced and FcγRIIa-binding activity is also enhanced, but the degree of enhancement of FcγRIIa-binding activity is lower than the degree of enhancement of FcγRIIb-binding activity; or
(iii) FcγRIIb-binding activity is decreased, but the degree of decrease of the binding activity is less than the degree of decrease of FcγRIIa-binding activity. Whether or not an Fc region variant of the present invention is a variant with improved binding selectivity for FcγRIIb rather than for FcγRIIa can be determined, for example, by comparing the ratio of the KD value for FcγRIIa to the KD value for FcγRIIb of the polypeptide comprising an Fc region variant of the present invention (KD value for FcγRIIa/KD value for FcγRIIb) with the ratio of the KD value for FcγRIIa to the KD value for FcγRIIb of the polypeptide comprising the parent Fc region (KD value for FcγRIIa/KD value for FcγRIIb), which were determined according to the above-mentioned examples. Specifically, when the value of the KD ratio for the polypeptide comprising the Fc region variant of the present invention is greater than that of the polypeptide comprising the parent Fc region, the polypeptide comprising the Fc region variant of the present invention can be determined to have an improved binding selectivity for FcγRIIb rather than for FcγRIIa in comparison with the polypeptide comprising the parent Fc region variant. In particular, since FcγRIIa (type R)-binding activity is likely to correlate with binding activity to FcγRIIb than to FcγRIIa (type H), finding amino acid alteration(s) that can enhance binding selectivity to FcγRIIb compared to FcγRIIa (type R) is important for enhancing binding selectivity to FcγRIIb compared to other FcγRs other than FcγRIIb.

The binding selectivity between FcγRIIa (type R) and FcγRIIb is, for example, a KD value ratio [KD value of the polypeptide comprising the Fc region variant for FcγRIIa (type R)]/[KD value of the polypeptide comprising the Fc region variant for FcγRIIb] of preferably 10.0 or more for the KD values measured by the measurement method described above, and more preferably 20.0 or more.

The binding selectivity between FcγRIIa (type H) and FcγRIIb is, for example, a KD value ratio [KD value of the polypeptide comprising the Fc region variant for FcγRIIa (type H)]/[KD value of the polypeptide comprising the Fc region variant for FcγRIIb] of preferably 100.0 or more, 200 or more, 300 or more, 400 or more, or 500 or more for the KD values measured by the measurement method described above, and more preferably 600 or more, 700 or more, 800 or more, or 900 or more.

Furthermore, whether or not the binding activities of the polypeptides of the present invention towards various FcγRs were maintained, enhanced, or decreased can be determined from the increase or decrease in the amount of binding of the various FcγRs to the polypeptides of the present invention, which were determined according to the examples described above. Here, the amount of binding of the various FcγRs to the polypeptides refers to values obtained by determining the difference in the RU values of sensorgrams that changed before and after interaction of various FcγRs as the analyte with each polypeptide, and dividing them by differences in the RU values of sensorgrams that changed before and after capturing polypeptides to the sensor chips.

Fc region variants of the present invention are not particularly limited in terms of their KD values (mol/L) for FcγRIIb, and for example, the values may be $9 \times 10^{-7}$ or less, preferably $5 \times 10^{-7}$ or less, more preferably $3 \times 10^{-7}$ or less, even more preferably $1 \times 10^{-7}$ or less, and yet even more preferably $5 \times 10^{-8}$ or less.

"Fc region" refers to the fragment consisting of a hinge portion or a part thereof, CH2 domain, and CH3 domain in an antibody molecule. According to EU numbering (herein, also called the EU INDEX) (see FIG. 21), an IgG-class Fc region refers to, for example, the region from cysteine at position 226 to the C terminus, or from proline at position 230 to the C terminus, but is not limited thereto.

The Fc region may be obtained preferably by re-eluting the fraction adsorbed onto protein A column after partially digesting IgG1, IgG2, IgG3, IgG4 monoclonal antibodies or such using a protease such as pepsin. The protease is not particularly limited as long as it can digest a full-length antibody so that Fab and F(ab')2 will be produced in a restrictive manner by appropriately setting the enzyme reaction conditions such as pH, and examples include pepsin and papain.

The present invention provides Fc region variants having a combination of alterations which includes alteration of amino acid at position 238 (EU numbering) to another amino acid and alteration of at least one amino acid selected from amino acids at positions 233, 234, 235, 237, 264, 265, 266, 267, 268, 269, 271, 272, 274, 296, 326, 327, 330, 331, 332, 333, 334, 355, 356, 358, 396, 409, and 419 (EU numbering) to another amino acid in the Fc region of a human IgG (IgG1, IgG2, IgG3, or IgG4). By combining alteration of amino acid at position 238 (EU numbering) to another amino acid with alteration of at least one amino acid selected from amino acids at positions 233, 234, 237, 264, 265, 266, 267, 268, 269, 271, 272, 274, 296, 326, 327, 330, 331, 332, 333, 334, 355, 356, 358, 396, 409, and 419 (EU numbering) to another amino acid in the human IgG Fc region, it is possible to provide a polypeptide comprising an Fc region variant with enhanced FcγRIIb-binding activity, and/or enhanced binding selectivity to FcγRIIb, compared to FcγRIIa, to FcγRIIa (type R) in particular, as compared to those of a polypeptide containing an Fc region to which an amino acid alteration(s) has not been introduced. Other amino acid alterations that are to be combined with the amino acid alteration at position 238 (EU numbering) are preferably those at positions 233, 237, 264, 267, 268, 271, 272, 296, 327, 330, 332, 333, and 396 (EU numbering), and particularly preferably those at positions 233, 237, 264, 267, 268, 271, 296, 330, and 396 (EU numbering). In particular, in terms of enhancement of FcγRIIb-binding activity, or enhancement of binding selectivity to FcγRIIb compared to FcγRIIa, an example of a preferred combination of amino acid alterations include combination of alterations at amino acid positions 238, 268, and 271 (EU numbering) with at least one amino acid position selected from 233, 237, 264, 267, 272, 296, 327, 330, 332, and 396 (EU numbering).

Amino acids to be altered are not particularly limited as long as they lead to enhancement of FcγRIIb-binding activity or enhancement of binding selectivity to FcγRIIb compared to FcγRIIa as compared to before the alteration, but it is preferred that the amino acid at position 238 is Asp, the amino acid at position 233 is Asp, the amino acid at position 234 is Tyr, the amino acid at position 235 is Phe, the amino acid at position 237 is Asp, the amino acid at position 264 is Ile, the amino acid at position 265 is Glu, the amino acid at position 266 is Phe, Leu, or Met, the amino acid at position 267 is Ala, Glu, Gly, or Gln, the amino acid at position 268 is Asp, Gln, or Glu, the amino acid at position 269 is Asp, the amino acid at position 271 is Gly, the amino acid at position 272 is Asp, Phe, Ile, Met, Asn, Pro, or Gln, the amino acid at position 274 is Gln, the amino acid at position 296 is Asp or Phe, the amino acid at position 326 is Ala or Asp, the amino acid at position 327 is Gly, the amino acid at position 330 is Lys, Arg, or Ser, the amino acid at position 331 is Ser, the amino acid at position 332 is Lys, Arg, Ser, or Thr, the amino acid at position 333 is Lys, Arg, Ser, or Thr, the amino acid at position 334 is Arg, Ser, or Thr, the amino acid at position 355 is Ala or Gln, the amino acid at position 356 is Glu, the amino acid at position 358 is Met, the amino acid at position 396 is Ala, Asp, Glu, Phe, Gly, His, Ile, Lys, Leu, Met, Asn, Gln, Arg, Ser, Thr, Val, Trp or Tyr, the amino acid at position 409 is Arg, and the amino acid at position 419 is Glu, according to EU numbering. In particular, when combining alterations at amino acid positions 238, 268, and 271 (EU numbering) with at least one amino acid position selected from 233, 264, 267, 272, 296, 327, 330, 332, and 396 (EU numbering), it is preferred that the amino acid at position 238 is Asp, the amino acid at position 268 is Asp or Glu, the amino acid at position 271 is Gly, the amino acid at position 233 is Asp, the amino acid at position 237 is Asp, the amino acid at position 264 is lie, the amino acid at position 267 is Ala or Gly, the amino acid at position 272 is Asp or Pro, the amino acid at position 296 is Asp, the amino acid at position 327 is Gly, the amino acid at position 330 is Arg, the amino acid at position 332 is Thr, and the amino acid at position 396 is Leu or Met, according to EU numbering.

In addition to these alterations, at least one different Fc region alteration may be added in the present invention. The added alteration is not particularly limited as long as FcγRIIb-binding activity is enhanced and/or binding selectivity to FcγRIIb compared to FcγRIIa is enhanced. Furthermore, alterations can be made by combining an alteration where a portion of an Fc region is substituted with a corresponding portion of Fc region of a different isotype. For example, it is possible to enhance FcγRIIb-binding activity and/or binding selectivity to FcγRIIb by combining the above-mentioned amino acid alterations with substitution of the amino acid sequence from Ala at position 118 to Thr at position 225 (EU numbering) in the IgG-derived Fc region with the amino acid sequence from Ala at position 118 to Pro at position 222 (EU numbering) in the IgG4-derived Fc region. A specific example includes a combination of amino acid alterations introduced into IL6R-BP230, and the alteration of substituting the amino acid sequence from Ala at position 118 to Thr at position 225 (EU numbering) in G1d with the amino acid sequence from Ala at position 118 to Pro at position 222 (EU numbering) in G4d, as of IL6R-BP478/IL6R-L described in Example 7.

Among them, alterations that lead to greater enhancement of FcγRIIb-binding activity, or lead to greater enhancement of binding selectivity to FcγRIIb compared to FcγRIIa (type R) are preferred. Examples of such a preferred combination of amino acid alterations include the following (a) to (x):

(a) amino acid alterations at positions 238, 233, 237, 268, 271, 296, and 330 (EU numbering) of an Fc region;
(b) amino acid alterations at positions 238, 237, 268, 271, 296, and 330 (EU numbering) of an Fc region;
(c) amino acid alterations at positions 238, 233, 237, 268, 271, 296, 330, and 332 (EU numbering) of an Fc region;
(d) amino acid alterations at positions 238, 233, 237, 264, 267, 268, 271, and 330 (EU numbering) of an Fc region;
(e) amino acid alterations at positions 238, 233, 237, 267, 268, 271, 296, 330, and 332 (EU numbering) of an Fc region;
(f) amino acid alterations at positions 238, 237, 267, 268, 271, 296, 330, and 332 (EU numbering) of an Fc region;
(g) amino acid alterations at positions 238, 233, 237, 268, 271, 296, 327, and 330 (EU numbering) of an Fc region;
(h) amino acid alterations at positions 238, 233, 237, 264, 267, 268, and 271 (EU numbering) of an Fc region;
(i) amino acid alterations at positions 238, 233, 237, 264, 267, 268, 271, 296, and 330 (EU numbering) of an Fc region;
(j) amino acid alterations at positions 238, 233, 237, 264, 267, 268, 271, 296, 330, and 396 (EU numbering) of an Fc region;
(k) amino acid alterations at positions 238, 237, 264, 267, 268, 271, and 330 (EU numbering) of an Fc region;
(l) amino acid alterations at positions 238, 237, 264, 267, 268, 271, 296, and 330 (EU numbering) of an Fc region;
(m) amino acid alterations at positions 238, 264, 267, 268, and 271 (EU numbering) of an Fc region;
(n) amino acid alterations at positions 238, 264, 267, 268, 271, and 296 (EU numbering) of an Fc region;
(o) amino acid alterations at positions 238, 237, 267, 268, 271, 296, and 330 (EU numbering) of an FE region;
(p) amino acid alterations at positions 238, 233, 237, 264, 267, 268, 271, 330, and 396 (EU numbering) of the Fc region;
(q) amino acid alterations at positions 238, 233, 237, 264, 267, 268, 271, 296, 327, 330, and 396 (EU numbering) of an Fc region;
(r) amino acid alterations at positions 238, 233, 237, 264, 267, 268, 271, 272, and 296 (EU numbering) of an Fc region;
(s) amino acid alterations at positions 238, 237, 264, 267, 268, 271, 272, and 330 (EU numbering) of an Fc region;
(t) amino acid alterations at positions 238, 237, 264, 267, 268, 271, 272, 296, and 330 (EU numbering) of an Fc region;
(u) amino acid alterations at positions 238, 233, 264, 267, 268, and 271 (EU numbering) of an Fc region;
(v) amino acid alterations at positions 238, 237, 267, 268, 271, 296, and 330 (EU numbering) of an Fc region;
(w) amino acid alterations at positions 238, 264, 267, 268, 271, 272, and 296 (EU numbering) of an Fc region; and
(x) amino acid alterations at positions 238, 233, 264, 267, 268, 271, and 296 (EU numbering) of an Fc region.

In addition, among these combinations, the following combinations of amino acid alterations (a) to (x) below are more preferred amino acid combinations:

(a) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, and the amino acid at position 330 is Arg, according to EU numbering, in an Fc region;
(b) an amino acid sequence in which the amino acid at position 238 is Asp, the amino acid at position 237 is Asp, the amino acid at position 268 is Asp or Glu, the amino acid at position 271 is Gly, the amino acid at position 296 is Asp, and the amino acid at position 330 is Arg, according to EU numbering, in an Fc region;
(c) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, the amino acid at position 330 is Arg, and the amino acid at position 332 is Thr, according to EU numbering, in an Fc region;
(d) an amino acid sequence in which the amino acid at position 238 is Asp, the amino acid at position 233 is Asp, the amino acid at position 237 is Asp, the amino acid at position 264 is Ile, the amino acid at position 267 is Gly or Ala, the amino acid at position 268 is Glu, the amino acid at position 271 is Gly, and the amino acid at position 330 is Arg, according to EU numbering, in an Fc region;
(e) an amino acid sequence in which the amino acid at position 238 is Asp, the amino acid at position 233 is Asp, the amino acid at position 237 is Asp, the amino acid at position 267 is Ala, the amino acid at position 268 is Glu, the amino acid at position 271 is Gly, the amino acid at position 296 is Asp, the amino acid at position 330 is Arg, and the amino acid at position 332 is Thr, according to EU numbering, in an Fc region;
(f) an amino acid sequence in which the amino acid at position 238 is Asp, the amino acid at position 237 is Asp, the amino acid at position 267 is Ala, the amino acid at position 268 is Glu, the amino acid at position 271 is Gly, the amino acid at position 296 is Asp, the amino acid at position 330 is Arg, and the amino acid at position 332 is Thr, according to EU numbering, in an Fc region;
(g) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, the amino acid at position 327 is Gly, and the amino acid at position 330 is Arg, according to EU numbering, in an Fc region;
(h) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, and the amino acid at position 271 is Gly, according to EU numbering, in an Fc region;
(i) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, and the amino acid at position 330 is Arg, according to EU numbering, in an Fc region;
(j) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, the amino acid at position 330 is Arg, and the amino acid at position 396 is Met or Leu, according to EU numbering, in the Fc region;
(k) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, and the amino acid at position 330 is Arg, according to EU numbering, in an Fc region;
(l) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, and the amino acid at position 330 is Arg, according to EU numbering, in an Fc region;
(m) an amino acid sequence in which the amino acid at position 238 is Asp, the amino acid at position 264 is Ile, the amino acid at position 267 is Ala, the amino acid at position 268 is Glu, and the amino acid at position 271 is Gly, according to EU numbering, in an Fc region;
(n) an amino acid sequence in which the amino acid at position 238 is Asp, the amino acid at position 264 is Ile, the amino acid at position 267 is Ala, the amino acid at position 268 is Glu, the amino acid at position 271 is Gly, and the amino acid at position 296 is Asp, according to EU numbering, in an Fc region;
(o) an amino acid sequence in which the amino acid at position 238 is Asp, the amino acid at position 237 is Asp, the amino acid at position 267 is Ala or Gly, the amino acid at position 268 is Glu, the amino acid at position 271 is Gly, the amino acid at position 296 is Asp, and the amino acid at position 330 is Arg, according to EU numbering, in an Fc region;
(p) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 330 is Arg, and the amino acid at position 396 is Met or Leu, according to EU numbering, in an Fc region;
(q) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, the amino acid at position 327 is Gly, the amino acid at position 330 is Arg, and the amino acid at position 396 is Met, according to EU numbering, in an Fc region;
(r) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Asp, and the amino acid at position 296 is Asp, according to EU numbering, in an Fc region;
(s) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Pro, and the amino acid at position 330 is Arg, according to EU numbering, in an Fc region;

(t) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Pro, the amino acid at position 296 is Asp, and the amino acid at position 330 is Arg, according to EU numbering, in an Fc region;

(u) an amino acid sequence in which the amino acid at position 238 is Asp, the amino acid at position 233 is Asp, the amino acid at position 264 is Ile, the amino acid at position 267 is Ala, the amino acid at position 268 is Glu, and the amino acid at position 271 is Gly, according to EU numbering, in an Fc region;

(v) an amino acid sequence in which the amino acid at position 238 is Asp, the amino acid at position 237 is Asp, the amino acid at position 267 is Gly, the amino acid at position 268 is Asp, the amino acid at position 271 is Gly, the amino acid at position 296 is Asp, and the amino acid at position 330 is Arg, according to EU numbering, in an Fc region;

(w) an amino acid sequence in which the amino acid at position 238 is Asp, the amino acid at position 264 is Ile, the amino acid at position 267 is Ala, the amino acid at position 268 is Glu, the amino acid at position 271 is Gly, the amino acid at position 272 is Asp, and the amino acid at position 296 is Asp, according to EU numbering, in an Fc region; and (x) an amino acid sequence in which the amino acid at position 238 is Asp, the amino acid at position 233 is Asp, the amino acid at position 264 is Ile, the amino acid at position 267 is Ala, the amino acid at position 268 is Glu, the amino acid at position 271 is Gly, and the amino acid at position 296 is Asp, according to EU numbering, in an Fc region.

In addition, amino acid alterations performed for other purpose(s) can be combined in polypeptides comprising an Fc region variant of the present invention. For example, amino acid substitutions that improve FcRn-binding activity (J. Immunol. 2006 Jan. 1; 176(1): 346-56; J Biol Chem. 2006 Aug. 18; 281(33): 23514-24; Int. Immunol. 2006 December; 18(12): 1759-69; Nat Biotechnol. 2010 February; 28(2): 157-9; WO/2006/019447; WO/2006/053301; and WO/2009/086320), and amino acid substitutions for improving antibody heterogeneity or stability (WO/2009/041613) may be added. Alternatively, polypeptides produced by conferring polypeptides comprising an Fc region variant of the present invention with the property of promoting disappearance of antigens, which are described in WO 2011/122011 or PCT/JP2011/072550, and polypeptides conferring the property for repeated binding to a plurality of antigen molecules, which are described in WO 2009/125825, WO 2012/073992 or WO 2013/047752, are also included in the present invention. Alternatively, with the objective of increasing plasma retention, amino acid alterations that decrease the pI of the constant region (WO/2012/016227) may be combined in a polypeptide comprising an Fc region variant of the present invention. Alternatively, with the objective of conferring binding ability to other antigens, the amino acid alterations disclosed in EP1752471 and EP1772465 may be combined in CH3 of a polypeptide comprising an Fc region variant of the present invention.

When a polypeptide comprising an Fc region variant of the present invention is an antigen-binding molecule such as an antibody, amino acid alterations of enhancing human FcRn-binding activity under an acidic pH range condition can be combined to enhance the effect of the antigen-binding molecule to eliminate antigens from plasma. More specifically, alterations used to enhance human FcRn-binding activity under an acidic pH range condition may be carried out on an IgG antibody, for example, by a method of substituting Leu for Met at position 428, and substituting Ser for Asn at position 434, according to EU numbering (Nat Biotechnol, 2010 28: 157-159); a method of substituting Ala for Asn at position 434 (Drug Metab Dispos. 2010 April; 38(4): 600-5); a method of substituting Tyr for Met at position 252, substituting Thr for Ser at position 254, and substituting Glu for Thr at position 256 (J Biol Chem, 2006, 281: 23514-23524); a method for substituting Gln for Thr at position 250, and substituting Leu for Met at position 428 (J Immunol. 2006, 176(1): 346-56); method of substituting His for Asn at position 434 (Clinical Pharmacology & Therapeutics (2011) 89(2): 283-290), or by using alterations such as those described in WO2010106180, WO2010045193, WO2009058492, WO2008022152, WO2006050166, WO2006053301, WO2006031370, WO2005123780, WO2005047327, WO2005037867, WO2004035752, WO2002060919, or such.

Furthermore, an antibody molecule produced by substituting His for Asn at position 434 (EU numbering) in humanized anti-CD4 antibody to enhance human FcRn-binding activity under an acidic pH range condition and to improve plasma retention properties was recently reported to bind to rheumatoid factors (RF) (Clin Pharmacol Ther. 2011 February; 89(2): 283-90). This antibody has a human IgG1 Fc region, but by substituting His for Asn at position 434 which is positioned at the FcRn-binding site, it has been shown to bind to rheumatoid factors that recognize this substituted site.

As described above, various alterations have been reported as alterations for enhancing human FcRn-binding activity under an acidic pH range condition; however, by introducing these alterations into the FcRn-binding site in an Fc region, affinity to rheumatoid factors which recognize this site may become enhanced.

However, by introducing alterations which do not reduce FcRn-binding activity and reduce only binding activity to rheumatoid factors into the site in the Fc region, antigen-binding molecules with enhanced human FcRn-binding activity under an acidic pH range condition and without affinity to rheumatoid factors can be produced.

For alterations that reduce binding activity to rheumatoid factors, alterations to positions 248-257, 305-314, 342-352, 380-386, 388, 414-421, 423, 425-437, 439, and 441-444 according to EU numbering are used. Preferably, alterations to positions 387, 422, 424, 426, 433, 436, 438, and 440 are used. Particularly preferably, alteration of substituting Glu or Ser for Val at position 422, alteration of substituting Arg for Ser at position 424, alteration of substituting Asp for His at position 433, alteration of substituting Thr for Tyr at position 436, alteration of substituting Arg or Lys for Gln at position 438, and alteration of substituting Glu or Asp for Ser at position 440 are used. These alterations may be used alone or by combining alterations at multiple positions.

Alternatively, to decrease binding activity to rheumatoid factors, an N-type glycosylation sequence may be introduced into this site. Specifically, Asn-Xxx-Ser/Thr (Xxx is any amino acid other than Pro) is known as an N-type glycosylation sequence. Adding an N-type sugar chain by introducing this sequence into the site in the Fc region enables inhibition of binding to RF by steric hindrance due to the N-type sugar chain. Alterations used to add an N-type sugar chain are preferably alteration which substitutes Asn for Lys at position 248, alteration which substitutes Asn for Ser at position 424, alteration which substitutes Asn for Tyr at position 436 and substitutes Thr for Gln at position 438, and alteration which substitutes Asn for Gln at position 438. Particularly preferably, the alteration which substitutes Asn for Ser at position 424 is used.

Preferred example of a polypeptide comprising an Fc region variant of the present invention includes a polypeptide comprising at least two Fc region variants wherein the two Fc region variants are associated, much like in an IgG antibody. When an IgG antibody is used as a polypeptide of the present invention, the type of constant region is not limited, and an IgG isotypes (subclasses) such as IgG1, IgG2, IgG3, and IgG4 can be used. IgG antibodies of the present invention are preferably human IgG, and more preferably human IgG1 and human IgG4. The amino acid sequences of the heavy-chain constant regions of human IgG1 and human IgG4 are known. A plurality of allotype sequences due to genetic polymorphisms have been described in Sequences of Proteins of Immunological Interest, NIH Publication No. 91-3242 for the human IgG1 constant region, and any of the sequences may be used in the present invention.

The two associated Fc region variants included in the aforementioned polypeptide may be Fc region variants introduced with the same amino acid alteration(s) (hereinafter, referred to as a polypeptide containing homologous Fc region variants) or Fc region variants comprising different amino acid sequences where each have been introduced with different amino acid alteration(s), or alternatively Fc region variants comprising different amino acid sequences where only one of the Fc regions has been introduced with amino acid alteration(s) (hereinafter, referred as a polypeptide containing heterologous Fc region variants). As the amino acid alteration to be introduced into only one of the Fc regions, alteration in the loop structure portion from positions 233 to 239 (EU numbering) in the Fc region CH2 domain involved in binding with FcγRIIb and FcγRIIa is preferred; and preferably, an alteration that enhances FcγRIIb-binding activity and/or enhances binding selectivity to FcγRIIb compared to FcγRIIa (type R) of the loop structure of the CH2 region of one of the Fc regions is introduced and an amino acid alteration that destabilizes the loop structure of the CH2 region of the other Fc region is introduced. Examples of amino acid alterations that can destabilize the loop structure of the CH2 region may be substitution of at least one amino acid selected from amino acids at positions 235, 236, 237, 238, and 239 to another amino acid. Specifically, the CH2 region loop structure can be destabilized, for example, by altering the amino acid at position 235 to Asp, Gln, Glu, or Thr, altering the amino acid at position 236 to Asn, altering the amino acid at position 237 to Phe or Trp, altering the amino acid at position 238 to Glu, Gly, or Asn, and altering the amino acid at position 239 to Asp or Glu, according to EU numbering.

To produce a polypeptide comprising heterologous Fc region variants of the present invention, it is required that Fc region variants having amino acids that differ from each other are associated, or a polypeptide comprising heterologous Fc region variants of interest is separated from other polypeptides comprising homologous Fc region variants.

For association of polypeptides having different amino acids from each other, a technique of suppressing unintended association between H chains by introducing electrostatic repulsion into the interface of the second constant region of the antibody H chain (CH2) or the third constant region of the H chain (CH3) (WO 2006/106905) can be applied.

In the technology of suppressing unintended association between H chains by introducing electrostatic repulsion into the interface of CH2 or CH3, examples of amino acid residues in contact at the interface of other constant regions of the H chain include the residue at position 356 (EU numbering), the residue at position 439 (EU numbering), the region facing the residue at position 357 (EU numbering), the residue at position 370 (EU numbering), the residue at position 399 (EU numbering), and the residue at position 409 (EU numbering) in the CH3 domain.

More specifically, for example, in an antibody containing two types of H chain CH3 domains, the antibody in which one to three pairs of amino acid residues selected from the amino acid residues shown below in (1) to (3) in the first H chain CH3 domain have the same type of charge can be produced:

(1) amino acid residues at positions 356 and 439 (EU numbering) which are amino acid residues contained in the H chain CH3 domain;
(2) amino acid residues at positions 357 and 370 (EU numbering) which are amino acid residues contained in the H chain CH3 domain; and
(3) amino acid residues at positions 399 and 409 (EU numbering) which are amino acid residues contained in the H chain CH3 domain.

Furthermore, an antibody can be produced in which one to three pairs of amino acid residues corresponding to the amino acid residue pairs indicated above in (1) to (3) having the same type of charge in the first H chain CH3 domain have charges opposite to the corresponding amino acid residues in the aforementioned first H chain CH3 domain, wherein the amino acid residue pairs are selected from the amino acid residue pairs indicated above in (1) to (3) in the second H chain CH3 domain which differs from the first H chain CH3 domain.

The respective amino acid residues of (1) to (3) mentioned above are positioned close to each other when associated. Those skilled in the art can find sites that correspond to the above-mentioned amino acid residues of (1) to (3) by homology modeling and such using commercially available software for the desired H chain CH3 domain or H chain constant region, and amino acid residues of these sites can be altered when appropriate.

In the above-mentioned antibodies, for example, "charged amino acid residues" are preferably selected from amino acid residues included in either of groups (X) or (Y) below:
(X) glutamic acid (E) and aspartic acid (D); and
(Y) lysine (K), arginine (R), and histidine (H).

In the above-mentioned antibodies, the phrase "having the same type of charge" means that, for example, all of the two or more amino acid residues are amino acid residues included in either of the above-mentioned groups (X) and (Y). The phrase "having the opposite charge" means that, for example, when at least one of the two or more amino acid residues is an amino acid residue included in either one of the above-mentioned groups (X) and (Y), the remaining amino acid residues are amino acid residues included in the other group.

In a preferred embodiment of the above-mentioned antibody, the first H chain CH3 domain and the second H chain CH3 domain may be cross-linked by disulfide bonds.

In the present invention, the amino acid residues to be altered are not limited to amino acid residues of the antibody constant region or antibody variable region described above.

Those skilled in the art can find amino acid residues that form the interface in polypeptide mutants or heteromultimers through homology modeling and such using commercially available software, and can alter the amino acid residues at those sites to regulate association.

Other known techniques can be used additionally for association of heterologous Fc region variants. Specifically, such a technique is conducted by substituting an amino acid side chain present in a variable region of one of the H chains in an antibody with a larger side chain (knob; which means "bulge"), and substituting an amino acid side chain present in a variable region of the other H chain with a smaller side chain (hole; which means "void"), to place the knob within the hole. This can promote efficient association between Fc-region-containing polypeptides having different amino acids (WO 1996/027011; Ridgway J B et al., Protein Engineering (1996) 9, 617-621; Merchant A M et al., Nature Biotechnology (1998) 16, 677-681).

In addition, other known techniques can also be used for heterologous association of Fc region variants. Association of polypeptides having different sequences can be induced efficiently by complementary association of CH3 by using a strand-exchange engineered domain CH3 produced by changing a portion of one of the H chain CH3 of an antibody to an IgA-derived sequence corresponding to that portion and introducing to the complementary portion of the other H chain CH3, an IgA-derived sequence corresponding to that portion (Protein Engineering Design & Selection, 23; 195-202, 2010). This known technique can also be used to efficiently induce association between Fc region-containing polypeptides having different amino acids from each other.

In addition, heterodimerized antibody production techniques that use association of antibody CH1 and CL, and association of VH and VL, which are described in W2011/028952, can also be used.

As with the method described in WO2008/119353 and WO2011/131746, it is also possible to use the technique of producing heterodimerized antibodies by producing two types of homodimerized antibodies in advance, incubating them under reducing conditions to dissociate them, and allowing them to associate again.

As with the method described in J. Mol. (2012) 420, 204-219, it is also possible to use the technique of producing heterodimerized antibodies by introducing charged residues such as Lys, Arg, Glu, and Asp so that electrostatic repulsion is introduced into CH3 of IgG1 and IgG2.

Furthermore, as with the method described in WO2012/058768, it is also possible to use the technique of producing heterodimerized antibodies by adding alterations to the CH2 and CH3 regions.

Furthermore, even in cases where polypeptides comprising heterologous Fc region variants cannot be formed efficiently, polypeptides comprising heterologous Fc region variants can be obtained by separating and purifying them from polypeptides comprising homologous Fc region variants. When producing a polypeptide comprising heterologous Fc region variants consisting of a first polypeptide and a second polypeptide which have different sequences from each other, polypeptides comprising homologous Fc region consisting of only two first polypeptides, and polypeptide comprising homologous Fc region consisting of only two second polypeptide are mixed in as impurities. Known technologies can be used as a method for efficiently removing these two types of polypeptides comprising homologous Fc region. A method has been reported to be able to purify two types of homodimers and the heterodimerized antibody of interest by ion exchange chromatography, by creating a difference in isoelectric points by introducing amino acid substitutions into the variable regions of the two types of H chains (WO 2007114325). To date, as a method for purifying heterodimerized antibodies, a method using Protein A has been reported to purify a heterodimerized antibody comprising a mouse IgG2a H chain that binds to Protein A and a rat IgG2b H chain that does not bind to Protein A (WO 98050431 and WO 95033844).

Furthermore, a heterodimerized antibody alone can be efficiently purified by using H chains in which amino acid residues at the IgG-Protein A binding site, positions 435 and 436 (EU numbering), are substituted with amino acids yielding different Protein A affinities such as Tyr or His to change interaction of each of the H chains with Protein A, and using a Protein A column.

A plurality of these substitutions and technologies, for example, two or more of them can be used in combination. Furthermore, these alterations can be made separately to the first polypeptide and the second polypeptide when necessary. Polypeptides of the present invention may also be those produced based on the products of the above-mentioned alterations.

In the present invention, amino acid alteration means any of substitution, deletion, addition, insertion, and modification, or a combination thereof. In the present invention, amino acid alteration may be rephrased as amino acid mutation, and they are used synonymously.

When substituting amino acid residues, substitution to a different amino acid residue is carried out with the objective of altering aspects such as (a)-(c) described below:
(a) polypeptide backbone structure in the sheet-structure or helical-structure region;
(b) electric charge or hydrophobicity at the target site; or
(c) size of the side chain.

Amino acid residues are classified into the following groups based on their general side chain properties:
(1) hydrophobic: norleucine, met, ala, val, leu, and ile;
(2) neutral hydrophilic: cys, ser, thr, asn, and gln;
(3) acidic: asp and glu;
(4) basic: his, lys, and arg;
(5) residues that affect the chain orientation: gly and pro; and
(6) aromatic: trp, tyr, and phe.

Substitution between amino acid residues within each of these amino acid groups is referred to as conservative substitution, and amino acid residue substitution between different groups is referred to as non-conservative substitution. Substitutions in the present invention may be conservative substitutions or non-conservative substitutions, or a combination of conservative substitutions and non-conservative substitutions.

Amino acid sequence alterations are produced by various methods known to those skilled in the art. Such methods include the site-directed mutagenesis method (Hashimoto-Gotoh, T, Mizuno, T, Ogasahara, Y, and Nakagawa, M. (1995) An oligodeoxyribonucleotide-directed dual amber method for site-directed mutagenesis. Gene 152: 271-275; Zoller, M J, and Smith, M. (1983) Oligonucleotide-directed mutagenesis of DNA fragments cloned into M13 vectors. Methods Enzymol. 100: 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12: 9441-9456; Kramer W, and Fritz H J (1987) Oligonucleotide-directed construction of mutations via gapped duplex DNA Methods. Enzymol. 154, 350-367; and Kunkel, TA (1985) Rapid and efficient site-specific mutagenesis without phenotypic selection. Proc Natl Acad Sci USA. 82: 488-

492), the PCR mutation method, and the cassette mutation method, but are not limited thereto.

Amino acid modification of the present invention includes post-translational modification. A specific post-translational modification may be addition or deletion of a sugar chain. For example, in the IgG1 constant region consisting of the amino acid sequence of SEQ ID NO: 11, the amino acid residue at position 297 (EU numbering) may be sugar chain-modified. The sugar-chain structure for the modification is not limited. Generally, antibodies expressed in eukaryotic cells comprise glycosylation in the constant region. Therefore, antibodies expressed in cells such as those below are normally modified by some type of sugar chain:

antibody-producing cells of mammals
    eukaryotic cells transformed with an expression vector comprising a DNA encoding an antibody Eukaryotic cells shown here include yeast and animal cells. For example, CHO cells and HEK293H cells are representative animal cells used in transformation with an expression vector comprising an antibody-encoding DNA. On the other hand, those without glycosylation at this site are also included in the constant region of the present invention. Antibodies whose constant region is not glycosylated can be obtained by expressing an antibody-encoding gene in prokaryotic cells such as *Escherichia coli*.

Specifically, for example, sialic acid may be added to the sugar chain of an Fc region (MAbs. 2010 September-October; 2(5): 519-27).

Furthermore, the present invention provides antibodies comprising any of Fc region variant described above.

The term "antibody/antibodies" in the present invention is used in the broadest sense, and as long as the desired biological activity is shown, it comprises any antibody such as monoclonal antibodies (including full-length monoclonal antibodies), polyclonal antibodies, antibody variants, antibody fragments, polyspecific antibodies (multi-specific antibodies) (for example, bispecific antibodies (diabodies)), chimeric antibodies, and humanized antibodies.

Regarding the antibodies of the present invention, the antigen type and antibody origin are not limited, and they may be any type of antibodies. The origin of the antibodies is not particularly limited, but examples include human antibodies, mouse antibodies, rat antibodies, and rabbit antibodies.

Methods for producing the antibodies are well known to those skilled in the art, and for example, monoclonal antibodies may be produced by the hybridoma method (Kohler and Milstein, Nature 256: 495 (1975)), or the recombination method (U.S. Pat. No. 4,816,567). Alternatively, they may be isolated from a phage antibody library (Clackson et al., Nature 352: 624-628 (1991); Marks et al., J. Mol. Biol. 222: 581-597 (1991)).

A humanized antibody is also called a reshaped human antibody. Specifically, humanized antibodies prepared by grafting the CDRs of a non-human animal antibody such as a mouse antibody to a human antibody and such are known. Common genetic engineering techniques for obtaining humanized antibodies are also known. Specifically, for example, overlap extension PCR is known as a method for grafting mouse antibody CDRs to human FRs.

A vector for expressing a humanized antibody can be produced by inserting a DNA encoding an antibody variable region in which three CDRs and four FRs are ligated and a DNA encoding a human antibody constant region into an expression vector so that these DNAs are fused in frame. After this integration vector is transfected into a host to establish recombinant cells, these cells are cultured, and the DNA encoding the humanized antibody is expressed to produce the humanized antibody in the culture of the cells (see, European Patent Publication No. EP 239,400, and International Patent Publication No. WO 1996/002576).

As necessary, an amino acid residue in an FR may be substituted so that the CDRs of a reshaped human antibody form an appropriate antigen-binding site. For example, a mutation can be introduced into the amino acid sequence of an FR by applying the PCR method used for grafting mouse CDRs to human FRs.

A desired human antibody can be obtained by DNA immunization using a transgenic animal having the complete repertoire of human antibody genes (see International Publication Nos. WO 1993/012227, WO 1992/003918, WO 1994/002602, WO 1994/025585, WO 1996/034096, and WO 1996/033735) as an animal for immunization.

Furthermore, technologies for obtaining a human antibody by panning using a human antibody library are known. For example, a human antibody V region is expressed on the surface of a phage as a single-chain antibody (scFv) by the phage display method. The scFv-expressing phage that binds to the antigen can be selected. The DNA sequence that encodes the V region of the antigen-bound human antibody can be determined by analyzing the genes of the selected phage. After determining the DNA sequence of the scFv that binds to the antigen, an expression vector can be prepared by fusing the V-region sequence in-frame with the sequence of a desired human antibody C region, and then inserting this into a suitable expression vector. The expression vector is introduced into suitable expression cells such as those described above, and the human antibody can be obtained by expressing the human antibody-encoding gene. These methods are already known (see, International Publication Nos. WO 1992/001047, WO 1992/020791, WO 1993/006213, WO 1993/011236, WO 1993/019172, WO 1995/001438, and WO 1995/15388).

Variable regions constituting the antibodies of the present invention can be variable regions that recognize any antigen.

Herein, there is no particular limitation on the antigen, and it may be any antigens. Examples of such antigens preferably include ligands (cytokines, chemokines, and such), receptors, cancer antigens, MHC antigens, differentiation antigens, immunoglobulins, and immune complexes partly containing immunoglobulins.

Examples of cytokines include interleukins 1 to 18, colony stimulating factors (G-CSF, M-CSF, GM-CSF, etc.), interferons (IFN-α, IFN-β, IFN-γ, etc.), growth factors (EGF, FGF, IGF, NGF, PDGF, TGF, HGF, etc.), tumor necrosis factors (TNF-α and TNF-β), lymphotoxin, erythropoietin, leptin, SCF, TPO, MCAF, and BMP.

Examples of chemokines include CC chemokines such as CCL1 to CCL28, CXC chemokines such as CXCL1 to CXCL17, C chemokines such as XCL1 to XCL2, and CX3C chemokines such as CX3CL1.

Examples of receptors include receptors belonging to receptor families such as the hematopoietic growth factor receptor family, cytokine receptor family, tyrosine kinase-type receptor family, serine/threonine kinase-type receptor family, TNF receptor family, G protein-coupled receptor family, GPI anchor-type receptor family, tyrosine phosphatase-type receptor family, adhesion factor family, and hormone receptor family. The receptors belonging to these receptor families and their characteristics have been described in many documents such as Cooke B A., King R J B., van der Molen H J. ed. New Comprehesive Biochemistry Vol. 18B "Hormones and their Actions Part II" pp. 1-46

(1988) Elsevier Science Publishers BV; Patthy (Cell (1990) 61 (1): 13-14); Ullrich et al. (Cell (1990) 61 (2): 203-212); Massagud (Cell (1992) 69 (6): 1067-1070); Miyajima et al. (Annu. Rev. Immunol. (1992) 10: 295-331); Taga et al. (FASEB J. (1992) 6, 3387-3396); Fantl et al. (Annu. Rev. Biochem. (1993), 62: 453-481); Smith et al. (Cell (1994) 76 (6): 959-962); and Flower D R. Flower (Biochim. Biophys. Acta (1999) 1422 (3): 207-234).

Examples of specific receptors belonging to the above-mentioned receptor families preferably include human or mouse erythropoietin (EPO) receptors (Blood (1990) 76 (1): 31-35; and Cell (1989) 57 (2): 277-285), human or mouse granulocyte-colony stimulating factor (G-CSF) receptors (Proc. Nat. Acad. Sci. USA. (1990) 87 (22): 8702-8706, mG-CSFR; Cell (1990) 61 (2): 341-350), human or mouse thrombopoietin (TPO) receptors (Proc Natl Acad Sci USA. (1992) 89 (12): 5640-5644; EMBO J. (1993) 12(7): 2645-53), human or mouse insulin receptors (Nature (1985) 313 (6005): 756-761), human or mouse Flt-3 ligand receptors (Proc. Natl. Acad. Sci. USA. (1994) 91 (2): 459-463), human or mouse platelet-derived growth factor (PDGF) receptors (Proc. Natl. Acad. Sci. USA. (1988) 85 (10): 3435-3439), human or mouse interferon (IFN)-α and β receptors (Cell (1990) 60 (2): 225-234; and Cell (1994) 77 (3): 391-400), human or mouse leptin receptors, human or mouse growth hormone (GH) receptors, human or mouse interleukin (IL)-10 receptors, human or mouse insulin-like growth factor (IGF)-I receptors, human or mouse leukemia inhibitory factor (LIF) receptors, and human or mouse ciliary neurotrophic factor (CNTF) receptors.

Cancer antigens are antigens that are expressed as cells become malignant, and they are also called tumor-specific antigens. Abnormal sugar chains that appear on cell surfaces or protein molecules when cells become cancerous are also cancer antigens, and they are also called sugar-chain cancer antigens. Examples of cancer antigens preferably include GPC3 which is a receptor belonging to the GPI anchor-type receptor family mentioned above, and is also expressed in several cancers including liver cancer (Int J Cancer. (2003) 103 (4): 455-65), as well as EpCAM which is expressed in several cancers including lung cancer (Proc Natl Acad Sci USA. (1989) 86 (1):27-31), CA19-9, CA15-3, and sialyl SSEA-1 (SLX).

MHC antigens are roughly classified into MHC class I antigens and MHC class II antigens. MHC class I antigens include HLA-A, -B, -C, -E, -F, -G, and -H, and MHC class II antigens include HLA-DR, -DQ, and -DP.

Differentiation antigens may include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Immunoglobulins include IgA, IgM, IgD, IgG, and IgE. Immune complexes include a component of at least any of the immunoglobulins.

Other antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Axl, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3(C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), PGF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, S100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEM5, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaRIIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alpha-beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TLIA/VEGI), TNFSF18 (GITR ligand AITR ligand, TL6), TNFSFIA (TNF-α Conectin, DIF, TNFSF2), TNFSFIB (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, A, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and SiP; and receptors for hormone and growth factors.

One or more amino acid residue alterations are allowed in the amino acid sequences constituting the variable regions as long as their antigen-binding activities are maintained. When altering a variable region amino acid sequence, there is no particularly limitation on the site of alteration and number of amino acids altered. For example, amino acids present in CDR and/or FR can be altered appropriately. When altering amino acids in a variable region, the binding activity is preferably maintained without particular limitation; and for example, as compared to before alteration, the binding activity is 50% or more, preferably 80% or more, and more preferably 100% or more. Furthermore, the binding activity may be increased by amino acid alterations. For example, the binding activity may be 2-, 5-, 10-times higher or such than that before alteration. In the antibodies of the present invention, alteration of amino acid sequence may be at least one of amino acid residue substitution, addition, deletion, and modification.

For example, the modification of the N-terminal glutamine of a variable region into pyroglutamic acid by pyroglutamylation is a modification well known to those skilled in the art. Thus, when the heavy-chain N terminus is glutamine, the antibodies of the present invention comprise the variable regions in which the glutamine is modified to pyroglutamic acid.

Antibody variable regions of the present invention may have any sequences, and they may be antibody variable regions of any origin, such as mouse antibodies, rat antibodies, rabbit antibodies, goat antibodies, camel antibodies, humanized antibodies produced by humanizing these non-human antibodies, and human antibodies. "Humanized antibodies", also referred to as "reshaped human antibodies", are antibodies in which the complementarity determining regions (CDRs) of an antibody derived from a non-human mammal, for example, a mouse antibody, are transplanted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342: 877). Their common genetic recombination techniques are also known (see, European Patent Application Publication No. EP 125023 and WO 96/02576). Furthermore, these antibodies may have various amino acid substitutions introduced into their variable regions to improve their antigen binding, pharmacokinetics, stability, and immunogenicity. Variable regions of the antibodies of the present invention may be able to bind antigens repeatedly due to their pH dependability in antigen binding (WO 2009/125825).

κ chain and λ chain-type constant regions are present in antibody light-chain constant regions, but either one of the light chain constant regions is acceptable. Furthermore, light-chain constant regions of the present invention may be light-chain constant regions with amino acid alterations such as substitutions, deletions, additions, and/or insertions.

For example, for the heavy chain constant regions of an antibody of the present invention, heavy chain constant regions of human IgG antibodies may be used and heavy chain constant regions of human IgG1 antibodies and those of human IgG4 antibodies are preferred.

Furthermore, Fc region variants of the present invention may be made into Fc fusion protein molecules by linking to other proteins, physiologically active peptides, and such. Herein, fusion protein refers to a chimeric polypeptide comprising at least two different polypeptides, which do not spontaneously link with each other in natural. Examples of the other proteins and biologically active peptides include receptors, adhesion molecules, ligands, and enzymes, but are not limited thereto.

Preferred examples of Fc fusion protein molecules of the present invention include proteins with Fc region fused to a receptor protein that binds to a target, and such examples include TNFR-Fc fusion protein, ILIR-Fc fusion protein, VEGFR-Fc fusion protein, and CTLA4-Fc fusion protein (Nat Med. 2003 January; 9(1): 47-52; BioDrugs. 2006; 20(3): 151-60).

Furthermore, a protein to be fused to a polypeptide of the present invention may be any molecule as long as it binds to a target molecule, and examples include scFv molecules (WO 2005/037989), single-domain antibody molecules (WO 2004/058821; WO 2003/002609), antibody-like molecules (Current Opinion in Biotechnology 2006, 17: 653-658; Current Opinion in Biotechnology 2007, 18: 1-10; Current Opinion in Structural Biology 1997, 7: 463-469; and Protein Science 2006, 15: 14-27) such as DARPins (WO 2002/020565), Affibody (WO 1995/001937), Avimer (WO 2004/044011; WO 2005/040229), and Adnectin (WO 2002/032925). Furthermore, antibodies and Fc fusion protein molecules may be multispecific antibodies that bind to multiple types of target molecules or epitopes.

Furthermore, the antibodies of the present invention include antibody modification products. Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. "Bispecific antibody" refers to an antibody that has in a single molecule variable regions that recognize different epitopes. The epitopes may be present in a single molecule or in different molecules.

The polypeptides of the present invention can be prepared by the methods known to those skilled in the art. For example, the antibodies can be prepared by the methods described below, but the methods are not limited thereto.

A DNA encoding an antibody heavy chain in which one or more amino acid residues in the Fc region have been substituted with other amino acids of interest and DNA encoding an antibody light chain, are expressed. A DNA encoding a heavy chain in which one or more amino acid residues in the Fc region are substituted with other amino acids of interest can be prepared, for example, by obtaining a DNA encoding the Fc region of a natural heavy chain, and introducing an appropriate substitution so that a codon encoding a particular amino acid in the Fc region encodes another amino acid of interest.

Alternatively, a DNA encoding a heavy chain in which one or more amino acid residues in the Fc region are substituted with other amino acids of interest can also be prepared by designing and then chemically synthesizing a DNA encoding a protein in which one or more amino acid residues in the Fc region of the natural heavy chain are substituted with other amino acids of interest. The position and type of amino acid substitution are not particularly limited. Furthermore, alteration is not limited to substitution, and alteration may be any of deletion, addition, or insertion, or combination thereof.

Alternatively, a DNA encoding a heavy chain in which one or more amino acid residues in the Fc region are substituted with other amino acids of interest can be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc region, but are not limited thereto. Furthermore, a DNA encoding a light chain can similarly be prepared as a combination of partial DNAs.

Methods for expressing the above-described DNAs include the methods described below. For example, a heavy chain expression vector is constructed by inserting a DNA encoding a heavy chain variable region into an expression vector along with a DNA encoding a heavy chain constant region. Likewise, a light chain expression vector is constructed by inserting a DNA encoding a light chain variable region into an expression vector along with a DNA encoding a light chain constant region. Alternatively, these heavy and light chain genes may be inserted into a single vector.

When inserting a DNA encoding the antibody of interest into an expression vector, the DNA is inserted so that the antibody is expressed under the control of an expression-regulating region such as an enhancer or promoter. Next, host cells are transformed with this expression vector to express the antibody. In such cases, an appropriate combination of host and expression vector may be used.

Examples of the vectors include M13 vectors, pUC vectors, pBR322, pBluescript, and pPCR-Script. Alternatively, when aiming to subclone and excise cDNA, in addition to the vectors described above, pGEM-T, pDIRECT, pT7, and such can be used.

Expression vectors are particularly useful when using vectors for producing the polypeptides of the present invention. For example, when a host cell is *E. coli* such as JM109, DH5a, HB101, and XL1-Blue, the expression vectors must carry a promoter that allows efficient expression in *E. coli*, for example, lacZ promoter (Ward et al., Nature (1989) 341: 544-546; FASEB J. (1992) 6: 2422-2427; its entirety are incorporated herein by reference), araB promoter (Better et al., Science (1988) 240: 1041-1043; its entirety are incorporated herein by reference), T7 promoter, or such. Such vectors include pGEX-5X-1 (Pharmacia), "QIAexpress system" (QIAGEN), pEGFP, or pET (in this case, the host is preferably BL21 that expresses T7 RNA polymerase) in addition to the vectors described above.

The vectors may contain signal sequences for polypeptide secretion. As a signal sequence for polypeptide secretion, a pelB signal sequence (Lei, S. P. et al J. Bacteriol. (1987) 169: 4379; its entirety are incorporated herein by reference) may be used when a polypeptide is secreted into the *E. coli* periplasm. The vector can be introduced into host cells by lipofectin method, calcium phosphate method, and DEAE-Dextran method, for example.

In addition to *E. coli* expression vectors, the vectors for producing the polypeptides of the present invention include mammalian expression vectors (for example, pcDNA3 (Invitrogen), pEGF-BOS (Nucleic Acids. Res. 1990, 18(17): p5322; its entirety are incorporated herein by reference), pEF, and pCDM8), insect cell-derived expression vectors (for example, the "Bac-to-BAC baculovirus expression system" (GIBCO-BRL) and pBacPAK8), plant-derived expression vectors (for example, pMH1 and pMH2), animal virus-derived expression vectors (for example, pHSV, pMV, and pAdexLcw), retroviral expression vectors (for example, pZIPneo), yeast expression vectors (for example, "*Pichia* Expression Kit" (Invitrogen), pNV11, and SP-QO1), and *Bacillus subtilis* expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277: 108; its entirety are incorporated herein by reference), MMTV-LTR promoter, EF1α promoter (Mizushima et al., Nucleic Acids Res. (1990) 18: 5322; its entirety are incorporated herein by reference), CAG promoter (Gene. (1990) 18: 5322; its entirety are incorporated herein by reference), and CMV promoter, and more preferably they have a gene for selecting transformed cells (for example, a drug resistance gene that allows evaluation using an agent (neomycin, G418, or such)). Vectors with such characteristics include pMAM, pDR2, pBK-RSV, pBK-CMV, pOPRSV, and pOP13, for example.

In addition, the following method can be used for stable gene expression and gene copy number amplification in cells: CHO cells deficient in a nucleic acid synthesis pathway are introduced with a vector that carries a DHFR gene which compensates for the deficiency (for example, pCHOI), and the vector is amplified using methotrexate (MTX). Alternatively, the following method can be used for transient gene expression: COS cells with a gene expressing SV40 T antigen on their chromosome are transformed with a vector with an SV40 replication origin (pcD and such). Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

Antibodies can be collected, for example, by culturing transformed cells, and then separating the antibodies from the inside of the transformed cells or from the culture media. Antibodies can be separated and purified using an appropriate combination of methods such as centrifugation, ammonium sulfate fractionation, salting out, ultrafiltration, lq, FcRn, protein A, protein G column, affinity chromatography, ion exchange chromatography, and gel filtration chromatography.

Furthermore, the present invention provides methods for producing a polypeptide comprising an antibody Fc region variant having enhanced FcγRIIb-binding activity in comparison with a polypeptide comprising a parent Fc region, which comprises adding at least one amino acid alteration to the Fc region variant.

Examples include production methods comprising the following steps:
(a) adding at least one amino acid alteration to an Fc region of polypeptides comprising the Fc region;
(b) measuring the FcγRIIb-binding activity of the polypeptides altered in step (a); and
(c) selecting polypeptides comprising an Fc region variant having enhanced FcγRIIb-binding activity in comparison with a polypeptide comprising a parent Fc region.

A preferred embodiment is a method for producing a polypeptide comprising an Fc region variant, which comprises the steps of:
(a) altering a nucleic acid encoding the polypeptide so that the FcγRIIb-binding activity is enhanced in comparison with the polypeptide comprising a parent Fc region;
(b) introducing the nucleic acid into host cells and culturing them to induce expression; and
(c) collecting the polypeptide from the host cell culture.

Furthermore, antibodies and Fc fusion protein molecules produced by this production method are also included in the present invention.

The present invention also provides a method of producing a polypeptide which comprises an Fc region variant with enhanced binding selectivity to FcγRIIb compared to FcγRIIa (type R) as compared to that of a polypeptide which comprises a parent Fc region, wherein the method comprises adding at least one amino acid alteration to an antibody Fc region variant in a polypeptide comprising the Fc region variant.

An example is a production method comprising the steps of:
(a) adding at least one amino acid alteration to an Fc region in a polypeptide comprising the Fc region;
(b) determining the FcγRIIa-binding activity and FcγRIIb-binding activity of the polypeptide altered in step (a); and
(c) selecting a polypeptide comprising an Fc region variant with enhanced binding selectivity to FcγRIIb compared to FcγRIIa (type R) as compared to that of a polypeptide comprising a parent Fc region.

In a preferred embodiment, it is a method of producing polypeptides comprising an Fc region variant, wherein the method comprises the steps of:
(a) modifying a nucleic acid encoding a polypeptide comprising a parent Fc region to achieve enhancement of binding selectivity to FcγRIIb compared to FcγRIIa (type R) as compared to that of the polypeptide;
(b) transfecting the nucleic acid into a host cell and culturing the cell for expression of the nucleic acid; and
(c) collecting the polypeptide from the host cell culture.

Antibodies and Fc fusion protein molecules produced by the production method are also included in the present invention.

Furthermore, the present invention provides a method of producing a polypeptide comprising an Fc region variant with enhanced FcγRIIb-binding activity and enhanced binding selectivity to FcγRIIb compared to FcγRIIa (type R) as compared to those of a polypeptide comprising a parent Fc region, wherein the method comprises adding at least one amino acid alteration to an antibody Fc region variant in a polypeptide comprising the antibody Fc region variant.

An example is a production method comprising the steps of:
(a) adding at least one amino acid alteration to an Fc region in a polypeptide comprising the Fc region;
(b) determining the FcγRIIa-binding activity and FcγRIIb-binding activity of the polypeptide altered in step (a); and
(c) selecting a polypeptide comprising an Fc region variant with enhanced FcγRIIb-binding activity and enhanced binding selectivity to FcγRIIb compared to FcγRIIa (type R) as compared to those of a polypeptide comprising a parent Fc region.

In a preferred embodiment, it is a method of producing polypeptides comprising an Fc region variant, wherein the method comprises the steps of:
(a) modifying nucleic acid encoding a polypeptide comprising a parent Fc region to achieve enhancement of FcγRIIb-binding activity and enhancement of binding selectivity to FcγRIIb compared to FcγRIIa (type R) as compared to those of the polypeptide;
(b) transfecting the nucleic acid into a host cell and culturing the cell for expression of the nucleic acid; and
(c) collecting the polypeptide from the host cell culture.

Antibodies and Fc fusion protein molecules produced by the production method are also included in the present invention.

The present invention also provides methods for producing a polypeptide in which antibody production against the polypeptide is suppressed compared with a polypeptide comprising a parent Fc region when administered in vivo, which comprise adding at least one amino acid alteration in the Fc region of a polypeptide comprising an antibody Fc region.

Examples include a production method comprising the following steps:
(a) adding at least one amino acid alteration in the Fc region of a polypeptide comprising an Fc region; and
(b) confirming that antibody production is suppressed when the polypeptide comprising an Fc region altered in step (a) is administered in vivo in comparison with a polypeptide comprising a parent Fc region.

Whether or not production of antibodies against the polypeptide has been suppressed can be confirmed by methods of administering the polypeptide to an animal and such.

Alternatively, suppression of antibody production can be determined by measuring the binding activities towards FcγRIIa and FcγRIIb, and observing an increase in the value obtained by dividing the KD value for FcγRIIa by the KD value for FcγRIIb. Such polypeptides are considered to be useful as pharmaceuticals since they can suppress antibody production without activating activating FcγR.

In the above-mentioned production methods, it is preferred that FcγRIIb-binding activity is enhanced and binding selectivity to FcγRIIb compared to FcγRIIa (type R) is enhanced.

An example of a preferred embodiment of the above-mentioned production method is altering an Fc region of human IgG so that alteration of the amino acid at position 238 (EU numbering) to another amino acid and alteration of at least one amino acid selected from amino acids at positions 233, 234, 235, 237, 264, 265, 266, 267, 268, 269, 271, 272, 274, 296, 326, 327, 330, 331, 332, 333, 334, 355, 356, 358, 396, 409, and 419 according to EU numbering to another amino acid are introduced into the Fc region. Other amino acid alterations that are combined with the amino acid alteration at position 238 (EU numbering) are preferably those at amino acid positions 233, 237, 264, 267, 268, 271, 272, 296, 327, 330, 332, 333, and 396 according to EU numbering, and in particular those at amino acid positions 233, 237, 264, 267, 268, 271, 296, 330, and 396. In particular, a preferred combination of amino acid alterations in terms of enhancement of FcγRIIb-binding activity or enhancement of binding selectivity to FcγRIIb compared to FcγRIIa includes, for example, the combination of amino acid alterations at amino acid positions 238, 268, and 271 (EU numbering) with at least one amino acid alteration selected from positions 233, 237, 264, 267, 272, 296, 327, 330, 332, and 396 (EU numbering).

The amino acids to be altered are not particularly limited as long as those enhance FcγRIIb-binding activity or enhance binding selectivity to FcγRIIb compared to FcγRIIa as compared to before the alteration, but preferably, the amino acid at position 238 is Asp, the amino acid at position 233 is Asp, the amino acid at position 234 is Tyr, the amino acid at position 237 is Asp, the amino acid at position 264 is Ile, the amino acid at position 265 is Glu, the amino acid at position 266 is Phe, Leu or Met, the amino acid at position 267 is Ala, Glu, Gly, or Gln, the amino acid at position 268 is Asp, Gln, or Glu, the amino acid at position 269 is Asp, the amino acid at position 271 is Gly, the amino acid at position 272 is Asp, Phe, Ile, Met, Asn, Pro, or Gln, the amino acid at position 274 is Gln, the amino acid at position 296 is Asp or Phe, the amino acid at position 326 is Ala or Asp, the amino acid at position 327 is Gly, the amino acid at position 330 is Lys, Arg, or Ser, the amino acid at position 331 is Ser, the amino acid at position 332 is Lys, Arg, Ser, or Thr, the amino acid at position 333 is Lys, Arg, Ser, or Thr, the amino acid at position 334 is Arg, Ser, or Thr, the amino acid at position 355 is Ala or Gln, the amino acid at position 356 is Glu, the amino acid at position 358 is Met, the amino acid at position 396 is Ala, Asp, Glu, Phe, Gly, His, Ile, Lys, Leu, Met, Asn, Gln, Arg, Ser, Thr, Val, Trp, or Tyr, the amino acid at position 409 is Arg, and the amino acid at position 419 is Glu. The amino acids to be altered are more preferably those that enhance FcγRIIb-binding activity and also enhance binding selectivity to FcγRIIb compared to FcγRIIa as compared to before the alteration. In particular, when combining alterations at amino acid positions 238, 268, and 271 (EU numbering) with at least one amino acid position selected from 233, 264, 267, 272, 296, 327, 330, 332, and 396 (EU numbering), it is preferred that the amino acid at position 238 is Asp, the amino acid at position 268 is Asp or Glu, the amino acid at position 271 is Gly, the amino acid at position 233 is Asp, the amino acid at position 237 is Asp, the amino acid at position 264 is Ile, the amino acid at position 267 is Ala or Gly, the amino acid at position 272 is Asp or Pro, the amino acid at position 296 is Asp, the amino acid at position 327 is Gly, the amino acid at position 330 is Arg, the amino acid at position 332 is Thr, and the amino acid at position 396 is Leu or Met, according to EU numbering.

Among these combinations, introducing alterations that lead to greater enhancement of FcγRIIb-binding activity, or lead to greater enhancement of binding selectivity to FcγRIIb compared to FcγRIIa (type R) are preferred. Examples of such a preferred combination of amino acid substitution as alterations include the following combinations (a) to (x):

(a) amino acid alterations at positions 238, 233, 237, 268, 271, 296, and 330 (EU numbering) of an Fc region;
(b) amino acid alterations at positions 238, 237, 268, 271, 296, and 330 (EU numbering) of an Fc region;
(c) amino acid alterations at positions 238, 233, 237, 268, 271, 296, 330, and 332 (EU numbering) of an Fc region;
(d) amino acid alterations at positions 238, 233, 237, 264, 267, 268, 271, and 330 (EU numbering) of an Fc region;
(e) amino acid alterations at positions 238, 233, 237, 267, 268, 271, 296, 330, and 332 (EU numbering) of an Fc region;
(f) amino acid alterations at positions 238, 237, 267, 268, 271, 296, 330, and 332 (EU numbering) of an Fc region;
(g) amino acid alterations at positions 238, 233, 237, 268, 271, 296, 327, and 330 (EU numbering) of an Fc region;
(h) amino acid alterations at positions 238, 233, 237, 264, 267, 268, and 271 (EU numbering) of an Fc region;
(i) amino acid alterations at positions 238, 233, 237, 264, 267, 268, 271, 296, and 330 (EU numbering) of an Fc region;
(j) amino acid alterations at positions 238, 233, 237, 264, 267, 268, 271, 296, 330, and 396 (EU numbering) of an Fc region;
(k) amino acid alterations at positions 238, 237, 264, 267, 268, 271, and 330 (EU numbering) of an Fc region;
(l) amino acid alterations at positions 238, 237, 264, 267, 268, 271, 296, and 330 (EU numbering) of an Fc region;
(m) amino acid alterations at positions 238, 264, 267, 268, and 271 (EU numbering) of an Fc region;
(n) amino acid alterations at positions 238, 264, 267, 268, 271, and 296 (EU numbering) of an Fc region;
(o) amino acid alterations at positions 238, 237, 267, 268, 271, 296, and 330 (EU numbering) of an Fc region;
(p) amino acid alterations at positions 238, 233, 237, 264, 267, 268, 271, 330, and 396 (EU numbering) of the Fe region;
(q) amino acid alterations at positions 238, 233, 237, 264, 267, 268, 271, 296, 327, 330, and 396 (EU numbering) of an Fc region;
(r) amino acid alterations at positions 238, 233, 237, 264, 267, 268, 271, 272, and 296 (EU numbering) of an Fc region;
(s) amino acid alterations at positions 238, 237, 264, 267, 268, 271, 272, and 330 (EU numbering) of an Fc region;
(t) amino acid alterations at positions 238, 237, 264, 267, 268, 271, 272, 296, and 330 (EU numbering) of an Fe region;
(u) amino acid alterations at positions 238, 233, 264, 267, 268, and 271 (EU numbering) of an Fe region;
(v) amino acid alterations at positions 238, 237, 267, 268, 271, 296, and 330 (EU numbering) of an Fc region;
(w) amino acid alterations at positions 238, 264, 267, 268, 271, 272, and 296 (EU numbering) of an Fc region; and
(x) amino acid alterations at positions 238, 233, 264, 267, 268, 271, and 296 (EU numbering) of an Fc region.

In addition, among these combinations, the following combinations of amino acid alterations (a) to (x) below are more preferred amino acid combinations:

(a) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, and the amino acid at position 330 is Arg, according to EU numbering, in an Fc region;
(b) an amino acid sequence in which the amino acid at position 238 is Asp, the amino acid at position 237 is Asp, the amino acid at position 268 is Asp or Glu, the amino acid at position 271 is Gly, the amino acid at position 296 is Asp, and the amino acid at position 330 is Arg, according to EU numbering, in an Fc region;
(c) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, the amino acid at position 330 is Arg, and the amino acid at position 332 is Thr, according to EU numbering, in an Fc region;
(d) an amino acid sequence in which the amino acid at position 238 is Asp, the amino acid at position 233 is Asp, the amino acid at position 237 is Asp, the amino acid at position 264 is Ile, the amino acid at position 267 is Gly or Ala, the amino acid at position 268 is Glu, the amino acid at position 271 is Gly, and the amino acid at position 330 is Arg, according to EU numbering, in an Fc region;
(e) an amino acid sequence in which the amino acid at position 238 is Asp, the amino acid at position 233 is Asp, the amino acid at position 237 is Asp, the amino acid at position 267 is Ala, the amino acid at position 268 is Glu, the amino acid at position 271 is Gly, the amino acid at position 296 is Asp, the amino acid at position 330 is Arg, and the amino acid at position 332 is Thr, according to EU numbering, in an Fc region;
(f) an amino acid sequence in which the amino acid at position 238 is Asp, the amino acid at position 237 is Asp, the amino acid at position 267 is Ala, the amino acid at position 268 is Glu, the amino acid at position 271 is Gly, the amino acid at position 296 is Asp, the amino acid at position 330 is Arg, and the amino acid at position 332 is Thr, according to EU numbering, in an Fc region;
(g) an amino acid sequence in which the amino acid at position 238 is Asp, the amino acid at position 233 is Asp, the amino acid at position 237 is Asp, the amino acid at position 268 is Asp, the amino acid at position 271 is Gly, the amino acid at position 296 is Asp, the amino acid at position 327 is Gly, and the amino acid at position 330 is Arg, according to EU numbering, in an Fc region;
(h) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, and the amino acid at position 271 is Gly, according to EU numbering, in an Fc region;
(i) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, and the amino acid at position 330 is Arg, according to EU numbering, in an Fc region;

(j) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, the amino acid at position 330 is Arg, and the amino acid at position 396 is Met or Leu, according to EU numbering, in the Fc region;

(k) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, and the amino acid at position 330 is Arg, according to EU numbering, in an Fc region;

(l) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, and the amino acid at position 330 is Arg, according to EU numbering, in an Fc region;

(m) an amino acid sequence in which the amino acid at position 238 is Asp, the amino acid at position 264 is Ile, the amino acid at position 267 is Ala, the amino acid at position 268 is Glu, and the amino acid at position 271 is Gly, according to EU numbering, in an Fc region; (n) an amino acid sequence in which the amino acid at position 238 is Asp, the amino acid at position 264 is Ile, the amino acid at position 267 is Ala, the amino acid at position 268 is Glu, the amino acid at position 271 is Gly, and the amino acid at position 296 is Asp, according to EU numbering, in an Fc region;

(o) an amino acid sequence in which the amino acid at position 238 is Asp, the amino acid at position 237 is Asp, the amino acid at position 267 is Ala or Gly, the amino acid at position 268 is Glu, the amino acid at position 271 is Gly, the amino acid at position 296 is Asp, and the amino acid at position 330 is Arg, according to EU numbering, in an Fc region;

(p) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 330 is Arg, and the amino acid at position 396 is Met or Leu, according to EU numbering, in an Fc region;

(q) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 296 is Asp, the amino acid at position 327 is Gly, the amino acid at position 330 is Arg, and the amino acid at position 396 is Met, according to EU numbering, in an Fc region;

(r) an amino acid sequence in which the amino acid at position 238 is Asp, the amino acid at position 233 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Asp, and the amino acid at position 296 is Asp, according to EU numbering, in an Fc region;

(s) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Pro, and the amino acid at position 330 is Arg, according to EU numbering, in an Fc region;

(t) an amino acid sequence in which the amino acid at position 238 is Asp, the amino acid at position 237 is Asp, the amino acid at position 264 is Ile, the amino acid at position 267 is Ala, the amino acid at position 268 is Glu, the amino acid at position 271 is Gly, the amino acid at position 272 is Pro, the amino acid at position 296 is Asp, and the amino acid at position 330 is Arg, according to EU numbering, in an Fc region;

(u) an amino acid sequence in which the amino acid at position 238 is Asp, the amino acid at position 233 is Asp, the amino acid at position 264 is Ile, the amino acid at position 267 is Ala, the amino acid at position 268 is Glu, and the amino acid at position 271 is Gly, according to EU numbering, in an Fc region;

(v) an amino acid sequence in which the amino acid at position 238 is Asp, the amino acid at position 237 is Asp, the amino acid at position 267 is Gly, the amino acid at position 268 is Asp, the amino acid at position 271 is Gly, the amino acid at position 296 is Asp, and the amino acid at position 330 is Arg, according to EU numbering, in an Fc region;

(w) an amino acid sequence in which the amino acid at position 238 is Asp, the amino acid at position 264 is Ile, the amino acid at position 267 is Ala, the amino acid at position 268 is Glu, the amino acid at position 271 is Gly, the amino acid at position 272 is Asp, and the amino acid at position 296 is Asp, according to EU numbering, in an Fc region; and (x) an amino acid sequence in which the amino acid at position 238 is Asp, the amino acid at position 233 is Asp, the amino acid at position 264 is Ile, the amino acid at position 267 is Ala, the amino acid at position 268 is Glu, the amino acid at position 271 is Gly, and the amino acid at position 296 is Asp, according to EU numbering, in an Fc region.

The present invention further provides a method of altering a polypeptide to produce a polypeptide with enhanced FcγRIIb-binding activity or enhanced binding selectivity to FcγRIIb compared to FcγRIIa (type R) as compared to those of a polypeptide containing a parent Fc region. The present invention also provides a method of altering a polypeptide to produce a polypeptide with enhanced FcγRIIb-binding activity and enhanced binding selectivity to FcγRIIb compared to FcγRIIa (type R) as compared to those of a polypeptide containing a parent Fc region.

The present invention also provides methods for altering a polypeptide for the production of a polypeptide whose antibody production is suppressed compared with that of a polypeptide comprising a parent Fc region when it is administered in vivo.

An example of a preferred embodiment includes the combination of amino acid alterations described in the method of producing polypeptides comprising Fc region variants with enhanced FcγRIIb-binding activity or enhanced binding selectivity to FcγRIIb compared to FcγRIIa (type R). An example of a more preferred embodiment includes the above-described combination of amino acid alterations described in the method of producing polypeptides comprising Fc region variants with enhanced FcγRIIb-binding activity and enhanced binding selectivity to FcγRIIb compared to FcγRIIa (type R).

Furthermore, the present invention provides a nucleic acid encoding a polypeptide comprising an Fc region having at least one amino acid alteration, wherein the polypeptide comprises an Fc region variant with enhanced FcγRIIb-binding activity or enhanced binding selectivity to FcγRIIb compared to FcγRIIa (type R) as compared to those of a polypeptide comprising a parent Fc region. The present invention also provides a nucleic acid encoding a polypeptide comprising an Fc region having at least one amino acid alteration, wherein the polypeptide comprises an Fc region variant with enhanced FcγRIIb-binding activity and enhanced binding selectivity to FcγRIIb compared to FcγRIIa (type R)-binding activity, as compared to those of a polypeptide comprising a parent Fc region. The nucleic acid of the present invention may be in any form such as DNA or RNA.

The present invention also provides vectors carrying the above-described nucleic acids of the present invention. The type of vector can be appropriately selected by those skilled in the art depending on the host cells to be introduced with the vector. The vectors include, for example, those described above.

Furthermore, the present invention relates to host cells transformed with the above-described vectors of the present invention. Appropriate host cells can be selected by those skilled in the art. The host cells include, for example, those described above. Specific examples include the following host cells.

When eukaryotic cells are used as host cells, animal cells, plant cells, or fungal cells can be appropriately used. Specifically, the animal cells include, for example, the following cells.
(1) mammalian cells: CHO (Chinese hamster ovary cell line), COS (Monkey kidney cell line), myeloma (Sp2/O, NS0, and such), BHK (baby hamster kidney cell line), Hela, Vero, HEK293 (human embryonic kidney cell line with sheared adenovirus (Ad)5 DNA), FreeStyle293™ cell line, PER.C6 cell (human embryonic retinal cell line transformed with the Adenovirus Type 5 (Ad5) E1A and E1B genes), and such (Current Protocols in Protein Science (May, 2001, Unit 5.9, Table 5.9.1));
(2) amphibian cells: *Xenopus oocytes*, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:
yeasts: the *Saccharomyces* genus such as *Saccharomyces serevisiae*, and the *Pichia* genus such as *Pichia pastoris*; and
filamentous fungi: the *Aspergillus* genus such as *Aspergillus niger*.

Furthermore, the present invention provides a method of enhancing FcγRIIb-binding activity and/or enhancing binding selectivity to FcγRIIb compared to FcγRIIa (type R)-binding activity, as compared to those of a polypeptide comprising a parent Fc region, wherein the method comprises adding at least one amino acid alteration to the Fc region in an Fc region-comprising polypeptide.

The present invention also provides methods for suppressing production of antibodies against a polypeptide comprising an Fc region, as compared with a polypeptide comprising a parent Fc region, when the polypeptide is administered in vivo, wherein the method comprises adding at least one amino acid alteration in the Fc region of the polypeptide.

An example of a preferred embodiment is the combination of amino acid alterations described in the method of producing polypeptides comprising Fc region variants with enhanced FcγRIIb-binding activity and/or enhanced binding selectivity to FcγRIIb compared to FcγRIIa (type R).

Polypeptides produced by any of the above-mentioned methods are also included in the present invention.

The present invention provides pharmaceutical compositions comprising the polypeptide comprising an Fc region variant of the present invention.

The pharmaceutical compositions of the present invention can be formulated, in addition to the antibody or Fc-fusion protein molecules of the present invention described above, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies or Fc-fusion protein molecules with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dosage of the pharmaceutical composition containing an antibody or a polynucleotide encoding an antibody can be selected, for example, from the range of 0.0001 mg to 1000 mg per kg of body weight. Alternatively, the dosage may be, for example, in the range of 0.001 to 100000 mg/patient. However, the dosage is not limited to these values. The dosage and method of administration vary depending on the patient's body weight, age, and symptoms, and can be appropriately selected by those skilled in the art.

The above-mentioned polypeptides comprising an Fc region variant of the present invention are useful as active ingredients of pharmaceutical agents that suppress the activation of B cells, mast cells, dendritic cells, and/or basophils. Polypeptides comprising an Fc region variant of the present invention can suppress the activation of B cells, mast cells, dendritic cells, and/or basophils, by selectively working on FcγRIIb without activating activating FcγR. B cell activation includes proliferation, IgE production, IgM production, and IgA production. The above-mentioned polypeptides comprising an Fc region variant of the present invention cross-link FcγRIIb with IgE to suppress IgE production of B cells, with IgM to suppress IgM production of B cells, and with IgA to suppress IgA production. Other than the above, suppressive effects similar to those mentioned above are exhibited by directly or indirectly cross-linking FcγRIIb with molecules that are expressed on B cells and comprise the ITAM domain inside the cell or interact with the ITAM domain such as BCR, CD19, and CD79b. Furthermore, activation of mast cells includes proliferation, activation by IgE and such, and degranulation. In mast cells, the above-mentioned polypeptides comprising an Fc region variant of the present invention can suppress proliferation, activation by IgE and such, and degranulation by directly or indirectly cross-linking FcγRIIb with IgE receptor molecules that are expressed on mast cells and comprise the ITAM domain or interact with the ITAM domain such as FcεRI, DAP12, and CD200R3. Activation of basophils includes proliferation and degranulation of basophils. Also in basophils, the above-mentioned polypeptides comprising an Fc region variant of the present invention can suppress proliferation, activation, and degranulation by directly or indirectly cross-linking FcγRIIb with molecules on the cell membrane, which comprise the ITAM domain inside the cell or interact with the ITAM domain. Activation of dendritic cells includes proliferation and degranulation of dendritic cells. Also in dendritic cells, the above-mentioned polypeptides comprising an Fc region variant of the present invention can suppress activation, degranulation, and proliferation by directly or indirectly cross-linking FcγRIIb with molecules on the cell membrane, which comprise the ITAM domain inside the cell or interact with the ITAM domain.

In the present invention, the polypeptides comprising an Fc region variant of the present invention mentioned above are useful as an active ingredient of therapeutic agents or preventive agents for immunological inflammatory diseases. As described above, since polypeptides comprising an Fc region variant of the present invention can suppress activation of B cells, mast cells, dendritic cells and/or basophils, administration of the polypeptides comprising an Fc region variant of the present invention as a result can treat or prevent immunological inflammatory diseases. Without being limited thereto, the term "immunological inflammatory diseases" comprises, rheumatoid arthritis, autoimmune hepatitis, autoimmune thyroiditis, autoimmune blistering diseases, autoimmune adrenocortical disease, autoimmune hemolytic anemia, autoimmune thrombocytopenic purpura, megalocytic anemia, autoimmune atrophic gastritis, autoimmune neutropenia, autoimmune orchitis, autoimmune encephalomyelitis, autoimmune receptor disease, autoimmune infertility, chronic active hepatitis, glomerulonephritis, interstitial pulmonary fibrosis, multiple sclerosis, Paget's disease, osteoporosis, multiple myeloma, uveitis, acute and chronic spondylitis, gouty arthritis, inflammatory bowel disease, adult respiratory distress syndrome (ARDS), psoriasis, Crohn's disease, Basedow's disease, juvenile diabetes, Addison's disease, myasthenia gravis, lens-induced uveitis, systemic lupus erythematosus, allergic rhinitis, allergic dermatitis, ulcerative colitis, hypersensitivity, muscle degeneration, cachexia, systemic scleroderma, localized scleroderma, Sjogren's syndrome, Behchet's disease, Reiter's syndrome, type I and type II diabetes, bone resorption disorder, graft-versus-host reaction, ischemia-reperfusion injury, atherosclerosis, brain trauma, cerebral malaria, sepsis, septic shock, toxic shock syndrome, fever, malgias due to staining, aplastic anemia, hemolytic anemia, idiopathic thrombocytopenia, Goodpasture's syndrome, Guillain-Barre syndrome, Hashimoto's thyroiditis, pemphigus, IgA nephropathy, pollinosis, antiphospholipid antibody syndrome, polymyositis, Wegener's granulomatosis, arteritis nodosa, mixed connective tissue disease, fibromyalgia, asthma, atopic dermatitis, chronic atrophic gastritis, primary biliary cirrhosis, primary sclerosing cholangitis, autoimmune pancreatitis, aortitis syndrome, rapidly progressive glomerulonephritis, megaloblastic anemia, idiopathic thrombocytopenic purpura, primary hypothyroidism, idiopathic Addison's disease, insulin-dependent diabetes mellitus, chronic discoid lupus erythematosus, pemphigoid, herpes gestationis, linear IgA bullous dermatosis, epidermolysis bullosa acquisita, alopecia areata, vitiligo vulgaris, leukoderma acquisitum centrifugum of Sutton, Harada's disease, autoimmune optic neuropathy, idiopathic azoospermia, habitual abortion, hypoglycemia, chronic urticaria, ankylosing spondylitis, psoriatic arthritis, enteropathic arthritis, reactive arthritis, spondyloarthropathy, enthesopathy, irritable bowel syndrome, chronic fatigue syndrome, dermatomyositis, inclusion body myositis, Schmidt's syndrome, Graves' disease, pernicious anemia, lupoid hepatitis, presenile dementia, Alzheimer's disease, demyelinating disorder, amyotrophic lateral sclerosis, hypoparathyroidism, Dressier's syndrome, Eaton-Lambert syndrome, dermatitis herpetiformis, alopecia, progressive systemic sclerosis, CREST syndrome (calcinosis, Raynaud's phenomenon, esophageal dysmotility, sclerodactyly, and telangiectasia), sarcoidosis, rheumatic fever, erythema multiforme, Cushing's syndrome, transfusion reaction, Hansen's disease, Takayasu arteritis, polymyalgia rheumatica, temporal arteritis, giant cell arthritis, eczema, lymphomatoid granulomatosis, Kawasaki disease, endocarditis, endomyocardial fibrosis, endophthalmitis, fetal erythroblastosis, eosinophilic fasciitis, Felty syndrome, Henoch-Schonlein purpura, transplant rejection, mumps, cardiomyopathy, purulent arthritis, familial Mediterranean fever, Muckle-Wells syndrome, and hyper-IgD syndrome.

Furthermore, in autoimmune diseases which may be caused by production of antibodies against autoantigens (autoantibodies), the polypeptides comprising an Fc region variant of the present invention mentioned above are useful as an active ingredient of pharmaceutical agents for treating or preventing the autoimmune diseases by suppressing production of those autoantibodies. Use of a molecule produced by fusing an antibody Fc portion with AchR (an autoantigen of myasthenia gravis) has been reported to suppress proliferation of B cells which express AchR-recognizing BCR, and induce apoptosis (J. Neuroimmunol, 227: 35-43, 2010). Use of a fusion protein formed between an antigen recognized by an autoantibody and an antibody Fc region of the present invention enables crosslinking of FcγRIIb with BCR of a B cell expressing BCR for that autoantigen, suppression of proliferation of B cells expressing BCR for the autoantigen, and induction of apoptosis. Such autoimmune diseases include Guillain-Barre syndrome, myasthenia gravis, chronic atrophic gastritis, autoimmune hepatitis, primary biliary cirrhosis, primary sclerosing cholangitis, autoimmune pancreatitis, aortitis syndrome, Goodpasture's syndrome, rapidly progressive glomerulonephritis, megaloblastic anemia, autoimmune hemolytic anemia, autoimmune neutropenia, idiopathic thrombocytopenic purpura, Basedow's disease, Hashimoto's thyroiditis, primary hypothyroidism, idiopathic Addison's disease, insulin-dependent diabetes mellitus, chronic discoid lupus erythematosus, localized scleroderma, pemphigus, pemphigoid, herpes gestationis, linear IgA bullous dermatosis, epidermolysis bullosa acquisita, alopecia areata, vitiligo vulgaris, leukoderma acquisitum centrifugum of Sutton, Harada's disease, autoimmune optic neuropathy, idiopathic azoospermia, habitual abortion, type II diabetes, hypoglycemia, and chronic urticaria; but are not limited thereto.

Furthermore, the above-mentioned polypeptides comprising an Fc Region variant of the present invention are useful as an active ingredient in therapeutic agents for diseases with deficiency of a biologically essential protein. For diseases with deficiency of a biologically essential protein, therapeutic methods that administer and supplement the protein as a pharmaceutical agent are used. However, since the patient lacks the protein from the beginning, the externally supplemented protein is recognized as a foreign substance and antibodies against that protein are produced. As a result, the protein becomes easily removed, and the effect as a pharmaceutical is reduced. Use of a fusion protein comprising such a protein and an antibody Fc region of the present invention enables crosslinking between FcγRIIb and BCR on B cells that recognize the protein, and enables suppression of antibody production against the protein. The proteins to be supplemented include Factor VIII, Factor IX, TPO, EPO, α-iduronidase, iduronate sulfatase, A-type heparan N-sulfatase, B type α-N-acetylglucosaminidase, C type acetyl CoA: α-glucosaminidase acetyltransferase, D type N-acetylglucosamine 6-sulfatase, galactose 6-sulfatase, N-acetylgalactosamine 4-sulfatase, β-glucuronidase, α-galactosidase, acidic α-galactosidase, and glucocerebrosidase. These proteins may be supplemented for diseases such as hemophilia, idiopathic thrombocytopenic purpura, renal anemia, and lysosomal disease (mucopolysaccharidosis, Fabry's disease, Pompe disease, and Gaucher's disease), without being limited thereto.

Furthermore, the above-mentioned polypeptides comprising an Fc region variant of the present invention are useful as an active ingredient for antiviral agents. Antibodies that comprise an Fc region of the present invention and are anti-virus antibodies can suppress antibody-dependent enhancement observed with anti-virus antibodies. Antibody-dependent enhancement is a phenomenon where a virus uses neutralizing antibodies against the virus to become phagocytosed via activating FcγRs, and infects FcγR-expressing cells so that the infection spreads. Binding of anti-dengue-virus neutralizing antibodies to FcγRIIb has been reported to play an important role in suppressing antibody-dependent enhancement (Proc. Natl. Acad. Sci. USA, 108: 12479-12484, 2011). Crosslinking FcγRIIb with an immune complex with dengue virus, which is formed by the anti-dengue-virus neutralizing antibodies, inhibits FcγR-mediated phagocytosis, resulting in the suppression of antibody-dependent enhancement. Examples of such viruses include dengue virus (DENV1, DENV2, and DENV4) and HIV, but are not limited thereto.

Furthermore, polypeptides comprising an Fc region variant of the present invention described above are useful as an active ingredient in preventive agents or therapeutic agents for arteriosclerosis. Antibodies against oxidized LDL, i.e., a cause for arteriosclerosis, which are antibodies comprising an Fc region of the present invention, can prevent FcγRIIa-dependent adhesion of inflammatory cells. It has been reported that while anti-oxidized LDL antibodies inhibit the interaction between oxidized LDL and CD36, anti-oxidized LDL antibodies bind to endothelial cells, and monocytes recognize their Fc portion in an FcγRIIa-dependent or FcγRI-dependent manner; and this leads to adhesion (Immunol. Lett., 108: 52-61, 2007). Using antibodies comprising an Fc region of the present invention for such antibodies may inhibit FcγRIIa-dependent binding and suppress monocyte adhesion by FcγRIIb-mediated inhibitory signals.

In the present invention, polypeptides comprising an Fc region variant of the present invention described above are useful as an active ingredient in therapeutic agents or preventive agents for cancer. As described above, it is known that enhancing the FcγRIIb binding enhances the agonistic activity of an agonist antibody, and enhances the antitumor effect of the antibody. Therefore, agonist antibodies using the Fc region variant of the present invention are useful for treatment or prevention of cancer. Specifically, the Fc region variant of the present invention enhances the agonistic activity of agonist antibodies against, for example, receptors of the TNF receptor family such as Aliases, CD120a, CD120b, Lymphotoxin β receptor, CD134, CD40, FAS, TNFRSF6B, CD27, CD30, CD137, TNFRSF10A, TNFRSF10B, TNFRSF10C, TNFRSF10D, RANK, Osteoprotegerin, TNFRSF12A, TNFRSF13B, TNFRSF13C, TNFRSF14, Nerve growth factor receptor, TNFRSF17, TNFRSF18, TNFRSF19, TNFRSF21, TNFRSF25, and Ectodysplasin A2 receptor and can be used for treating or preventing cancer. Furthermore, in addition to the above, agonistic activity is also enhanced for agonist antibodies against molecules which need to interact with FcγRIIb for exhibiting its agonistic activity. In addition, by incorporating the Fc region variant of the present invention into a polypeptide having binding activity to a molecule such as Kit, a type of receptor tyrosine kinase (RTK), which suppresses cell proliferation upon crosslinking with FcγRIIb, inhibitory effect against cells expressing such molecule may be enhanced. Without being limited thereto, cancer includes lung cancer (including small cell lung cancer, non-small cell lung cancer, pulmonary adenocarcinoma, and squamous cell carcinoma of the lung), large intestine cancer, rectal cancer, colon cancer, breast cancer, liver cancer, gastric cancer, pancreatic cancer, renal cancer, prostate cancer, ovarian cancer, thyroid cancer, cholangiocarcinoma, peritoneal cancer, mesothelioma, squamous cell carcinoma, cervical cancer, endometrial cancer, bladder cancer, esophageal cancer, head and neck cancer, nasopharyngeal cancer, salivary gland tumor, thymoma, skin cancer, basal cell tumor, malignant melanoma, anal cancer, penile cancer, testicular cancer, Wilms' tumor, acute myeloid leukemia (including acute myeloleukemia, acute myeloblastic leukemia, acute promyelocytic leukemia, acute myelomonocytic leukemia, and acute monocytic leukemia), chronic myelogenous leukemia, acute lymphoblastic leukemia, chronic lymphatic leukemia, Hodgkin's lymphoma, non-Hodgkin's lymphoma (Burkitt's lymphoma, chronic lymphocytic leukemia, mycosis fungoides, mantle cell lymphoma, follicular lymphoma, diffuse large-cell lymphoma, marginal zone lymphoma, pilocytic leukemia plasmacytoma, peripheral T-cell lymphoma, and adult T cell leukemia/lymphoma), Langerhans cell histiocytosis, multiple myeloma, myelodysplastic syndrome, brain tumor (including glioma, astroglioma, glioblastoma, meningioma, and ependymoma), neuroblastoma, retinoblastoma, osteosarcoma, Kaposi's sarcoma, Ewing's sarcoma, angiosarcoma, and hemangiopericytoma.

Furthermore, the present invention relates to methods for treating or preventing immunological inflammatory diseases, which comprise the step of administering to a subject (patient) a polypeptide comprising an Fc region variant of the present invention or a polypeptide comprising an Fc region variant produced by production methods of the present invention.

The present invention also provides kits for use in the therapeutic methods or preventive methods of the present invention, which comprises at least a polypeptide comprising an Fc region variant of the present invention or a polypeptide comprising an Fc region variant produced by production methods of the present invention, or a pharmaceutical composition of the present invention. In addition, pharmaceutically acceptable carriers, media, instructions on the method of use, and such may be included in the kit. Furthermore, the present invention relates to use of a polypeptide comprising an Fc region variant of the present invention or a polypeptide comprising an Fc region variant produced by production methods of the present invention in the production of agents for treating or preventing immunological inflammatory diseases. The present invention also relates to polypeptides comprising an Fc region variant of the present invention or polypeptides comprising an Fc region variant produced by production methods of the present invention for use in the therapeutic methods or preventive methods of the present invention.

As used herein, the three-letter and single-letter codes for respective amino acids are as follows:

Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

Herein below, the present invention will be specifically described further with reference to the Examples, but it is not to be construed as being limited thereto.

[Example 1] Assessment of Platelet Aggregation Ability of Existing Antibodies Comprising an Fc with Enhanced FcgRIIb-Binding As shown in Table 16 in Reference Example 4, an existing FcgRIIb enhancement technique which introduces alterations involving substitution of Glu for Ser at position 267 and substitution of Phe for Leu at position 328 (EU numbering) into native human IgG1 (Non-patent Document 28) shows 408-fold enhanced binding to FcgRIIb and 0.51-fold decreased binding to FcgRIIaH, while showing 522-fold enhanced binding to FcgRIIaR, as compared to those of IgG1. As described in "Background Art", even if FcgRIIb-binding is enhanced, when it comes to cells such as platelets which only express FcgRIIa, only enhancement effects on FcgRIIa may be affected. That is, existing techniques which enhance binding to FcgRIIaR have the danger of enhancing platelet-aggregating activity and increasing the risk for developing thrombosis. To confirm this, it was assessed whether platelet-aggregating activity is actually enhanced when FcgRIIa-binding of an antibody is enhanced.

Using the method of Reference Example 1, omalizumab_VH-G1d (SEQ ID NO: 25) was produced as the heavy chain and omalizumab_VL-CK (SEQ ID NO: 26) was produced as the light chain of a human IgG1 antibody that binds to IgE. Furthermore, to enhance human FcγRIIb-binding activity of omalizumab_VH-G1d, omalizumab_VH-G1d-v3 was produced by substituting Glu for Ser at position 267 and Phe for Leu at position 328 according to EU numbering in omalizumab_VH-G1d. Using the method of Reference Example 1, omalizumab-G1d-v3 which contains omalizumab_VH-G1d-v3 as the heavy chain and omalizumab_VL-CK as the light chain was produced. Platelet-aggregating ability was assessed using this antibody.

Platelet aggregation was assayed using the platelet aggregometer HEMA TRACER 712 (LMS Co.). First, about 50 ml of whole blood was collected at a fixed amount into 4.5-ml evacuated blood collection tubes containing 0.5 ml of 3.8% sodium citrate, and this was centrifuged at 200 g for 15 minutes. The resultant supernatant was collected and used as platelet-rich plasma (PRP). After PRP was washed with buffer 1 (137 mM NaCl, 2.7 mM KCl, 12 mM NaHCO$_3$, 0.42 mM NaH$_2$PO$_4$, 2 mM MgCl$_2$, 5 mM HEPES, 5.55 mM dextrose, 1.5 U/ml apyrase, 0.35% BSA), the buffer was replaced with buffer 2 (137 mM NaCl, 2.7 mM KCl, 12 mM NaHCO$_3$, 0.42 mM NaH$_2$PO$_4$, 2 mM MgCl$_2$, 5 mM HEPES, 5.55 mM dextrose, 2 mM CaCl$_2$, 0.35% BSA) to prepare about 300,000/μl washed platelets. 156 μl of the washed platelets was aliquoted into assay cuvettes containing a stir bar set in the platelet aggregometer.

The platelets were stirred at 1000 rpm with the stir bar in the cuvettes maintained at 37.0° C. in the platelet aggregometer. 44 μl of the immune complex of omalizumab-G1d-v3 and IgE at a molar ratio of 1:1 (prepared at final concentrations of 600 μg/ml and 686 μg/ml, respectively) was added to the cuvettes. The platelets were reacted with the immune complex for five minutes. Then, at a concentration that does not allow secondary platelet aggregation, adenosine diphosphate (ADP, SIGMA) was added to the reaction mixture to test whether the aggregation is enhanced.

Figure 1:
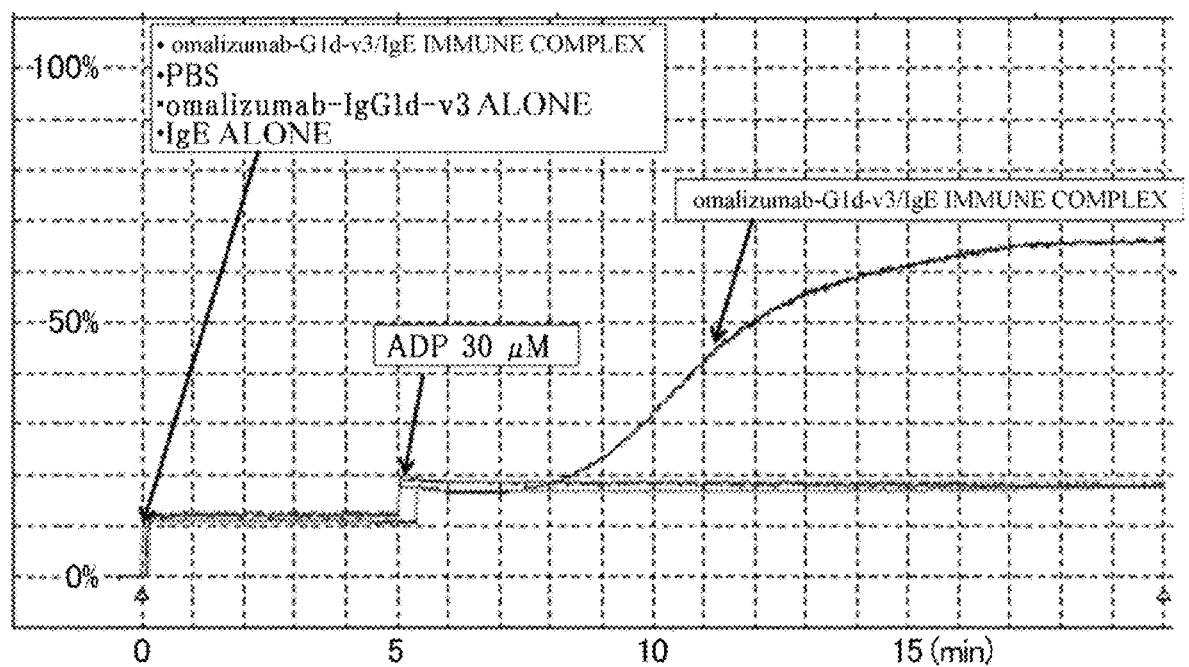
FIG. 1 is a graph showing the results of evaluating platelet aggregation due to the omalizumab-G1d-3/IgE immune complex in a platelet aggregation assay using platelets derived from a donor having FcγRIIa (R/H) polymorphism.
Figure 2:
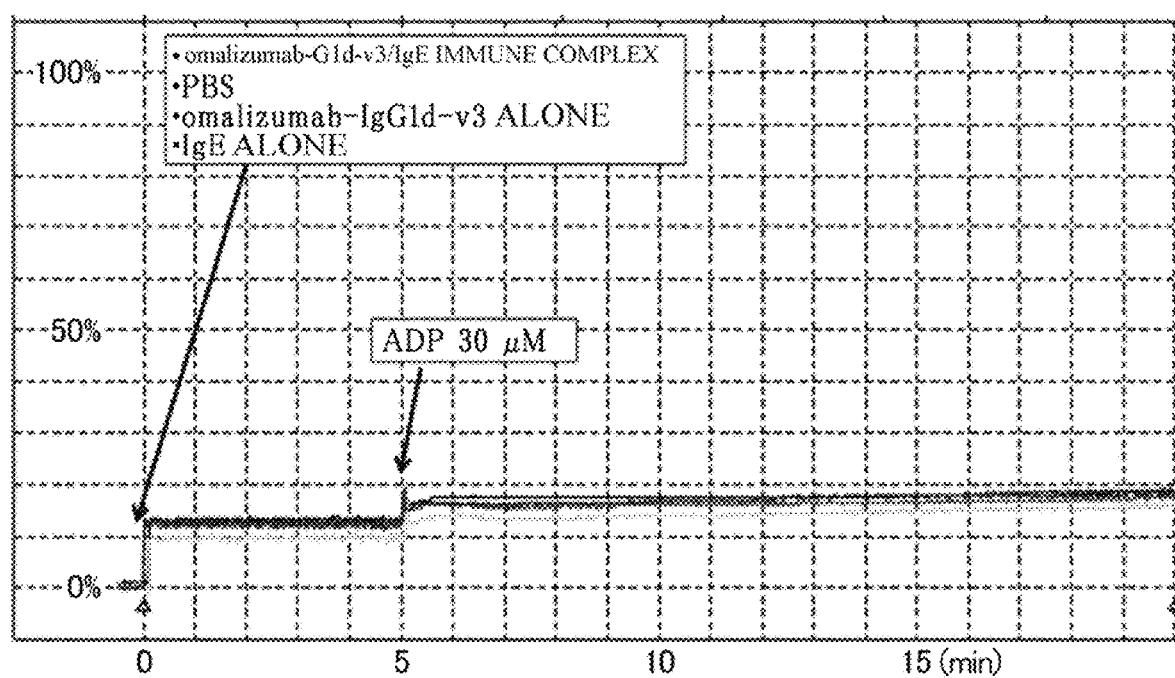
FIG. 2 is a graph showing the results of evaluating platelet aggregation due to the omalizumab-G1d-3/IgE immune complex in a platelet aggregation assay using platelets derived from a donor having FcγRIIa (H/H) polymorphism.

The result for each donor with an FcγRIIa polymorphic form (H/H or R/H) obtained from the above assay is shown in FIGS. 1 and 2. From the result in FIG. 1, it is shown that platelet aggregation was enhanced with the FcγRIIa polymorphic form (R/H) when the immune complex is added. Meanwhile, as shown in FIG. 2, platelet aggregation was not enhanced with the FcγRIIa polymorphic form (H/H).

Next, platelet activation was assessed using activation markers. Platelet activation can be measured based on the increased expression of an activation marker such as CD62p (p-selectin) or active integrin on the platelet membrane surface. 2.3 μl of the immune complex was added to 7.7 μl of the washed platelets prepared by the method described above. After five minutes of reaction at room temperature, activation was induced by adding ADP at a final concentration of 30 μM, and whether the immune complex enhances the ADP-dependent activation was assessed. A sample added with phosphate buffer (pH 7.4; Gibco), instead of the immune complex, was used as a negative control. Staining was performed by adding, to each post-reaction sample, PE-labeled anti-CD62 antibody (BECTON DICKINSON), PerCP-labeled anti-CD61 antibody, and FITC-labeled PAC-1 antibody (BD bioscience). Each of the fluorescence intensities was measured using a flow cytometer (FACS CantoII™ flow cytometer, BD bioscience).

Figure 3:
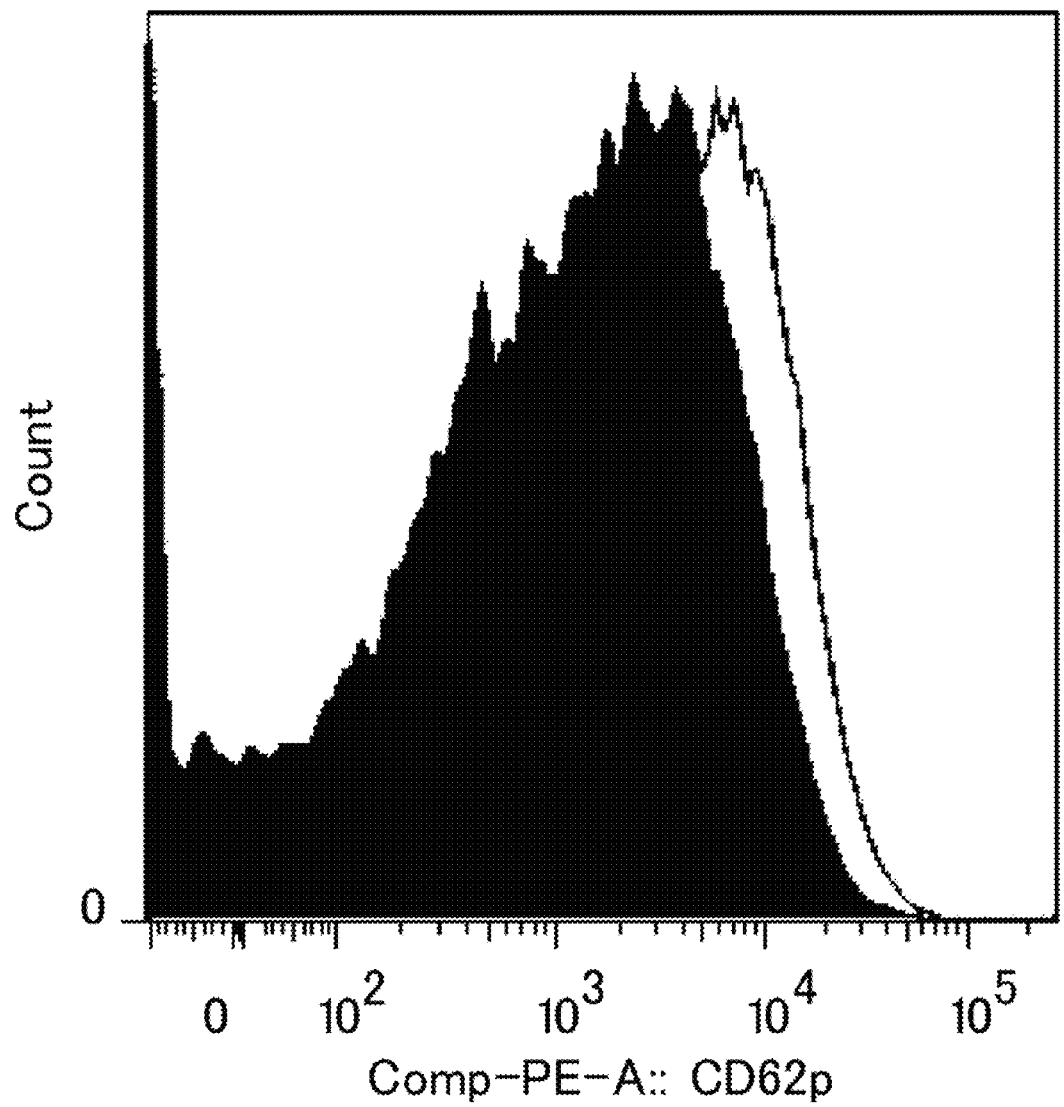
FIG. 3 is a graph showing the results of evaluating CD62p expression on a washed platelet membrane surface. The black-filled curve indicates the result obtained when reaction with PBS was followed by stimulation by ADP addition, and the unfilled curve indicates the result obtained when reaction with an immune complex was followed by stimulation with ADP.
Figure 4:
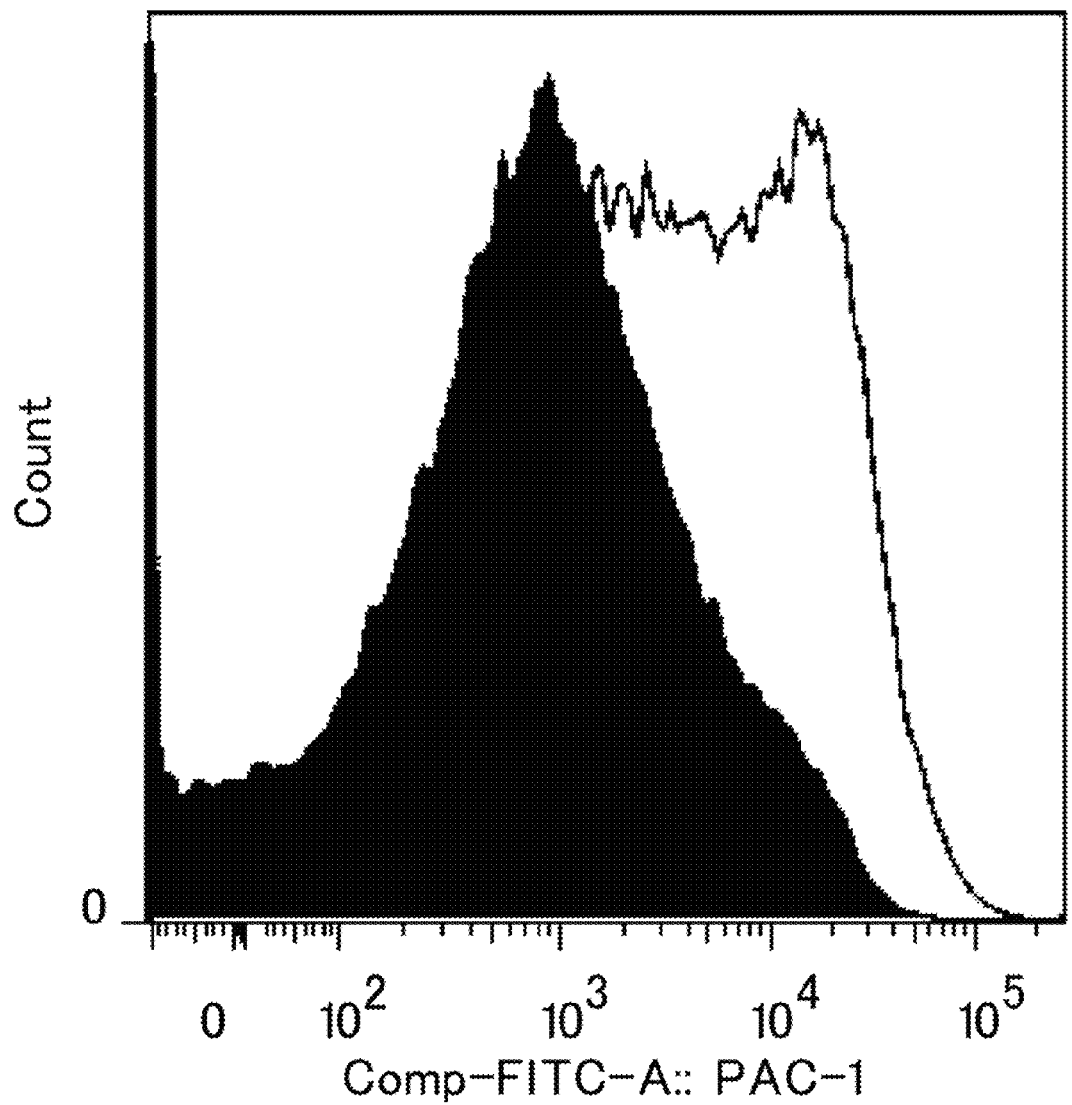
FIG. 4 is a graph showing the results of evaluating active integrin expression on a washed platelet membrane surface. The black-filled curve indicates the result obtained when reaction with PBS was followed by stimulation by ADP addition, and the unfilled curve indicates the result obtained when reaction with an immune complex was followed by stimulation with ADP.

The result on CD62p expression, obtained by the above assay method, is shown in FIG. 3. The result on the activated integrin expression is shown in FIG. 4. The washed platelets used were obtained from a healthy person with the FcγRIIa polymorphic form R/H. Both CD62p and active integrin expressed on platelet membrane surface, which is induced by ADP stimulation, was enhanced in the presence of the immune complex.

From these results, in existing antibodies having an Fc with enhanced human FcγRIIb-binding, which have an Fc produced by introducing substitution of Ser at position 267 with Glu and Leu at position 328 with Phe (EU numbering) into an IgG1 Fc, the genetic polymorphs of FcγRIIa whose amino acid at position 131 is R showed enhanced platelet-aggregating activity compared to when the amino acid at position 131 is H. That is, existing antibodies having an Fc with enhanced human FcγRIIb binding was suggested to have the danger of increasing the risk for developing thrombosis due to platelet aggregation in humans carrying FcγRIIa type R, elucidating the value of an Fc with enhanced selective binding to FcγRIIb that overcomes this problem.

[Example 2] Production of Variants with Enhanced Binding to FcgRIIb

As shown in Example 1, when enhancing binding to FcgRIIb, it is necessary to enhance FcgRIIb-binding while also suppressing binding to other activating FcgRs as much as possible. Therefore, production of variants with enhanced binding or selectivity to FcgRIIb was examined by combining alterations having the effect of enhancing binding or improving selectivity to FcgRIIb. Specifically, using as a base the P238D alteration, which shows excellent effects in both enhancement of binding and improvement of selectivity to FcgRIIb, alterations found to be effective upon combination with P238D in Reference Examples 6, 8, and 9 were further combined.

The variable region of IL6R-H (SEQ ID NO: 18), which is disclosed in WO2009/125825 and which is the variable region of an antibody against the human interleukin 6 receptor was produced as the antibody H chain variable region, and IL6R-G1d (SEQ ID NO: 19) which has G1d produced by removing the C-terminal Gly and Lys of human IgG1 was produced as the antibody H chain constant region. Furthermore, IL6R-B3 (SEQ ID NO: 23) was produced by introducing K439E into IL6R-G1d. Then, variants were produced from IL6R-B3 by combining E233D, L234Y, G237D, S267Q, H268D, P271G, Y296D, K326D, K326A, A330R, A330K, which are alterations found to be effective upon combination with P238D in Reference Examples 6, 8, and 9. IL6R-L (SEQ ID NO: 21) was commonly used as the antibody L chain.

These variants were used for antibody expression and purification according to the method of Reference Example 1, and binding to each FcgR (FcgRIa, FcgRIIa type H, FcgRIIa type R, FcgRIIb, and FcgRIIIa type V) were assessed by the method of Reference Example 2.

The KD values of each variant for each FcgR are shown in Table 1. "Alteration" in the Table refers to alterations introduced into IL6R-B3 (SEQ ID NO: 23). Meanwhile, IL6R-B3/IL6R-L which is used as a template for producing each of the variants is indicated by an asterisk (*). "KD(IIaR)/KD(IIb)" in the Table shows the value obtained by dividing the KD of each variant for FcgRIIaR by the KD of each variant for FcgRIIb. The greater this value is, the higher the selectivity to FcgRIIb is. "Parent polypeptide KD(Ib)/altered polypeptide KD(Ib)" refers to a value obtained by dividing the KD value of IL6R-B3/IL6R-L for FcgRIIb by the KD value of each variant for FcgRIIb. Furthermore, "parent polypeptide KD(IIaR)/altered polypeptide KD(IIaR)" refers to a value obtained by dividing the KD value of IL6R-B3/IL6R-L for FcgR IIaR by the KD value of that variant for FcgRIIaR. In Table 1, values shown in bold italicized font were calculated using the following equation $$KD = C \cdot R_{max}/(R_{eq} - RI) - C \quad \text{[Equation 2]}$$

described in Reference Example 2 since the binding of FcgR to IgG was determined to be too weak to analyze accurately by kinetic analysis.

TABLE 1

| VARIANT NAME | ALTERATION | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/KD(IIb) | KD(IIb) OF PARENT POLYPEPTIDE/ KD(IIb) OF ALTERED POLYPEPTIDE | KD(IIaR) OF PARENT POLYPEPTIDE/ KD(IIaR) OF ALTERED POLYPEPTIDE |
|---|---|---|---|---|---|---|---|---|---|
| IL6R-G1d/IL6R-L | | 3.2E-10 | 1.0E-06 | 6.7E-07 | 2.6E-06 | 3.5E-07 | 0.4 | 1.2 | 1.1 |
| IL6R-B3/IL6R-L | * | 4.2E-10 | 1.1E-06 | 7.7E-07 | 3.1E-06 | 3.3E-07 | 0.3 | 1.0 | 1.0 |
| IL6R-BF648/IL6R-L | P238D | 1.1E-08 | 1.5E-05 | *4.0E-05* | 1.2E-06 | *7.1E-05* | 12.5 | 2.6 | 0.1 |
| IL6R-BP215/ | G237D/P238D/H268D/ | 4.3E-08 | 1.3E-06 | *1.4E-05* | 4.1E-08 | *6.7E-05* | 31.7 | 75.6 | 0.8 |

TABLE 1-continued

| VARIANT NAME | ALTERATION | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIb) OF PARENT POLYPEPTIDE/ KD(IIb) OF ALTERED POLYPEPTIDE | KD(IIaR) OF PARENT POLYPEPTIDE/ KD(IIaR) OF ALTERED POLYPEPTIDE |
|---|---|---|---|---|---|---|---|---|---|
| IL6R-BP216/ IL6R-L | P271G/Y296D/A330K G237D/P238D/S267Q/ H268D/P271G/A330K | 6.2E−07 | 2.9E−06 | 2.6E-05 | 1.4E−07 | 5.3E−05 | 20.7 | 22.1 | 0.4 |
| IL6R-BP217/ IL6R-L | G237D/P238D/S267Q/ H268D/P271G/Y296D/ A330K | 2.8E−06 | 3.6E−06 | 2.8E-05 | 1.5E−07 | 6.0E−05 | 24.0 | 20.7 | 0.3 |
| IL6R-BP218/ IL6R-L | G237D/P238D/H268D/ P271G/K326D/A330K | 3.7E−08 | 1.5E−06 | 1.2E-05 | 7.6E−08 | 3.8E−05 | 19.7 | 40.8 | 0.7 |
| IL6R-BP219/ IL6R-L | L234Y/G237D/P238D/ H268D/P271G/A330K | 4.6E−08 | 6.1E−07 | 2.5E-06 | 3.4E−08 | 2.9E−05 | 17.9 | 91.2 | 1.8 |
| IL6R-BP220/ IL6R-L | E233D/G237D/P238D/ H268D/P271G/Y296D/ A330K | 2.0E−08 | 1.1E−06 | 1.2E-05 | 3.6E−08 | 5.8E−05 | 30.6 | 86.1 | 1.0 |
| IL6R-BP221/ IL6R-L | L234Y/G237D/P238D/ Y296D/K326A/A330R | 1.3E−07 | 7.1E−07 | 2.5E-06 | 2.8E−08 | 4.6E−05 | 25.4 | 110.7 | 1.5 |
| IL6R-BP222/ IL6R-L | L234Y/G237D/P238D/ P271G/K326A/A330R | 5.1E−08 | 7.1E−07 | 2.6E-06 | 3.4E−08 | 4.7E−05 | 20.9 | 91.2 | 1.5 |
| IL6R-BP223/ IL6R-L | L234Y/G237D/P238D/ H268D/P271G/K326A/ A330R | 2.7E−08 | 6.0E−07 | 2.8E-06 | 2.5E−08 | 3.2E−05 | 24.0 | 124.0 | 1.8 |
| IL6R-BP224/ IL6R-L | L234Y/G237D/P238D/ S267Q/H268D/P271G/ K326A/A330R | 6.2E−09 | 4.5E−07 | 9.5E-06 | 3.5E−08 | 4.1E−05 | 12.9 | 88.6 | 2.4 |
| IL6R-BP225/ IL6R-L | L234Y/G237D/P238D/ K326D/A330R | 6.5E−08 | 6.9E−07 | 2.8E-06 | 3.5E−08 | 3.2E−05 | 19.7 | 88.6 | 1.6 |
| IL6R-BP226/ IL6R-L | L234Y/G237D/P238D/ P271G/K326D/A330R | 5.2E−08 | 5.7E−07 | 2.4E-06 | 3.3E−08 | 3.6E−05 | 17.3 | 93.9 | 1.9 |
| IL6R-BP227/ IL6R-L | L234Y/G237D/P238D/ H268D/P271G/K326D/ A330R | 2.7E−08 | 6.2E−07 | 2.9E-06 | 3.2E−08 | 2.6E−05 | 19.4 | 96.9 | 1.8 |
| IL6R-BP228/ IL6R-L | L234Y/G237D/P238D/ S267Q/H268D/P271G/ K326D/A330R | 5.5E−09 | 4.2E−07 | 1.1E-05 | 4.0E−08 | 3.2E−05 | 10.5 | 77.5 | 2.6 |
| IL6R-BP229/ IL6R-L | E233D/L234Y/G237D/ P238D/P271G/K326A/ A330R | 5.6E−08 | 8.1E−07 | 3.3E-06 | 4.2E−08 | 3.7E−05 | 19.3 | 73.8 | 1.4 |
| IL6R-BP230/ IL6R-L | E233D/G237D/P238D/ H268D/P271G/Y296D/ A330R | 1.4E−08 | 5.7E−07 | 9.6E-06 | 2.1E−08 | 6.7E−05 | 27.1 | 147.6 | 1.9 |
| IL6R-BP231/ IL6R-L | G237D/P238D/H268D/ P271G/Y296D/A330R | 9.4E−09 | 7.4E−07 | 1.1E-05 | 2.3E−08 | 4.0E−05 | 32.2 | 134.8 | 1.5 |
| IL6R-BP232/ IL6R-L | L234Y/G237D/P238D/ P271G/K236A/A330K | 7.6E−08 | 8.4E−07 | 3.3E-06 | 5.6E−08 | 4.5E−05 | 15.0 | 55.4 | 1.3 |
| IL6R-BP233/ IL6R-L | L234Y/G237D/P238D/ P271G/A330K | 7.0E−08 | 6.9E−07 | 2.8E-06 | 3.7E−08 | 5.1E−05 | 18.6 | 83.8 | 1.6 |
| IL6R-BP234/ IL6R-L | E233D/L234Y/G237D/ P238D/S267Q/H268D/ P271G/Y296D/K326D/ A330K | 6.5E−09 | 1.2E−06 | 2.0E-05 | 1.2E−07 | 3.1E−05 | 10.0 | 25.8 | 0.9 |
| IL6R-BP235/ IL6R-L | E233D/L234Y/G237D/ P238D/H268D/P271G/ Y296D/K326D/A330R | 3.5E−09 | 6.8E−07 | 7.5E-06 | 4.4E−08 | 2.5E−05 | 15.5 | 70.5 | 1.6 |
| IL6R-BP236/ IL6R-L | E233D/L237Y/G237D/ P238D/S267Q/H268D/ P271G/Y296D/K326D/ A330R | 7.7E−09 | 8.4E−07 | 1.9E-05 | 6.5E−08 | 3.9E−05 | 12.9 | 47.7 | 1.3 |
| IL6R-BP237/ IL6R-L | E233D/L237Y/G237D/ P238D/S267Q/H268D/ P271G/Y296D/K326A/ A330K | 4.1E−09 | 1.1E−06 | 1.9E-05 | 1.0E−07 | 3.5E−05 | 11.0 | 31.0 | 1.0 |
| IL6R-BP238/ IL6R-L | E233D/L237Y/G237D/ P238D/H268D/P271G/ Y296D/K326A/A330R | 2.4E−09 | 6.4E−07 | 7.0E-06 | 3.6E−08 | 2.7E−05 | 17.8 | 86.1 | 1.7 |
| IL6R-BP239/ IL6R-L | E233D/L237Y/G237D/ P238D/S267Q/H268D/ P271G/Y296D/K326A/ A330R | 7.6E−09 | 8.1E−07 | 1.7E-05 | 6.0E−08 | 4.8E−05 | 13.5 | 51.7 | 1.4 |
| IL6R-BP240/ IL6R-L | E233D/G237D/P238D/ S267Q/H268D/P271G/ A330R | 7.6E−09 | 1.5E−06 | 2.6E-05 | 9.5E−08 | 5.2E−05 | 15.8 | 32.6 | 0.7 |

TABLE 1-continued

| VARIANT NAME | ALTERATION | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIb) OF PARENT POLYPEPTIDE/ KD(IIb) OF ALTERED POLYPEPTIDE | KD(IIaR) OF PARENT POLYPEPTIDE/ KD(IIaR) OF ALTERED POLYPEPTIDE |
|---|---|---|---|---|---|---|---|---|---|
| IL6R-BP241/ IL6R-L | E233D/G237D/P238D/ H268D/P271G/K326D/ A330R | 1.1E−09 | 6.8E−07 | 9.0E-06 | 4.5E−08 | 3.1E−05 | 15.1 | 68.9 | 1.6 |
| IL6R-BP242/ IL6R-L | E233D/G237D/P238D/ H268D/P271G/K326A/ A330R | 1.9E−09 | 7.5E−07 | 8.6E-06 | 5.1E−08 | 2.9E−05 | 14.7 | 60.8 | 1.5 |
| IL6R-BP243/ IL6R-L | E233D/L237Y/G237D/ P238D/H268D/P271G/ A330R | 3.0E−09 | 5.4E−07 | 6.0E-06 | 3.6E−08 | 2.5E−05 | 15.0 | 86.1 | 2.0 |
| IL6R-BP244/ IL6R-L | E233D/G237D/P238D/ S267Q/H268D/P271G/ Y296D/A330R | 7.8E−09 | 1.8E−06 | 2.6E-05 | 1.1E−07 | 4.6E−05 | 16.4 | 28.2 | 0.6 |
| IL6R-BP245/ IL6R-L | E233D/G237D/P238D/ S267Q/H268D/P271G/ Y296D/K326D/A330R | 6.3E−09 | 1.4E−06 | 2.5E-05 | 8.3E−08 | 3.9E−05 | 16.9 | 37.3 | 0.8 |
| IL6R-BP246/ IL6R-L | E233D/G237D/P238D/ S267Q/H268D/P271G/ Y296D/K326A/A330R | 8.0E−09 | 1.6E−06 | 2.3E-05 | 9.2E−08 | 4.4E−05 | 17.4 | 33.7 | 0.7 |
| IL6R-BP247/ IL6R-L | E233D/G237D/P238D/ H268D/P271G/Y296D/ K326D/A330R | 7.5E−09 | 8.1E−07 | 1.2E-05 | 3.7E−08 | 4.4E−05 | 21.9 | 83.8 | 1.4 |
| IL6R-BP248/ IL6R-L | E233D/G237D/P238D/ H268D/P271G/Y296D/ K326A/A330R | 1.7E−09 | 8.2E−07 | 1.1E-05 | 3.5E−08 | 4.4E−05 | 23.4 | 88.6 | 1.3 |
| IL6R-BP249/ IL6R-L | E233D/L234Y/G237D/ P238D/H268D/P271G/ Y296D/A330R | 7.0E−09 | 6.2E−07 | 7.2E-06 | 3.7E−08 | 2.8E−05 | 16.8 | 83.8 | 1.8 |

Binding of IL6R-G1d/IL6R-L which carries the native human IgG1 sequence was 1.3 fold for FcgRIa, 1.1 fold for FcgRIIaR, 1.1 fold for FcgRIIaH, 1.2 fold for FcgRIIb, and 0.9 fold for FcgRIIIaV, when binding of IL6R-B3/IL6R-L produced by introducing K439E into IL6R-G1d/IL6R-L to the respective FcgRs was defined as 1, and all of the binding to FcgRs were equivalent to that of IL6R-G1d/IL6R-L. Therefore, comparing binding of each variant with that of the IL6R-B3/IL6R-L prior to alteration can be considered to be equivalent to comparing each variant with IL6R-G1d/IL6R-L which carries the native human IgG1 sequence. Accordingly, in the Examples hereafter, binding activity of each variant is compared with that of the IL6R-B3/IL6R-L prior to alteration.

Table 1 shows that all variants showed improved affinity to FcgRIIb in comparison with the IL6R-B3 prior to alteration, and IL6R-BF648/IL6R-L showed 2.6 fold improved affinity which was the lowest and IL6R-BP230/IL6R-L showed 147.6 fold improved affinity which was the highest. Furthermore, the value of KD(IIaR)/KD(IIb), which shows the degree of selectivity, is 10.0 for IL6R-BP234/IL6R-L which showed the lowest value, and 32.2 for IL6R-BP231/IL6R-L which showed the highest value, and all variants improved their selectivity compared to the IL6R-B3/IL6R-L prior to alteration, which showed a value of 0.3. All variants showed lower binding to FcgRIa, FcgRIIaH, and FcgRIIIaV compared to the IL6R-B3/IL6R-L prior to alteration.

[Example 3] X-Ray Structure Analysis of a Complex Formed Between an Fc with Enhanced FcγRIIb Binding and the Extracellular Region of FcγRIIb and a Complex Formed Between this Fc and the Extracellular Region of FcγRIIaR The IL6R-BP230/IL6R-L variant showing the highest enhanced FcgRIIb binding in Example 2 showed approximately 150-fold enhanced binding to FcgRIIb and binding to FcgRIIa type R was suppressed to about 1.9-fold increase when compared to the IL6R-B3/IL6R-L prior to alteration. Therefore, IL6R-BP230/IL6R-L is an excellent variant in terms of both binding and selectivity to FcgRIIb; however, to produce more excellent variants, it is preferred that FcgRIIb binding is further enhanced as well as binding to FcgRIIaR is suppressed as much as possible.

Figure 28:
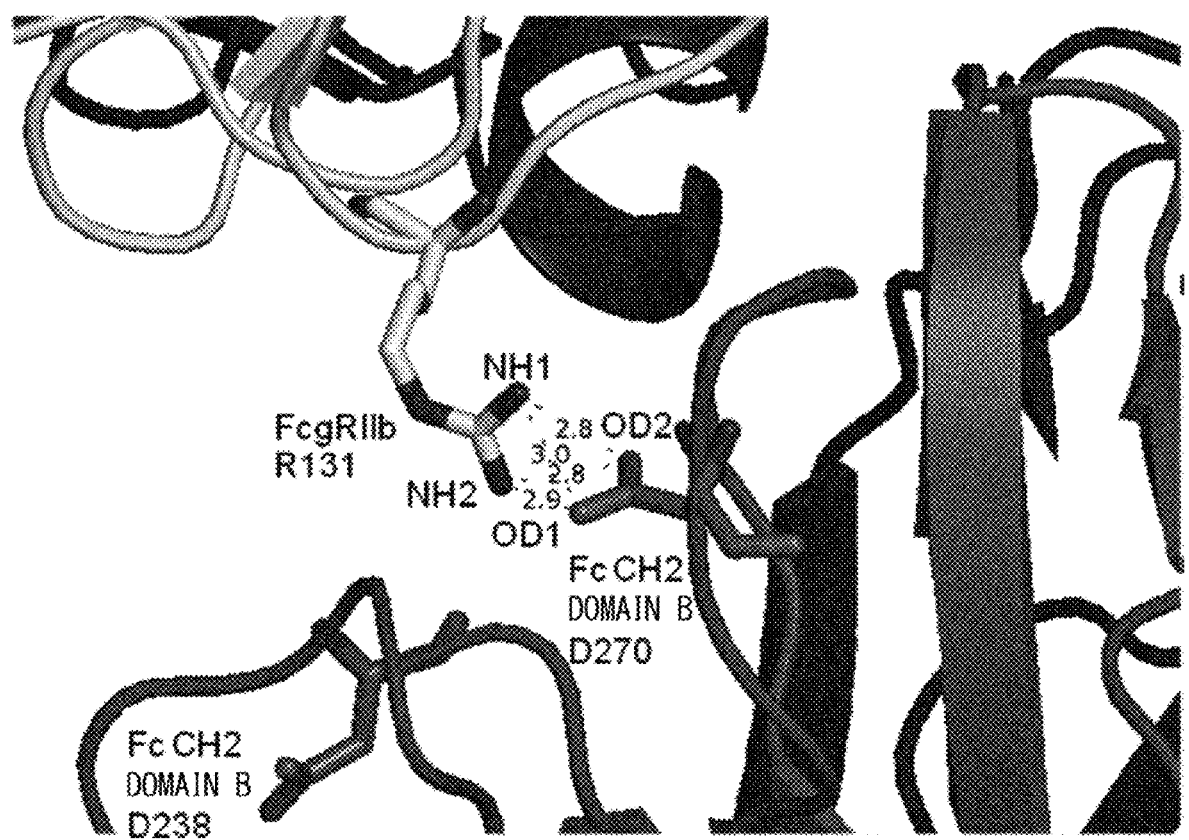
FIG. 28 shows that an electrostatic interaction is found between Asp at position 270 (EU numbering) in Fc CH2 domain B, and Arg at position 131 in FcγRIIb in the crystal structure of the Fc(P238D)/FcγRIIb extracellular region complex.

As shown in FIG. 28 of Reference Example 7, in Fc having the P238D alteration, formation of a strong electrostatic interaction is observed between Asp at position 270 (EU numbering) of the CH2 domain B and Arg at position 131 of FcγRIIb. While this residue at position 131 is His in FcγRIIIa and FcγRIIa type H, it is Arg in FcγRIIa type R as in the case with FcγRIb. As a result, there are no differences in the interactions at this portion, and this is the reason that it is difficult to bring about selectivity for FcγRIIa type R.

Meanwhile, the extracellular regions of FcγRIIa and FcγRIIb match 93% in amino acid sequence, that is, have very high homology. When the crystal structure of the complex formed between the native IgG1 Fc (hereinafter "Fc(WT)") and the extracellular region of FcγRIIa type R (J. Imunol. 2011, 187, 3208-3217) was analyzed, amino acid differences around an interacting interface were found to be only three (Gln127, Leu132, and Phe160) between FcγRIIa type R and FcγRIIb, and improvement of selectivity over FcγRIIa type R was expected to be very difficult.

Therefore, to achieve further improvement of selectivity and enhancement of FcγRIIb-binding activity, the present inventors considered that the amino acid mutations to be introduced must be examined in detail by conformationally elucidating the subtle differences in interactions caused by the difference in receptors by obtaining not only the three-dimensional structure of the complex formed between an Fc with enhanced FcγRIIb binding and the extracellular region of FcγRIIb, but also simultaneously, the three-dimensional structure of a complex formed with the extracellular region of FcγRIIa type R for which improvement of selectivity is considered most difficult. Then, X-ray structure analyses were performed on a complex formed between the extracellular region of FcγRIIb and Fc(P208), in which the K439E alteration is removed from the Fc of IL6R-BP208/IL6R-L (produced in Reference Example 9) which is a variant used as the basis for production of IL6R-BP230/IL6R-L, and a complex formed between the extracellular region of FcγRIIa type R and Fc(P208).

Figure 5:
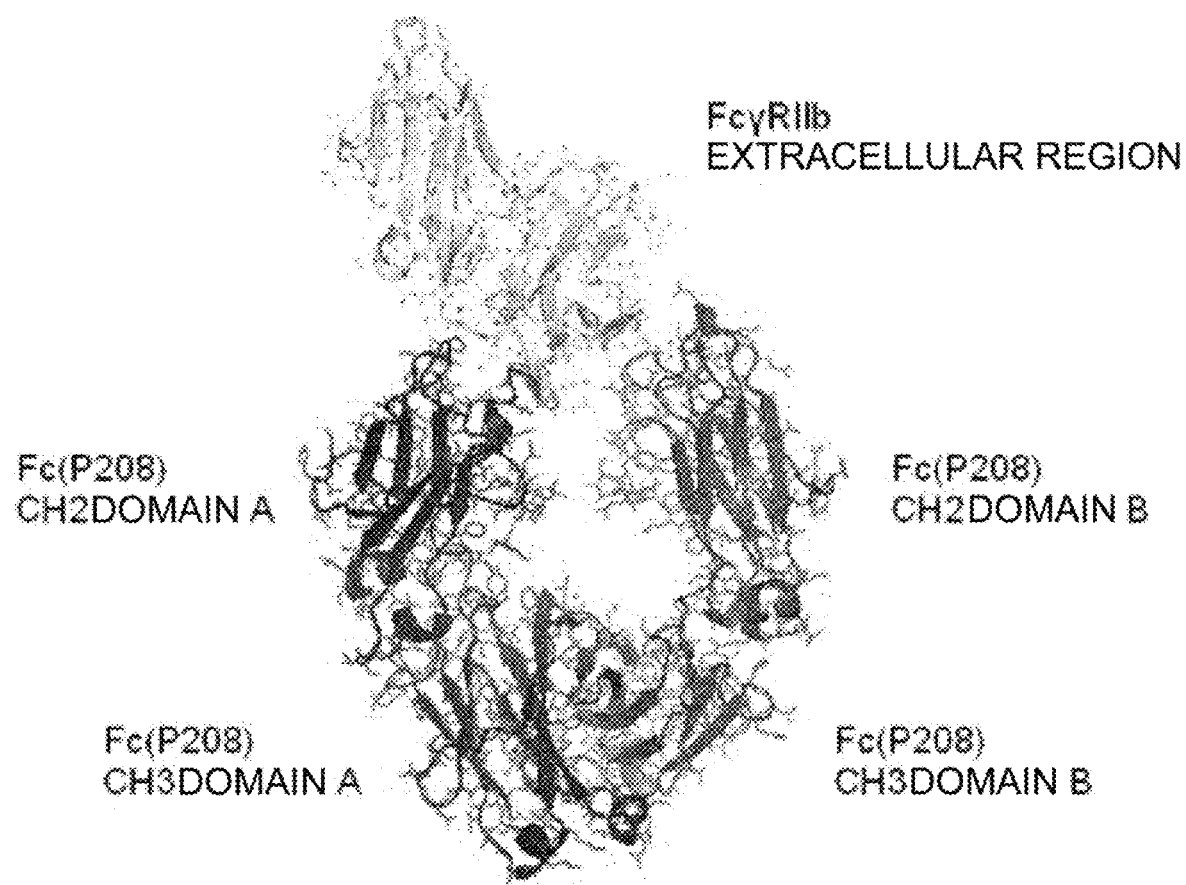
FIG. 5 shows the Fc(P208)/FcγRIIb extracellular region complex as determined by X-ray crystal structure analysis. For each of the Fc-region CH2 domain and CH3 domain, the portion shown on the left was defined as domain A and the portion shown on the right was defined as domain B.

3-1. X-Ray Structure Analysis of a Complex Formed Between Fc(P208) and the Extracellular Region of FcγRIIb The three-dimensional structure of the Fc(P208)/FcγRIIb extracellular region complex was determined by X-ray structure analysis at 2.81 Å resolution. The structure obtained as a result of this analysis is shown in FIG. 5. The extracellular region of FcγRIIb is bound between two Fc CH2 domains, and this is similar to the three-dimensional structures of complexes formed between Fc(WT) which is an Fc of a native IgG and the respective extracellular region of FcγRIIIa (Proc. Natl. Acad. Sci. USA, 2011, 108, 12669-126674), FcγRIIb (Nature, 2000, 400, 267-273; J. Biol. Chem. 2011, 276, 16469-16477), or FcγRIIa analyzed so far.

Figure 6:
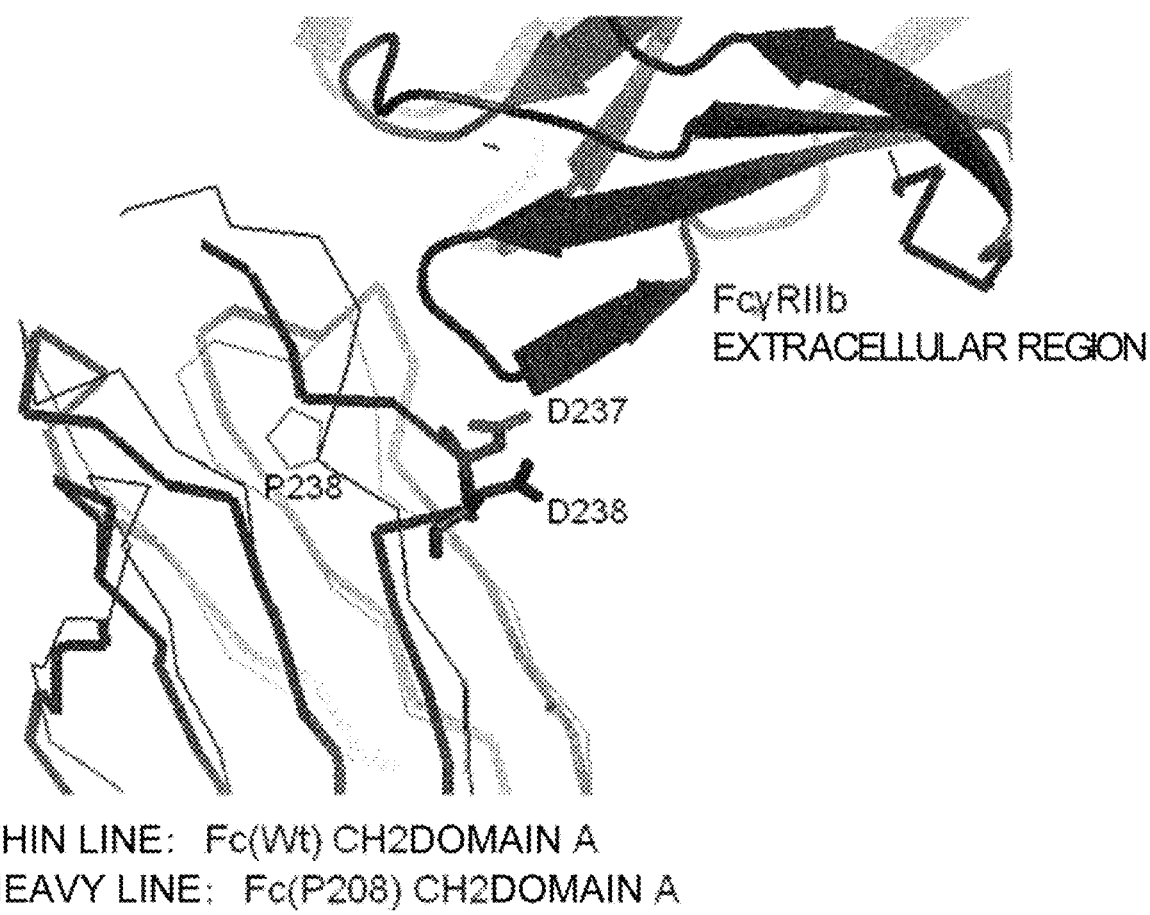
FIG. 6 shows a comparison made by superimposing the X-ray crystal structure of the Fc(P208)/FcγRIIb extracellular region complex and the structure of the Fc(WT)/FcγRIIa extracellular region complex (PDB code: 3RY6), with respect to Fc CH2 domain A by least square fitting based on Cα atom pair distances. In the figure, the Fc(P208)/FcγRIIb extracellular region complex structure is depicted using thick lines and the Fc(WT)/FcγRIIa extracellular region complex structure is depicted using thin lines. Regarding the structure of the Fc(WT)/FcγRIIa extracellular region complex, only the Fc portion CH2 domain A is depicted.
Figure 7:
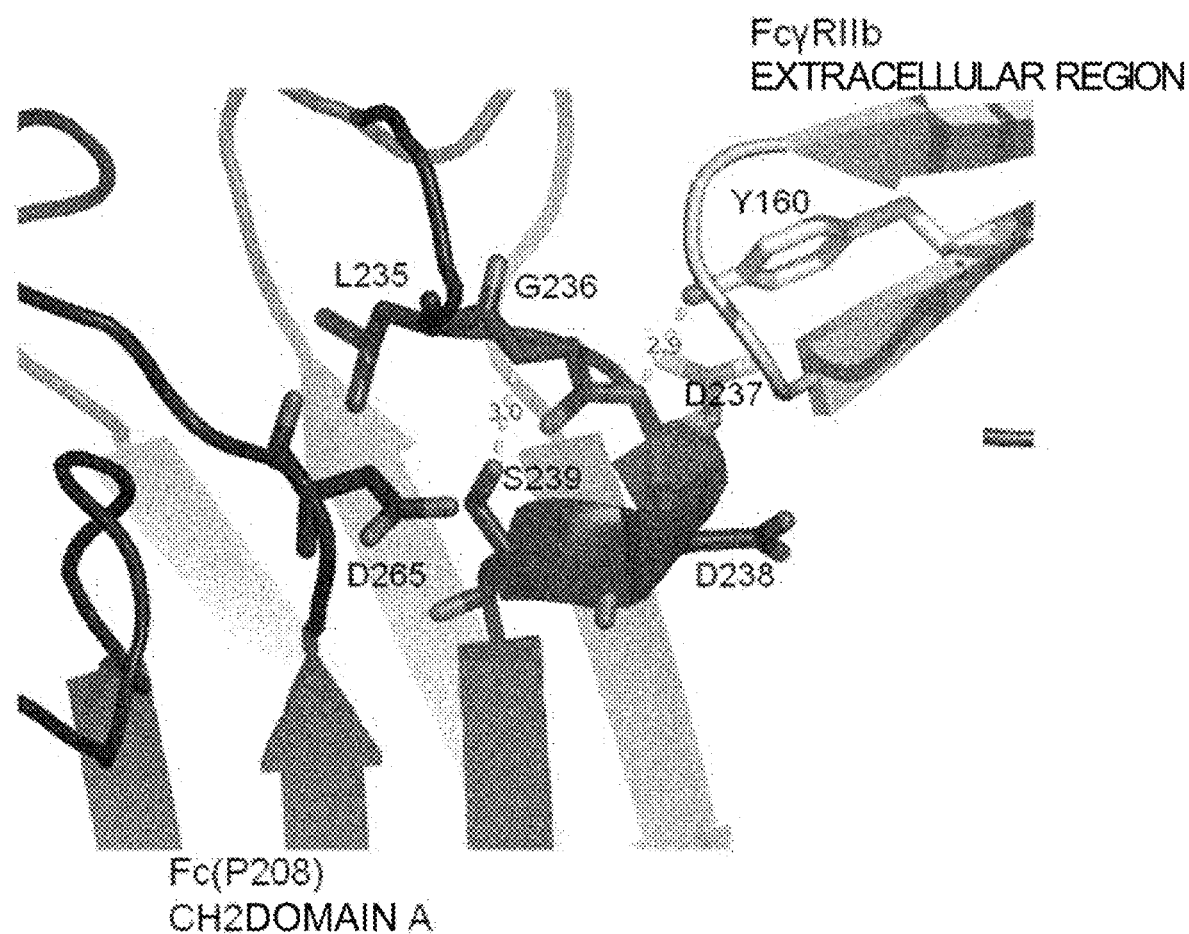
FIG. 7 shows the detailed structure around Asp at position 237 (EU numbering) in Fc portion CH2 domain A whose main chain forms a hydrogen bond with Tyr at position 160 of FcγRIIb in the X-ray crystal structure of the Fc(P208)/FcγRIIb extracellular region complex.

However, detailed analysis revealed that in the Fc(P208)/FcγRIIb extracellular region complex, the loop structure of positions 233 to 239 (EU numbering) continuing from the hinge region of Fc CH2 domain A was changed compared to that of the Fc(WT)/FcγRIIa type R extracellular region complex due to introduction of the G237D and P238D mutations (FIG. 6). As a result, formation of a strong hydrogen bond was observed between the main chain of Asp at position 237 (EU numbering) of Fc(P208) and the side chain of Tyr at position 160 of FcγRIIb (FIG. 7). As this Tyr160 is Phe in both the type H and type R of FcγRIIa, hydrogen bond formation is impossible. Therefore, this hydrogen bond was considered to have an important contribution to acquisition of selectivity which refers to enhancement of FcγRIIb-binding activity and decrease in FcγRIIa-binding activity.

Figure 8:
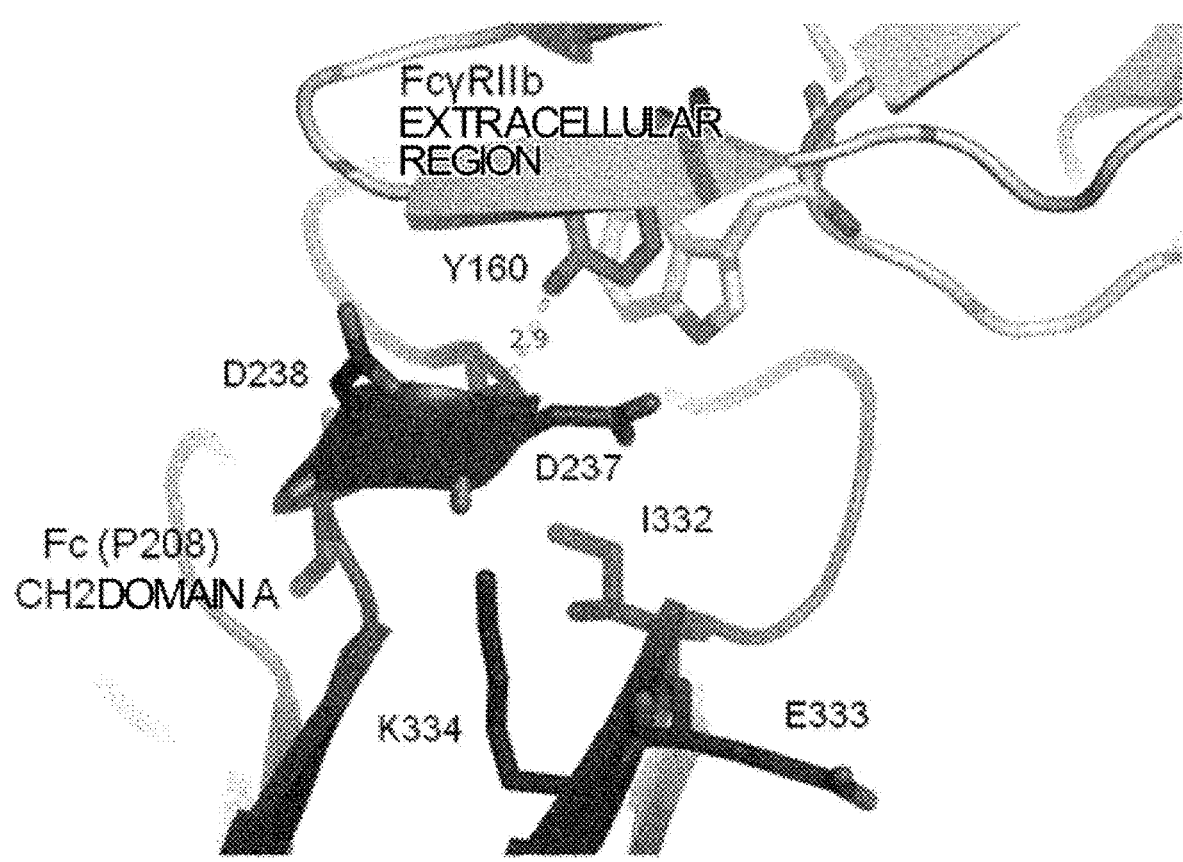
FIG. 8 shows the structure of amino acid residues around the side chain of Asp at position 237 (EU numbering) in Fc portion CH2 domain A whose main chain forms a hydrogen bond with Tyr at position 160 of FcγRIIb in the X-ray crystal structure of the Fc(208)/FcγRIIb extracellular region complex.

On the other hand, the side chain of Asp at position 237 (EU numbering) of Fc(P208) does not show remarkable interaction with FcγRIIb, and no interaction was observed with residues within Fc. Ile at position 332 (EU numbering), Glu at position 333 (EU numbering), and Lys at position 334 (EU numbering) in Fc were positioned in close proximity around this Asp at position 237 (EU numbering) (FIG. 8). If the loop structure can be stabilized by substituting these positions with hydrophilic resides to form interaction with the side chain of Asp at position 237 (EU numbering), entropic energy loss accompanying formation of hydrogen bond with Tyr at position 160 of FcγRIIb can be decreased, and this may lead to increase in the binding free energy, that is, enhancement of binding activity.

Figure 9:
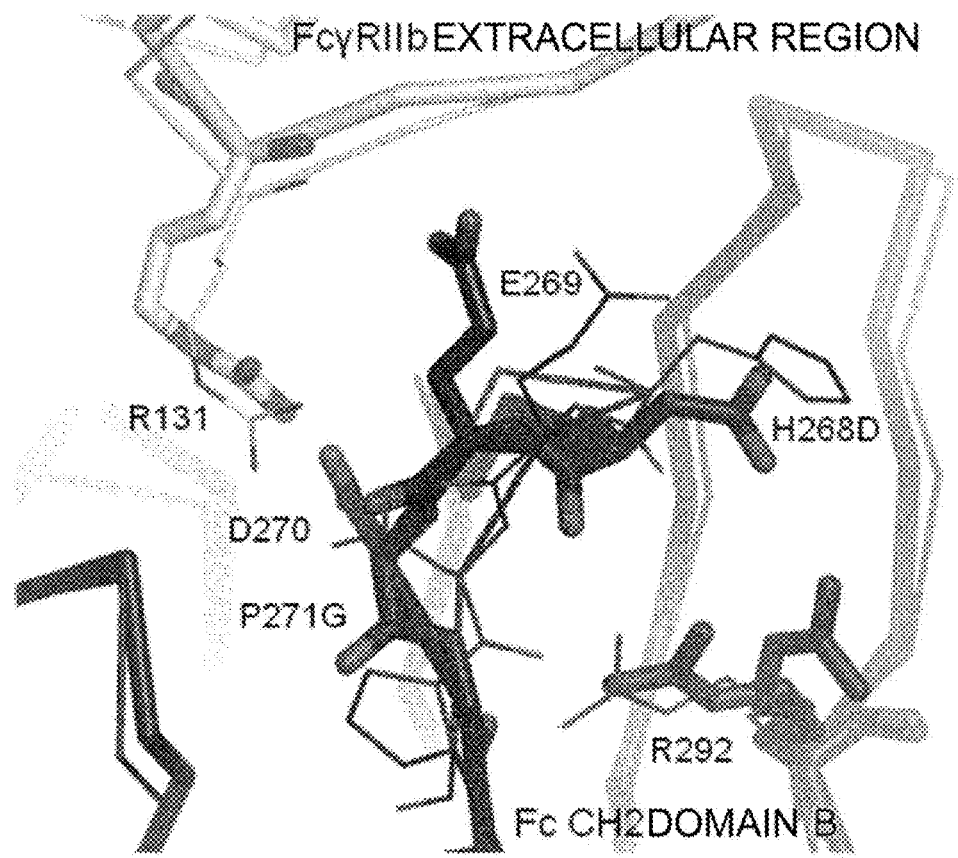
FIG. 9 shows an image of superimposing the X-ray crystal structure of the Fc(P238D)/FcγRIIb extracellular region complex shown in Reference Example 7 and the X-ray crystal structure of the Fc(P208)/FcγRIIb extracellular region complex, with respect to Fc portion CH2 domain B by least square fitting based on Cα atom pair distances, to compare the region around the loop of positions 266 to 271 according to EU numbering. In the loop, Fc(P208) has an H268D alteration at position 268 (EU numbering) and a P271G alteration at position 271 (EU numbering) when compared to Fc(P238D).

Comparison of the X-ray crystal structure of the complex formed between Fc(P238D) carrying the P238D alteration and the extracellular region of FcγRIIb, which is shown in Reference Example 7, and the X-ray crystal structure of the complex formed between Fc(P208) and the extracellular region of FcγRIIb, showed that compared to Fc(P238D), Fc(P208) contains five new mutations, and most of them were only changes at the side-chain level. However, by altering Pro at position 271 (EU numbering) to Gly in the CH2 domain B of Fc, change in location was observed at the main-chain-level, and structural changes had taken place at the upstream loop formed by positions 266-270 (EU numbering) (FIG. 9). As shown in Reference Example 8, in Fc(P238D), it has been suggested that the Pro portion at position 271 (EU numbering) may be stereochemically strained when Asp at position 270 (EU numbering) forms a strong electrostatic interaction with Arg at position 131 of FcγRIIb. Structural changes observed this time by introducing Gly at position 271 (EU numbering) may be the result of releasing structural strain accumulated at the Pro portion prior to alteration, and the amount of release of strain is considered to have led to improvement of binding free energy with FcγRIIb, that is, the enhancement of binding activity.

Furthermore, Arg at position 292 (EU numbering) was confirmed to undergo structural changes with taking two forms as a result of structural changes of the loop at positions 266-271 (EU numbering). In this case, Arg at position 292 (EU numbering) forms electrostatic interaction with Asp at position 268 (EU numbering) which is one of the other altered residues in Fc(P208) (FIG. 9), and this may contribute to the stabilization of this loop structure. The electrostatic interaction formed between Asp at position 270 (EU numbering) in this loop and Arg at position 131 of FcγRIIb greatly contributes to FcγRIIb-binding activity; therefore, introduction of the H268D alteration may have led to reduction of entropic energy loss accompanying binding and increase in binding free energy, that is, enhancement of binding activity by stabilizing the conformation of this loop structure to its FcγRIIb-bound form.

Figure 10:
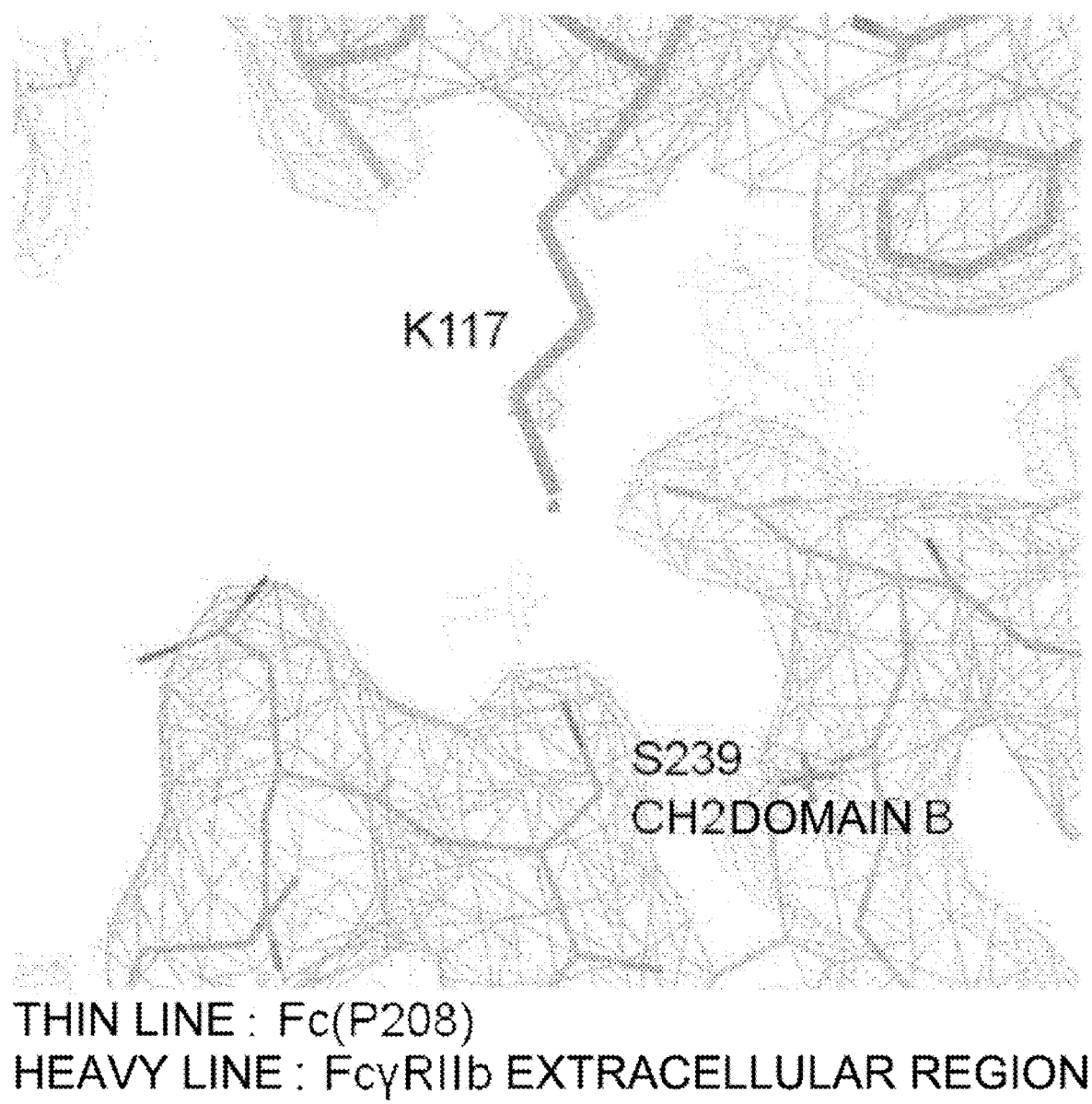
FIG. 10 shows the structure around Ser239 of the Fc portion CH2 domain B along with electron density obtained by X-ray crystal structure analysis which uses 2Fo-Fc as the coefficient in the X-ray crystal structure of the Fc(P208)/FcγRIIb extracellular region complex.

When further investigations for the possibility of alterations aimed at further improving the activity were carried out based on the structural analysis results, Ser at position 239 (EU numbering) was found as one of the candidate positions for introducing alterations. As shown in FIG. 10, this Ser at position 239 (EU numbering) of CH2 domain B is positioned in the direction where Lys at position 117 of FcγRIIb extends in a most structurally natural manner. However, as the electron density of Lys at position 117 of FcγRIIb was not detected in this analysis, this Lys residue does not form a steady structure. Thus, currently, involvement of this Lys residue in the interaction with Fc(P208) is considered to be limited; however, if this Ser at position 239 (EU numbering) of CH2 domain B is altered to negatively-charged Asp or Glu, electrostatic interaction with the positively-charged Lys at position 117 of FcγRIIb can be expected, and as a result, FcγRIIb-binding activity can be expected to become enhanced.

On the other hand, observing the structure of Ser at position 239 (EU numbering) in CH2 domain A, it is considered that the side chain of this amino acid forms hydrogen bonds with the main chain of Gly at position 236 (EU numbering) and stabilizes the loop structure from positions 233 to 239 which continues from the hinge region and includes Asp at position 237 (EU numbering) which forms a hydrogen bond with the FcγRIIb Tyr160 side chain (FIG. 7). Stabilizing this loop structure to the conformation taken during binding may lead to reduction of entropic energy loss accompanying binding, and as a result, enhancement of binding free energy, that is, enhancement of binding activity. On the other hand, if this Ser at position 239 (EU numbering) in CH2 domain A is altered to Asp or Glu, the hydrogen bond with the main chain of Gly at position 239 (EU numbering) may be lost, and may cause electrostatic repulsion between Asp at position 265 (EU numbering) which is present in close proximity, and thus may lead to large destabilization of the loop structure. This destabilized energy operates to decrease the binding free energy with FcγRIIb; therefore, this may lead to decrease in binding activity.

[Expression and Purification of Fc(P208)]

Fc(P208) was prepared as follows. First, IL6R-P208 was produced by altering Glu at position 439 (EU numbering) of IL6R-BP208 (SEQ ID NO: 24) to Lys, which is the sequence of a native human IgG1. Then, Cys at position 220 (EU numbering) of IL6R-P208 was substituted with Ser. Then, genetic sequence of Fc(P208) from Glu at position 216 (EU numbering) to its C terminal was cloned by PCR. Using this cloned genetic sequence, production of expression vectors, and expression and purification of Fc(P208) were carried out according to the method of Reference Example 1. Cys at position 220 (EU numbering) forms a disulfide bond with Cys of the L chain in general IgG1. The L chain is not co-expressed when Fc alone is prepared, and therefore, this residue was substituted with Ser to avoid formation of unnecessary disulfide bonds.

[Expression and Purification of the FcγRIIb Extracellular Region]

This was prepared according to the method of Reference Example 2.

[Purification of the Fc(P208)/FcγRIIb Extracellular Region Complex]

To 1.5 mg of the FcγRIIb extracellular region sample obtained for crystallization, 0.15 mg of Endo F1 (Protein Science 1996, 5: 2617-2622) expressed and purified from *Escherichia coli* as a glutathione S-transferase fusion protein was added. This was allowed to remain at room temperature for three days in 0.1 M Bis-Tris buffer at pH 6.5, and the N-linked oligosaccharide was cleaved, leaving N-acetylglucosamine directly bound to Asn. Next, this FcγRIIb extracellular region sample subjected to carbohydrate cleavage treatment was concentrated by ultrafiltration with 5000 MWCO, and purified by gel filtration chromatography (Superdex® 200 10/300 chromatography) using a column equilibrated in 20 mM HEPES at pH 7.5 containing 0.1 M NaCl. Furthermore, to the obtained carbohydrate-cleaved FcγRIIb extracellular region fraction, Fc(P208) was added so that the molar ratio of the FcγRIIb extracellular region would be present in slight excess, and after concentration by ultrafiltration with 10000 MWCO, a sample of the Fc(P208)/FcγRIIb extracellular region complex was obtained through purification by gel filtration chromatography (Superdex® 200 10/300 chromatography) using a column equilibrated in 25 mM HEPES at pH 7.5 containing 0.1 M NaCl.

[Crystallization of the Fc(P208)/FcγRIIb Complex Extracellular Region Complex]

A sample of Fc(P208)/FcγRIIb extracellular region complex were concentrated to about 10 mg/ml using 10000MWCO ultrafiltration filter, and crystallized using the hanging drop vapor diffusion method in combination with the seeding method. VDXm plate (Hampton Research) was used for crystallization. Using a reservoir solution containing 0.1 M Bis-Tris (pH 6.5), 19% (w/v) PEG3350, and 0.2 M potassium phosphate dibasic, crystallization drops were prepared at a mixing ratio of reservoir solution:crystallization sample=0.85 μl:0.85 μl. Crystals of the complex obtained under the same condition were crushed with Seed Bead (Hampton Research) to prepare a seed crystal solution. 0.15 μl of a diluted solution produced from the seed crystal solution was added to the crystallization drops, which were sealed in the wells containing reservoirs, and allowed to stand at 20° C. This successfully yielded plate-like crystals.

[Measurement of X-Ray Diffraction Data from an Fc(P208)/FcγRIIb Extracellular Region Complex Crystal]

One of the obtained single crystals of the Fc(P208)/FcγRIIb extracellular region complex was soaked into a solution of 0.1 M Bis-Tris pH 6.5, 24% (w/v) PEG3350, 0.2 M potassium phosphate dibasic, 20% (v/v) ethylene glycol. The crystal was fished out of the solution using a pin with attached tiny nylon loop, and frozen in liquid nitrogen; and then X-ray diffraction data was measured by BL32XU at Spring-8. During the measurement, the crystal was constantly placed in a nitrogen stream at −178° C. to maintain in a frozen state, and a total of 300 X ray diffraction images were collected using MX-225HE CCD detector (RAY-ONIX) attached to a beam line with rotating the crystal 0.6° at a time. Determination of cell parameters, indexing of diffraction spots, and diffraction data processing from the obtained diffraction images were performed using the Xia2 program (J. Appl. Cryst. 2010, 43: 186-190), XDS Package (Acta. Cryst. 2010, D66: 125-132) and Scala (Acta. Cryst. 2006, D62: 72-82); and finally, diffraction intensity data up to 2.81 Å resolution was obtained. The crystal belongs to the space group C222$_1$, and has the following cell parameters; a=156.69 Å, b=260.17 Å, c=56.85 Å, α=90°, β=90°, γ=90°.

[X Ray Structure Analysis of the Fc(P208)/FcγRIIb Extracellular Region Complex]

Crystal structure of the Fc(P208)/FcγRIIb extracellular region complex was determined by the molecular replacement method using the program Phaser (J. Appl. Cryst. 2007, 40: 658-674). From the size of the obtained crystal lattice and the molecular weight of the Fc(P208)/FcγRIIb extracellular region complex, the number of complexes in the asymmetric unit was predicted to be one. From the structural coordinates of PDB code: 3SGJ which is the crystal structure of the Fc(WT)/FcγRIIIa extracellular region complex, the amino acid residue portions of the A chain positions 239-340 and the B chain positions 239-340 were taken out as separate coordinates, and they were used respectively as models for searching the Fc CH2 domains. The amino acid residue portions of the A chain positions 341-444 and the B chain positions 341-443 were taken out as a single set of coordinates from the same structural coordinates of PDB code: 3SGJ; and this was used as a model for searching the Fc CH3 domains. Finally, from the structural coordinates of PDB code: 2FCB which is a crystal structure of the FcγRIIb extracellular region, the amino acid residue portions of the A chain positions 6-178 was taken out and used as a model for searching the Fc(P208). The present inventors tried to determine the orientations and positions of each search model of Fc CH3 domains, FcγRIIb extracellular region, and Fc CH2 domain in the crystal lattices using rotation function and translation function, but failed to determine the position of one of the CH2 domains. Then, with reference to the crystal structure of the complex of Fc(WT)/FcγRIIIa extracellular region, the position of the last CH2 domain was determined from an electron density map that was calculated based on the phase determined from the remaining three parts. Thus, the present inventors obtained an initial model for the crystal structure of the Fc(P208)/FcγRIIb extracellular region complex. When rigid body refinement which moves the two Fc CH2 domains, the two Fc CH3 domains, and the FcγRIIb extracellular region was performed on the obtained initial model, the crystallographic reliability factor, R value became 42.6%, and the Free R value became 43.7% to diffraction intensity data from 25 Å to 3.0 Å at this point. Furthermore, structural refinement using the program REFMAC5 (Acta Cryst. 2011, D67, 355-367), and revision of the model to observe the electron density maps whose coefficient have 2Fo-Fc or Fo-Fc, which are calculated based on the experimentally determined structural factor Fo, the calculated structural factor Fc and the calculated phase using the model, was carried out by the Coot program (Acta Cryst. 2010, D66:

486-501), and model refinement was carried out by repeating these steps. Finally, as a result of incorporation of water molecules into the model based on the electron density maps which use 2Fo-Fc or Fo-Fc as the coefficient, and the following refinement, the crystallographic reliability factor, R values and the Free R value of the model containing 4786 non-hydrogen atoms became 24.5% and 28.2% to 27259 diffraction intensity data from 25 Å to 2.81 Å resolution, respectively.

Figure 11:
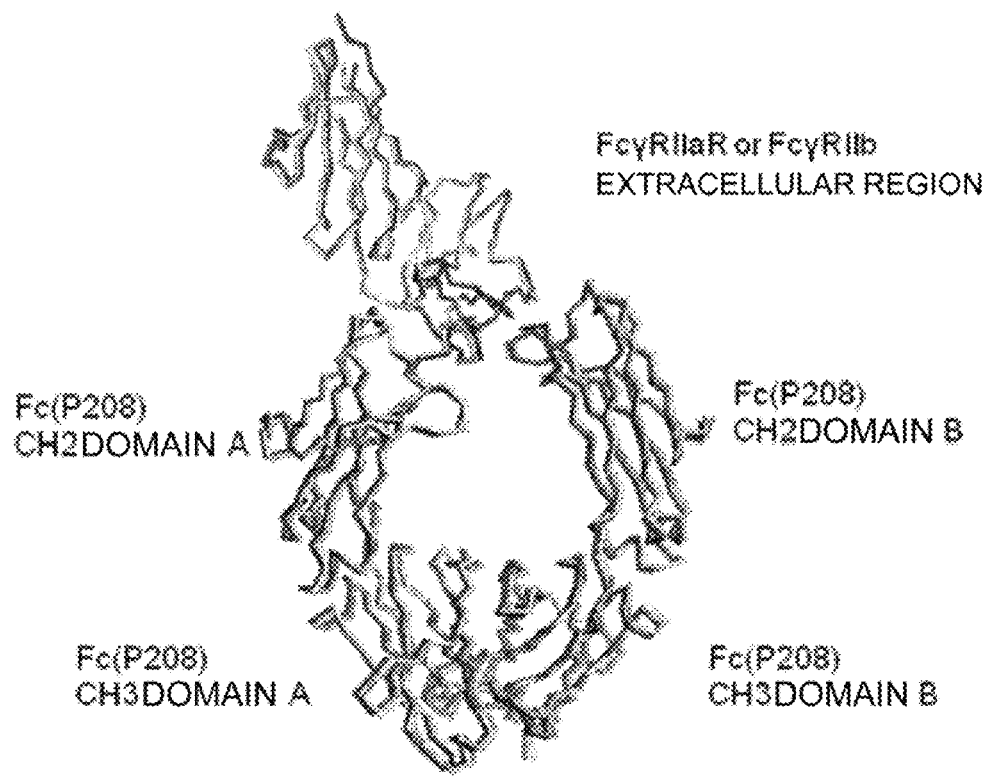
FIG. 11 shows a comparison made by superimposing the three-dimensional structure of the Fc(P208)/FcγRIIa type R extracellular region complex and three-dimensional structure of the Fc(P208)/FcγRIIb extracellular region complex, which are determined by X-ray crystal structure analysis, by least square fitting based on Cα atom pair distances.
Figure 12:
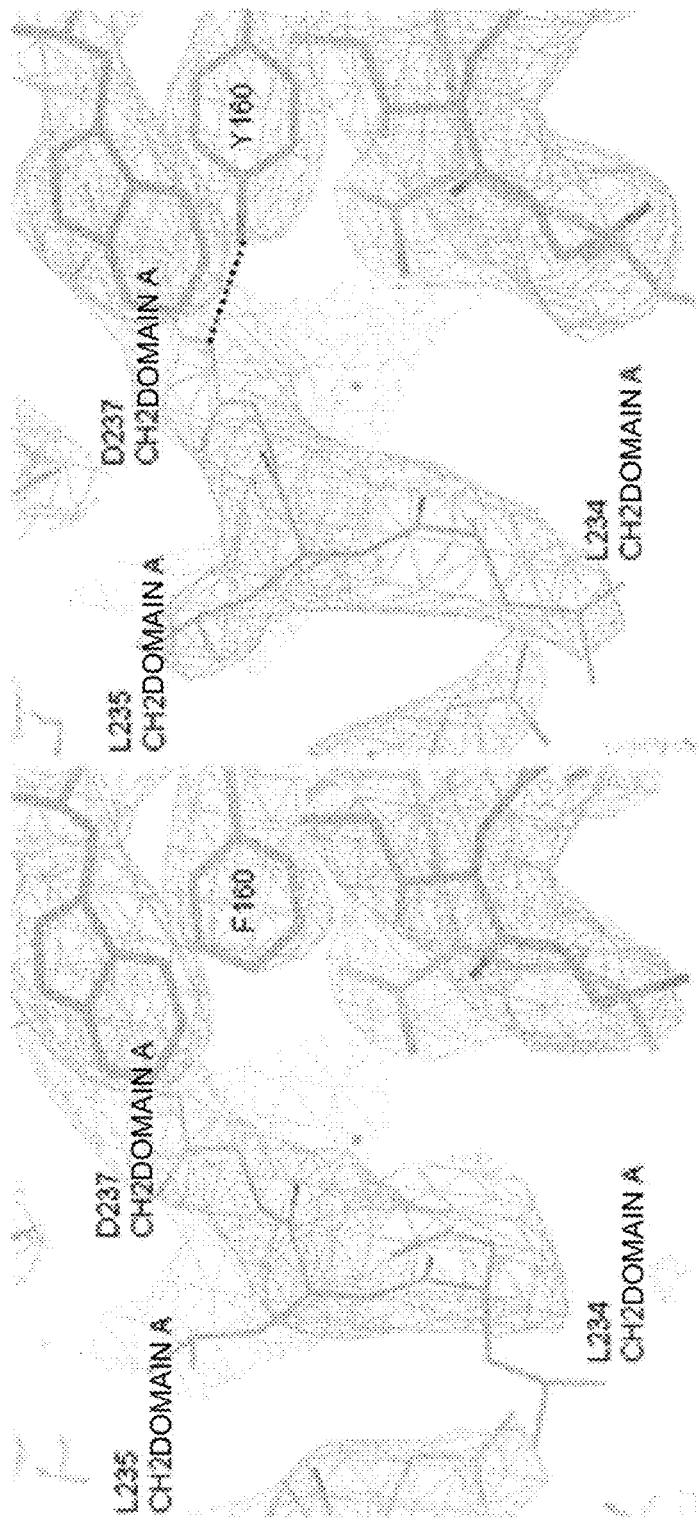
FIG. 12 shows a comparison of the X-ray crystal structure of the Fc(P208)/FcγRIa type R extracellular region complex and the X-ray crystal structure of the Fc(P208)/FcγRIIb extracellular region complex around Asp at position 237 (EU numbering) in Fc portion CH2 domain A, along with electron density obtained by X-ray crystal structure analysis which uses 2Fo-Fc as the coefficient.

3-2. X-Ray Structure Analysis of a Complex Formed Between Fc(P208) and the Extracellular Region of FcγRIIa Type R As a result of structural analysis, the crystal structure of the Fc(P208)/FcγRIIa type R extracellular region complex was determined at 2.87 Å resolution. The crystal structure of the Fc(P208)/FcγRIIa type R extracellular region complex was compared with the crystal structure of the Fc(P208)/FcγRIIb extracellular region complex shown in Example 3-1, and reflecting the very high amino acid homology of the two receptors, hardly any differences were observed for the overall structures (FIG. 11). However, when the structure was examined in detail at the electron density level, differences that may be used for improving selectivity were found. In FcγRIIa type R, the residue at position 160 was Phe instead of Tyr, and as shown in FIG. 12, this Phe cannot form a hydrogen bond with the main chain of amino acid residue at position 237 (EU numbering) of the Fc CH2 domain A, that was present in binding between FcgRIIb and Fc containing the P238D alteration. While this may be the major factor for improvement of selectivity for FcγRIIa type R by introduction of the P238D alteration, further comparison at the electron density level showed that in the complex formed with FcγRIIb, the electron density of the side chains of Leu at position 235 (EU numbering) and Leu at position 234 (EU numbering) in the Fc CH2 domain A can be confirmed, whereas the electron densities of these side chains were not clear in the complex formed with FcγRIIa type R, and the loop around position 237 (EU numbering) seems to be fluctuating as a result of decrease in interaction with FcgRIIa type R around this region. On the other hand, when structures of the same region are compared for CH2 domain B (FIG. 13), the electron density to Asp at position 237 (EU numbering) can be confirmed in the structure of the complex formed with FcγRIIb, whereas the electron density to about three residues upstream of Asp at position 237 (EU numbering) can be confirmed for the complex formed with FcγRIIa type R, and compared to binding with FcgRIIb, a wider region seems to be used for the interaction. The above suggested that in the region of positions 234 to 238 (EU numbering) of Fc(P208), the CH2 domain A side may largely contribute to binding with FcγRIIb, and the CH2 domain B side may largely contribute to binding with FcγRIIaR.

[Expression and Purification of FcγRIIa Type R Extracellular Region]

This was prepared according to the method of Reference Example 2.

[Purification of the Fc(P208)/FcγRIIa Type R Extracellular Region Complex]

To 1.5 mg of the purified FcγRIIa type R extracellular region sample, 0.15 mg of Endo F1 (Protein Science 1996, 5, 2617-2622) expressed and purified from *Escherichia coli* as a fusion protein with glutathione S-transferase and 20 μL of 5U/mL Endo F2 (QA-bio) and 20 μL of 5U/mL Endo F3 (QA-bio) were added. This was left to stand at room temperature for nine days in 0.1 M sodium acetate buffer (pH 4.5) condition, and then 0.07 mg of Endo F1 (Protein Science 1996, 5, 2617-2622) expressed and purified from *Escherichia coli* as a fusion protein with glutathione S-transferase and 7.5 μL of 5U/mL Endo F2 (QA-bio) and 7.5 μL of 5U/mL Endo F3 (QA-bio) were added. This was left to stand for three more days, and the N-linked oligosaccharide was cleaved, while leaving N-acetylglucosamine directly bound to Asn. Next, this FcγRIIa type R extracellular domain sample subjected to sugar chain cleavage treatment was concentrated using 10000 MWCO ultrafiltration filter, and purified by gel filtration chromatography (Superdex® 200 10/300 chromatography) using a column equilibrated with 25 mM HEPES (pH 7), 0.1 M NaCl. Furthermore, to the obtained sugar chain-cleaved FcγRIIa type R extracellular region fraction, Fc(P208) was added so that the molar ratio of FcγRIIa type R extracellular region would be present in slight excess, and after concentration using 10000 MWCO ultrafiltration filter, a sample of the Fc(P208)/FcγRIIa type R extracellular region complex was obtained through purification by gel filtration chromatography (Superdex® 200 10/300 chromatography) using a column equilibrated with 25 mM HEPES (pH 7), 0.1 M NaCl.

[Crystallization of the complex of Fc(P208)/FcγRIIaR type extracellular region] A sample of Fc(P208)/FcγRIIa R type extracellular region complex concentrated to about 10 mg/ml with a 10000 MWCO ultrafiltration filter was crystallized using the sitting drop vapor diffusion method. Using a reservoir solution of 0.1 M Bis-Tris (pH 7.5), 26% (w/v) PEG3350, 0.2 M ammonium sulfate, crystallization drops were prepared at a mixing ratio of reservoir solution:crystallization sample=0.8 μl:1.0 μl. The drops were then tightly sealed and allowed to stand at 20° C. This succeeded in yielding plate-like crystals.

[X-Ray Diffraction Data Measurement from Fc(P208)/FcγRIIa Type R Extracellular Region Complex Crystal]

A single crystal of Fc(P208)/FcγRIIa type R extracellular region complex prepared was soaked into a solution of 0.1 M Bis-Tris (pH 7.5)), 27.5% (w/v) PEG3350, 0.2 M ammonium sulfate, 20% (v/v) glycerol. Then, the crystal was fished out of the solution using a pin with attached tiny nylon loop, and frozen in liquid nitrogen. X-ray diffraction data of the single crystal was measured at synchrotron radiation facility Photon Factory BL-17A in the High Energy Accelerator Research Organization. The crystal was constantly placed in a nitrogen stream at −178° C. to maintain in a frozen state during the measurement. A total of 225 X-ray diffraction images from the single crystal were collected using CCD detector Quantum 315r (ADSC) equipped to the beam line with rotating the single crystal at 0.6° at a time. Based on the obtained diffraction images, lattice constant determination, diffraction spot indexing, and diffraction data processing were performed using programs Xia2 (J. Appl. Cryst. (2010) 43, 186-190), XDS Package (Acta Cryst. (2010) D66, 125-132), and Scala (Acta Cryst. (2006) D62, 72-82). Finally, diffraction intensity data up to 2.87 Å resolution was obtained. The crystal belongs to the space group $C222_1$ with lattice constant a=154.31 Å, b=257.61 Å, c=56.19 Å, α=90°, β=90°, and γ=90°.

[X-Ray Crystal Structure Analysis of Fc(P208)/FcγRIIa Type R Extracellular Region Complex]

The structure was determined by a molecular replacement method using program Phaser (J. Appl. Cryst. (2007) 40, 658-674). The number of complexes in an asymmetrical unit was estimated to be one from the size of the obtained crystal lattice and the molecular weight of Fc(P208)/FcγRIIa type R extracellular region complex. Using, as a search model, the crystallographic structure of Fc(P208)/FcγRIIb extracellular region complex obtained as described in Example 3-1, the orientation and position in the crystal lattices were determined based on the rotation function and translation function. The crystallographic reliability factor R value for the data of diffracted intensity at 25 to 3.0 Å was 38.4% and Free R value was 38.0% after rigid body refinement of the obtained initial model which moves the two CH2 domains and two CH3 domains of the Fc, and the extracellular region of FcγRIIa type R. Then, structural model refinement was achieved by repeating structural refinement using program REFMAC5 (Acta Cryst. (2011) D67, 355-367) followed by revision of the model performed using program Coot (Acta Cryst. (2010) D66, 486-501) with reference to the electron density maps where the coefficients 2Fo-Fc and Fo-Fc were calculated using experimentally determined structural factor Fo, structural factor Fc calculated according to the model, and the phases calculated according to the model. Finally, as a result of incorporation of water molecules into the model based on the electron density maps which use 2Fo-Fc or Fo-Fc as the coefficient, and the following refinement, the crystallographic reliability factor, R values and the Free R value of the model containing 4758 non-hydrogen atoms became 26.3% and 29.8% to 24838 diffraction intensity data from 25 Å to 2.87 Å resolution, respectively.

[Example 4] Fc Variants Whose Alteration Sites were Determined Based on Crystal Structures As shown in Example 3, it was suggested that electrostatic interaction between Asp at position 268 (EU numbering) and Arg at position 292 (EU numbering) is formed as a result of structural changes nearby which accompany introduction of the P271G alteration into the CH2 domain B of the FcgRIIb-binding-enhanced variant Fc(P208) (FIG. 9). This interaction functions to stabilize the loop structure of positions 266 to 271 (EU numbering), and as a result it may have contributed to the enhancement of FcγRIIb binding. Accordingly, it was examined whether strengthening the electrostatic interaction with Arg at position 292 (EU numbering) to stabilize this loop structure by altering Asp at position 268 (EU numbering) to Glu leads to enhancement of interaction with FcgRIIb. Furthermore, as shown in FIG. 8, Tyr at position 160 (EU numbering) of FcgRIIb forms hydrogen bonds with the main chain of Asp at position 237 (EU numbering) of the Fc(P208) CH2 domain A, and plays an important role in binding with FcgRIIb. While the side chain portion of Asp at position 237 (EU numbering) does not form a particular interaction, Ile at position 332 (EU numbering), Glu at position 333 (EU numbering), and Lys at position 334 (EU numbering) are positioned nearby in the molecule. Examination of whether substituting these sites with hydrophilic residues to strengthen the interaction with Asp at position 237 (EU numbering) and stabilize the loop structure near this residue will enhance interaction with Tyr at position 160 of FcγRIIb were carried out.

Variants were produced by introducing H268E, I332T, I332S, I332E, I332K, E333K, E333R, E333S, E333T, K334S, K334T, and K334E individually into IL6R-BP230/IL6R-L (SEQ ID NO: 27/SEQ ID NO: 21) which was produced in Example 2. IL6R-L (SEQ ID NO: 21) was commonly used as the antibody L chain. These variants were used for antibody expression and purification according to the method of Reference Example 1, and binding to each FcgR (FcgRIa, FcgRIIa type H, FcgRIIa type R, FcgRIIb, and FcgRIIIa type V) was assessed using the method of Reference Example 2.

The KD of each variant to each FcgR is shown in Table 2. In the table, "alteration" refers to an alteration introduced into IL6R-BP3 (SEQ ID NO: 23). IL6R-B3/IL6R-L which is used as the template to produce IL6R-BP230 is indicated by an asterisk (*). "KD (IIb) of parent polypeptide/KD (Ib) of altered polypeptide" in the table shows the value obtained by dividing the KD value of IL6R-B3/IL6R-L for FcgRIIb by the KD value of each variant for FcgRIIb. Meanwhile, "KD (IIaR) of parent polypeptide/KD (IIaR) of altered polypeptide" shows the value obtained by dividing the KD value of IL6R-B3/IL6R-L for FcgR IIaR by the KD value of each variant for FcgR IIaR. "KD (IIaR)/KD (IIb)" shows the value obtained by dividing the KD of each variant for FcgRIIaR by the KD of the variant for FcgRIIb. The greater the value, the higher the selectivity to FcgRIIb is. In Table 2, values shown in bold italicized font are ones for which the binding of FcgR to IgG was concluded to be too weak to analyze correctly by kinetic analysis and thus was calculated using:

$$KD = C \cdot R_{max}/(R_{eq}-RI)-C \qquad \text{[Equation 2]}$$

described in Reference Example 2.

TABLE 2

| VARIANT NAME | ALTERATION ADDED TO IL6R-BP230 | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|---|
| IL6R-G1d/IL6R-1L |  | 3.2E-10 | 1.0E-06 | 6.7E-07 | 2.6E-06 | 3.5E-07 | 0.4 | 1.1 | 1.2 |
| IL6R-B3/IL6R-L | * | 4.2E-1.0 | 1.1E-06 | 7.7E-07 | 3.1E-06 | 3.3E-07 | 0.3 | 1.0 | 1.0 |
| IL6R-BP230/IL6R-L |  | 1.4E-08 | 5.7E-07 | *9.6E-06* | 2.1E-08 | *6.7E-05* | 27.5 | 1.9 | 149.0 |
| IL6R-BP264/IL6R-L | H268E | 6.5E-09 | 4.8E-07 | *9.2E-06* | 1.2E-08 | *5.2E-05* | 40.6 | 2.3 | 265.0 |
| IL6R-BP384/IL6R-L | K334R | 3.0E-09 | 1.3E-06 | *1.8E-05* | 7.1E-08 | *4.5E-05* | 17.7 | 0.9 | 43.5 |
| IL6R-BP390/IL6R-L | I332S | 1.6E-09 | 4.9E-07 | *7.3E-06* | 2.1E-08 | *2.9E-05* | 22.9 | 2.2 | 144.9 |
| IL6R-BP391/IL6R-L | I332T | 9.6E-10 | 3.4E-07 | *4.4E-06* | 1.3E-08 | *1.9E-05* | 26.6 | 3.2 | 242.2 |
| IL6R-BP392/IL6R-L | I332K | 7.9E-09 | 7.3E-06 | *2.8E-05* | 9.9E-07 | *2.9E-05* | 7.3 | 0.2 | 3.1 |
| IL6R-BP393/IL6R-L | I332R | 1.1E-08 | 3.9E-06 | *4.6E-05* | 2.7E-06 | *4.8E-05* | 1.4 | 0.3 | 1.2 |
| IL6R-BP465/IL6R-L | E333K | 1.6E-08 | 6.1E-07 | *1.5E-05* | 2.1E-08 | *6.7E-05* | 29.8 | 1.8 | 151.2 |
| IL6R-BP466/IL6R-L | E333R | 1.5E-08 | 5.2E-07 | *1.1E-05* | 1.7E-08 | *2.9E-05* | 30.4 | 2.1 | 181.3 |
| IL6R-BP467/IL6R-L | K334S | 8.9E-10 | 1.1E-06 | *1.2E-05* | 4.1E-08 | *3.2E-05* | 25.8 | 1.0 | 75.4 |
| IL6R-BP468/IL6R-L | K334T | 9.7E-10 | 1.1E-06 | *9.7E-06* | 4.0E-08 | *2.7E-05* | 26.3 | 1.0 | 77.7 |

TABLE 2-continued

| VARIANT NAME | ALTERATION ADDED TO IL6R-BP230 | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|---|
| IL6R-BP469/IL6R-L | E333S | 1.3E−08 | 6.0E−07 | *1.2E-05* | 2.3E−08 | *3.7E-05* | 26.4 | 1.8 | 136.6 |
| IL6R-BP470/IL6R-L | E333T | 1.5E−08 | 4.9E−07 | *1.0E-05* | 1.6E−08 | *3.7E-05* | 30.6 | 2.2 | 192.5 |

Both FcgRIIb binding and FcgRIIb selectivity of IL6R-BP264/IL6R-L, IL6R-BP465/IL6R-L, IL6R-BP466/IL6R-L, and IL6R-BP470, resulting from introducing H268E, E333K, E333R, and E333T, respectively, into IL6R-BP230/IL6R-L were increased as compared to those of IL6R-BP230/IL6R-L. The FcgRIIb selectivity of IL6R-BP391/IL6R-L introduced with the I332T was reduced while its FcgRIIb binding was increased as compared to IL6R-BP230/IL6R-L.

[Example 5] Introduction of Comprehensive Alterations into the Area Around Position 271 (EU Numbering)

When the X-ray crystal structure of the complex formed between Fc(P238D) carrying the P238D alteration and the FcγRIIb extracellular region and the X-ray crystal structure of the complex formed between Fc(P208) and the FcγRIIb extracellular region were compared, the structure near position 271 (EU numbering) showed the greatest structural change (FIG. 9). As shown in Reference Example 8, in Fc(P238D), it was suggested that when Asp at position 270 (EU numbering) forms a strong electrostatic interaction with Arg at position 131 of FcγRIIb, the Pro at position 271 (EU numbering) portion may be stereochemically strained. In the structure of Fc(P208)/FcγRIIb, introduction of the P271G alteration causes positional changes at the main-chain level to remove this structural strain. As a result, the structure near position 271 (EU numbering) may have been largely changed. If alterations that further stabilize this changed structure can be efficiently introduced, entropic energy loss accompanying formation of electrostatic interaction with Arg at position 131 of FcγRIIb can be reduced, and this may lead to enhancement of binding activity. Accordingly, comprehensive alterations were introduced into the area around position 271 (EU numbering) to screen for alterations that show effects of enhancing binding to FcgRIIb or improving selectivity to FcgRIIb.

IL6R-BP267 (SEQ ID NO: 29) produced by introducing E233D, G237D, P238D, H268E, and P271G into IL6R-B3 (SEQ ID NO: 23) was used as the template for introducing comprehensive alterations. Amino acids at positions 264, 265, 266, 267, 269, and 272 (EU numbering)) in IL6R-BP267 were individually substituted with any of the 18 amino acids other than the original amino acids and Cys. IL6R-L (SEQ ID NO: 21) was commonly used as the antibody L chain. These variants were used for antibody expression and purification according to the method of Reference Example 1, and binding to each FcgR (FcgRIa, FcgRIIa type H, FcgRIIa type R, FcgRIIb, and FcgRIIIa type V) was assessed using the method of Reference Example 2. From among the obtained variants, those that enhanced FcgRIIb-binding or improved selectivity to FcgRIIb compared to those of the IL6R-BP267/IL6R-L prior to alteration introduction are summarized in Table 3.

TABLE 3

| VARIANT NAME | ALTERATION ADDED TO IL6R-BP230 | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|---|
| IL6R-BP/IL6R-L | * | 4.2E−10 | 1.1E−06 | 7.7E−07 | 3.1E−06 | 3.3E−07 | 0.3 | 1.0 | 1.0 |
| IL6R-BP267/IL6R-L |  | 4.0E−09 | 1.7E−06 | *1.9E-05* | 1.3E−07 | *5.3E-05* | 13.0 | 0.7 | 24.3 |
| IL6R-BP348/IL6R-L | S267A | 5.5E−10 | 7.0E−07 | *2.2E-05* | 4.6E−08 | *2.7E-05* | 15.3 | 1.5 | 67.6 |
| IL6R-BP300/IL6R-L | V264I | 9.6E−09 | 6.9E−07 | *2.2E-05* | 5.8E−08 | *5.6E-05* | 11.9 | 1.6 | 53.3 |
| IL6R-BP367/IL6R-L | E269D | 3.1E−09 | 1.2E−06 | *4.6E-05* | 1.0E−07 | *5.3E-05* | 11.7 | 0.9 | 30.6 |
| IL6R-BP350/IL6R-L. | S267E | 8.9E−10 | 1.5E−07 | *8.3E-05* | 1.0E−07 | *8.9E-05* | 1.5 | 7.0 | 30.0 |
| IL6R-BP333/IL6R-L | V266F | 9.1E−09 | 1.5E−06 | *3.4E-05* | 1.2E−07 | *5.9E-05* | 12.5 | 0.7 | 26.4 |
| IL6R-BP352/IL6R-L | S267G | 1.8E−09 | 1.9E−06 | *2.8E-05* | 1.2E−07 | *4.3E-05* | 15.7 | 0.6 | 25.3 |
| IL6R-BP339/IL6R-L | V266M | 4.6E−09 | 1.4E−06 | *1.8E-05* | 1.3E−07 | *2.4E-05* | 11.3 | 0.8 | 24.5 |
| IL6R-BP520/IL6R-L | E272M | 3.9E−09 | 3.0E−06 | *3.1E-05* | 1.7E−07 | *4.7E-05* | 17.5 | 0.4 | 17.8 |
| IL6R-BP523/IL6R-L | E272Q | 3.7E−09 | 2.7E−06 | *2.9E-05* | 1.7E−07 | *4.1E-05* | 15.9 | 0.4 | 18.4 |
| IL6R-BP313/IL6R-L | D265E | 2.6E−08 | 1.3E−05 | *4.7E-05* | 8.4E−07 | *3.8E-05* | 15.6 | 0.1 | 3.7 |
| IL6R-BP513/IL6R-L | E272O | 3.8E−09 | 1.7E−06 | *3.9E-05* | 1.1E−07 | *7.5E-05* | 15.4 | 0.6 | 28.1 |
| IL6R-BP521/IL6R-L | E272N | 3.6E−09 | 2.9E−06 | *4.4E-05* | 1.9E−07 | *9.9E-05* | 15.2 | 0.4 | 16.0 |
| IL6R-BP338/IL6R-L | V266L | 1.5E−08 | 2.2E−06 | *2.2E-05* | 1.5E−07 | *2.5E-05* | 15.0 | 0.5 | 21.3 |
| IL6R-BP517/IL6R-L | E272I | 3.2E−09 | 2.1E−06 | *2.2E-05* | 1.4E−07 | *3.5E-05* | 14.7 | 0.5 | 21.5 |
| IL6R-BP514/IL6R-L | E272F | 4.3E−09 | 3.0E−06 | *6.4E-05* | 2.1E−07 | *9.1E-05* | 14.0 | 0.4 | 14.6 |

The KD value of each variant to each FcgR is shown in Table 3. In the table, "alteration added to IL6R-BP267" refers to an alteration introduced into IL6R-BP267 (SEQ ID NO: 29), which was used as a template. IL6R-B3/IL6R-L which is used as the parent to produce IL6R-B3 is indicated by asterisk (*). In the table, "KD (IIb) of parent polypeptide/ KD (IIb) of altered polypeptide" shows the value obtained by dividing the KD value of IL6R-B3/IL6R-L for FcgRIIb by the KD value of each variant for FcgRIIb. Meanwhile, "KD (IIaR) of parent polypeptide/KD (IIaR) of altered polypeptide" shows the value obtained by dividing the KD of IL6R-B3/IL6R-L for FcgRIIaR by the KD of each variant for FcgR IIaR. "KD (IIaR)/KD (IIb)" shows the value obtained by dividing the KD value of each variant for FcgRIIaR by the KD value of the variant for FcgRIIb. The greater the value is, the higher the selectivity to FcgRIIb is. In Table 3, the values shown in bold italicized font are ones for which the binding of FcgR to IgG was concluded to be too weak to analyze correctly by kinetic analysis and thus was calculated using:

$$KD = C \cdot R_{max}/(R_{eq}-RI) - C \quad \text{[Equation 2]}$$

described in Reference Example 2.

All the binding of variants shown in Table 3 to FcgRIa, FcgRIIaH, and FcgRIIIaV were comparable or reduced as compared to that of IL6R-B3/IL6R-L. Meanwhile, the FcgRIIb binding of variants resulting from adding the S267A, V264I, E269D, S267E, V266F, S267G, and V266M, respectively, to IL6R-BP267/IL6R-L was increased as compared to that of IL6R-BP267/IL6R-L prior to addition of alteration. Meanwhile, the KD (IIaR)/KD (IIb) values of variants resulting from adding the S267A, S267G, E272M, E272Q, D265E, E272D, E272N, V266L, E272, and E272F alterations, respectively, to IL6R-BP267/IL6R-L were increased as compared to that of IL6R-BP267/IL6R-L prior to addition of alteration, demonstrating the effect to improve the FcgRIIb selectivity.

[Example 6] Enhancement of the FcgRIIb Binding by Introducing Alterations into CH3 Region An alteration substituting Leu for Pro at position 396 (EU numbering) has been reported to enhance the FcgRIIb binding (Cancer Res. (2007) 67, 8882-8890). Position 396 (EU numbering) is present at a position which is not directly involved in the interaction with FcgR. However, the amino acid can be assumed to have an effect on the interaction with FcgR by changing the antibody structure. Thus, the present inventors assessed whether the FcgRIIb binding is enhanced or its FcgRIIb selectivity is increased by comprehensive introduction of amino acid alterations at position 396 (EU numbering).

IL6R-BP423 (SEQ ID NO: 33) produced by introducing E233D, G237D, P238D, S267A, H268E, P271G, and A330R into IL6R-B3 (SEQ ID NO: 23) was used as the template. Variants were produced by substituting the amino acid at position 396 (EU numbering)) in IL6R-BP423 with any of the 18 amino acids other than the original amino acid and cysteine. IL6R-L (SEQ ID NO: 21) was commonly used as the antibody L chain. These variants were used for antibody expression and purification according to the method of Reference Example 1, and binding to each FcgR (FcgRIa, FcgRIIa type H, FcgRIIa type R, FcgRIIb, and FcgRIIIa type V) was assessed using the method of Reference Example 2. Binding of the obtained variants to each FcgR are summarized in Table 4.

TABLE 4

| VARIANT NAME | ALTERATION ADDED TO IL6R-BP423 | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|---|
| IL6R-G1d/IL6R-L |  | 3.2E−10 | 1.0E−06 | 6.7E−07 | 2.6E−06 | 3.5E−07 | 0.4 | 1.1 | 1.2 |
| IL6R-B3/IL6R-L | * | 4.2E−10 | 1.1E−06 | 7.7E−07 | 3.1E−06 | 3.3E−07 | 0.3 | 1.0 | 1.0 |
| IL6R-BP423/IL6R-L |  | 7.78-10 | 1.8E−07 | *2.0E-06* | 5.1E−09 | *1.6E-05* | 34.2 | 6.3 | 604 |
| IL6R-BP447/IL6R-L | P396A | 9.0E−10 | 1.6E−07 | *2.0E-06* | 5.3E−09 | *2.5E-05* | 29.7 | 7.0 | 584 |
| IL6R-BP448/IL6R-L | P396D | 7.5E−10 | 1.3E−07 | *1.4E-06* | 4.1E−09 | *9.7E-06* | 31.7 | 8.5 | 759 |
| IL6R-BP449/IL6R-L | P396E | 9.1E−10 | 1.4E−07 | *1.5E-06* | 4.6E−09 | *1.2E-05* | 29.8 | 8.0 | 667 |
| IL6R-BP450/IL6R-L | P396F | 8.4E−10 | 1.2E−07 | *1.3E-06* | 4.1E−09 | *9.6E-06* | 29.4 | 9.2 | 763 |
| IL6R-BP451/IL6R-L | P396G | 9.8E−10 | 1.8E−07 | *2.0E-06* | 6.2E−09 | *1.2E-05* | 29.2 | 6.1 | 499 |
| IL6R-BP452/IL6R-L | P396H | 7.5E−10 | 1.3E−07 | *1.5E-06* | 5.1E−09 | *1.1E-05* | 25.9 | 8.3 | 602 |
| IL6R-BP453/IL6R-L | P396I | 7.5E−10 | 1.2E−07 | 9.3E−07 | 4.6E−09 | *7.4E-06* | 25.5 | 9.4 | 675 |
| IL6R-BP454/IL6R-L | P396K | 8.2E−09 | 1.3E−07 | *1.4E-06* | 4.8E−09 | *9.1E-06* | 27.5 | 8.4 | 649 |
| IL6R-BP455/IL6R-L | P396L | 7.5E−10 | 1.3E−07 | *1.6E-06* | 4.0E−09 | *8.5E-06* | 31.8 | 8.6 | 767 |
| IL6R-BP456/IL6R-L | P396M | 6.0E−10 | 1.2E−07 | *2.0E-06* | 3.5E−09 | *9.2E-06* | 35.3 | 8.9 | 888 |
| IL6R-BP457/IL6R-L | P396N | 9.1E−10 | 1.5E−07 | *2.6E-06* | 5.2E−09 | *1.3E-05* | 28.9 | 7.3 | 591 |
| IL6R-BP458/IL6R-L | P396Q | 7.8E−10 | 1.4E−07 | *1.4E-06* | 4.5E−09 | *1.1E-05* | 31.1 | 7.9 | 687 |
| IL6R-BP459/IL6R-L | P396R | 1.1E−09 | 1.5E−07 | *1.4E-06* | 5.1E−09 | *1.2E-05* | 28.9 | 7.5 | 607 |
| IL6R-BP460/IL6R-L | P396S | 8.7E−10 | 1.6E−07 | *3.2E-06* | 6.5E−09 | *1.4E-05* | 25.2 | 6.7 | 478 |
| IL6R-BP461/IL6R-L | P396T | 1.3E−09 | 1.3E−07 | *1.5E-06* | 5.1E−09 | *9.9E-06* | 24.4 | 8.8 | 602 |
| IL6R-BP462/IL6R-L | P396V | 9.7E−10 | 1.3E−07 | *1.4E-06* | 5.2E−09 | *9.0E-06* | 25.0 | 8.5 | 593 |
| IL6R-BP463/IL6R-L | P396W | 1.3E−09 | 1.6E−07 | *1.9E-06* | 5.6E−09 | *1.2E-05* | 28.1 | 7.0 | 554 |
| IL6R-BP464/IL6R-L | P396Y | 1.1E−09 | 1.3E−07 | *2.1E-06* | 4.0E−09 | *9.9E-06* | 31.5 | 8.7 | 773 |

In the Table, "alteration added to IL6R-BP423" refers to an alteration introduced into IL6R-BP423. IL6R-B3/IL6R-L which was used as the template to produce IL6R-BP423 is indicated by asterisk (*). In the table, "KD (IIb) of parent polypeptide/KD (IIb) of altered polypeptide" shows the value obtained by dividing the KD value of IL6R-B3/ IL6R-L for FcgRIIb by the KD value of each variant for FcgRIIb. Meanwhile, "KD (IIaR) of parent polypeptide/KD (IIaR) of altered polypeptide" shows the value obtained by dividing the KD value of IL6R-B3/IL6R-L for FcgR IIaR by the KD value of each variant for FcgR IIaR. "KD (IIaR)/KD (IIb)" shows the value obtained by dividing the KD of each variant for FcgRIIaR by the KD of the variant for FcgRIIb. The greater the value, the higher the selectivity to FcgRIIb is. In Table 4, the values shown in bold italicized font are ones for which the binding of FcgR to IgG was concluded to be too weak to analyze correctly by kinetic analysis and thus was calculated using:

$$KD = C \cdot R_{max}/(R_{eq}-RI)-C \qquad \text{[Equation 2]}$$

described in Reference Example 2.

The result shown in Table 4 demonstrates that: the FcgRIIb-binding activity of IL6R-BP456/IL6R-L resulting from introducing P396M into IL6R-BP423/IL6R-L, IL6R-BP455/IL6R-L resulting from introducing P396L into IL6R-BP423/IL6R-L, IL6R-BP464/IL6R-L resulting from introducing P396Y into IL6R-BP423/IL6R-L, IL6R-BP450/IL6R-L resulting from introducing P396F into IL6R-BP423/IL6R-L, IL6R-BP448/IL6R-L resulting from introducing P396D into IL6R-BP423/IL6R-L, IL6R-BP458/IL6R-L resulting from introducing P396Q into IL6R-BP423/IL6R-L, IL6R-BP453/IL6R-L resulting from introducing P396I into IL6R-BP423/IL6R-L, IL6R-BP449/IL6R-L resulting from introducing P396E into IL6R-BP423/IL6R-L, IL6R-BP454/IL6R-L resulting from introducing P396K into IL6R-BP423/IL6R-L, and IL6R-BP459/IL6R-L resulting from introducing P396R into IL6R-BP423/IL6R-L was all increased as compared to that of IL6R-BP423/IL6R-L prior to introduction of the alterations. Meanwhile, the KD (IIaR)/KD (IIb) value of IL6R-BP456/IL6R-L resulting from introducing P396M into IL6R-BP423/IL6R-L was larger as compared to that of IL6R-BP423/IL6R-L prior to introduction of the alteration, demonstrating the improved FcgRIIb selectivity. As seen in Table 4, the affinity of the prepared variants to FcgRIa, FcgRIIaH, and FcgRIIIaV was all lower than that of IL6R-B3/IL6R-L, which was the parent polypeptide.

[Example 7] Preparation of Variants with Enhanced FcgRIIb Binding Using Subclass Sequences Subclass exists in human IgG and its FcgR binding profile varies. The present inventors assessed whether the difference in the affinity to each FcgR between IgG1 and IgG4 could be utilized to increase the FcgRIIb binding and/or improve the selectivity.

First, IgG1 and IgG4 were analyzed for their affinity to each FcgR. IL6R-G4d (SEQ ID NO: 30) containing G4d was constructed as the antibody H chain. G4d lacks the C-terminal Gly and Lys and contains a substitution of Pro for Ser at position 228 (EU numbering) in human IgG4. IL6R-L (SEQ ID NO: 21) was commonly used as the antibody L chain. IL6R-G1d/IL6R-L and IL6R-G4d/IL6R-L were expressed and purified according to the method described in Reference Example 1. These were assessed for their binding to each FcgR (FcgRIa, FcgRIIa type H, FcgRIIa type R, FcgRIIb, or FcgRIIIa type V) by the method described in Reference Example 2. The binding of the resulting variants to each FcgR is summarized in Table 5.

TABLE 5

| VARIANT NAME | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) |
|---|---|---|---|---|---|
| IL6R-G1d/ IL6R-L | 1.2E-10 | 9.7E-07 | 6.5E-07 | 3.9E-06 | 4.2E-07 |
| IL6R-G4d/ IL6R-L | 6.6E-10 | 2.1E-06 | 3.4E-06 | 2.6E-06 | 3.4E-06 |

Compared to IL6R-G1d/IL6R-L, IL6R-G4d/IL6R-L was found to have 1.5-fold stronger binding to FcgRIIb and 2.2-fold weaker binding to FcgRIIaR. Furthermore, compared to IL6R-G1d/IL6R-L, IL6R-G4d/IL6R-L had weaker affinity to FcgRIa, FcgRIIaH, and FcgRIIIaV. The above-mentioned results revealed that compared to IL6R-G1d, IL6R-G4d has excellent selectivity and binding to FcgRIIb.

FIG. 14 shows the comparison of the sequences of G1d and G4d from CH1 to the C terminus (positions 118 to 445 (EU numbering)). The boxed amino acids in FIG. 14 show residues that are different between G1 d and G4d. Several sites predicted to be involved in interaction with FcgR were selected from among these different amino acids, and whether further improvement of selectivity and binding is possible was examined by transferring the sequence of G4d having excellent selectivity and binding to FcgRIIb into FcgRIIb-enhanced variants.

Specifically, IL6R-BP473 was produced by introducing A327G into IL6R-BP230, IL6R-BP472 was produced by introducing A330S into IL6R-BP230, IL6R-BP471 was produced by introducing P331S into IL6R-BP230, IL6R-BP474 was produced by introducing A330S and P331S into IL6R-BP230, IL6R-BP475 was produced by introducing A327G and A330S into IL6R-BP230, IL6R-BP476 was produced by introducing A327G, A330S, and P331S into IL6R-BP230, and IL6R-BP477 was produced by introducing A327G and P331S into IL6R-BP230. Furthermore IL6R-BP478 (SEQ ID NO: 31) was produced by substituting Ala at position 118 to Thr at position 225 (EU numbering) in IL6R-BP230 with a G4d sequence (Ala at position 118 to Pro at position 222 (EU numbering)). IL6R-L (SEQ ID NO: 21) was commonly used as the antibody L chain. These variants were used for antibody expression and purification according to the method of Reference Example 1, and binding to each FcgR (FcgRIa, FcgRIIa type H, FcgRIIa type R, FcgRIIb, and FcgRIIIa type V) was assessed using the method of Reference Example 2.

The KD value of each variant to each FcgR is shown in Table 6. "KD (IIb) of parent polypeptide/KD (IIb) of altered polypeptide" in the table shows the value obtained by dividing the KD value of IL6R-B3/IL6R-L for FcgRIIb by the KD value of each variant for FcgRIIb. "Alteration(s) added to IL6R-BP230" refers to an alteration introduced into IL6R-BP230. IL6R-B3/IL6R-L used as the template to produce IL6R-BP230 is indicated by *1. Meanwhile, IL6R-BP478 (SEQ ID NO: 31), in which the segment from Ala at position 118 up to Thr at position 225 (EU numbering) in IL6R-BP230 is substituted with the sequence of G4d (Ala at position 118 up to Pro at position 222 (EU numbering)), is indicated by *2. "KD (IIaR) of parent polypeptide/KD (IIaR) of altered polypeptide" shows the value obtained by dividing the KD value of IL6R-B3/IL6R-L for FcgR IIaR by the KD value of the variant for FcgRIIaR. "KD (IIaR)/KD (IIb)" shows the value obtained by dividing the KD of each variant for FcgRIIaR by the KD of the variant for FcgRIIb. The greater the value, the higher the selectivity to FcgRIIb is. In Table 6, the values shown in bold italicized font are ones for which the binding of FcgR to IG was concluded to be too weak to analyze correctly by kinetic analysis and thus was calculated using:

$$KD = C \cdot R_{max}/(R_{eq}-RI)-C \qquad \text{[Equation 2]}$$

described in Reference Example 2.

TABLE 6

| VARIANT NAME | ALTERATION(S) ADDED TO IL6R-BP230 | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|---|
| IL6R-G1d/IL6R-L | | 3.2E−10 | 1.0E−06 | 6.7E−07 | 2.6E−06 | 3.5E−07 | 0.4 | 1.1 | 1.2 |
| IL6R-B3/IL6R-L | *1 | 4.2E−10 | 1.1E−06 | 7.7E−07 | 3.1E−06 | 3.3E−07 | 0.3 | 1.0 | 1.0 |
| IL6R-BP230/IL6R-L | | 1.4E−08 | 5.7E−07 | *9.6E-06* | 2.1E−08 | *6.7E-05* | 27.5 | 1.9 | 149.0 |
| IL6R-BP471/IL6R-L | P331S | 7.3E−09 | 8.0E−07 | *1.2E-05* | 3.5E−08 | *7.1E-05* | 22.7 | 1.4 | 88.1 |
| IL6R-BP472/IL6R-L | A330S | 5.2E−09 | 3.3E−06 | *2.4E-05* | 1.5E−07 | *3.8E-05* | 21.5 | 0.3 | 20.3 |
| IL6R-BP473/IL6R-L | A327G | 6.2E−09 | 3.8E−07 | *4.8E-06* | 1.8E−08 | *3.6E-05* | 21.1 | 2.9 | 172.2 |
| IL6R-BP474/IL6R-L | A330S/P331S | 4.1E−09 | 3.0E−06 | *3.7E-05* | 1.8E−07 | *5.5E-05* | 16.6 | 0.4 | 16.9 |
| IL6R-BP475/IL6R-L | A327G/A330S | 4.9E−09 | 1.0E−06 | *1.5E-05* | 1.1E−07 | *4.6E-05* | 9.7 | 1.1 | 29.2 |
| IL6R-BP476/IL6R-L | A327G/A330S/P331S | 5.9E−09 | 1.3E−06 | *1.9E-05* | 1.3E−07 | *4.9E-05* | 9.7 | 0.9 | 23.7 |
| IL6R-BP477/IL6R-L | A327G/P331S | 9.2E−09 | 5.1E−07 | *7.6E-06* | 3.7E−08 | *5.8E-05* | 14.0 | 2.2 | 84.9 |
| IL6R-BP478/IL6R-L | *2 | 7.7E−09 | 5.4E−07 | *6.7E-06* | 1.9E−08 | *3.5E-05* | 28.0 | 2.0 | 160.6 |

Of the variants shown in Table 6, IL6R-BP473/IL6R-L introduced with A327G showed FcgRIIb binding increased by 1.2 times compared to that of IL6R-BP230/IL6R-L. Compared to IL6R-BP230/IL6R-L, IL6R-BP478/IL6R-L produced by substituting Ala at position 118 to Thr at position 225 (EU numbering) in IL6R-BP230 with a G4d sequence (Ala at position 118 to Pro at position 222 (EU numbering)), showed 1.1-fold increase in both FcgRIIb-binding and FcgRIIaR-binding. Compared to IL6R-B3/IL6R-L which is the parent peptide, all variants had lower affinity to FcgRIa, FcgRIIaH, and FcgRIIIaV.

Furthermore, as shown in FIG. 14, the other sites where the amino acids are different between G1d and G4d include positions 268, 274, 296, 355, 356, 358, 409, 419, and 445 (EU numbering). Therefore, by substituting these sites with IgG4-derived amino acids, selectivity and binding to FcgRIIb may be enhanced.

In the examination carried out so far, transferring A327G, which is in the human IgG4 sequence, to the variant IL6R-BP230/IL6R-L was shown to enhance FcγRIIb-binding activity. A further examination was performed for portions that do not match between the IgG4 and IgG1 sequences.

Specifically, variants were produced by introducing the following alterations into IL6R-BP230 as the antibody H chain: K274Q was introduced to produce IL6R-BP541; Y296F was introduced to produce IL6R-BP542; H268Q was introduced to produce IL6R-BP543; R355Q was introduced to produce IL6R-BP544; D356E was introduced to produce IL6R-BP545; L358M was introduced to produce IL6R-BP546; K409R was introduced to produce IL6R-BP547; and Q419E was introduced to produce IL6R-BP548. Meanwhile, IL6R-L was used as the common antibody L chain. Antibodies that contain the above heavy chain variant and the light chain IL6R-L were purified according to the methods described in Reference Example 1. The purified antibodies were assessed for their binding to each FcγR (FcγRIa, FcγRIIaH, FcγRIIaR, FcγRIIb, or FcγRIIIaV) by the method of Reference Example 2.

The KD of each variant for each FcγR is shown in Table 7. In this Table, "parent polypeptide KD(IIb)/altered polypeptide KD(IIb)" refers to a value obtained by dividing the KD value of IL6R-B3/IL6R-L for FcγRIIb by the KD value of each variant for FcγRIIb. In the Table, "alterations added to IL6R-BP230" indicate alterations introduced into IL6R-BP230. Meanwhile, IL6R-B3/IL6R-L used as a template when producing IL6R-BP230 was indicated as *1. "Parent polypeptide KD(IIaR)/altered polypeptide KD(IIaR)" refers to a value obtained by dividing the KD value of IL6R-B3/IL6R-L for FcγRIIaR by the KD value of each variant for FcγRIIaR. "KD(IIaR)/KD(IIb)" is a value obtained by dividing the KD of each variant for FcγRIIaR by the KD of this variant for FcγRIIb. The larger this value is, the higher the selectivity to FcγRIIb is. The Table 7 values shown in bold italicized font were calculated using the following equation $$KD = C \cdot R_{max}/(R_{eq}-RI)-C \quad \text{[Equation 2]}$$

shown in Reference Example 2 since the binding of FcγR to IgG was determined to be too weak to analyze correctly by kinetic analysis.

TABLE 7

| VARIANT NAME | ALTERATION(S) ADDED TO IL6R-BP230 | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|---|
| IL6R-G1d/IL6R-L | | 3.2E−10 | 1.0E−06 | 6.7E−07 | 2.6E−06 | 3.5E−07 | 0.4 | 1.1 | 1.2 |
| IL6R-B3/IL6R-L | *1 | 4.2E−10 | 1.1E−06 | 7.7E−07 | 3.1E−06 | 3.3E−07 | 0.3 | 1.0 | 1.0 |
| IL6R-B230/IL6R-L | | 1.0E−08 | 4.9E−07 | *9.7E-06* | 1.8E−08 | *3.9E-05* | 28.0 | 2.2 | 175.6 |
| IL6R-BP541/IL6R-L | K274Q | 1.1E−08 | 4.5E−07 | *9.3E-06* | 1.6E−08 | *4.1E-05* | 27.8 | 2.4 | 189.6 |
| IL6R-BP542/IL6R-L | Y296F | 1.3E−08 | 4.9E−07 | *9.7E-06* | 2.0E−08 | *4.3E-05* | 24.4 | 2.2 | 153.7 |

TABLE 7-continued

| VARIANT NAME | ALTERATION(S) ADDED TO IL6R-BP230 | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|---|
| IL6R-BP543/ IL6R-L | H268Q | 2.3E−08 | 5.6E−07 | *7.4E-06* | 2.0E−08 | *4.6E-05* | 27.3 | 1.9 | 151.5 |
| IL6R-BP544/ IL6R-L | R355Q | 9.8E−09 | 4.8E−07 | *1.2E-05* | 1.7E−08 | *4.5E-05* | 28.8 | 2.2 | 183.9 |
| IL6R-BP545/ IL6R-L | D356E | 9.9E−09 | 5.7E−07 | *9.1E-06* | 1.7E−08 | *4.5E-05* | 32.7 | 1.9 | 178.6 |
| IL6R-BP546/ IL6R-L | L358M | 9.0E−09 | 5.0E−07 | *1.0E-05* | 1.5E−08 | *3.7E-05* | 32.8 | 2.2 | 204.6 |
| IL6R-BP547/ IL6R-L | K409R | 1.2E−08 | 4.9E−07 | *7.5E-06* | 1.9E−08 | *3.5E-05* | 25.5 | 2.2 | 162.6 |
| IL6R-BP548/ IL6R-L | Q419E | 1.2E−08 | 5.0E−07 | *9.4E-06* | 1.9E−08 | *3.4E-05* | 26.2 | 2.2 | 161.8 |

As shown in Table 7, compared to the IL6R-BP230/IL6R-L prior to alteration, IL6R-BP541/IL6R-L produced by introducing K274Q into IL6R-BP230/IL6R-L, IL6R-BP544/IL6R-L produced by introducing R355Q into IL6R-BP230/IL6R-L, IL6R-BP545/IL6R-L produced by introducing D356E into IL6R-BP230/IL6R-L, and IL6R-BP546/IL6R-L produced by introducing L358M into IL6R-BP230/IL6R-L, had enhanced FcγRIIb-binding. Among them, IL6R-BP544/IL6R-L produced by introducing R355Q into IL6R-BP230/IL6R-L, IL6R-BP545/IL6R-L produced by introducing D356E into IL6R-BP230/IL6R-L, and IL6R-BP546/IL6R-L produced by introducing L358M into IL6R-BP230/IL6R-L show increased KD(IIaR)/KD(IIb) values when compared to that of the IL6R-BP230/IL6R-L prior to alteration, showing that these alterations enhance selectivity to FcγRIIb as well.

[Example 8] Examination of Combining Alterations that Bring about Improvement of Selectivity and Enhancement of Binding to FcgRIIb The combinations of alterations that were found in the examinations carried out so far to improve selectivity or binding activity to FcγRIIb were examined to achieve further optimization.

Combination of alterations that achieves improvement of selectivity and/or enhancement of binding to FcγRIIb in the examinations carried out so far was introduced into IL6R-B3. As a comparative control, IL6R-BP253 was produced by introducing the S267E and L328F alterations, which are known to enhance binding to FcγRIIb (Seung et al., Mol. Immunol. (2008) 45, 3926-3933), into IL6R-B3. IL6R-L was used for the antibody L chain. An antibody containing the above-mentioned heavy-chain variant and the light chain of IL6R-L, which was expressed according to the method of Reference Example 1, was purified. Binding of the purified antibody to each FcγR (FcγRIa, FcγRIIaH, FcγRIIaR, FcγRIIb, and FcγRIIIaV) was assessed using the method of Reference Example 2.

The KD of each variant for each FcγR is shown in Table 8. "Alteration" in the Table refers to alterations introduced into IL6R-B3. Meanwhile, IL6R-B3/IL6R-L used as a template for producing each of the variants is indicated by an asterisk (*). "Parent polypeptide KD(IIb)/altered polypeptide KD(IIb)" refers to a value obtained by dividing the KD value of IL6R-B3/IL6R-L for FcγRIIb by the KD value of each variant for FcγRIIb. Furthermore, "parent polypeptide KD(IIaR)/altered polypeptide KD(IIaR)" refers to a value obtained by dividing the KD value of IL6R-B3/IL6R-L for FcγR IIaR by the KD of the respective variant for FcγRIIaR. "KD(IIaR)/KD(IIb)" shows a value obtained by dividing the KD of each variant for FcγRIIaR by the KD of the respective variant for FcγRIIb. The larger this value is, the higher the selectivity to FcγRIIb compared to FcγRIIaR is. "KD(IIaH)/KD(IIb)" shows a value obtained by dividing the KD of each variant for FcγRIIaH by the KD of the respective variant for FcγRIIb. The larger this value is, the higher the selectivity to FcγRIIb compared to FcγRIIaH is. The values shown in bold italicized font in Table 8 were calculated using the following equation $$KD = C \cdot R_{max}/(R_{eq}-RI)-C \qquad \text{[Equation 2]}$$

shown in Reference Example 2 since the binding of FcγR to IgG was determined to be too weak to correctly analyze by kinetic analysis.

TABLE 8

| VARIANT | | KD (mol/L) | | | | | KD(IIaR)/ | | KD(IIaR) OF THE PARENT POLYPEPTIDE/ | KD(IIb) OF THE PARENT POLYPEPTIDE/ |
|---|---|---|---|---|---|---|---|---|---|---|
| NAME | ALTERATION | FcγRIa | FcγRIIaR | FcγRIIaH | FcγRIIb | FcγRIIIaV | KD(IIb) | KD(IIaH)/KD(IIb) | KD(IIaR) OF THE ALTERED POLYPEPTIDE | KD(IIb) OF THE ALTERED POLYPEPTIDE |
| G1d | G1d | 3.2E−10 | 1.0E−06 | 6.7E−07 | 2.6E−06 | 3.5E−07 | 0.4 | 0.3 | 1.1 | 1.2 |
| B3 | B3 | 4.2E−10 | 1.1E−06 | 7.7E−07 | 3.1E−06 | 3.3E−07 | 0.3 | 0.2 | 1.0 | 1.0 |
| BP253 | S267E/L328F | 6.7E−11 | 2.1E−09 | 1.2E−06 | 1.1E−08 | 3.6E−06 | 0.2 | 107.1 | 528.8 | 276.8 |
| BP262 | G237D/P238D/H268E/P271G | 1.0E−08 | 2.0E−06 | *4.5E−05* | 1.2E−07 | *5.6E−05* | 17.0 | 375.0 | 0.5 | 25.8 |
| BP264 | E233D/G237D/P238D/H268E/ P271G/Y296D/A330R | 7.4E−09 | 3.5E−07 | *2.8E−05* | 1.2E−08 | *2.6E−05* | 28.3 | 227.6 | 3.2 | 252.0 |
| BP265 | G237D/P238D/H268E/P271G/ Y296D/A330R | 2.3E−08 | 6.3E−07 | *1.2E−05* | 1.5E−08 | *9.6E−05* | 41.2 | 789.5 | 1.8 | 203.9 |
| BP266 | E233D/G237D/P238D/H268E/ P271G/A330R | 1.4E−08 | 3.2E−07 | *1.1E−05* | 1.8E−08 | *4.0E−05* | 18.0 | 621.5 | 3.4 | 175.1 |
| BP268 | E233D/G237D/P238D/H268E/ P271G/Y296D | 4.5E−09 | 1.8E−06 | *2.1E−05* | 9.2E−08 | *2.8E−05* | 19.6 | 228.3 | 0.6 | 33.7 |
| BP269 | G237D/P238D/H268E/P271G/ Y296D | 1.4E−08 | 2.2E−06 | *7.2E−05* | 1.1E−07 | *1.4E−04* | 19.6 | 637.2 | 0.5 | 27.4 |
| BP423 | E233D/G237D/P238D/S267A/ H268E/P271G/A330R | 7.7E−10 | 1.8E−07 | *2.0E−06* | 5.1E−09 | *1.6E−05* | 34.2 | 390.6 | 6.3 | 605.5 |
| BP425 | E233D/G237D/P238D/V266L/ S267A/H268E/P271G/A330R | 4.1E−09 | 2.2E−07 | *1.5E−05* | 9.1E−09 | *4.2E−05* | 23.6 | 1644.7 | 5.1 | 339.9 |
| BP426 | E233D/G237D/P238D/S267A/ H268E/E269D/P271G/A330R | 1.0E−09 | 1.6E−07 | *4.9E−05* | 5.9E−09 | *4.1E−05* | 27.6 | 8361.8 | 6.8 | 529.0 |
| BP428 | E233D/G237D/P238D/S267G/ H268E/P271G/A330R | 4.9E−09 | 3.9E−07 | *4.2E−05* | 1.4E−08 | *3.6E−05* | 28.0 | 3000.0 | 2.8 | 221.4 |
| BP429 | E233D/G237D/P238D/V264I/ S267G/H268E/P271G/A330R | 6.2E−09 | 1.7E−07 | *3.5E−06* | 5.4E−09 | *6.8E−05* | 31.5 | 648.1 | 6.5 | 574.1 |
| BP430 | E233D/G237D/P238D/V266L/ S267G/H268E/P271G/A330R | 1.7E−08 | 2.2E−07 | *1.1E−05* | 1.2E−08 | *3.5E−05* | 18.5 | 909.1 | 4.9 | 256.2 |
| BP431 | E233D/G237D/P238D/S267G/ H268E/E269D/P271G/A330R | 3.6E−09 | 4.1E−07 | *7.6E−06* | 1.2E−08 | *3.2E−05* | 34.6 | 649.6 | 2.7 | 265.0 |
| BP433 | E233D/G237D/P238D/H268D/ P271G/Y296D/A330K/I332T | 7.5E−10 | 6.8E−07 | *7.3E−06* | 3.4E−08 | *2.6E−05* | 20.0 | 216.0 | 1.6 | 91.7 |
| BP434 | E233D/G237D/P238D/H268D/ P271G/Y296D/K326D/A330R/ I332T | 5.5E−10 | 3.4E−07 | *4.1E−06* | 1.2E−08 | *2.5E−05* | 27.2 | 333.3 | 3.3 | 252.0 |
| BP435 | E233D/G237D/P238D/H268D/ P271G/Y296D/K326A/A330R/ I332T | 1.0E−09 | 4.2E−07 | *3.4E−06* | 1.6E−08 | *2.2E−05* | 27.1 | 217.9 | 2.6 | 198.7 |
| BP436 | E233D/G237D/P238D/S267A/ H268E/P271G/Y296D/A330R/ I332T | 2.6E−10 | 2.2E−07 | 2.1E−06 | 5.1E−09 | *1.3E−05* | 43.8 | 411.0 | 4.9 | 606.7 |
| BP437 | G237D/P238D/S267A/H268E/ P271G/Y296D/A330R/I332T | 7.5E−10 | 2.2E−07 | *1.4E−06* | 5.9E−09 | *1.1E−05* | 37.7 | 236.5 | 4.9 | 523.6 |
| BP438 | E233D/G237D/P238D/S267A/ H268E/P271G/A330R/I332T | 2.1E−10 | 1.8E−07 | 1.6E−06 | 5.5E−09 | *6.8E−06* | 32.7 | 293.6 | 6.2 | 568.8 |
| BP439 | E233D/G237D/P238D/V264I/ V266L/S267A/H268E/P271G/ A330R | 8.7E−09 | 1.3E−07 | *2.8E−06* | 6.1E−09 | *6.6E−05* | 20.9 | 460.5 | 8.7 | 509.9 |

TABLE 8-continued

| VARIANT NAME | ALTERATION | KD (mol/L) FcγRIa | FcγRIIaR | FcγRIIaH | FcγRIIb | FcγRIIIaV | KD(IIaR)/KD(IIb) | KD(IIaH)/KD(IIb) | KD(IaR) OF THE PARENT POLYPEPTIDE/ KD(IIaR) OF THE ALTERED POLYPEPTIDE | KD(IIb) OF THE PARENT POLYPEPTIDE/ KD(IIb) OF THE ALTERED POLYPEPTIDE |
|---|---|---|---|---|---|---|---|---|---|---|
| BP440 | E233D/G237D/P238D/V264I/H268E/P271G/A330R | 8.7E-09 | 1.3E-07 | 1.6E-06 | 5.2E-09 | 2.8E-05 | 24.0 | 307.1 | 8.8 | 595.0 |
| BP441 | E233D/G237D/P238D/V266L/H268E/P271G/A330R | 1.7E-08 | 3.6E-07 | 8.8E-06 | 1.5E-08 | 3.7E-05 | 24.0 | 582.8 | 3.0 | 205.3 |
| BP442 | E233D/G237D/P238D/H268E/E269D/P271G/A330R | 4.5E-09 | 3.8E-07 | 4.7E-06 | 1.2E-08 | 2.5E-05 | 30.6 | 379.0 | 2.9 | 250.0 |
| BP443 | E233D/G237D/P238D/V266L/H268E/E269D/P271G/A330R | 1.8E-08 | 5.1E-07 | 9.5E-06 | 2.3E-08 | 2.3E-05 | 21.7 | 406.0 | 2.2 | 132.5 |
| BP445 | E233D/G237D/P238D/V264I/S267A/H268E/P271G/A330R | 2.0E-09 | 8.0E-08 | 1.5E-06 | 2.6E-09 | 2.4E-05 | 31.0 | 581.4 | 13.8 | 1201.6 |
| BP479 | E233D/G237D/P238D/V264I/V266L/S267A/H268E/P271G | 5.3E-08 | 9.0E-07 | 1.5E-05 | 5.6E-08 | 4.0E-05 | 16.1 | 268.3 | 1.2 | 55.5 |
| BP480 | E233D/G237D/P238D/V266L/H268E/E269D/P271G | 1.3E-08 | 6.3E-06 | 2.1E-05 | 2.0E-07 | 4.6E-05 | 32.1 | 107.7 | 0.2 | 15.9 |
| BP481 | E233D/G237D/P238D/V264I/S267A/H268E/P271G | 1.0E-08 | 4.0E-07 | 6.8E-06 | 1.9E-08 | 2.4E-05 | 20.5 | 350.5 | 2.8 | 159.8 |
| BP483 | E233D/G237D/P238D/V266L/S267A/H268E/P271G | 1.3E-09 | 1.3E-06 | 1.8E-05 | 7.8E-08 | 2.5E-05 | 16.8 | 230.8 | 0.8 | 39.7 |
| BP484 | E233D/G237D/P238D/S267A/H268E/E269D/P271G | 8.2E-10 | 7.8E-07 | 1.1E-05 | 4.6E-08 | 2.5E-05 | 17.1 | 240.7 | 1.4 | 67.8 |
| BP487 | E233D/G237D/P238D/V264I/H268E/P271G/A330R/P396M | 1.2E-09 | 3.9E-08 | 8.4E-07 | 1.2E-09 | 1.0E-05 | 33.8 | 730.4 | 28.3 | 2695.7 |
| BP488 | E233D/G237D/P238D/V264I/S267A/H268E/P271G/Y296D/A330R | 2.2E-08 | 7.4E-08 | 1.6E-06 | 1.9E-09 | 2.0E-05 | 40.1 | 864.9 | 14.8 | 1675.7 |
| BP489 | E233D/G237D/P238D/V264I/S267A/H268E/P271G/Y296D/A330R/P396M | 1.3E-08 | 4.3E-08 | 8.7E-07 | 1.0E-09 | 1.2E-05 | 42.8 | 870.0 | 25.7 | 3100.0 |
| BP490 | G237D/P238D/V264I/S267A/H268E/P271G/A330R | 4.5E-09 | 1.1E-07 | 2.4E-06 | 2.4E-09 | 2.3E-05 | 46.7 | 1000.0 | 9.8 | 1291.7 |
| BP491 | G237D/P238D/V264I/S267A/H268E/P271G/Y296D/A330R | 5.3E-09 | 1.2E-07 | 2.2E-06 | 3.0E-09 | 2.1E-05 | 38.8 | 723.7 | 9.3 | 1019.7 |
| BP492 | P238D/V264I/S267A/H268E/P271G | 7.9E-10 | 9.2E-07 | 1.6E-05 | 2.4E-08 | 3.6E-05 | 38.8 | 678.0 | 1.2 | 131.4 |
| BP493 | P238D/V264I/S267A/H268E/P271G/Y296D | 8.2E-10 | 1.1E-06 | 1.9E-05 | 2.1E-08 | 3.5E-05 | 52.1 | 900.5 | 1.0 | 146.9 |
| BP494 | G237D/P238D/S267A/H268E/P271G/Y296D/A330R | 3.9E-09 | 2.5E-07 | 5.4E-06 | 6.6E-09 | 4.0E-05 | 38.6 | 820.7 | 4.3 | 471.1 |
| BP495 | G237D/P238D/S267G/H268E/P271G/Y296D/A330R | 8.3E-09 | 4.9E-07 | 1.2E-05 | 9.7E-09 | 3.3E-05 | 50.9 | 1243.5 | 2.2 | 321.2 |
| BP496 | E233D/G237D/P238D/V264I/P271G/Y296D | 1.2E-09 | 4.7E-07 | 3.7E-06 | 1.8E-08 | 3.0E-05 | 25.5 | 201.1 | 2.3 | 168.5 |
| BP497 | E233D/G237D/P238D/V264I/S267A/H268E/P271G/Y296D | 2.1E-09 | 8.5E-08 | 9.6E-07 | 4.1E-09 | 2.8E-05 | 21.0 | 236.5 | 12.9 | 763.5 |
| BP498 | E233D/G237D/P238D/V264I/S267A/H268E/P271G/A330R/P396L | 1.3E-09 | 5.1E-08 | 9.3E-07 | 1.7E-09 | 1.0E-05 | 30.8 | 563.6 | 21.7 | 1878.8 |

TABLE 8-continued

| VARIANT NAME | ALTERATION | KD (mol/L) | | | | | KD(IIaR)/ KD(IIb) | KD(IIaR)/ KD(IIb) OF THE PARENT POLYPEPTIDE/ KD(IIaR)/ KD(IIb) OF THE ALTERED POLYPEPTIDE | KD(IIaR) OF THE PARENT POLYPEPTIDE/ KD(IIaR) OF THE ALTERED POLYPEPTIDE |
| --- | --- | --- | --- | --- | --- | --- | --- | --- | --- |
| | | FcγRIa | FcγRIIaR | FcγRIIaH | FcγRIIb | FcγRIIIaV | | | |
| BP499 | E233D/G237D/P238D/V264I/S267A/H268E/P271G/Y296D/A330R/P396L | 1.2E−09 | 4.9E−08 | 1.0E−06 | 1.5E−09 | 1.2E−05 | 33.8 | 684.9 | 22.3 |
| BP500 | G237D/P238D/V264I/S267A/H268E/P271G/Y296D | 2.3E−09 | 7.2E−07 | 2.5E−05 | 2.4E−08 | 3.9E−05 | 29.9 | 1033.1 | 1.5 |
| BP501 | G237D/P238D/V264I/S267A/H268E/P271G | 2.1E−09 | 6.3E−07 | 1.4E−05 | 2.5E−08 | 1.9E−05 | 25.1 | 555

TABLE 8-continued

| VARIANT NAME | ALTERATION | KD (mol/L) FcγRIa | FcγRIIaR | FcγRIIaH | FcγRIIb | FcγRIIIaV | KD(IIaR) KD(IIb) | KD(IIaR)/ KD(IIb) OF THE ALTERED POLYPEPTIDE | KD(IIaR) OF THE PARENT POLYPEPTIDE/ KD(IIaR) OF THE ALTERED POLYPEPTIDE | KD(IIb) OF THE PARENT POLYPEPTIDE/ KD(IIb) OF THE ALTERED POLYPEPTIDE |
|---|---|---|---|---|---|---|---|---|---|---|
| BP535 | E233D/G237D/P238D/V264I/S267G/H268E/P271G/Y296D/A327G/A330R/P396M | 1.1E-08 | 9.2E-08 | 3.2E-06 | 4.0E-09 | 3.3E-05 | 23.2 | 806.0 | 11.9 | 780.9 |
| BP536 | E233D/G237D/P238D/V264I/H268E/P271G/Y296D/A327G/A330R/P396M | 8.9E-09 | 7.9E-08 | 1.3E-06 | 3.0E-09 | 2.3E-05 | 26.6 | 437.7 | 13.9 | 1043.8 |
| BP537 | G237D/P238D/V264I/S267G/H268E/P271G/A330R | 2.9E-08 | 2.7E-07 | 3.1E-06 | 6.9E-09 | 3.6E-05 | 39.1 | 447.3 | 4.1 | 447.3 |
| BP538 | G237D/P238D/V264I/H268E/P271G/A330R | 5.5E-08 | 2.0E-07 | 3.0E-06 | 5.3E-09 | 3.3E-05 | 38.6 | 568.2 | 5.4 | 587.1 |
| BP539 | G237D/P238D/V264I/S267G/H268E/P271G/E272P/Y296D/A330R | 6.4E-08 | 3.3E-07 | 5.6E-06 | 8.4E-09 | 3.4E-05 | 39.0 | 666.7 | 3.4 | 369.0 |
| BP540 | G237D/P238D/V264I/H268E/P271G/E272P/Y296D/A330R | 9.6E-08 | 2.1E-07 | 4.6E-06 | 5.7E-09 | 3.9E-05 | 36.6 | 802.8 | 5.2 | 541.0 |
| BP549 | G237D/P238D/S267G/H268E/P271G/A330R | 1.8E-08 | 5.7E-08 | 1.1E-05 | 1.6E-08 | 2.4E-05 | 35.9 | 696.2 | 1.9 | 196.2 |
| BP550 | G237D/P238D/V264I/S267G/H268E/P271G/E272D/Y296D/A330R | 2.5E-08 | 3.4E-07 | 5.0E-06 | 7.6E-09 | 4.8E-05 | 44.2 | 655.3 | 3.3 | 406.3 |
| BP551 | G237D/P238D/V264I/H268E/P271G/E272D/Y296D/A330R | 3.2E-08 | 2.5E-07 | 2.8E-06 | 6.4E-09 | 4.8E-05 | 38.1 | 435.5 | 4.5 | 482.1 |
| BP552 | E233D/G237D/P238D/V264I/P271G/E272D/Y296D/A330R | 3.2E-09 | 9.7E-08 | 1.9E-06 | 2.6E-09 | 3.0E-05 | 37.3 | 733.6 | 11.4 | 1196.9 |
| BP553 | E233D/G237D/P238D/V264I/S267A/H268E/P271G/E272D/A330R | 3.4E-09 | 8.6E-08 | 1.4E-06 | 3.1E-09 | 2.0E-05 | 27.8 | 453.1 | 12.8 | 1003.2 |
| BP554 | G237D/P238D/V264I/S267A/H268E/P271G/E272D/A330R | 8.0E-09 | 1.5E-07 | 2.3E-06 | 4.4E-09 | 2.4E-05 | 32.7 | 518.0 | 7.6 | 698.2 |
| BP555 | G237D/P238D/V264I/S267A/P271G/E272D/A330R | 9.4E-09 | 1.6E-07 | 3.2E-06 | 4.1E-09 | 3.0E-05 | 39.7 | 778.6 | 6.7 | 754.3 |
| BP556 | G237D/P238D/V264I/S267G/H268E/P271G/Y296D/A330R | 4.3E-08 | 3.0E-07 | 5.8E-06 | 8.4E-09 | 6.0E-05 | 35.4 | 692.1 | 3.7 | 369.9 |
| BP557 | G237D/P238D/S267G/H268D/P271G/Y296D/A330R | 1.3E-08 | 8.5E-08 | 1.5E-05 | 2.0E-08 | 2.9E-05 | 42.0 | 746.3 | 1.3 | 154.2 |
| BP558 | G237D/P238D/V264I/S267G/P271G/E272D/A330R | 1.3E-08 | 3.3E-07 | 4.9E-06 | 9.0E-09 | 3.6E-05 | 36.4 | 543.2 | 3.4 | 343.7 |
| BP559 | P238D/V264I/S267A/H268E/P271G/E272D/Y296D | 1.1E-09 | 1.6E-06 | 2.0E-05 | 2.8E-08 | 4.4E-05 | 58.4 | 711.7 | 0.7 | 110.3 |

TABLE 8-continued

| VARIANT NAME | ALTERATION | KD (mol/L) FcγRIa | FcγRIIaR | FcγRIIaH | FcγRIIb | FcγRIIIaV | KD(IIaR)/KD(IIb) | KD(IIaH)/KD(IIb) | KD(IIaR) OF THE PARENT POLYPEPTIDE/ KD(IIaR) OF THE ALTERED POLYPEPTIDE | KD(IIb) OF THE PARENT POLYPEPTIDE/ KD(IIb) OF THE ALTERED POLYPEPTIDE |
|---|---|---|---|---|---|---|---|---|---|---|
| BP560 | P238D/S267G/H268E/P271G/Y296D/A330R | 5.6E-09 | 4.2E-06 | 3.1E-05 | 1.8E-07 | 4.1E-05 | 22.8 | 168.5 | 0.3 | 16.8 |
| BP561 | E233D/G237D/P238D/H268D/P271G/E272D/Y296D/A330R | 9.4E-09 | 5.1E-07 | 5.3E-06 | 1.8E-08 | 3.7E-05 | 28.0 | 291.2 | 2.2 | 170.3 |
| BP562 | G237D/P238D/H268D/P271G/E272D/Y296D/A330R | 2.5E-08 | 6.8E-07 | 1.1E-05 | 2.4E-08 | 5.3E-05 | 29.0 | 466.1 | 1.6 | 131.4 |
| BP563 | E233D/G237D/P238D/H268E/P271G/E272D/Y296D/A330R | 1.2E-08 | 4.6E-07 | 8.3E-06 | 1.6E-08 | 3.8E-05 | 29.1 | 525.3 | 2.4 | 196.2 |
| BP564 | G237D/P238D/H268E/P271G/E272D/Y296D/A330R | 3.1E-08 | 5.8E-07 | 1.0E-05 | 2.2E-08 | 4.9E-05 | 26.2 | 454.5 | 1.9 | 140.9 |
| BP565 | E233D/G237D/P238D/S267A/H268E/P271G/Y296D/A330R | 2.4E-09 | 2.3E-07 | 4.7E-06 | 5.5E-09 | 2.1E-05 | 41.5 | 856.1 | 4.8 | 564.7 |
| BP567 | E233D/P238D/V264I/S267A/H268E/P271G/Y296D | 2.1E-10 | 8.9E-07 | 1.7E-05 | 1.4E-08 | 3.9E-05 | 64.4 | 1231.9 | 1.2 | 224.6 |
| BP568 | E233D/P238D/V264I/S267A/H268E/P271G | 1.9E-10 | 6.8E-07 | 1.1E-05 | 1.5E-08 | 2.5E-05 | 46.1 | 748.3 | 1.6 | 210.9 |

Among the variants described in Table 8, IL6R-BP253/IL6R-L produced by adding known alterations that enhance FcγRIIb binding showed 277-fold and 529-fold enhanced binding activities to FcγRIIb and FcγRIIaR, respectively, compared to those of the IL6R-B3/IL6R-L prior to alteration. Furthermore, FcγRIa-binding activity of IL6R-BP253/IL6R-L was also enhanced compared to that of IL6R-B3/IL6R-L. On the other hand, binding of IL6R-BP253/IL6R-L to FcγRIIaH and FcγRIIIaV was decreased compared to those of IL6R-B3/IL6R-L. Among the other variants, binding to FcγRIa was slightly enhanced for IL6R-BP436/IL6R-L, IL6R-BP438/IL6R-L, IL6R-BP567/IL6R-L, and IL6R-BP568/IL6R-L, compared to that of the IL6R-B3/IL6R-L prior to alteration but FcγRIa binding was decreased in all of the other variants. Furthermore, binding to FcγRIIaH and FcγRIIIaV were decreased in all variants when compared to those of IL6R-B3/IL6R-L.

Comparison of variants produced in this examination with the existing variant IL6R-BP253/IL6R-L having enhanced FcγRIIb binding showed that the value of KD (IIaH)/KD (IIb) is 107.7 for IL6R-BP480/IL6R-L which showed the lowest value and is 8362 for IL6R-BP426/IL6R-L which showed the highest value, and the values for all variants were higher than 107.1 for IL6R-BP253/IL6R-L. Furthermore, the value of KD (IIaR)/KD (IIb) is 16.1 for IL6R-BP479/IL6R-L which showed the lowest value and is 64.4 for IL6R-BP567/IL6R-L which showed the highest value, and the values for all variants were higher than 0.2 for IL6R-BP253/IL6R-L. From these results, all of the variants shown in Table 8 have been shown to be variants with improved selectivity to FcγRIIb as compared to the existing variant into which alteration(s) to enhance FcγRIIb binding is introduced. In particular, IL6R-BP559/IL6R-L, IL6R-BP493/IL6R-L, IL6R-BP557/IL6R-L, IL6R-BP492/IL6R-L, IL6R-BP500/IL6R-L, and IL6R-BP567/IL6R-L all have FcγRIIaR binding maintained at not more than 1.5 times that of IL6R-B3/IL6R-L, and at the same time FcγRIIb-binding activity enhanced by 100 times or more; therefore, these variants were expected to show effects yielded by enhanced binding to FcγRIIb while avoiding side effects caused by enhanced binding to FcγRIIaR.

In addition, regarding IL6R-BP489/IL6R-L, IL6R-BP487/IL6R-L, IL6R-BP499/IL6R-L, IL6R-BP498/IL6R-L, IL6R-BP503/IL6R-L, IL6R-BP488/IL6R-L, IL6R-BP490/IL6R-L, IL6R-BP445/IL6R-L, IL6R-BP552/IL6R-L, IL6R-BP507/IL6R-L, IL6R-BP536/IL6R-L, IL6R-BP534/IL6R-L, IL6R-BP491/IL6R-L, IL6R-BP553/IL6R-L, IL6R-BP532/IL6R-L, IL6R-BP506/IL6R-L, IL6R-BP511/IL6R-L, IL6R-BP502/IL6R-L, IL6R-BP531/IL6R-L, IL6R-BP510/IL6R-L, IL6R-BP535/IL6R-L, IL6R-BP497/IL6R-L, IL6R-BP533/IL6R-L, IL6R-BP555/IL6R-L, IL6R-BP554/IL6R-L, IL6R-BP436/IL6R-L, IL6R-BP423/IL6R-L, IL6R-BP440/IL6R-L, IL6R-BP538/IL6R-L, IL6R-BP429/IL6R-L, IL6R-BP438/IL6R-L, IL6R-BP565/IL6R-L, IL6R-BP540/IL6R-L, IL6R-BP426/IL6R-L, IL6R-BP437/IL6R-L, IL6R-BP439/IL6R-L, IL6R-BP551/IL6R-L, IL6R-BP494/IL6R-L, IL6R-BP537/IL6R-L, IL6R-BP550/IL6R-L, IL6R-BP556/IL6R-L, IL6R-BP539/IL6R-L, IL6R-BP558/IL6R-L, IL6R-BP425/IL6R-L, and IL6R-BP495/IL6R-L, their FcγRIIb binding was higher than that of IL6R-BP253/IL6R-L added with the existing alteration that enhances the FcγRIIb binding. Further, the enhancement of the FcγRIIb binding ranges from 321 times (lowest) to 3100 times (highest), compared to the binding of IL6R-B3/IL6R-L (which is defined to be 1), from IL6R-BP495/IL6R-L to IL6R-BP489/IL6R-L, respectively.

Therefore, one may say that these variants are superior to existing technology with regard to both selectivity and binding to FcγRIIb.

Here, variants related to IL6R-BP567/IL6R-L which is considered to be the best in terms of selectivity for FcγRIIb were studied from the perspective of immunogenicity. The Y296D alteration has been introduced into IL6R-BP567/IL6R-L which showed the highest selectivity and into IL6R-BP493/IL6R-L which showed FcγRIIaR binding that is completely equivalent to that of the native form and showed 147-fold enhanced binding to FcγRIIb. Y296 has been reported to be included in a Tregitope sequence (De Groot et al., Blood (2008) 112, 3303-3311), and introducing alterations into this site may lead to loss of immunosuppressive functions that a native IgG1 normally have. Therefore, from the perspective of immunogenicity, variants that do not include the Y296D alteration are more preferred. IL6R-BP568/IL6R-L and IL6R-BP492/IL6R-L were produced by removing the Y296D alteration from IL6R-BP567/IL6R-L and IL6R-BP493/IL6R-L, respectively. Considering the selectivity and binding activity to FcγRIIb, removing the Y296D alteration from IL6R-BP492/IL6R-L and IL6R-BP568/IL6R-L decreased both selectivity and binding activity compared to when Y296D was included. However, compared to the native form, binding to FcγRIIaR is 1.6-fold and binding to FcγRIIb is 211-fold for IL6R-BP568/IL6R-L, and binding to FcγRIIaR is 1.2-fold and binding to FcγRIIb is 131-fold for IL6R-BP492/IL6R-L, and therefore high selectivity and binding activity were still maintained. These results allow one to say that IL6R-BP568/IL6R-L and IL6R-BP492/IL6R-L are excellent variants not only in terms of selectivity and binding activity to FcγRIIb but also in terms of immunogenicity.

Figure 26:
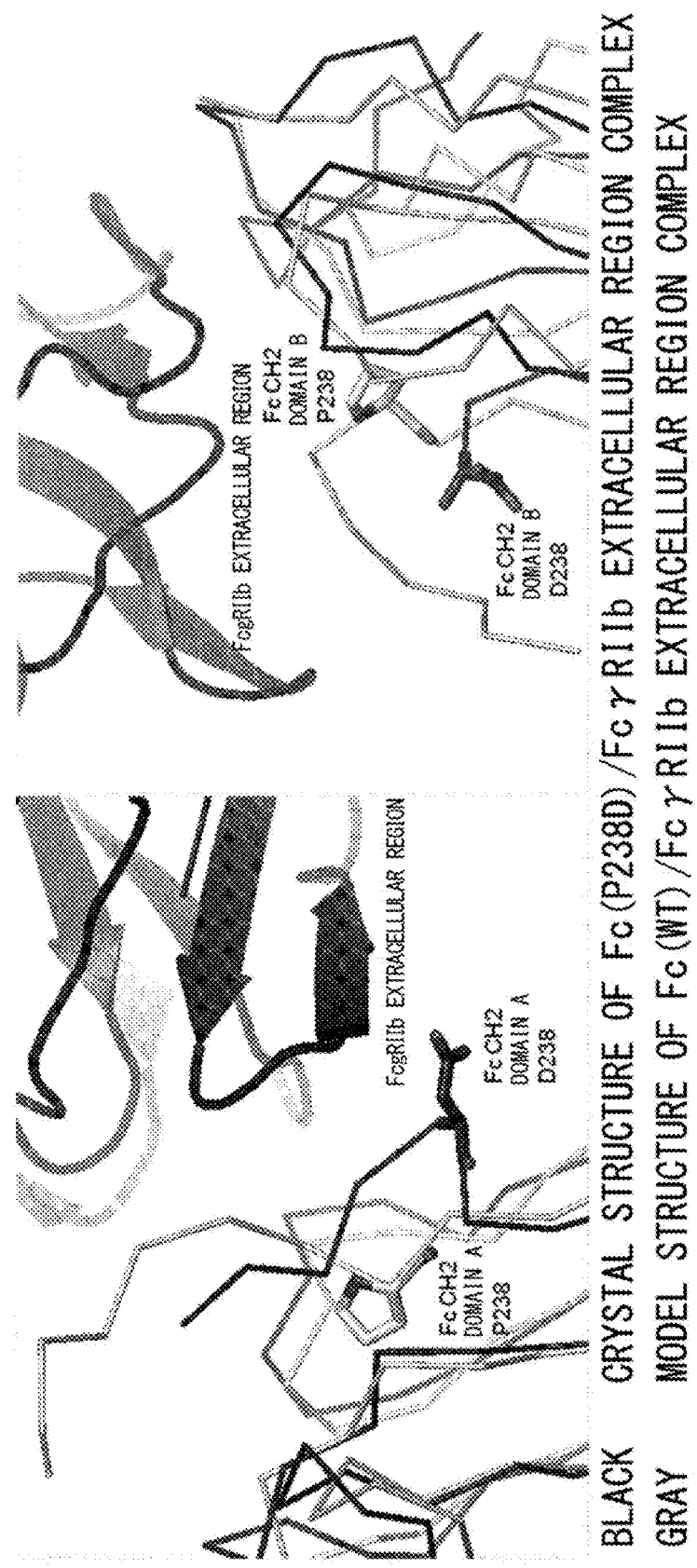
FIG. 26 shows comparison of the detailed structure around P238D after superimposing the crystal structure of the Fc(P238D)/FcγRIIb extracellular region complex and the model structure of the Fc(WT)/FcγRIIb extracellular region complex with respect to the only Fc CH2 domain A or the only Fc CH2 domain B by least square fitting based on Cα atom pair distances.
Figure 27:
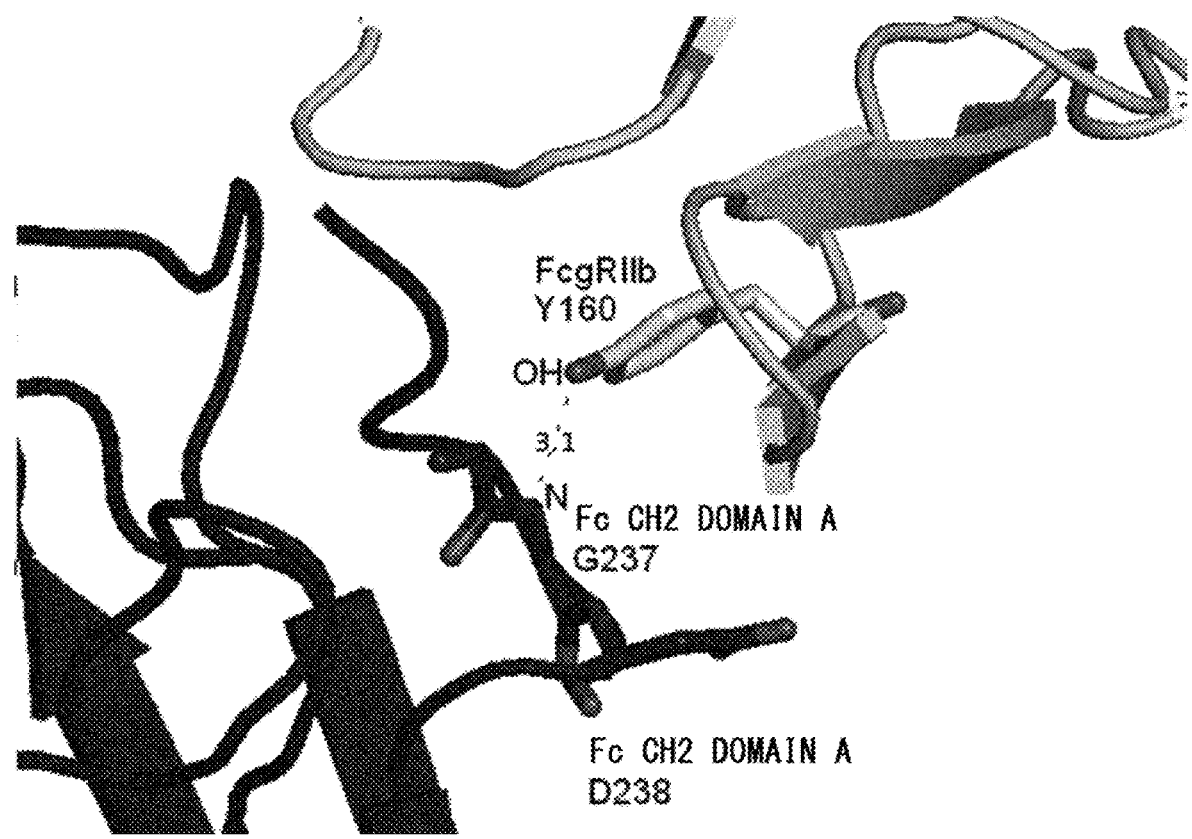
FIG. 27 shows that a hydrogen bond is found between the main chain of Gly at position 237 (EU numbering) in Fc CH2 domain A, and Tyr at position 160 in FcγRIIb in the crystal structure of the Fc(P238D)/FcγRIIb extracellular region complex.

[Example 9] Enhancement of Binding to FcgRIIb by a Heterodimerized Antibody 9-1. Examination of Introducing P238D into Only One of the Chains As shown in FIG. 26 in Reference Example 7, the reason why Fc(P238D) acquired high binding to FcgRIIb is by introducing the P238D alteration, the region that had formed a hydrophobic core with the surrounding residues in the case of Pro could no longer exist in the hydrophobic core upon change to Asp and directed to the solvent side, and resulting in the great change in the loop structure of domain A. However, whether it is necessary to introduce the P238D alteration into both chains or whether it is acceptable to introduce P238D into one of the chains and introduce other alterations into the other chain still has to be verified. Accordingly, heterodimerized antibodies with different alterations introduced into each of the antibody H chains were used for this verification.

The variable region (SEQ ID NO: 15) of a glypican 3 antibody comprising the CDRs of GpH7 which is an anti-glypican 3 antibody with improved plasma kinetics disclosed in WO 2009/041062 was used as the antibody H chain. GpH7-A5 (SEQ ID NO: 35) produced by introducing the D356K and H435R alterations into GpH7-G1d (SEQ ID NO: 34) in which Gly and Lys are removed from the C terminus of IgG1 carrying GpH7 as the variable region, and GpH7-B3 (SEQ ID NO: 17) produced by introducing the K439E alteration into GpH7-G1d were used. The D356K and K439E alterations introduced into the respective H chains were introduced to efficiently form the heterodimers for each H chain when producing heterodimerized antibodies comprising two H chains (WO2006/106905). H435R is an alteration that inhibits binding to Protein A, and was introduced to efficiently separate the dimeric heteromer comprising two H chains each introduced with different alterations from the dimeric homomer comprising two H chains each introduced with the same alterations. Variants in which the amino acids at positions 236, 237, and 238 (EU numbering) in GpH7-B3 (SEQ ID NO: 17) produced in Reference Example 3 were substituted with any of the 18 amino acids other than the original amino acid and Cys were used as one of the H chains. GpH7-AP001 produced by introducing P238D into GpH7-A5 (SEQ ID NO: 35) was used as the other chain. GpL16-k0 (SEQ ID NO: 16) of glypican 3 antibody with improved plasma kinetics disclosed in WO 2009/041062 was commonly used as the antibody L chain. These variants were expressed and purified according to the method of Reference Example 1, and binding to each of the FcgRIIa type R and FcgRIIb was assessed using the method of Reference Example 2. The amount binding to FcgR of each variant is shown in FIG. 15.

Figure 15:
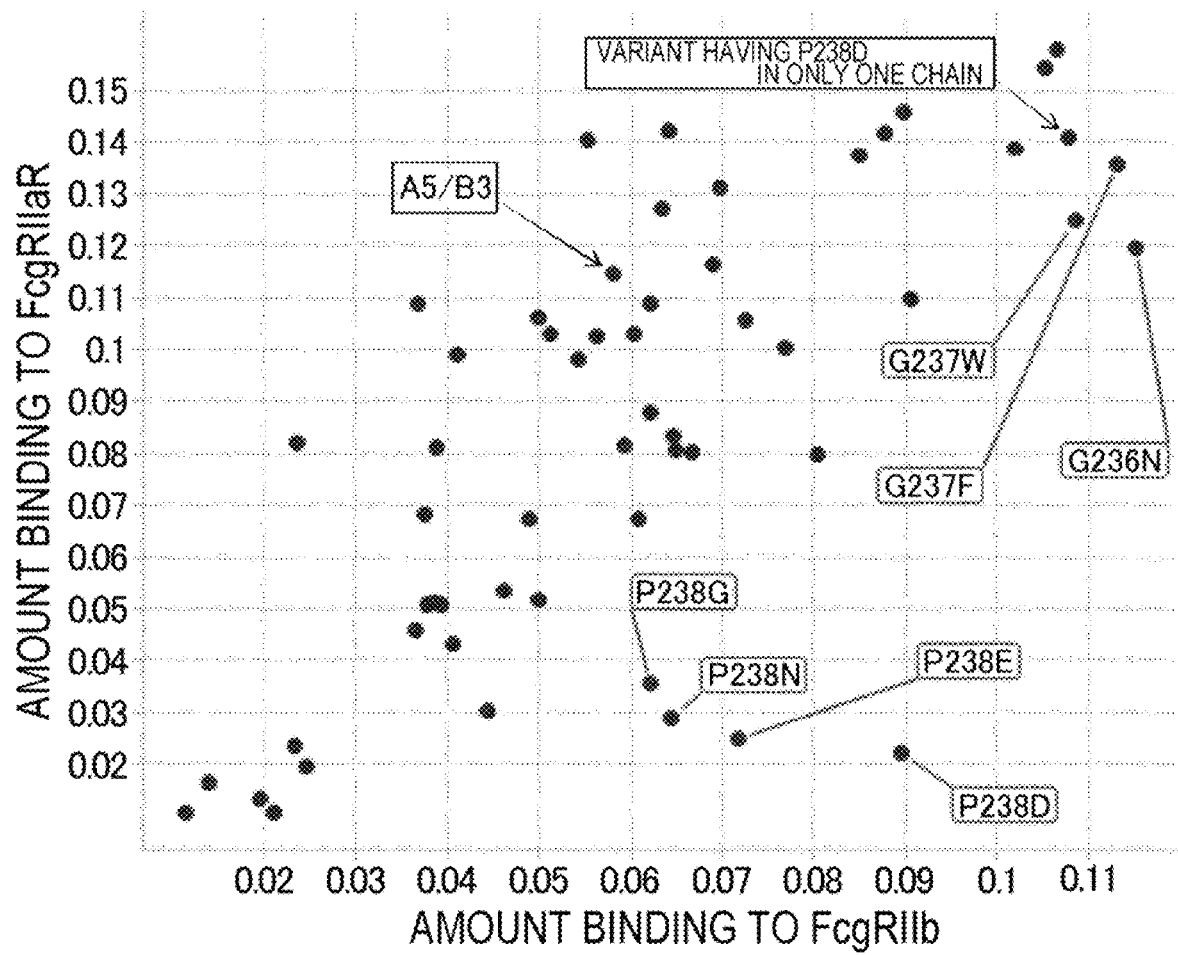
FIG. 15 shows the values of the binding amount of each variant to FcgRIIb on the horizontal axis, and the binding amount of each variant to FcgRIIaR on the vertical axis. The alterations indicated in the figure, G237W, G237F, G236N, P238G, P238N, P238E, and P238D, refer to alterations introduced into GpH7-B3. A5/B3 refers to GpH7-A5/GpH7-B3/GpL16-k0 without any introduction of alterations to both chains, and a variant containing P238D in only one of the chains refers to GpH7-A5/GpH7-BF648/GpL16-k0.

The G237W, G237F, G236N, P238G, P238N, P238E, and P238D alterations shown in FIG. 15 refer to alterations introduced into GpH7-B3. A5/B3 refers to GpH7-A5/GpH7-B3/GpL16-k0 which has no alterations introduced into both chains, and a variant containing P238D in only one of the chains refers to GpH7-A5/GpH7-BF648/GpL16-k0. Their results are shown in Table 9.

has the P238D alteration in both chains, high selectivity to FcgRIIb was maintained. Furthermore, since GpH7-AP001/GpH7-BF648/GpL16-k0 having the P238D alteration in both chains also maintained 69% or greater affinity for FcgRIIb, one can say that if the P238D alteration is present in one of the chains, the other chain may have the P238E, P238N, or P238G alteration. In addition, focusing on FcgRIIb-binding, compared to GpH7-AP001/GpH7-BF648/GpL16-k0 having P238D in both chains, GpH7-A5/GpH7-BF648/GpL16-k0 which has P238D only in one of the chains and does not have alteration in the other chain showed stronger binding to FcgRIIb; and GpH7-AP001/GpH7-BP032/GpL16-k0, GpH7-AP001/GpH7-BP044/GpL16-k0, and GpH7-AP001/GpH7-BP057/GpL16-k0 which have P238D in one of their chains and have G236N, G237F, and G237W, respectively, in the other chain were found to bind more strongly to FcgRIIb.

9-2. Verification of Alterations Based on the Structural Information of Fc(P208)/FcgRIIb As shown in FIG. 10, in the crystal structure of Fc(P208)/FcgRIIb, electron density of Lys at position 117 of FcgRIIb was not observed, and this residue was considered not to be largely involved in binding with Fc(P208); but by substituting Asp or Glu for Ser at position 239 (EU numbering) of the CH2 domain B, which is positioned nearby, an electrostatic interaction may be formed with this Lys at position

TABLE 9

| VARIANT NAME | ALTERATION INTRODUCED INTO GpH7-A5 | ALTERATION INTRODUCED INTO GpH7-B3 | BINDING AMOUNT OF ALTERED POLYPEPTIDE TO FcgRIIaR WHEN THAT OF GpH7-AP001/GpH7-BF-648 IS DEFINED AS 100 | BINDING AMOUNT OF ALTERED POLYPEPTIDE TO FcgRIIb WHEN THAT OF GpH7-AP001/GpH7-BF648 IS DEFINED AS 100 | AMOUNT BINDING TO FcgRIIb/AMOUNT BINDING TO FcgRIIaR |
|---|---|---|---|---|---|
| GpH7-G1d/GpL16-k0 | * | * | 515 | 65 | 0.5 |
| GpH7-A5/GpH7-B3/GpL16-k0 | | | 570 | 77 | 0.5 |
| GpH7-A5/GpH7-BF648/GpL16-k0 | | P238D | 677 | 131 | 0.8 |
| GpH7-AP001/GpH7-BF648/GpL16-k0 | P238D | P238D | 100 | 100 | 4.0 |
| GpH7-AP001/GpH7-BP032/GpL16-k0 | P238D | G236N | 538 | 129 | 1.0 |
| GpH7-AP001/GpH7-BP044/GpL16-k0 | P238D | G237F | 609 | 127 | 0.8 |
| GpH7-AP001/GpH7-BP057/GpL16-k0 | P238D | G237W | 561 | 121 | 0.9 |
| GpH7-AP001/GpH7-BP061/GpL16-k0 | P238D | P238E | 111 | 80 | 2.9 |
| GpH7-AP001/GpH7-BP063/GpL16-k0 | P238D | P238G | 161 | 69 | 1.7 |
| GpH7-APC01/GpH7-BP069/GpL16-k0 | P238D | P238N | 131 | 72 | 2.2 |

In Table 9, "amount binding to FcgRIIb/amount binding to FcgRIIaR" are values obtained by dividing the amount binding to FcgRIIb of each variant by the amount binding to FcgRIIaR of each variant, and shows that the higher the value is, the higher selectivity to FcgRIIb is. Furthermore, while the phrases "alteration introduced into GpH7-A5" and "alteration introduced into GpH7-1B3" indicate alterations introduced into GpH7-A5 and GpH7-B33, respectively; and GpH7-G1d which was used as the template when producing GpH7-A5 and GpH7-3 is indicated by an asterisk (*). From the results of Table 9, GpH7-AP001/GpH7-BF648/GpL16-k0 having the P238D alteration in both chains had the highest selectivity to FcgRIIb. GpH7-AP001/GpH7-BP061/GpL16-k0, GpH7-AP001/GpH7-BP069/GpL16-k0, and GpH7-AP001/GpH7-BP063/GpL16-k which have P238E, P238N, and P238G in the other chain show the values of "amount binding to FcgRIIb/amount binding to FcgRIIaR" that are 2.9, 2.2, and 1.7, respectively, and even when compared to GpH7-AP001/GpH7-BF648/GpL16-k0 which 117 of FcgRIIb. On the other hand, as shown in FIG. 7, in CH2 domain A, Ser at position 239 (EU numbering) forms a hydrogen bond with Gly at position 236 (EU numbering), and stabilization of the loop structure from positions 233 to 239 (EU numbering) may contribute to strengthen the binding with Tyr at position 160 (EU numbering), and substitutions in this portion is predicted to cause decrease in binding activity accompanying destabilization of the loop structure in CH2 domain A, and these effects were predicted to cancel each other in homologous alterations. Accordingly, in this examination, the S239D alteration or the S239E alteration was introduced only into one of the chains by heterodimerization, and effects of enhancement of binding to FcgRIIb were examined.

As one of the antibody H chains, IL6R-BP256 and IL6R-BP257 were produced by introducing S239D and S239E, respectively, into IL6R-BP208 (SEQ ID NO: 24). Similarly, S239D was introduced into IL6R-BP230 (SEQ ID NO: 27) to produce IL6R-BP259, and S239E was introduced into IL6R-BP230 to produce IL6R-BP260. IL6R-AP002 was produced by introducing the same alterations as those included in CH2 of IL6R-BP208, which are E233D, G237D, P238D, H268D, P271G, and A330R, into IL6R-A5 (SEQ ID NO: 69), and IL6R-AP009 was produced by introducing the same alterations as those included in CH2 of IL6R-BP230, which are E233D, G237D, P238D, H268D, P271G, Y296D, and A330R, into IL6R-A5, and they were used as the other antibody H chain. As a comparison, IL6R-BP253 (SEQ ID NO: 32) was produced by introducing S267E and L328F, which is a known FcgRIIb enhancement technique (Non-patent Document 28), into IL6R-B3. IL6R-L (SEQ ID NO: 21) was commonly used as the antibody L chain. Antibodies were expressed using these variants and then purified according to the method of Reference Example 1, and binding to each FcgR (FcgRIa, FcgRIIa type H, FcgRIIa type R, FcgRIIb, and FcgRIIIa type V) was assessed using the method of Reference Example 2.

The KD values of each variant for each FcgR are shown in Table 10. "Parent polypeptide KD(IIb)/altered polypeptide KD(IIb)" refers to a value obtained by dividing the KD value of IL6R-B3/IL6R-L for FcgRIIb by the KD value of each variant for FcgRIIb. Furthermore, "parent polypeptide KD(IIaR)/altered polypeptide KD(IIaR)" refers to a value obtained by dividing the KD value of IL6R-B3/IL6R-L for FcgRIIaR by the KD value of each variant for FcgRIIaR. "KD(IIaR)/KD(IIb)" is a value obtained by dividing the KD of each variant for FcgRIIaR by the KD of each variant for FcgRIIb. The larger this value is, the higher the selectivity to FcgRIIb is. The Table 10 values shown in bold italicized font were calculated using the following equation $$KD = C \cdot R_{max}/(R_{eq}-RI) - C \quad \text{[Equation 2]}$$

shown in Reference Example 2 since the binding of FcgR to IgG was too weak to accurately analyze by kinetic analysis.

BP256/IL6R-L produced by introducing S239D into both chains of IL6R-BP208/IL6R-L and IL6R-BP257/IL6R-L produced by introducing S239E into both chains of IL6R-BP208/IL6R-L had significantly decreased. This way, when S239D or S239E was introduced into only one of the chains, effects of enhancing binding to FcgRIIb was observed, whereas when S239D or S239E was introduced into both chains, binding to FcgRIIb significantly decreased. The main reason why this happened may be, as described previously, the destabilization of loop structure in CH2 domain A. Similar results were observed when S239D and S239E were introduced using IL6R-BP230/IL6R-L as the template. IL6R-AP009/IL6R-BP259/IL6R-L and IL6R-AP009/IL6R-BP260/IL6R-L produced by introducing S239D and S239E, respectively, into one of the chains of IL6R-BP230/IL6R-L showed both higher selectivity and binding to FcgRIIb than those of IL6R-BP230/IL6R-L. On the other hand, IL6R-BP259/IL6R-L and IL6R-BP260/IL6R-L produced by introducing S239D and S239E respectively into both chains showed greatly decreased selectivity and binding to FcgRIIb as compared to those of IL6R-BP230/IL6R-L. Furthermore, variants produced by introducing S239D or S239E into one of the chains of IL6R-BP208/IL6R-L and IL6R-BP230/IL6R-L all showed greater selectivity as well as binding to FcgRIIb as compared to those of IL6R-BP253/IL6R-L utilizing a known FcgRIIb-enhancement technique.

9-3. Verification of Alterations Based on Structural Information on Fc(P208)/FcgRIIaR Comparison of the crystal structures of Fc(P208) with FcgRIIb and with FcgRIIaR in Example 3 showed that there is a difference in electron density around position 237 (EU numbering) where a hydrogen bond is formed with Tyr at position 160 of FcgRIIb, and the CH2 domain A side was suggested to have a larger contribution to binding with FcgRIIb, and the CH2 domain B side was suggested to have

TABLE 10

| VARIANT NAME | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|
| IL6R-G1d/IL6R-L | 3.2E−10 | 1.0E−06 | 6.7E−07 | 2.6E−06 | 3.5E−07 | 0.4 | 1.1 | 1 |
| IL6R-B3/IL6R-L | 4.2E−10 | 1.1E−06 | 7.7E−07 | 3.1E−06 | 3.3E−07 | 0.3 | 1.0 | 1 |
| IL6R-BP253/IL6R-L | 5.0E−11 | 2.3E−09 | 8.6E−07 | 8.9E−09 | 4.0E−07 | 0.3 | 480.0 | 349 |
| IL6R-BP208/IL6R-L | 1.9E−08 | 8.5E−07 | *8.3E−06* | 3.2E−08 | *5.3E−05* | 26.3 | 1.3 | 95 |
| IL6R-BP256/IL6R-L | 2.0E−09 | 7.3E−07 | *2.1E−05* | 8.7E−08 | *1.1E−05* | 8.4 | 1.5 | 36 |
| IL6R-BP257/IL6R-L | 3.1E−10 | 1.3E−06 | *3.9E−05* | 4.3E−07 | *1.9E−05* | 3.0 | 0.9 | 7 |
| IL6R-AP002/IL6R-BP256/IL6R-L | 3.6E−09 | 1.4E−07 | 4.2E−06 | 4.1E−09 | *1.7E−05* | 34.3 | 7.7 | 752 |
| IL6R-AP002/IL6R-BP257/IL6R-L | 1.9E−09 | 1.3E−07 | 4.9E−06 | 4.7E−09 | *1.4E−05* | 27.7 | 8.3 | 657 |
| IL6R-BP230/IL6R-L | 1.4E−08 | 5.7E−07 | *9.6E−06* | 2.1E−08 | *6.7E−05* | 27.5 | 1.9 | 149 |
| IL6R-BP259/IL6R-L | 3.1E−09 | 8.6E−07 | *1.8E−05* | 1.1E−07 | *1.1E−05* | 8.0 | 1.3 | 29 |
| IL6R-BP260/IL6R-L | 3.1E−10 | 1.2E−06 | *3.9E−05* | 3.8E−07 | *2.1E−05* | 3.2 | 0.9 | 8 |
| IL6R-AP009/IL6R-BP259/IL6R-L | 3.5E−09 | 1.9E−07 | 6.6E−06 | 3.9E−09 | *2.2E−05* | 47.7 | 5.8 | 788 |
| IL6R-AP009/IL6R-BP260/IL6R-L | 1.7E−09 | 1.4E−07 | 5.4E−06 | 4.2E−09 | *1.6E−05* | 34.2 | 7.6 | 739 |

Figure 13:
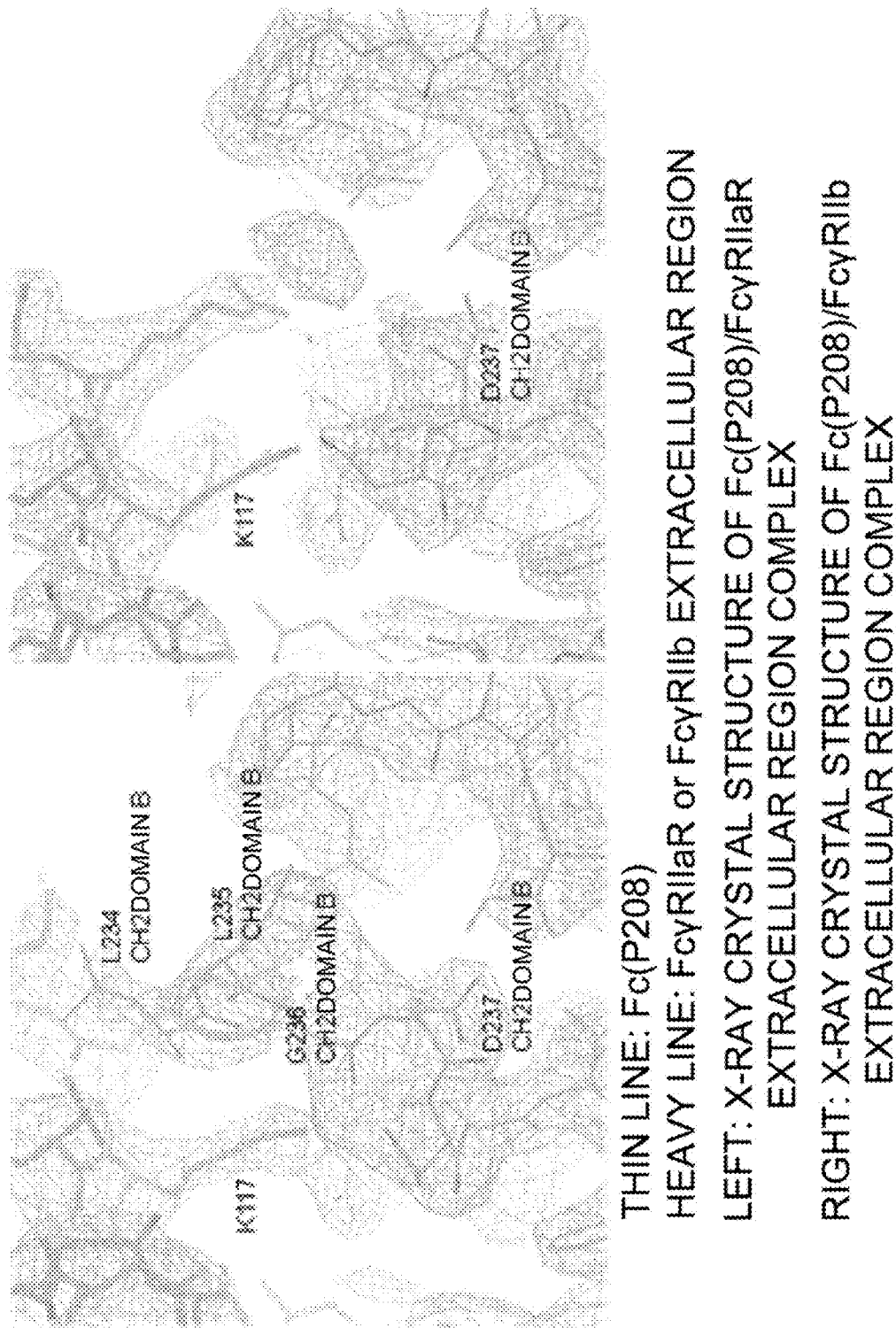
FIG. 13 shows a comparison of the X-ray crystal structure of the Fc(P208)/FcγRIIa type R extracellular region complex and the X-ray crystal structure of the Fc(P208)/FcγRIIb extracellular region complex around Asp at position 237 (EU numbering) in Fc portion CH2 domain B, along with electron density obtained by X-ray crystal structure analysis which uses 2Fo-Fc as the coefficient.

As shown in Table 10, compared to IL6R-BP208/IL6R-L, both IL6R-AP002/IL6R-BP256/IL6R-L and IL6R-AP002/IL6R-BP257/IL6R-L produced by introducing S239D and S239E, respectively, into one of the chains of IL6R-BP208/IL6R-L showed enhanced binding to FcgRIIb. Furthermore, the value of KD(IIaR)/KD(IIb) was greater than that of IL6R-BP256/IL6R-L, and selectivity to FcgRIIb was also improved. On the other hand, compared to IL6R-BP208/IL6R-L, both selectivity and binding to FcgRIIb of IL6R- a larger contribution to binding with FcgRIIaR (FIGS. 12 and 13). For example, from how the electron density looks, in the binding with the FcgRIIa type R, Leu at position 234 and Leu at position 235 (EU numbering) in CH2 domain B are considered to be involved in binding with the receptor, whereas these residues may only have little involvement in the binding to FcgRIIb. Then, by substituting these two residues with residues other than hydrophobic residues, interaction with FcgRIIa type R may be reduced by a greater degree. However, at the CH2 domain A side, the residues of Leu at position 234 and Leu at position 235 (EU numbering) are considered to contribute to stabilization of the loop structure around position 237 (EU numbering), and in particular, it is highly likely that they are more greatly involved in binding with FcgRIIb. Therefore, substituting these residues with residues other than hydrophobic residues may decrease interaction of CH2 domain A with FcgRIIb. In particular, Leu at position 235 (EU numbering) forms a favorable hydrophobic interaction in CH2 domain A of a complex structure formed with FcgRIIb, and since it is considered to have a large contribution to stabilization of the loop structure around position 237 (EU numbering), this residue was examined by substituting a residue in only one of the chains with a non-hydrophobic residue. If the hydrophobic interaction at the CH2 domain A in particular can further be strengthened to further stabilize the loop structure around position 237 (EU numbering) by substituting Leu at position 235 (EU numbering) with hydrophobic amino acids other than Leu in both chains, that may lead to reduction of entropic energy loss accompanying hydrogen bond formation with Tyr at position 160 of FcgRIIb and may cause enhancement of selectivity and binding to FcgRIIb; therefore, these were examined as well.

As the antibody H chain, IL6R-BP264 (SEQ ID NO: 28) was produced by introducing E233D, G237D, P238D, H268E, P271G, Y296D, and A330R into IL6R-B3 (SEQ ID NO: 23) was used as the template. Variants in which Leu at position 234 (EU numbering) of IL6R-BP264 individually was substituted with Asn, Ser, Asp, Gln, Glu, Thr, Arg, His, Gly, Lys, and Tyr were produced. Variants in which the amino acid at position 235 (EU numbering) in IL6R-BP264 was substituted with any of the 18 amino acids other than the original amino acid and Cys were also produced. For the other antibody H chain, IL6R-AP029 (SEQ ID NO: 42) was produced by introducing E233D, G237D, P238D, H268E, P271G, Y296D, and A330R into IL6R-A5 (SEQ ID NO: 69). IL6R-L (SEQ ID NO: 21) was commonly used as the antibody L chain. Variants produced by introducing L234N, L234S, L234D, L234Q, L234E, L234T, L234R, L234H, L234G, L234K, and L234Y into IL6R-BP264 and variants produced by introducing L235W, L235M, L235P, L235F, L235A, L235V, and L235I, respectively, into IL6R-BP264 were prepared as homologous antibodies containing the same alteration in both chains and variants produced by introducing L235N, L235S, L235D, L235Q, L235E, L235T, L235R, L235H, L235G, L235K, and L235Y, respectively, were combined with IL6R-AP029 to prepare heterodimeric antibodies, and those were then subjected to examination.

Figure 16:
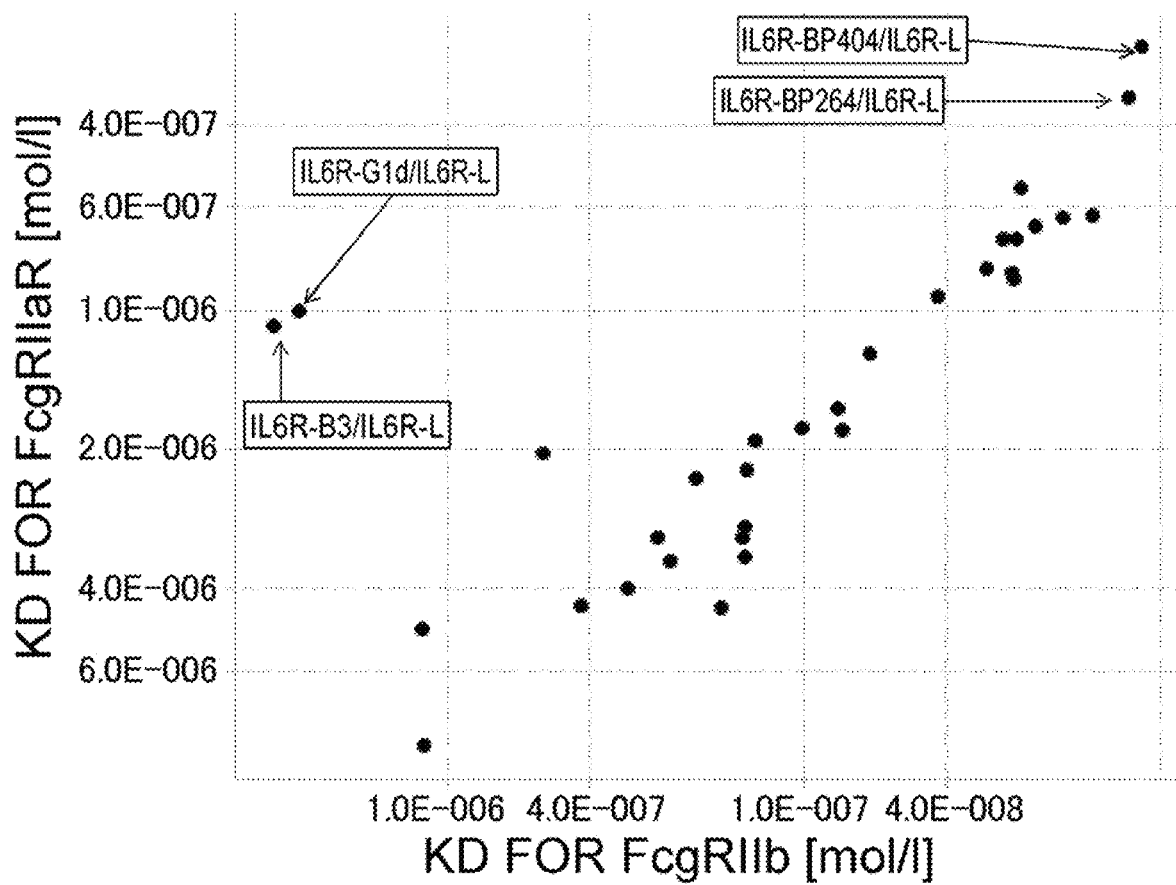
FIG. 16 shows the KD values of each variant for FcgRIIb on the horizontal axis, and the KD values of each variant for FcgRIIaR on the vertical axis. IL6R-B3/IL6R-L and IL6R-G1d/IL6R-L in the figure refer to antibodies having native human IgG sequences which serve as a comparison control when evaluating each of the variants. IL6R-BP264/IL6R-L is an original variant when producing each of the variants. IL6R-BP404/IL6R-L is a variant introduced with L234Y into both chains of IL6R-BP264/IL6R-L, which has improved FcgRIIb binding compared to that of the IL6R-BP264/IL6R-L before introducing alteration.
Figure 17:
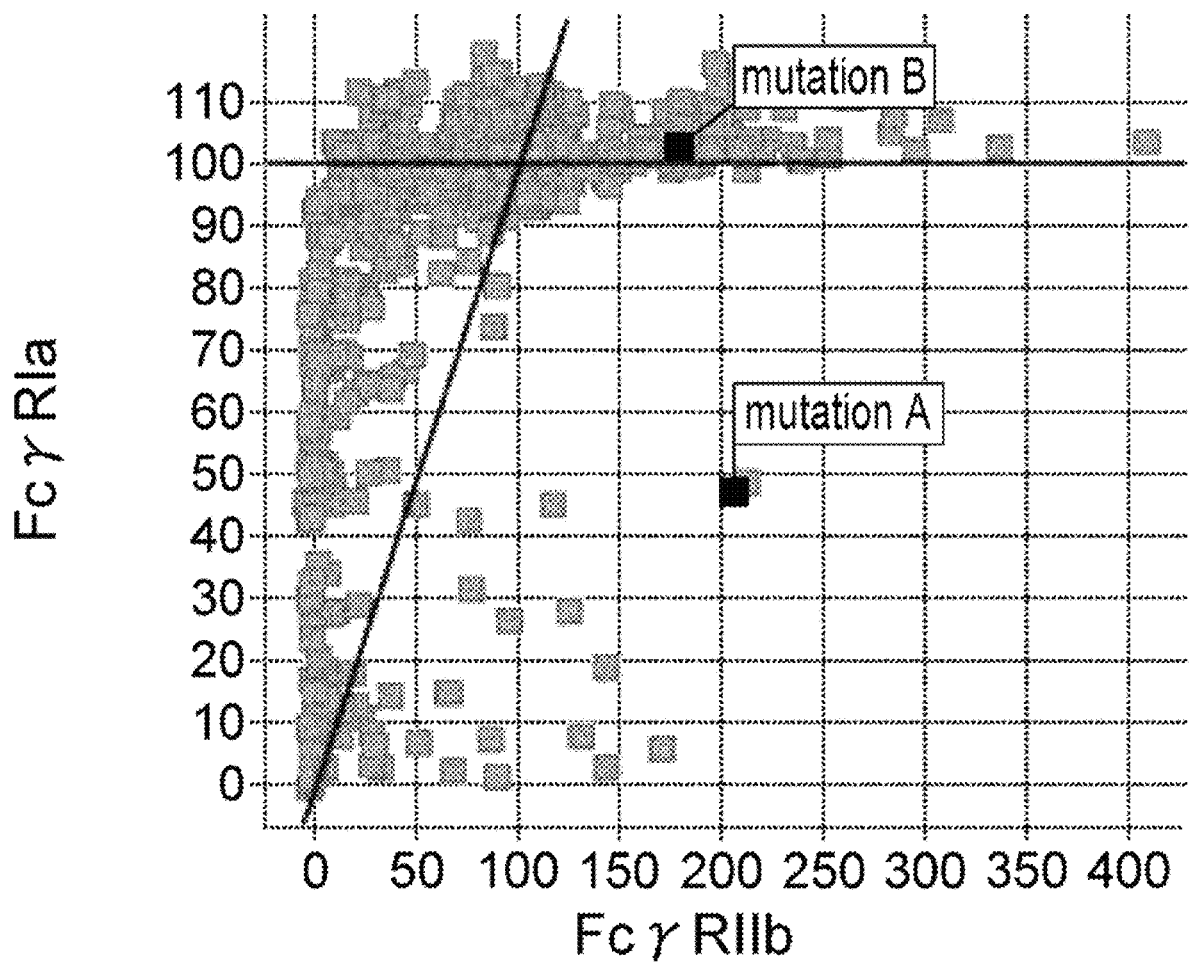
FIG. 17 shows comparison of FcγRIa binding and FcγRIIb binding. Binding of the antibody with substitution of Pro at position 238 (EU numbering) with Asp, and binding of the antibody with substitution of Leu at position 328 (EU numbering) with Glu have been labeled. "Mutation A" refers to an alteration produced by substituting Pro at position 238 (EU numbering) with Asp and "mutation B" refers to an alteration produced by substituting Leu at position 328 (EU numbering) with Glu.
Figure 18:
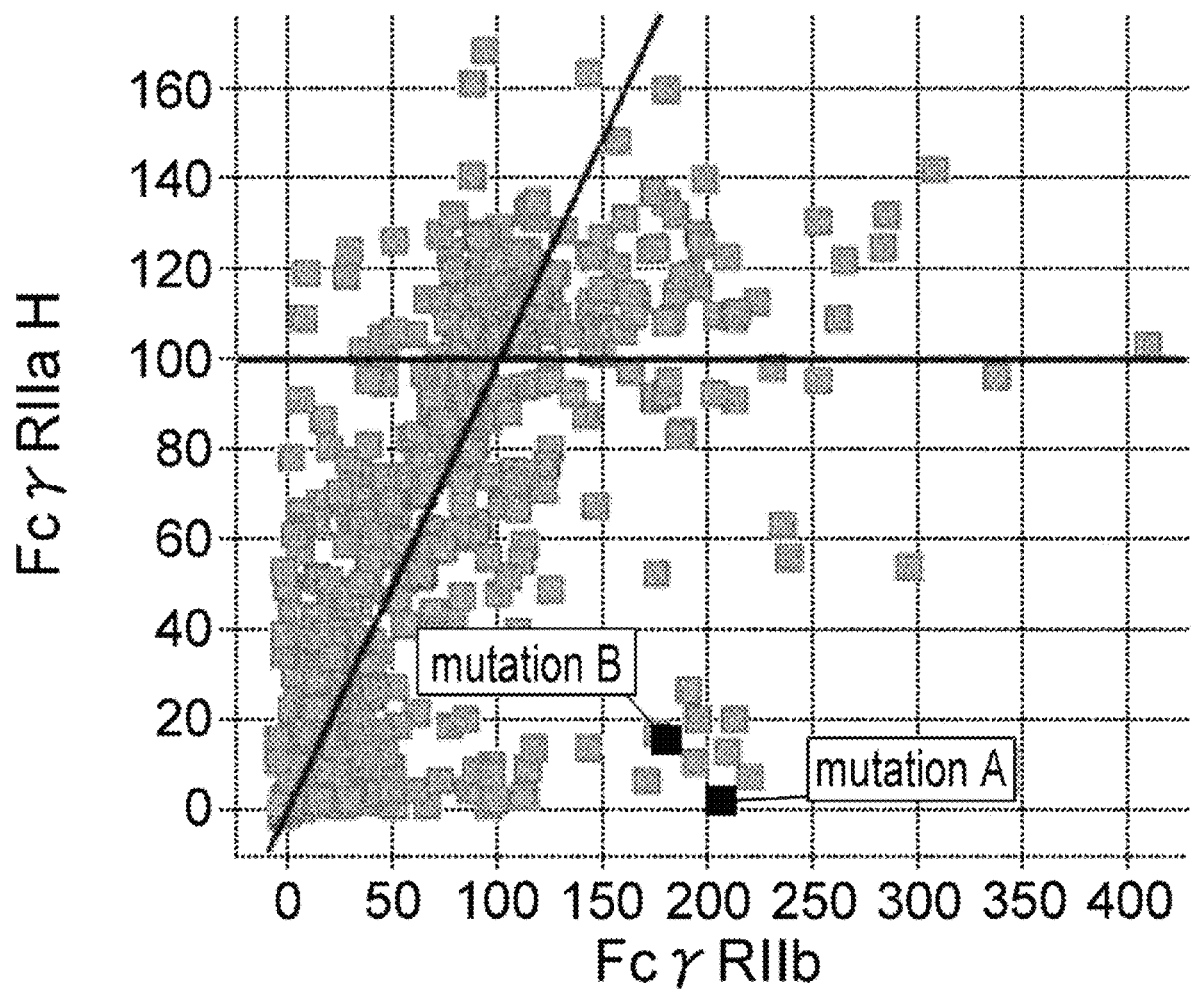
FIG. 18 shows comparison of FcγRIIa type H binding and FcγRIIb binding. Binding of the antibody with substitution of Pro at position 238 (EU numbering) with Asp, and binding of the antibody with substitution of Leu at position 328 (EU numbering) with Glu have been labeled. "Mutation A" refers to an alteration produced by substituting Pro at position 238 (EU numbering) with Asp, and "mutation B" refers to an alteration produced by substituting Leu at position 328 (EU numbering) with Glu.
Figure 19:
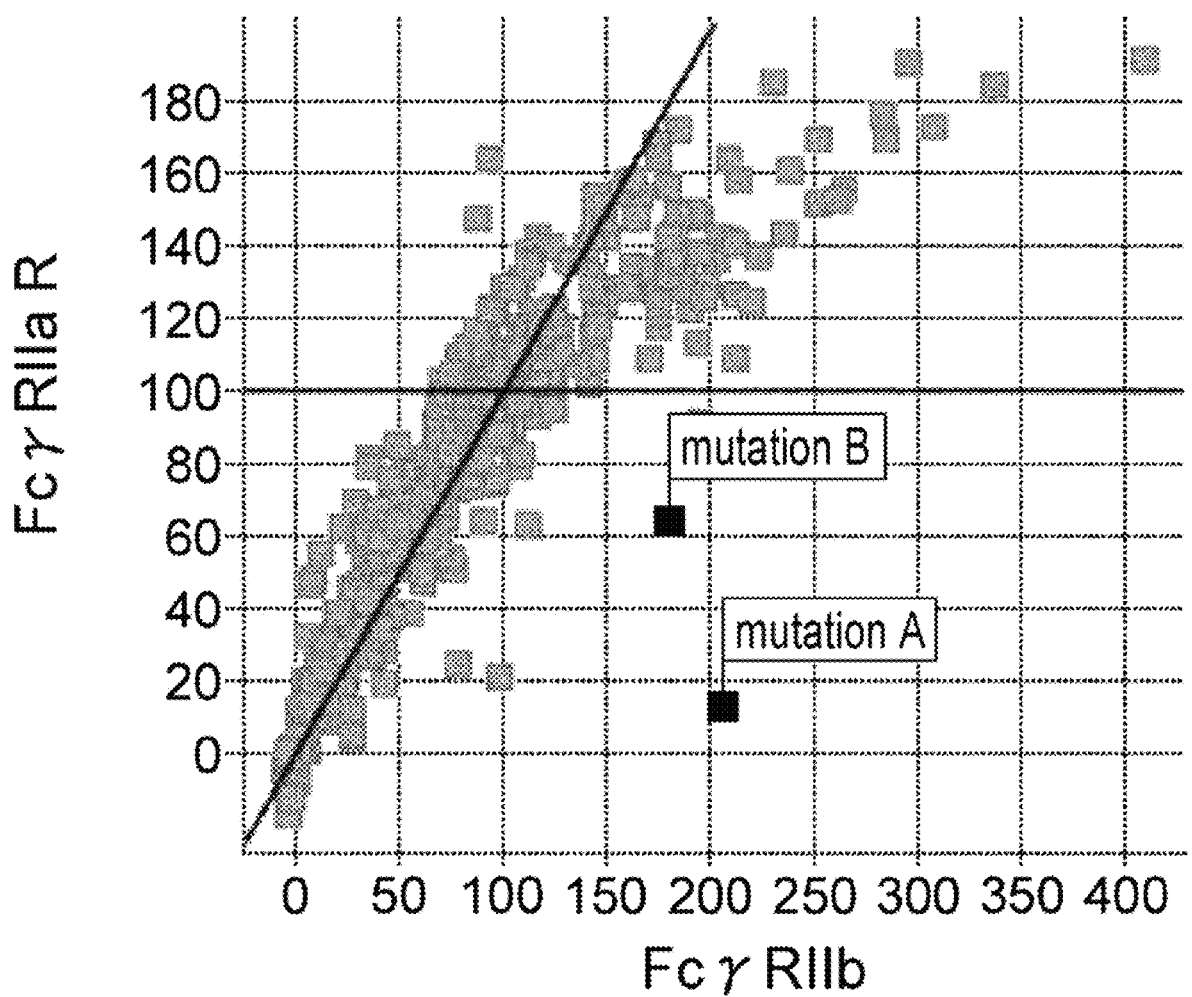
FIG. 19 shows comparison of FcγRIIa type R binding and FcγRIIb binding. Binding of the antibody with substitution of Pro at position 238 (EU numbering) with Asp, and binding of the antibody with substitution of Leu at position 328 (EU numbering) with Glu have been labeled. "Mutation A" refers to an alteration produced by substituting Pro at position 238 (EU numbering) with Asp, and "mutation B" refers to an alteration produced by substituting Leu at position 328 (EU numbering) with Glu.
Figure 20:
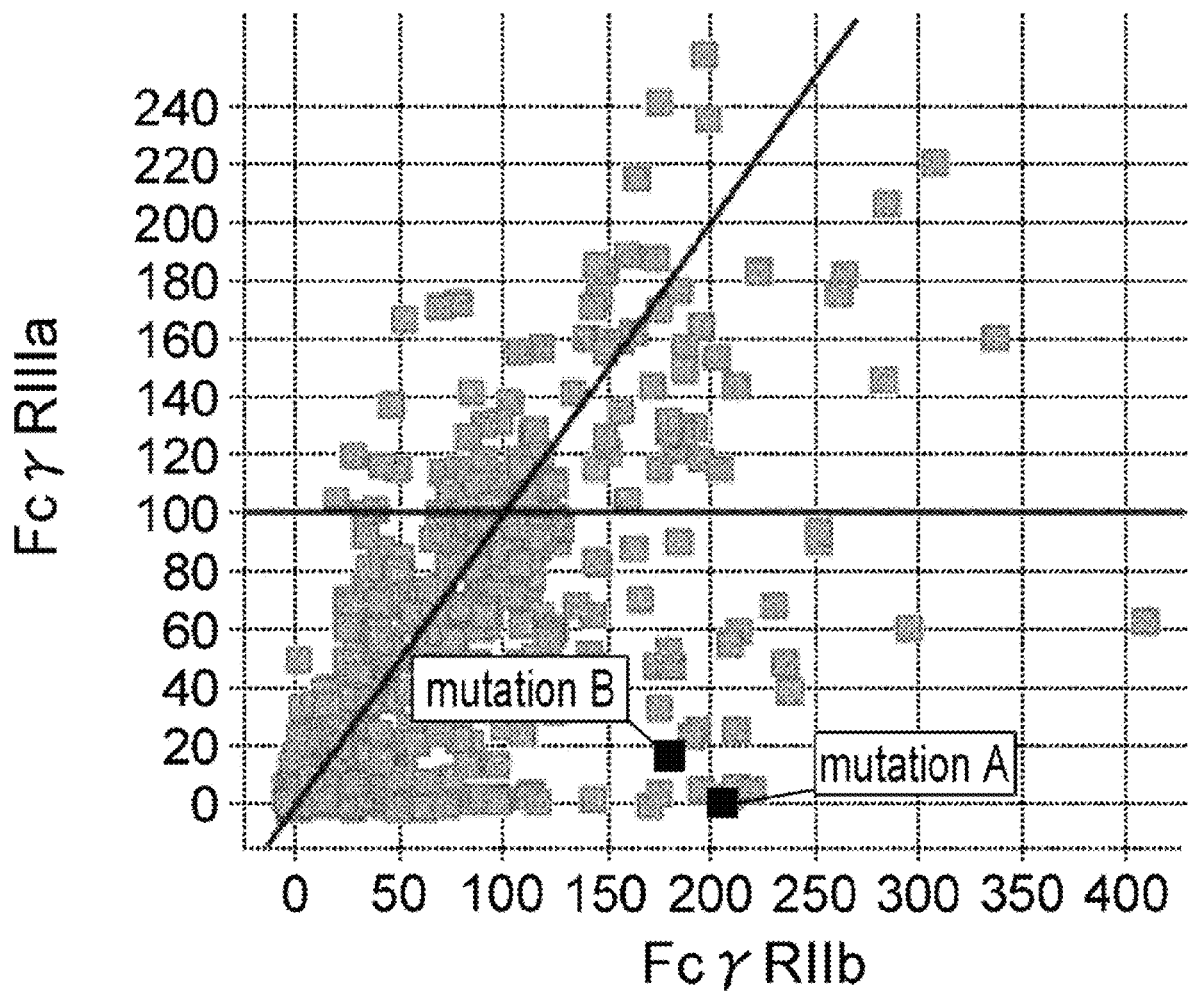
FIG. 20 shows comparison of FcγRIIIa binding and FcγRIIb binding. Binding of the antibody with substitution of Pro at position 238 (EU numbering) with Asp, and binding of the antibody with substitution of Leu at position 328 (EU numbering) with Glu have been labeled. "Mutation A" refers to an alteration produced by substituting Pro at position 238 (EU numbering) with Asp, and "mutation B" refers to an alteration produced by substituting Leu at position 328 (EU numbering) with Glu.

These variants were used for antibody expression and purification according to the method of Reference Example 1, and binding to each FcgR (FcgRIa, FcgRIIa type H, FcgRIIa type R, FcgRIIb, and FcgRIIIa type V) was assessed using the method of Reference Example 2. FIG. 16 shows a graph in which KD values of each variant for FcgRIIb are shown on the horizontal axis and the KD values of each variant for FcgRIIaR are shown on the vertical axis.

As shown in FIG. 16, IL6R-BP404/IL6R-L produced by introducing L234Y into both chains of IL6R-BP264/IL6R-L showed slightly enhanced binding to FcgRIIb as compared to that of the IL6R-BP264/IL6R-L prior to alteration.

From among these variants, IL6R-BP404/IL6R-L with enhanced FcgRIIb binding and variants with improved selectivity to FcgRIIb are summarized in Table 11. In this Table, "parent polypeptide KD (IIb)/altered polypeptide KD (IIb)" refers to a value obtained by dividing the KD value of IL6R-B3/IL6R-L for FcgRIIb by the KD value of each variant for FcgRIIb. "Parent polypeptide KD (IIaR)/altered polypeptide KD (IIaR)" refers to a value obtained by dividing the KD value of IL6R-B3/IL6R-L for FcgR IIaR by the KD value of each variant for FcgRIIaR. "KD (IIaR)/KD (IIb)" is a value obtained by dividing the KD of each variant for FcgRIIaR by the KD of each variant for FcgRIIb. The larger this value is, the higher the selectivity to FcgRIIb is. The Table 11 values shown in bold italicized font were calculated using the following equation $$KD = C \cdot R_{max}/(R_{eq}-RI)-C \qquad \text{[Equation 2]}$$

shown in Reference Example 2 since the binding of FcgR to IgG was too weak to accurately analyze by kinetic analysis.

TABLE 11

| VARIANT NAME | KD FOR FcgRIa (mol/L) | KD FOR FcgRIIaR (mol/L) | KD FOR FcgRIIaH (mol/L) | KD FOR FcgRIIb (mol/L) | KD FOR FcgRIIIaV (mol/L) | KD(IIaR)/ KD(IIb) | KD(IIaR) OF PARENT POLYPEPTIDE/ KD(IIaR) OF ALTERED POLYPEPTIDE | KD(IIb) OF PARENT POLYPEPTIDE/ KD(IIb) OF ALTERED POLYPEPTIDE |
|---|---|---|---|---|---|---|---|---|
| IL6R-G1d/IL6R-L | 3.2E−10 | 1.0E−06 | 6.7E−07 | 2.6E−06 | 3.5E−07 | 0.4 | 1.1 | 1.2 |
| IL6R-B3/IL6R-L | 4.2E−10 | 1.1E−06 | 7.7E−07 | 3.1E−06 | 3.3E−07 | 0.3 | 1.0 | 1.0 |
| IL6R-BP264/IL6R-L | 7.4E−09 | 3.5E−07 | *2.8E−06* | 1.2E−08 | *2.6E−05* | 28.3 | 3.2 | 252.0 |
| IL6R-BP404/IL6R-L | 1.0E−08 | 3.6E−07 | *3.4E−06* | 1.1E−08 | *3.3E−05* | 32.1 | 3.1 | 276.8 |
| IL6R-BP408/IL6R-L | 1.4E−07 | 3.4E−05 | *7.7E−05* | 7.2E−07 | *5.0E−05* | 47.0 | 0.03 | 4.3 |
| IL6R-BP419/IL6R-L | 4.0E−08 | 8.3E−07 | *3.8E−05* | 2.6E−08 | *3.8E−05* | 32.0 | 1.3 | 118.8 |
| IL6R-AP029/IL6R-BP407/IL6R-L | 1.3E−08 | 6.3E−07 | *8.9E−06* | 1.9E−08 | *2.3E−05* | 33.5 | 1.7 | 164.0 |
| IL6R-AP029/IL6R-BP408/IL6R-L | 2.0E−08 | 8.6E−07 | *8.2E−06* | 2.6E−08 | *3.1E−05* | 33.6 | 1.3 | 121.1 |
| IL6R-AP029/IL6R-BP409/IL6R-L | 1.9E−08 | 6.3E−07 | *9.4E−06* | 1.5E−08 | *2.8E−05* | 40.8 | 1.8 | 201.3 |
| IL6R-AP029/IL6R-BP410/IL6R-L | 1.7E−08 | 6.6E−07 | *5.1E−06* | 2.2E−08 | *2.1E−05* | 29.7 | 1.7 | 139.0 |

As shown in Table 11, IL6R-BP404/IL6R-L produced by introducing L234Y into both chains of IL6R-BP264/IL6R-L showed 1.1-fold increase in FcgRIIb binding as compared to that of the IL6R-BP264/IL6R-L prior to introduction of alterations. IL6R-BP408/IL6R-L produced by introducing L235Q into both chains of IL6R-BP264/IL6R-L, IL6R-BP419/IL6R-L produced by introducing L235F into both chains of IL6R-BP264/IL6R-L, IL6R-AP029/IL6R-BP407/IL6R-L produced by introducing L235D into one of the chains of IL6R-BP264/IL6R-L, IL6R-AP029/IL6R-BP408/IL6R-L produced by introducing L235Q into one of the chains of IL6R-BP264/IL6R-L, IL6R-AP029/IL6R-BP409/IL6R-L produced by introducing L235E into one of the chains of IL6R-BP264/IL6R-L, and IL6R-AP029/IL6R-BP410/IL6R-L produced by introducing L235T into one of the chains of IL6R-BP264/IL6R-L all showed KD(IIaR)/

KD(IIb) values that were larger compared to that of the IL6R-BP264/IL6R-L prior to introduction of alteration, and they were variants with improved selectivity to FcgRIIb.

[Example 10] Assessment of Immunogenicity of Fc Variants with Enhanced FcgRIIb Binding Using an In Silico Immunogenicity Prediction Tool When using the Fc variants described in this Example as therapeutic antibodies, it is preferred that production of anti-drug antibodies that weaken their pharmacological effect is not induced. Since antibodies with high immunogenicity tend to induce production of anti-drug antibodies, immunogenicity of therapeutic antibodies is preferably as low as possible. As efforts to avoid increase in immunogenicity of the variants as much as possible, one can use in silico immunogenicity prediction tools that predict T-cell epitopes such as Epibase™ and EpiMatrix prediction tools. Epibase™ Light (Lonza) is an in silico immunogenicity prediction tool to calculate the binding ability of 9-mer peptide to MHC class II which contains major DRB1 alleles using the FASTER algorithm (Expert Opin Biol Ther. 2007 March; 7(3): 405-18). This tool can identify T-cell epitopes with strong binding (strong epitopes) and medium binding (medium epitopes) to MHC class II.

DRB1 allotype population frequency is reflected in the calculation, and for this, Caucasian population frequency shown in Table 12 below can be used.

TABLE 12

| | |
|---|---|
| DRB1*1501 | 24.5% |
| DRB1*0301 | 23.7% |
| DRB1*0701 | 23.3% |
| DRB1*0401 | 16.2% |
| DRB1*0101 | 15.0% |
| DRB1*1101 | 11.6% |
| DRB1*1301 | 10.9% |
| DRB1*1302 | 8.2% |
| DRB1*0404 | 5.9% |
| DRB1*1104 | 5.8% |
| DRB1*1601 | 5.0% |
| DRB1*1401/1454 | 4.9% |
| DRB1*0801 | 4.9% |
| DRB1*0102 | 3.8% |
| DRB1*1201/1206/1210 | 3.3% |
| DRB1*0407 | 2.7% |
| DRB1*0901 | 2.3% |
| DRB1*1303 | 2.0% |
| DRB1*1001 | 1.9% |
| DRB1*0405 | 1.5% |
| DRB1*0403 | 1.0% |
| DRB1*1102 | 0.7% |
| DRB1*0802 | 0.7% |
| DRB1*1502 | 0.5% |
| DRB1*0804 | 0.4% |
| DRB1*1404 | 0.4% |
| DRB1*0803 | 0.3% |
| DRB1*0406 | 0.2% |
| DRB1*1402 | 0.2% |
| DRB1*1602 | 0.2% |
| DRB1*1202 | 0.1% |
| DRB1*0304 | 0.1% OR LESS |
| DRB1*1405 | 0.1% OR LESS |
| DRB1*0410 | 0.1% OR LESS |
| DRB1*1503 | 0.1% OR LESS |
| DRB1*1106 | 0.1% OR LESS |
| DRB1*1504 | 0.1% OR LESS |
| DRB1*1304 | 0.1% OR LESS |
| DRB1*1110 | 0.1% OR LESS |
| DRB1*1406 | 0.1% OR LESS |
| DRB1*0411 | 0.1% OR LESS |
| DRB1*0302 | 0.1% OR LESS |
| DRB1*1312 | 0.1% OR LESS |

This tool was used to compare the total number of T-cell epitopes with strong binding and medium binding that are included in the sequences (the sequence from position 118 to the C terminus (EU numbering)) of various Fc variants reported so far and Fc variants with selectively enhanced binding to FcgRIIb described in the Example. Specifically, the following antibodies were produced as comparison controls for evaluating pre-existing techniques: Fc(DLE) (SEQ ID NO: 78) which is an antibody Fc region introduced with the S239D, A330L, and I332E alterations, which has been previously reported to enhance FcgRIIIa-binding (Proc Natl Acad Sci USA. 2006, 103: 4005-10); Fc(YTE) (SEQ ID NO: 79) which is an antibody Fc region introduced with the M252Y, S254T, and T256E alterations, which has been previously reported to enhance FcRn-binding (J Biol Chem. 2006, 281: 23514-24); Fc(EF) (SEQ ID NO: 80) which is an antibody Fc region introduced with the S267E and L328F alterations, which has been reported to enhance FcgRIIb-binding (Mol Immunol. 2008, 45: 3926-33); and Fc(P208) (SEQ ID NO: 81) which is an Fc region of an antibody introduced with the E233D, G237D, P238D, H268D, P271G, and A330R alterations, which has been reported to enhance FcgRIIb-binding and is described in WO2012/115241. Furthermore, Fc(P587) (SEQ ID NO: 70), which is an antibody Fc region introduced with the E233D, P238D, S264I, S267A, H268E, and P271G alterations in a similar manner to the BP568 variant, which enhances FcgRIIb-binding and is described in the Examples, and Fc(P588) (SEQ ID NO: 71), which is an antibody Fc region introduced with the P238D, S264I, S267A, H268E, and P271G alterations in a similar manner to BP492, were produced. The total number of strong and medium binding epitopes in these Fc variants was compared using the Epibase™ prediction tool. The results are shown in Table 13.

TABLE 13

| | NUMBER OF T-cell epitope |
|---|---|
| Fc (DLE) | 2 |
| Fc (YTE) | 5 |
| Fc (EF) | 4 |
| Fc (P208) | 5 |
| Fc (P587) | 2 |
| Fc (P588) | 2 |

These results indicate that among the existing Fc variants, Fc(P587) and Fc(P588) which are Fc regions of variants described in the Examples have small number of T-cell epitopes and low immunogenicity risk. When using the variants as pharmaceuticals, this property indicates that the possibility of inducing anti-drug antibodies is lowered and that the variants have excellent properties.

[Example 11] Assessment of Blood Kinetics of Fc Variants with Enhanced Human FcgRIIb Binding Using Human FcgRIIb Transgenic Mice (11-1) Outline of the Examination As indicated in WO2013/047752, compared to a native human IgG, the plasma concentration of a target soluble antigen can be reduced significantly in a living organism by administering an antigen-binding molecule having human-FcRn-binding activity under an acidic pH range condition and comprising an antigen-binding domain whose antigen binding activity of the antigen-binding molecule changes depending on an ion concentration condition, and an FcgR-binding domain with higher FcgR-binding activity than the FcgR-binding domain of a native human IgG Fc region, wherein the sugar chain linked to position 297 (EU numbering) is a fucose-containing sugar chain. It has also been reported that when an antigen-binding molecule that has enhanced binding activity particularly to FcgRIIb among the FcgRs is administered in vivo, elimination of soluble antigens in plasma is accelerated, and the concentration of soluble antigens in plasma can be reduced effectively. In this Example, an Fc variant with enhanced binding to human FcgRIIb was administered to genetically-modified transgenic mice introduced with human FcgRIIb to test whether the elimination rate of the target soluble antigens can be accelerated by the Fc variant with actually enhanced binding to human FcgRIIb described herein.

(11-2) Preparation of Antibodies with Enhanced Binding to FcgRIIb

The following antibodies were used as the Fc variants with enhanced human FcgRIIb-binding:

IL6R-P587 was produced by introducing the E233D, P238D, S264I, S267A, H268E, and P271G alterations in a similar manner to BP568 into IL6R-G1d (SEQ ID NO: 19) consisting of a constant region of G1d which has the C-terminal Gly and Lys removed from human IgG1, and a variable region of an antibody against human interleukin-6 receptor (human IL-6R) disclosed in WO2009/125825. Fv4-P587 comprising IL-6R-P587 as the antibody H chain and IL6R-L2 (SEQ ID NO: 74) which is the L chain of an anti-human IL-6R antibody disclosed in WO2009/125825 as the antibody L chain was prepared according to the method of Reference Example 1. As a comparison control, Fv4-IgG1 comprising IL6R-G1d (SEQ ID NO: 19) and IL6R-L2 (SEQ ID NO: 74) as the antibody H chain and L chain, respectively, was prepared similarly according to the method of Reference Example 1. As described in WO2009/125825, Fv4-G1d and Fv4-P587 prepared herein comprises an antigen-binding domain whose antigen-binding activity of the antigen-binding molecule changes depending on the condition of proton ion concentration, that is, the antigen-binding activity of the antigen-binding domain binds to a human IL-6R (antigen) under acidic pH conditions weaker than under neutral pH conditions.

(11-3) Production of Human FcgRIIb Transgenic Mice

Human FcgRIIb transgenic mice were produced by the following method.

Transgenic mice were produced by introducing the human FcgRIIb gene into C57BL/6(B6) mice. Production of transgenic mice was carried out in accordance with the procedure described in "Nagy et al., (Manipulating the mouse embryo, CSHL press. (2003) 399-506)" and in "Ueda et al. (Latest Technology for Gene Targeting", Yodosha. (2000) 190-207)". More specifically, transgenic mice were produced by microinjecting into pronuclear fertilized eggs of B6 mice a bacterial artificial chromosome into which the genomic region of the human FcgRIIb gene (GeneBank #NW_004077999: 18,307,411-18,381,603) was cloned. Mice transferred with the human FcgRIIb gene were selected from the obtained mice by Southern blotting using a probe that specifically hybridizes with the human FcgRIIb gene and by performing PCR. Blood and liver were collected from the human FcgRIIb transgenic mice, and expression of the human FcgRIIb gene was confirmed by Reverse Transcription Polymerase Chain Reaction (RT-PCR) using primers that specifically amplify the human FcgRIIb gene. As a result, expression of the human FcgRIIb gene was detected. Furthermore, mouse peripheral blood mononuclear cells (PBMC) were isolated from the blood of the human FcgRIIb transgenic mice, and the expression of human FcgRIIb in PBMC was confirmed by fluorescence activated cell sorting (FACS) analyses. As a result, expression of human FcgRIIb was detected. The above confirmed that human FcgRIIb transgenic mice which express human FcgRIIb were established.

(11-4) In Vivo Test of Simultaneous Administration of Antigens and Antibodies Using the Human FcgRIIb Transgenic Mice Using the human FcgRIIb transgenic mice produced in (11-3), soluble human IL-6R which is the antigen and the anti-human IL-6R antibody prepared in (11-2) were administered simultaneously, and the plasma concentrations of soluble human IL-6R and anti-human IL-6R antibody after the administration were evaluated.

A mixed solution of soluble human IL-6R and anti-human IL-6R antibody (5 μg/mL and 0.1 mg/mL, respectively) was administered in a single dose at 10 mL/kg to the tail vein. In this case, since anti-human IL-6R antibody is present sufficiently in excess with respect to soluble human IL-6R, almost all of the soluble human IL-6R is considered to be bound to the antibody. Blood was collected five minutes, 1 hour, 4 hours, 7 hours, 1 day, 3 days, 7 days, 14 days, 21 days, and 28 days after administration. The collected blood was immediately centrifuged at 4° C. and 15,000 rpm for 15 minutes to obtain the plasma. The separated plasma was stored in a freezer set at −20° C. or lower until the time of measurement. The above-described Fv4-P587 and Fv4-IgG1 were used for the anti-human IL-6R antibody.

(11-5) Measurement of Plasma Anti-Human IL-6R Antibody Concentration by ELISA

Figure 33:
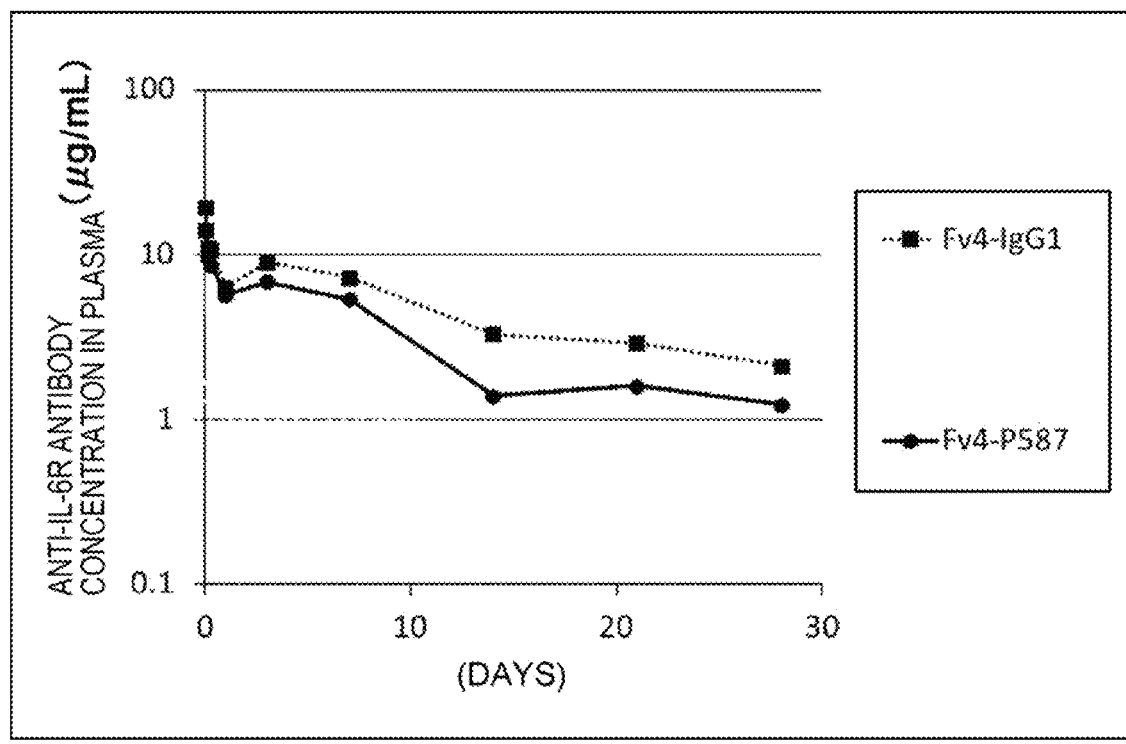
FIG. 33 shows the change in plasma concentrations of the administered antigen-binding molecules of human FcgRIIb transgenic mice when Fv4-IgG1 or Fv4-P587 was administered to the mice.

Concentration of anti-human IL-6R antibody in mouse plasma was measured by ELISA. First, anti-human IgG (γ-chain specific) antibody F(ab')2 fragment (Sigma) was aliquoted into a Nunc-Immuno™ MaxiSorp™ plate (Nalge Nunc International), followed by allowing to stand overnight at 4C to prepare an anti-human IgG-immobilized plate. Calibration curve samples of plasma concentration at 0.8, 0.4, 0.2, 0.1, 0.05, 0.025 and 0.0125 μg/mL and mouse plasma assay samples diluted to 100-fold or more were prepared. Mixtures obtained by adding 200 μL of 20 ng/mL soluble human IL-6R to 100 μl of the calibration curve samples or plasma assay samples were then stirred for 1 hour at room temperature. Subsequently, the anti-human IgG-immobilized plate in which the mixtures had been dispensed was further stirred for one hour at room temperature. Then, a biotinylated anti-human IL-6R antibody (R&D) was reacted with the samples at room temperature for one hour and Streptavidin-PolyHRP80 (Stereospecific Detection Technologies) was reacted with the samples at room temperature for one hour. The chromogenic reaction was carried out using TMB One Component HRP Microwell Substrate (BioFX Laboratories) as substrate. After the reaction was stopped by adding 1N sulfuric acid (Showa Chemical), absorbance at 450 nm was measured with a microplate reader. Antibody concentrations in the mouse plasma were calculated from absorbance values of the calibration curve using the SOFTmax™ PRO analysis software (Molecular Devices). The time course of plasma antibody concentration in human FcgRIIb transgenic mice after intravenous administration measured by this method is shown in FIG. 33.

Figure 34:
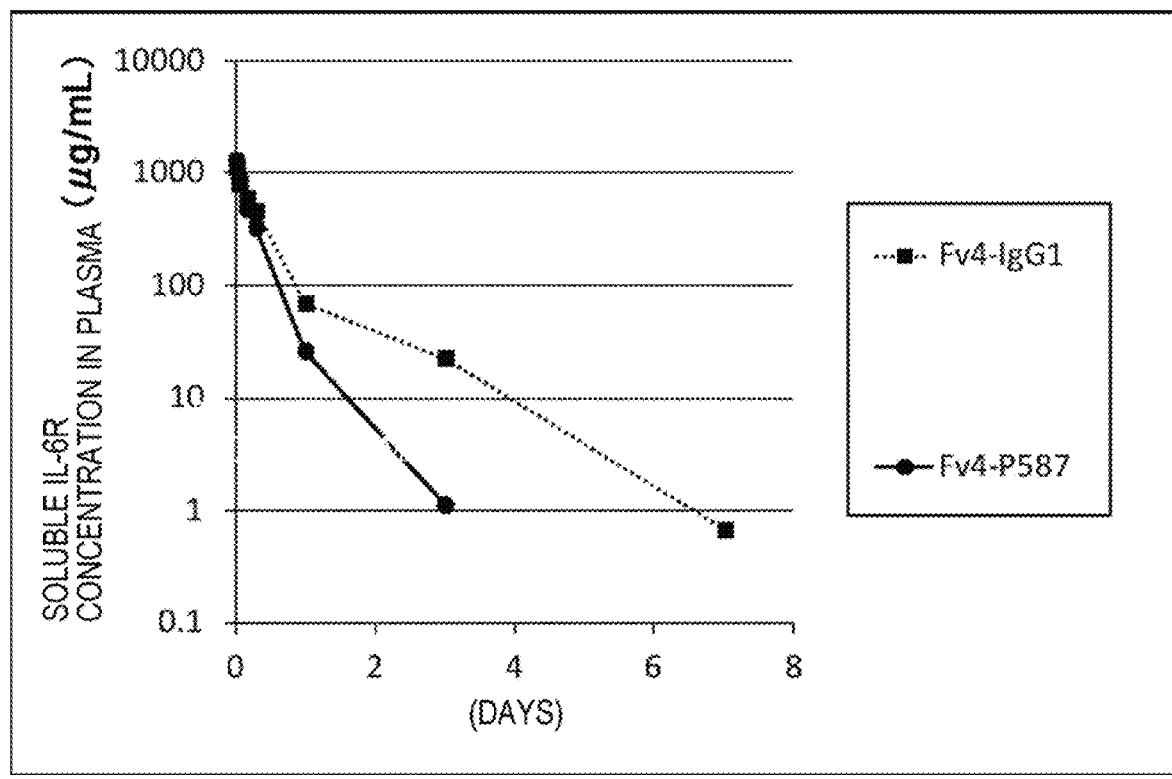
FIG. 34 shows the change in plasma concentrations of the administered human IL-6R of human FcgRIIb transgenic mice when Fv4-IgG1 or Fv4-P587 was administered to the mice.

(11-5) Measurement of Plasma Human IL-6R Concentration by Electrochemiluminescence The human IL-6R concentration in mouse plasma was measured by electrochemiluminescence. Calibration curve samples of human IL-6R were prepared at plasma concentrations of 12.5, 6.25, 3.13, 1.56, 0.781, 0.391, and 0.195 ng/mL, and mouse plasma assay samples were prepared by diluting 50 fold or more. Monoclonal Anti-human IL-6R Antibody (R&D) which has been ruthenium-labeled using SULFO-TAG NHS Ester (Meso Scale Discovery), Biotinylated Anti-human IL-6 R Antibody (R&D), and tocilizumab solution were mixed in and allowed to react overnight at 37° C. Then, the mixed solution was aliquoted into the Streptavidin Gold Multi-ARRAY Plate (Meso Scale Discovery) subjected to blocking using a TBS-Tween solution containing 0.5% BSA (w/v) overnight at 5° C. After allowing to react for two more hours at room temperature, the plate was washed. Immediately after the Read Buffer T (×2) (Meso Scale Discovery) was aliquoted into the plate, and measurements were carried out using the SECTOR® Imager 2400 (Meso Scale Discovery). The hSIL-6R concentrations were calculated based on the response from the calibration curve using the analytical software SOFTmax™ PRO (Molecular Devices). Time course of the soluble human IL-6R concentration in plasma of human FcgRIIb transgenic mice after intravenous administration, which was measured by this method, is shown in FIG. 34.

(11-6) Effects of Enhancing Human FcgRIIb Binding

The in vivo test results were compared for Fv4-P587 whose human FcgRIIb-binding has been enhanced and Fv4-IgG1. As shown in FIG. 33, the plasma retention of both antibodies were nearly equal; however, as shown in FIG. 34, elimination of human IL-6R was confirmed to be accelerated when human IL-6R was administered simultaneously with Fv4-P587 having enhanced human FcgRIIb-binding as compared to when human IL-6R was administered simultaneously with Fv4-IgG1. More specifically, an antibody that binds to human IL-6R in a pH-dependent manner was found to be able to decrease the concentration of soluble human IL-6R by enhancing its binding ability to human FcgRIIb.

Figure 35:
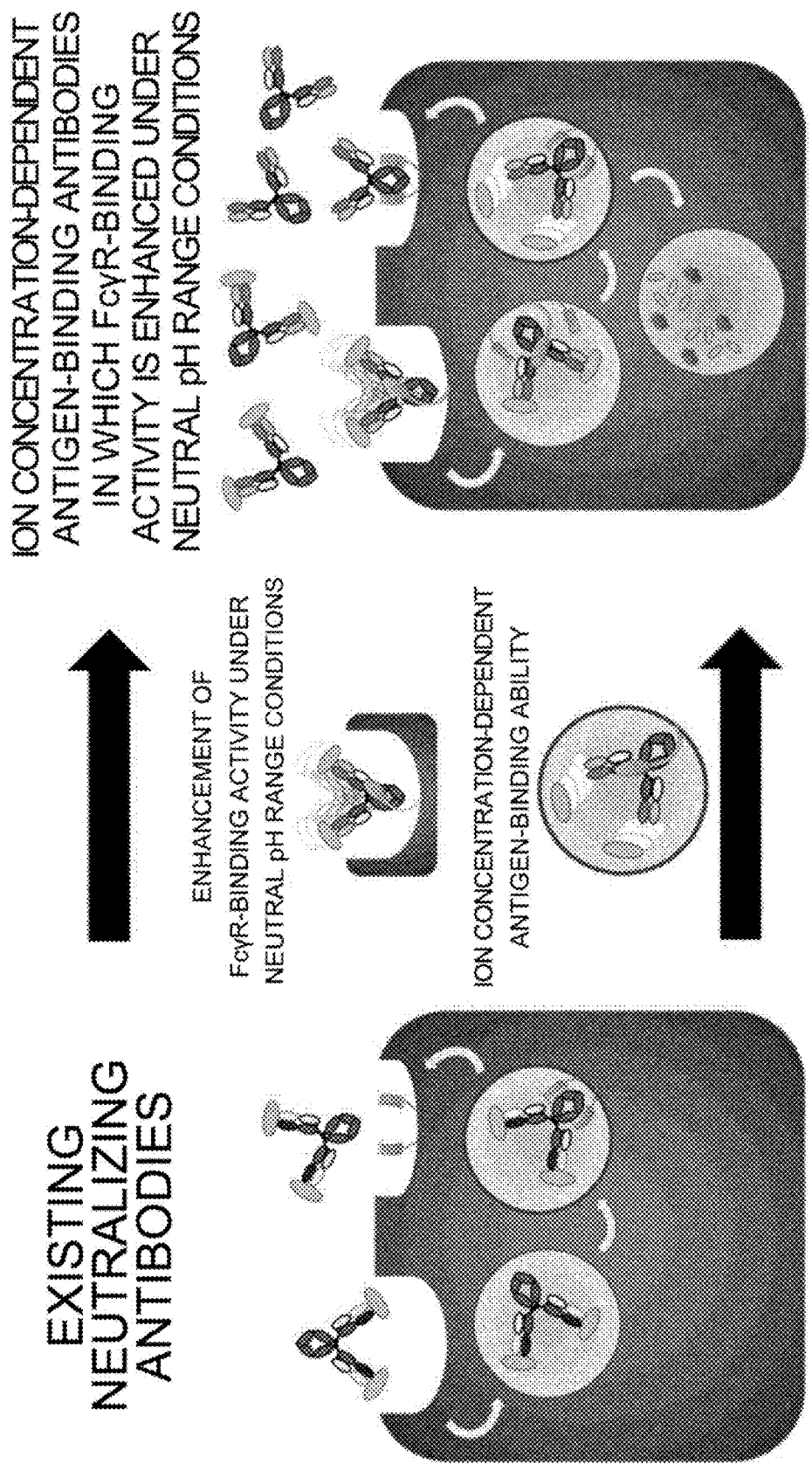
FIG. 35 shows a non-limiting action mechanism for the elimination of soluble antigens from plasma by administration of antibodies that bind to antigens in an ion-concentration-dependent manner, which are antibodies with enhanced FcγR-binding at neutral pH as compared to that of existing neutralizing antibodies.

Without being bound by a particular theory, one may consider from this result that according to the mechanism indicated in FIG. 35, the soluble antigens in plasma that bind to this antibody disappear as a result of being incorporated into FcγRIIb-expressing cells via human FcγRIIb.

Soluble human IL-6R bound to an antibody that binds soluble human IL-6R is recycled into plasma by FcRn along with the antibody. In contrast, Fv4-IgG1 which is an antibody that binds to soluble human IL-6R in a pH-dependent manner dissociates the antibody-bound soluble human IL-6R under acidic conditions in the endosome. Since the dissociated soluble human IL-6R is degraded by the lysosome, elimination of soluble human IL-6R can be significantly accelerated, and Fv4-IgG1 which is an antibody that binds to soluble human IL-6R in a pH-dependent manner binds to FcRn in the endosome and is then recycled into plasma. This recycled antibody can bind again to soluble human IL-6R; therefore, antigen (soluble human IL-6R)-binding and recycling into plasma by FcRn are repeated. It is considered that as a result, single antibody molecule can bind to the soluble human IL-6R several times repeatedly. Furthermore, it is considered that by enhancing the FcgRIIb-binding activity of Fv4-IgG1 which shows pH-dependent antigen binding, a complex formed between an antibody that binds to the soluble human IL-6R and a soluble human IL-6R is quickly incorporated into cells via FcgRIIb to enable decrease in the soluble human IL-6R concentration more efficiently (FIG. 35).

[Example 12] Evaluation of Blood Kinetics of Fc Variants with Enhanced Binding to Human FcgRIIb Using Human FcgRIIb and Human FcRn Transgenic Mice (12-1) Outline of the Examination As indicated in WO2013/047752, use of an antigen-binding molecule having higher FcγR-binding activity than that of the native IgG Fc region and whose human FcRn-binding activity under an acidic pH range condition is enhanced confirmed that plasma retention properties are improved compared to antigen-binding molecules whose human FcRn-binding activity under an acidic pH range condition is not enhanced. On the other hand, there have been reports that an antigen-binding molecule having higher FcγR-binding activity than that of the native human IgG Fc region and whose human FcRn-binding activity under an acidic pH range condition is enhanced showed decreased plasma concentration of target antigen as compared to an antigen-binding molecule having higher FcγR-binding activity than that of the native human IgG Fc region and whose human FcRn-binding activity under an acidic pH range condition is not enhanced. Accordingly, whether the antigen-binding molecules carrying the Fc region variants with enhanced human FcgRIIb binding described in the Examples have similar properties was investigated.

(12-2) Production of an Antigen-Binding Molecule Having Higher FcγR-Binding Activity than that of a Native Human IgG Fc Region and Whose Human FcRn-Binding Activity Under an Acidic pH Range Condition is Enhanced In addition to Fv4-IgG1 and Fv4-P587 described in Example 11-2, Fv4-P587-LS was prepared according to the method of Reference Example 1, where Fv4-P587-LS contains IL6R-L2 as the antibody L chain and IL6R-P587-LS (SEQ ID NO: 73) as the antibody H chain. IL6R-P587-LS was produced by introducing into IL6R-P587, the H chain of Fv4-P587, alterations consisting of substitution of Met at position 428 with Leu and substitution of Asn at position 434 with Ser, according to EU numbering, which are substitutions that have been previously reported to improve blood kinetics of antibodies (Nat. Biotechnol. 2010. 28; 157-159).

(12-3) Analysis of Interaction with Human FcRn

Analysis of interaction between a prepared antibody and the human FcRn was carried out using a Biacore™ T200 surface plasmon resonance system. An appropriate amount of protein L (BioVision) was immobilized onto Sensor Chip CM4 (GE Healthcare) by the amine coupling method and the antibodies of interest were captured onto it. Next, a diluted FcRn and a running buffer (used as a control solution) were injected to allow interaction of the antibodies captured onto this sensor chip with human FcRn. 50 mmol/L sodium phosphate, 150 mmol/L NaCl, and 0.05% (w/v) Tween20 (pH 6.0) was used as the running buffer, and this running buffer was also used to dilute FcRn. 10 mmol/L glycine-HCl(pH 1.5) was used for chip regeneration. All measurements were performed at 25° C. Kinetic parameters such as association rate constants ka (1/Ms) and dissociation rate constants kd (1/s) were determined from the sensorgram obtained from the measurements, and the KD (M) of each antibody for human FcRn were determined from the values of these constants. The Biacore™ T200 Evaluation Software (GE Healthcare) was used to calculate each parameter. KD values of the antibodies prepared this time for human FcRn as measured by this method are shown in Table 14. As shown in Table 14, compared to Fv4-P587, Fv4-P587-LS was confirmed to have enhanced FcRn binding under acidic conditions.

TABLE 14

| | KD FOR HUMAN FcRn AT pH 6.0 (μmol/L) |
|---|---|
| IgG1 | 1.4 |
| P587 | 1.5 |
| P587-LS | 0.12 |

(12-4) Production of Human FcgRIIb and Human FcRn Transgenic Mice

Human FcgRIIb and human FcRn transgenic mice, and mouse FcRn knockout mice were produced by the following method.

First, mouse FcRn knockout mice were produced. Production of knockout mice was carried out according to the procedure described in "Nagy et al., (Manipulating the mouse embryo, CSHL press. (2003) 399-506)". More specifically, a targeting vector to destroy the mouse FcRn gene is prepared and introduced into ES cells (derived from C57BL/6 mice) to destroy mouse FcRn gene by homologous recombination. RNA was extracted from the liver of the established mouse FcRn knockout mice, and by using cDNA synthesized from this RNA as a template, RT-PCR was carried out using primers that specifically amplify mouse FcRn. As a result, the mouse FcRn gene was not detected from mouse FcRn knockout mice. Next, transgenic mice were produced by introducing the human FcgRIIb and human FcRn genes into the mouse FcRn knockout mice. Transgenic mice were produced according to the procedures described in "Nagy et al., (Manipulating the mouse embryo, CSHL press. (2003) 399-506)" and in "Ueda et al. (Latest Technology for Gene Targeting, Yodosha. (2000) 190-207)". More specifically, the mice were produced by microinjecting into pronuclear fertilized eggs of mouse FcRn knockout mice a bacterial artificial chromosome into which the genomic regions of the human FcRn gene (GeneBank #NC_000019.9: 50,000,108-50,039,865) and the human FcgRIIb gene (GeneBank #NW_004077999:18,307,411-18,381,603) were cloned. Mice introduced with the human FcRn gene and the human FcgRIIb gene and made to be homozygous for the mouse FcRn knockout allele were selected from the obtained mice by Southern blotting using a probe that specifically hybridizes with each gene and by PCR. Blood was collected from the human FcgRIIb and human FcRn transgenic mice and mouse FcRn knockout mice, and expression of the human FcRn gene and the human FcgRIIb gene were confirmed by RT-PCR using primers that specifically amplify the human FcRn gene and the human FcgRIIb gene. As a result, expressions of the human FcRn gene and the human FcgRIIb gene were detected. The above confirmed that human FcgRIIb and human FcRn transgenic mice and mouse FcRn knockout mice which express human FcRn and human FcgRIIb and do not express mouse FcRn were established.

Figure 36:
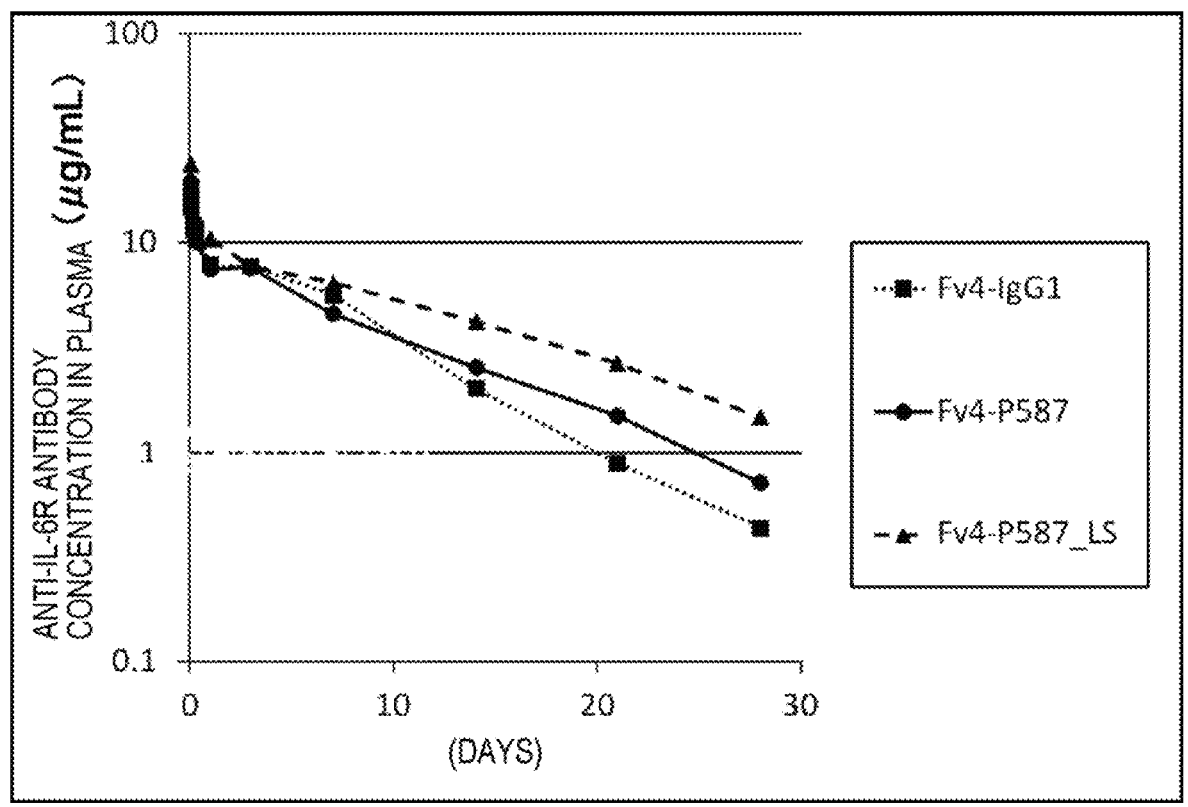
FIG. 36 shows the change in plasma concentrations of the administered antigen-binding molecules of human FcgRIIb and human FcRn transgenic mice when Fv4-IgG1, Fv4-P587, or Fv4-P587_LS was administered to the mice.
Figure 37:
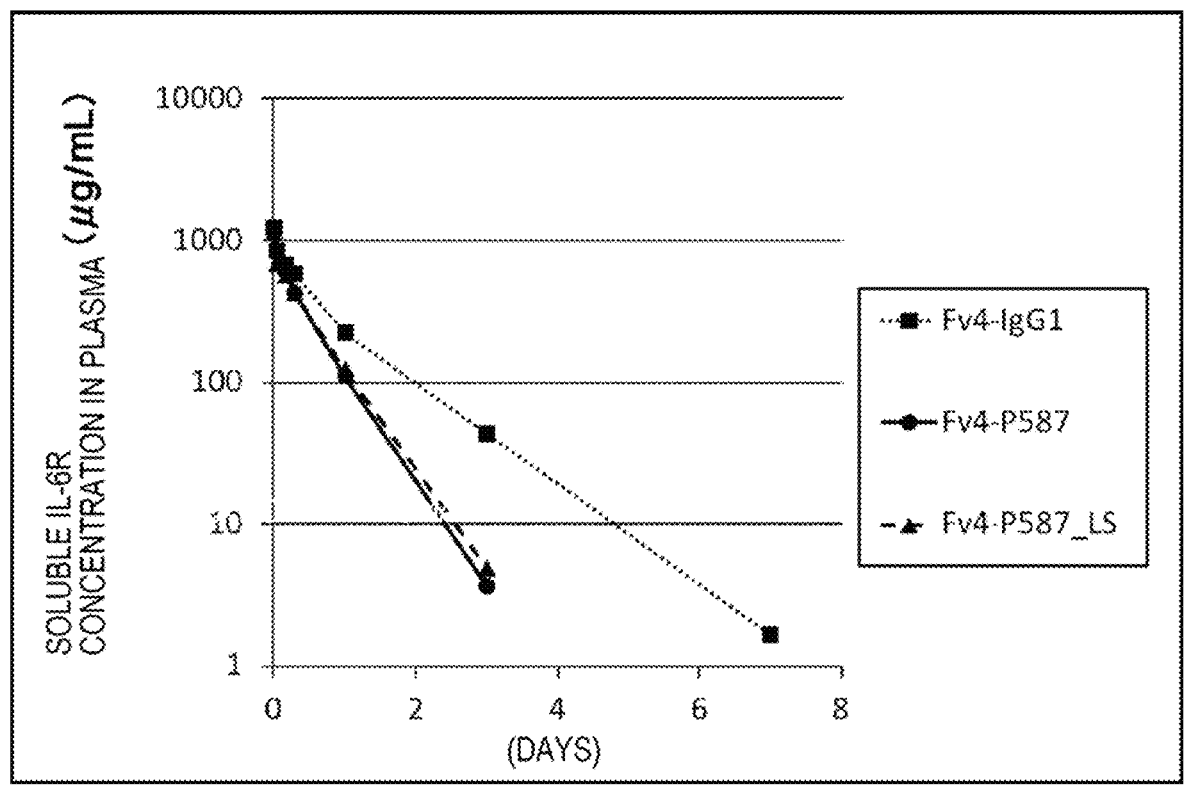
FIG. 37 shows the change in plasma concentrations of the administered human IL-6R of human FcgRIIb and human FcRn transgenic mice when Fv4-IgG1, Fv4-P587, or Fv4-P587_LS was administered to the mice.

(12-5) Improvement of Pharmacokinetics by Enhancing Human FcRn-Binding Activity Under an Acidic pH Range Condition In vivo examination was carried out in a manner similar to the method of Example 11 by administering Fv4-IgG1, Fv4-P587, and Fv4-P587-LS individually to human FcgRIIb and human FcRn transgenic mice, and plasma concentrations of soluble IL-6R and anti-human IL-6R antibody were measured for the mouse groups. The results of measuring the plasma concentrations of anti-human IL-6R antibody and soluble IL-6R are shown in FIG. 36 and FIG. 37, respectively.

In the group of mice administered with Fv4-P587-LS in which the binding activity of Fv4-P587 to human FcRn under an acidic pH range condition has been enhanced, plasma retention of antibodies was found to be improved compared to that in the group of mice administered with Fv4-P587. In addition, Fv4-P587-LS showed improved plasma retention than Fv4-IgG1. On the other hand, the plasma concentration of soluble IL-6R in the group of Fv4-P587-LS-administered mice was equivalent to that in the group of Fv4-P587-administered mice. In the group of Fv4-P587-LS- or Fv4-P587-administered mice, plasma concentration of soluble IL-6R was decreased compared to in the group of Fv4-IgG-administered mice.

Accordingly, administration of antibody in which the human FcRn-binding activity of an antigen-binding molecule under an acidic pH range condition has been enhanced, wherein human FcγRIIb-binding activity of the antigen-binding molecule is higher than that of a native human IgG Fc region, showed that plasma retention of the administered antigen molecule can be improved in a living organism receiving the administration. Furthermore, even if the plasma retention is improved in a living organism administered with the antigen-binding molecule, the antigen-eliminating effect of the living organism was shown not to decrease, but rather can be maintained.

Alterations to enhance the human FcRn-binding activity under an acidic pH range condition are not particularly limited; and include: the method for substituting Leu for Met at position 428 and Ser for Asn at position 434 (EU numbering) in an IgG antibody (Nat. Biotechnol, (2010) 28, 157-159); the method for substituting Ala for Asn at position 434 (Drug. Metab. Dispos. (2010) 38 (4), 600-605); the method for substituting Tyr for Met at position 252, Thr for Ser at position 254, and Glu for Thr at position 256 (J. Biol. Chem. (2006) 281, 23514-23524); the method for substituting Gln for Thr at position 250 and Leu for Met at position 428 (J. Immunol. (2006) 176 (1) 346-356); the method for substituting His for Asn at position 434 (Clin. Pharm. & Ther. (2011) 89 (2) 283-290.); and alterations disclosed in W2010/106180, WO2010/045193, WO2009/058492, WO2008/022152, WO2006/050166, WO2006/053301, WO2006/031370, WO2005/123780, WO2005/047327, WO2005/037867, WO2004/035752, WO2002/060919, and such.

[Reference Example 1] Construction of Antibody Expression Vectors; and Expression and Purification of Antibodies Synthesis of full-length genes encoding the nucleotide sequences of the H chain and L chain of the antibody variable regions was carried out by production methods known to those skilled in the art using Assemble PCR and such. Introduction of amino acid substitutions was carried out by methods known to those skilled in the art using PCR or such. The obtained plasmid fragment was inserted into an animal cell expression vector, and the H-chain expression vector and L-chain expression vector were produced. The nucleotide sequence of the obtained expression vector was determined by methods known to those skilled in the art. The produced plasmids were introduced transiently into the HEK293H cell line derived from human embryonic kidney cancer cells (Invitrogen) or into FreeStyle293™ cells (Invitrogen) for antibody expression. The obtained culture supernatant was collected, and then passed through a 0.22 μm MILLEX(R)-GV filter (Millipore), or through a 0.45 μm MILLEX(R)-GV filter (Millipore) to obtain the culture supernatant. Antibodies were purified from the obtained culture supernatant by methods known to those skilled in the art using a Protein A Sepharose® 4 Fast Flow gel filtration medium (GE Healthcare) or a Protein G Sepharose® 4 Fast Flow gel filtration medium (GE Healthcare). For the concentration of the purified antibodies, their absorbance at 280 nm was measured using a spectrophotometer. From the obtained value, the extinction coefficient calculated by the methods such as PACE was used to calculate the antibody concentration (Protein Science 1995; 4: 2411-2423).

[Reference Example 2] Method for Preparing FcγR and Method for Analyzing the Interaction Between an Altered Antibody and FcγR Extracellular domains of FcγRs were prepared by the following method. First, a gene of the extracellular domain of FcγR was synthesized by a method well known to those skilled in the art. At that time, the sequence of each FcγR was produced based on the information registered at NCBI. Specifically, FcγRI was produced based on the sequence of NCBI Accession No. NM_000566.3, FcγRIIa was produced based on the sequence of NCBI Accession No. NM_001136219.1, FcγRIIb was produced based on the sequence of NCBI Accession No. NM_004001.3, FcγRIIIa was produced based on the sequence of NCBI Accession No. NM_001127593.1, and FcγRIIIb was produced based on the sequence of NCBI Accession No. NM_000570.3, and a His tag was attached to the C terminus. Furthermore, polymorphism is known for FcγRIIa, FcγRIIIa, and FcγRIIIb, and the polymorphic sites were produced by referring to J. Exp. Med., 1990, 172: 19-25 for FcγRIIa; J. Clin. Invest., 1997, 100 (5): 1059-1070 for FcγRIIIa; and J. Clin. Invest., 1989, 84, 1688-1691 for FcγRIIIb.

The obtained gene fragments were inserted into an animal cell expression vector, and expression vectors were produced. The produced expression vectors were introduced transiently into human embryonic kidney cancer cell line-derived FreeStyle293™ cells (Invitrogen) to express the proteins of interest. Regarding FcγRIIb used for crystallographic analysis, the protein of interest was expressed in the presence of Kifunensine at a final concentration of 10 μg/mL, so that the sugar chain added to FcγRIIb will be the high-mannose type. Cells were cultured, and after collection of the obtained culture supernatant, this was passed through a 0.22 μm filter to obtain the culture supernatant. In principle, the obtained culture supernatants were purified in the following four steps. The steps carried out were, cation exchange column chromatography (SP Sepharose® 4 FF gel filtration medium) in step 1, affinity column chromatography (HisTrap™ HP affinity column) for His tag in step 2, gel filtration column chromatography (Superdex® 200gel filtration column) in step 3, and aseptic chromatography in step 4. However, for FcγRI, anion exchange column chromatography using Q Sepharose® 4 FF chromatography medium was performed as step 1. The purified proteins were subjected to absorbance measurements at 280 nm using a spectrophotometer; and from the obtained values, the concentrations of the purified proteins were calculated using the absorption coefficient calculated using methods such as PACE (Protein Science 1995; 4: 2411-2423).

Analysis of interaction between each altered antibody and the Fcγ receptor prepared as mentioned above was carried out using a Biacore™ T100 surface plasmon resonance system (GE Healthcare), a Biacore™ T200 surface plasmon resonance system (GE Healthcare), a Biacore™ A100 surface plasmon resonance system, and Biacore™ 4000 surface plasmon resonance system. HBS-EP+ (0.01 M HEPES pH 7.4, 0.15 M NaCl, 3 mM ethylene diamine tetraacetic acid (EDTA), 0.05% polysorbate 20) (GE Healthcare) was used as the running buffer, and the measurement temperature was set to 25° C. Chips produced by immobilizing the antigen peptide, Protein A (Thermo Scientific), Protein A/G (Thermo Scientific), and Protein L (ACTIGEN or BioVision) by the amine coupling method to a Series S sensor Chip CM5 (GE Healthcare) or Series S sensor Chip CM4 (GE Healthcare), or alternatively, chips produced by allowing preliminarily biotinylated antigen peptides to interact with and immobilize onto a Series S Sensor Chip SA (certified) (GE Healthcare) were used.

After capturing of antibodies of interest onto these sensor chips, an Fcγ receptor diluted with the running buffer was allowed to interact, the amount bound to an antibody was measured, and the antibodies were compared. However, since the amount of Fcγ receptor bound depends on the amount of the captured antibodies, the amount of Fcγ receptor bound was divided by the amount of each antibody captured to obtain corrected values, and these values were compared. Furthermore, antibodies captured onto the chips were washed by reaction with 10 mM glycine-HC, pH 1.5, and the chips were regenerated and used repeatedly.

Kinetic analyses for calculating the KD values of each altered antibody for FcγR were performed according to the following method. First, antibodies of interest were captured onto the above-mentioned sensor chips, and an Fcγ receptor diluted with the running buffer was allowed to interact. The Biacore™ Evaluation Software was used to globally fit the measured results to the obtained sensorgram using the 1:1 Langmuir binding model, and the association rate constant ka (L/mol/s) and the dissociation rate constant kd (1/s) were calculated; and from those values the dissociation constants KD (mol/L) were calculated.

When the interaction between each of the altered antibodies and FcγR was weak, and correct analysis was determined to be impossible by the above-mentioned kinetic analysis, the KD for such interactions were calculated using the following 1:1 binding model equation described in the Biacore™ T100 Software Handbook BR1006-48 Edition AE.

The behavior of interacting molecules according to the 1:1 binding model on a Biacore™ surface plasmon resonance system can be described by Equation 1 shown below.

$$R_{eq} = C \cdot R_{max}/(KD+C) + RI \qquad \text{[Equation 1]}$$

$R_{eq}$: a plot of steady-state binding levels against analyte concentration
C: concentration
RI: bulk refractive index contribution in the sample
$R_{max}$: analyte binding capacity of the surface When this equation is rearranged, KD can be expressed as Equation 2 shown below.

$$KD = C \cdot R_{max}/(R_{eq}-RI) - C \qquad \text{[Equation 2]}$$

KD can be calculated by substituting the values of $R_{max}$, RI, and C into this equation. The values of RI and C can be determined from the sensorgram of the measurement results and measurement conditions. $R_{max}$ was calculated according to the following method. As a target of comparison, for antibodies that had sufficiently strong interactions as evaluated simultaneously in the same round of measurement, the $R_{max}$ value was obtained through global fitting using the 1:1 Langmuir binding model, and then it was divided by the amount of the comparison antibody captured onto the sensor chip, and multiplied by the captured amount of an altered antibody to be evaluated.

[Reference Example 3] Comprehensive Analysis of the Binding of Fc Variants to FcγR Mutations were introduced into IgG1 antibodies to generate antibodies that have decreased Fc-mediated binding towards activating FcγR, specifically both allotypes of FcγRIIa, types H and R, as well as enhanced FcγRIIb binding relative to IgG1; and binding to each FcγR was analyzed comprehensively.

The variable region (SEQ ID NO: 15) of a glypican 3 antibody comprising the CDR of GpH7 which is an anti-glypican 3 antibody with improved plasma kinetics disclosed in WO 2009/041062 was used as the common antibody H chain. Similarly, for the common antibody L chain, GpL16-k0 (SEQ ID NO: 16) of the glypican 3 antibody with improved plasma kinetics disclosed in WO 2009/041062 was used. Furthermore, B3 in which a K439E mutation has been introduced into G1d produced by removing the C terminal Gly and Lys of IgG1 was used as the antibody H chain constant region. This H chain is referred to as GpH7-B3 (SEQ ID NO: 17), and the L chain is referred to as GpL16-k0 (SEQ ID NO: 16).

With respect to GpH7-B3, the amino acids that are considered to be involved in FcγR binding and the surrounding amino acids (positions 234 to 239, 265 to 271, 295, 296, 298, 300, and 324 to 337, according to EU numbering) were substituted respectively with 18 types of amino acids excluding the original amino acids and Cys. These Fc variants are referred to as B3 variants. B3 variants were expressed and purified using the method of Reference Example 1, and the binding to each FcγR (FcγRIa, FcγRIIa type H, FcγRIIa type R, FcγRIIb, and FcγRIIIa) was comprehensively evaluated using the method of Reference Example 2.

Figures were produced based on the results of interaction analysis with each FcγR by the method below. The value of the amount of FcγR binding of each B3 variant-derived antibody was divided by the value of the amount of FcγR binding of the antibody used for comparison which does not have mutations introduced into B3 (an antibody having the sequence of a naturally-occurring human IgG1 at positions 234 to 239, 265 to 271, 295, 296, 298, 300, and 324 to 337, according to EU numbering). The value obtained by multiplying this value by 100 was used as an indicator of the relative FcγR-binding activity of each variant. The horizontal axis shows the value of the relative FcγRIIb-binding activity of each variant, and the vertical axis shows the value of the respective relative binding activity of each variant towards activating FcγRs: FcγRIa, FcγRIIa type H, FcγRIIa type R, and FcγRIIIa (FIGS. 17, 18, 19, and 20).

As shown by labels in FIGS. 17-20, the results show that of all alterations, when only mutations called mutation A (alteration produced by substituting Pro at position 238 (EU numbering) with Asp) and mutation B (alteration produced by substituting Leu at position 328 (EU numbering) with Glu) were introduced, there were remarkable enhancement of binding to FcγRIIb and remarkable suppression of binding to both types of FcγRIIa compared with before the introduction.

[Reference Example 4] SPR Analysis of Variants that Selectively Bind to FcγRIIb

With regard to the alteration identified in Example 1 where Pro at position 238 (EU numbering) is substituted with Asp, the binding to each FcγR was analyzed in detail.

The variable region of IL6R-H (SEQ ID NO: 18), which is the variable region of the antibody against the human interleukin 6 receptor disclosed in WO 2009/125825, was used as the antibody H chain variable region, and IL6R-G1d (SEQ ID NO: 19) which comprises G1d with deletion of C-terminal Gly and Lys of human IgG1 was used as the antibody H chain constant region in the IgG1 H chain. Pro at position 238 (EU numbering) in IL6R-G1d was substituted with Asp to produce IL6R-G1d-v1 (SEQ ID NO: 20). Next, Leu at position 328 (EU numbering) in IL6R-G1d was substituted with Glu to produce IL6R-G1d-v2. Furthermore, for comparison, Ser at position 267 (EU numbering) was substituted with Glu, and Leu at position 328 (EU numbering) was substituted with Phe in IL6R-G1d to produce IL6R-G1d-v3 as described in Non-patent Document 28. IL6R-L (SEQ ID NO: 21), which is the L chain of tocilizumab, was utilized as a mutual antibody L chain; and together with each H chain, the antibodies were expressed and purified according to the method of Reference Example 1. The obtained antibodies which comprise an amino acid sequence derived from IL6R-G1d, IL6R-G1d-v1, IL6R-G1d-v2, or IL6R-G1d-v3 as the antibody H chain are referred to as IgG1, IgG-v1, IgG1-v2, and IgG1-v3, respectively.

Next, kinetic analysis of interactions between these antibodies and FcγR was carried out using a Biacore™ T100 surface plasmon resonance system (GE Healthcare). HBS-EP+(GE Healthcare) was used as the running buffer, and the measurement temperature was set to 25° C. A chip produced by immobilizing Protein A onto a Series S Sensor Chip CM5 (GE Healthcare) by the amine-coupling method was used. An antibody of interest was captured onto this chip to interact with each FcγR that had been diluted with the running buffer, and binding to the antibody was measured. After the measurement, the antibody captured on the chip was washed off by allowing reaction with 10 mM glycine-HCl, pH 1.5, and the chip was regenerated and used repeatedly. The sensorgrams obtained as measurement results were analyzed by the 1:1 Langmuir binding model using the Biacore™ Evaluation Software to calculate the binding rate constant ka (L/mol/s) and dissociation rate constant kd (1/s), and the dissociation constant KD (mol/L) was calculated from these values.

This time, since the binding of IgG1-v1 and IgG1-v2 to FcγRIIa type H and to FcγRIIIa was weak, kinetic parameters such as KD could not be calculated from the above-mentioned analytical method. Regarding such interactions, KD values were calculated using the following 1:1 binding model described in the Biacore™ T100 Software Handbook BR1006-48 Edition AE.

The behavior of interacting molecules according to the 1:1 binding model on a Biacore™ surface plasmon resonance system can be described by Equation 1 shown below.

$$R_{eq}=C \cdot R_{max}/(KD+C)+RI \quad \text{[Equation 1]}$$

$R_{eq}$: a plot of steady-state binding levels against analyte concentration
C: concentration
RI: bulk refractive index contribution in the sample
$R_{max}$: analyte binding capacity of the surface When this equation is rearranged, KD can be expressed as Equation 2 shown below.

$$KD=C \cdot R_{max}/(R_{eq}-RI)-C \quad \text{[Equation 2]}$$

KD can be calculated by substituting the values of $R_{max}$, RI, and C into this equation. From the current measurement conditions, RI=0, C=2 μmol/L can be used. Furthermore, the $R_{max}$ value obtained when globally fitting the sensorgram obtained as a result of analyzing the interaction of each FcγR with IgG1 using the 1:1 Langmuir binding model was divided by the amount of IgG1 captured, this was multiplied by the amount of IgG-v1 and IgG-v2 captured, and the resulting value was used as $R_{max}$. This calculation is based on the hypothesis that the limit quantity of each FcγR that can be bound by IgG1 remains unchanged for all variants produced by introducing mutations into IgG1, and the $R_{max}$ at the time of measurement is proportional to the amount of antibody bound on the chip at the time of measurement. $R_{eq}$ was defined as the amount of binding of each FcγR to each variant on the sensor chip observed at the time of measurement.

Under these measurement conditions, the amount of binding ($R_{eq}$) of IgG1-v1 and IgG1-v2 to FcγRIIa type H was approximately 2.5 RU and 10 RU, respectively, and the amount of binding ($R_{eq}$) of IgG1-v1 and IgG1-v2 to FcγRIIIa was approximately 2.5 RU and 5 RU, respectively. The amount of IgG1, IgG1-v1, and IgG1-v2 captured in the analysis of interactions with H-type FcγRIIa was 452 RU, 469.2 RU, and 444.2 RU, respectively, and the amount of IgG1, IgG1-v1, and IgG-v2 captured in the analysis of interactions with FcγRIIIa was 454.5 RU, 470.8 RU, and 447.1 RU, respectively. The $R_{max}$ values obtained from global fitting of sensorgrams obtained as a result of analyzing the interaction of IgG1 with H-type FcγRIIa and FcγRIIIa using the 1:1 Langmuir binding model were 69.8 RU and 63.8 RU, respectively. When these values were used, the calculated $R_{max}$ values of IgG1-v1 and IgG1-v2 to FcγRIIa type H were 72.5 RU and 68.6 RU, respectively, and the calculated $R_{max}$ values of IgG1-v1 and IgG1-v2 to FcγRIIIa were 66.0 RU and 62.7 RU, respectively. These values were substituted into Equation 2 to calculate the KD of IgG1-v1 and IgG1-v2 for FcγRIIa type H and FcγRIIIa.

$$KD = C \cdot R_{max}/(R_{eq}-RI) - C \qquad \text{[Equation 2]}$$

The KD values of IgG1, IgG1-v1, IgG1-v2, and IgG1-v3 for each FcγR (the KD values of each antibody for each FcγR) are shown in Table 15, and the relative KD values of IgG1-v, IgG1-v2, and IgG1-v3 obtained by taking the KD values of IgG1 for each FcγR and dividing them by the KD values of IgG1-v1, IgG1-v2, and IgG-v3 for each FcγR (the relative KD values of each antibody for each FcγR) are shown in Table 16.

TABLE 15

|  | IgG1 | IgG1-v1 | IgG1-v2 | IgG1-v3 |
| --- | --- | --- | --- | --- |
| FcγRIa | 3.4E−10 | 7.3E−09 | 4.6E−10 | 1.9E−10 |
| FcγRIIa R | 1.2E−06 | 1.2E−05 | 2.9E−06 | 2.3E−09 |
| FcγRIIa H | 7.7E−07 | 5.6E−05* | 1.2E−05* | 1.5E−06 |
| FcγRIIb | 5.3E−06 | 1.1E−06 | 2.3E−06 | 1.3E−08 |
| FcγRIIIa | 3.1E−06 | 5.1E−05* | 2.3E−05* | 8.8E−06 |

(mol/L)

In Table 15 shown above, "*" means that the KD value was calculated using Equation 2 because binding of FcγR to IgG was not sufficiently observed.

$$KD = C \cdot R_{max}/(R_{eq}-RI) - C \qquad \text{[Equation 2]}$$

TABLE 16

|  | IgG1-v1 | IgG1-v2 | IgG1-v3 |
| --- | --- | --- | --- |
| FcγRIa | 0.047 | 0.74 | 1.8 |
| FcγRIIa R | 0.10 | 0.41 | 522 |
| FcγRIIa H | 0.014 | 0.064 | 0.51 |
| FcγRIIb | 4.8 | 2.3 | 408 |
| FcγRIIIa | 0.061 | 0.14 | 0.35 |

(THE VALUE OBTAINED BY DIVIDING THE KD VALUE OF IgG1 FOR EACH FcγR BY THE KD VALUE OF EACH ANTIBODY IgG1 FOR EACH FcγR)

According to Table 16, when compared with that of IgG1, the binding activity of IgG1-v1 was decreased to 0.047-fold for FcγRIa, decreased to 0.10-fold for FcγRIIa type R, decreased to 0.014-fold for FcγRIIa type H, decreased to 0.061-fold for FcγRIIIa, and increased to 4.8-fold for FcγRIIb.

Furthermore, according to Table 16, when compared with that of IgG1, the binding activity of IgG1-v2 was decreased to 0.74-fold for FcγRIa, decreased to 0.41-fold for FcγRIIa type R, decreased to 0.064-fold for FcγRIIa type H, decreased to 0.14-fold for FcγRIIIa, and increased to 2.3-fold for FcγRIIb.

More specifically, these results demonstrated that IgG1-v1 having an alteration of substituting Pro at position 238 (EU numbering) with Asp and IgG1-v2 having an alteration of substituting Leu at position 328 (EU numbering) with Glu have the properties of weakening the binding to all activating FcγRs including both allotypes of FcγRIIa, while enhancing the binding to FcγRIIb which is an inhibitory FcγR.

Next, selectivity of the obtained variant to FcγRIIb was evaluated by using the ratio of FcγRIIb-binding activity to the binding activity towards type R or type H of FcγRIIa as the indicator. Specifically, I/A(R) or I/A(H), which is a value obtained by dividing the KD value for FcγRIIa type R or type H by the KD value for FcγRIIb, was used as an indicator for the selectivity of FcγRIIb with respect to each FcγRIIa. This indicator has a greater value when the KD value for FcγRIIb becomes smaller or when the KD value for FcγRIIa becomes larger. That is, a variant that shows a larger value shows an increased binding activity for FcγRIIb relative to FcγRIIa. These indicators are summarized in Table 17 for each variant.

TABLE 17

|  | IgG1 | IgG1-v1 | IgG1-v2 | IgG1-v3 |
| --- | --- | --- | --- | --- |
| I/A (R) | 0.23 | 11 | 1.3 | 0.18 |
| I/A (H) | 0.15 | 51 | 5.2 | 115 |

According to the results of Table 17, in comparison with IgG1, IgG1-v3 which was produced by applying the existing technology showed a greater I/A(H) value than that of IgG1 and a greater selectivity for FcγRIIb, but a smaller I/A(R) value than that of IgG1 and an improved selectivity for FcγRIIb. On the other hand, IgG1-v1 and IgG1-v2 found in the Examples have larger I/A(R) and I/A(H) values than those of IgG1, and improved selectivity for FcγRIIb over both allotypes of FcγRIIa.

So far, alterations having such properties have not been reported, and they are in fact very rare as shown in FIGS. 17, 18, 19, and 20. Alterations produced by substituting Pro at position 238 (EU numbering) with Asp or substituting Leu at position 328 (EU numbering) with Glu are very useful for the development of therapeutic agents for immunological inflammatory diseases and such Furthermore, Table 16 shows that IgG1-v3 described in Non-patent Document 28 certainly shows a 408-fold enhanced binding to FcγRIIb, while the binding to FcγRIIa type H is decreased to 0.51 fold, and the binding to FcγRIIa type R is enhanced to 522 fold. According to these results, since IgG1-v1 and IgG1-v2 suppress their binding to both FcγRIIa types R and H, and enhance their binding to FcγRIIb, they are considered to be variants that bind with a greater FcγRIIb selectivity compared with IgG1-v3. Specifically, alterations produced by substituting Pro at position 238 (EU numbering) with Asp or substituting Leu at position 328 (EU numbering) with Glu are very useful for the development of therapeutic agents for immunological inflammatory diseases and such.

[Reference Example 5] Effects of Combining FcγRIIb-Selective Binding Alterations with Other Fc Region Amino Acid Substitutions Further enhancement of the selectivity for FcγRIIb was attempted based on the variant which has improved selectivity for FcγRIIb and has a substitution of Pro at position 238 (EU numbering) with Asp found in Reference Examples 3 and 4.

First, into IL6R-G1d_v1 (SEQ ID NO: 20) produced by introducing into IL6R-G1d the alteration produced by substituting Pro at position 238 (EU numbering) with Asp, the substitution of Leu at position 328 (EU numbering) with Glu as described in Reference Example 4 which enhances selectivity for FcγRIIb was introduced to produce the IL6R-G1d-v4 variant. This was combined with IL6R-L (SEQ ID NO: 21) and prepared according to the method of Reference Example 1. The obtained antibody having the amino acid sequence derived from IL6R-G1d-v4 as the antibody H chain has been named IgG1-v4. The binding activities of IgG1, IgG1-v1, IgG1-v2, and IgG1-v4 to FcγRIIb were evaluated according to the method of Reference Example 2, and those results are shown in Table 18.

TABLE 18

| Variant | Alteration | KD for FcγRIIb (mol/L) | Relative KD for FcγRIIb (KD of IgG1/KD of each variant) |
|---|---|---|---|
| IgG1 | — | 5.30E−06 | 1 |
| IgG1-v1 | Substitution of Pro at position 238 (EU numbering) with Asp | 1.10E−06 | 4.8 |
| IgG1-v2 | Substitution of Leu at position 328 (EU numbering) with Glu | 2.30E−06 | 2.3 |
| IgG1-v4 | Substitution of Pro at position 238 (EU numbering) with Asp and substitution of Leu at position 328 (EU numbering) with Glu | 1.10E−05 | 0.47 |

From the results of Table 18, since L328E improves the FcγRIIb-binding activity by 2.3 fold compared with IgG1, combining it with P238D which similarly improves the FcγRIIb-binding activity by 4.8 fold compared with IgG1 was anticipated to further increase the degree of improvement of FcγRIIb-binding activity; however, in reality, the FcγRIIb-binding activity of the variant containing a combination of these alterations was decreased to 0.47 fold compared with that of IgG1. This result is an effect that could not have been predicted from the respective alterations.

Similarly, into IL6R-G1d-v1 (SEQ ID NO: 20) produced by introducing into IL6R-G1d the alteration produced by substituting Pro at position 238 (EU numbering) with Asp, the substitutions of Ser at position 267 (EU numbering) with Glu and of Leu at position 328 (EU numbering) with Phe as described in Reference Example 4 which improve FcγRIIb-binding activity were introduced, and the IL6R-G1d-v5 variant was prepared according to the method of Reference Example 1. The obtained antibody having the amino acid sequence derived from IL6R-G1d-v5 as the antibody H chain has been named IgG1-v5. The FcγRIIb-binding activities of IgG1, IgG1-v1, IgG-v3, and IgG1-v5 were evaluated according to the method of Reference Example 2, and those results are shown in Table 19.

S267E/L328F which had an enhancing effect on FcγRIIb in Reference Example 4 was introduced into the P238D variant and its FcγRIIb-binding activities before and after introducing this alteration were evaluated. The results are shown in Table 19.

TABLE 19

| Variant | Alteration | KD for FcγRIIb (mol/L) | Relative KD for FcγRIIb (KD of IgG1/KD of each variant) |
|---|---|---|---|
| IgG1 | — | 5.30E−06 | 1 |
| IgG1-v1 | Substitution of Pro at position 238 (EU numbering) with Asp | 1.10E−06 | 4.8 |
| IgG1-v3 | Substitution of Ser at position 267 (EU numbering) with Glu and substitution of Leu at position 328 (EU numbering) with Phe | 1.30E−08 | 408 |
| IgG1-v5 | Substitution of Pro at position 238 (EU numbering) with Asp, substitution of Ser at position 267 (EU numbering) with Glu, and substitution of Leu at position 328 (EU numbering) with Phe | 4.50E−07 | 12 |

From the results of Table 19, since S267E/L328F improves the FcγRIIb-binding activity by 408 fold compared with IgG1, combining it with P238D which similarly improves the FcγRIIb-binding activity by 4.8 fold as compared with IgG1 was anticipated to further increase the degree of improvement of FcγRIIb-binding activity; however, in reality, in a similar manner to the former example, the FcγRIIb-binding activity of the variant containing a combination of these alterations was improved only 12 fold or so as compared with that of IgG. This result is also an effect that could not have been predicted from the effects of the respective alterations.

These results showed that while the substitution of Pro at position 238 (EU numbering) with Asp alone improves FcγRIIb-binding activity, the effect is not exhibited when it is combined with other alterations that improve the FcγRIIb-binding activity. A reason for this may be that the structure at the interacting interface between Fc and FcγR is changed by introducing the substitution of Pro at position 238 (EU numbering) with Asp and the effects of alterations observed in the naturally-occurring antibody are no longer reflected in the results. Accordingly, it was considered to be extremely difficult to create an Fc with excellent selectivity for FcγRIIb using an Fc comprising substitution of Pro at position 238 (EU numbering) with Asp as a template, since the information on effects of alterations obtained with naturally-occurring antibodies could not be applied.

[Reference Example 6] Comprehensive Analysis of FcγRIIb Binding of Variants Introduced with an Alteration at the Hinge Portion in Addition to the P238D Alteration As shown in Reference Example 5, in an Fc produced by substituting Pro at position 238 (EU numbering) with Asp in a naturally-occurring human IgG1, an anticipated combinatorial effect could not be obtained even by combining it with another alteration predicted to further increase FcγRIIb binding. Therefore, based on the Fc variant produced by substituting Pro at position 238 (EU numbering) with Asp, examination was carried out by comprehensively introducing alterations into the Fc to find variants that further enhance FcγRIIb binding. For the antibody H chains, IL6R-F11 (SEQ ID NO: 22) was produced by introducing an alteration of substituting Met at position 252 (EU numbering) with Tyr and an alteration of substituting Asn at position 434 (EU numbering) with Tyr into IL6R-G1d (SEQ ID NO: 19), and IL6R-F652 was prepared by introducing an additional alteration of substituting Pro at position 238 (EU numbering) with Asp. Expression plasmids containing an antibody H chain sequence were prepared for each of the antibody H chain sequences produced by substituting the region near the residue at position 238 (EU numbering) (positions 234 to 237, and 239 (EU numbering)) in IL6R-F652 each with 18 amino acids excluding the original amino acids and cysteine. IL6R-L (SEQ ID NO: 21) was utilized as a common antibody L chain for all of the antibodies. These variants were expressed, purified, and expressed by the method of Reference Example 1. These Fc variants are called PD variants. Interactions of each PD variant with FcγRIIa type R and FcγRIIb were comprehensively evaluated by the method of Reference Example 2.

Figure 22:
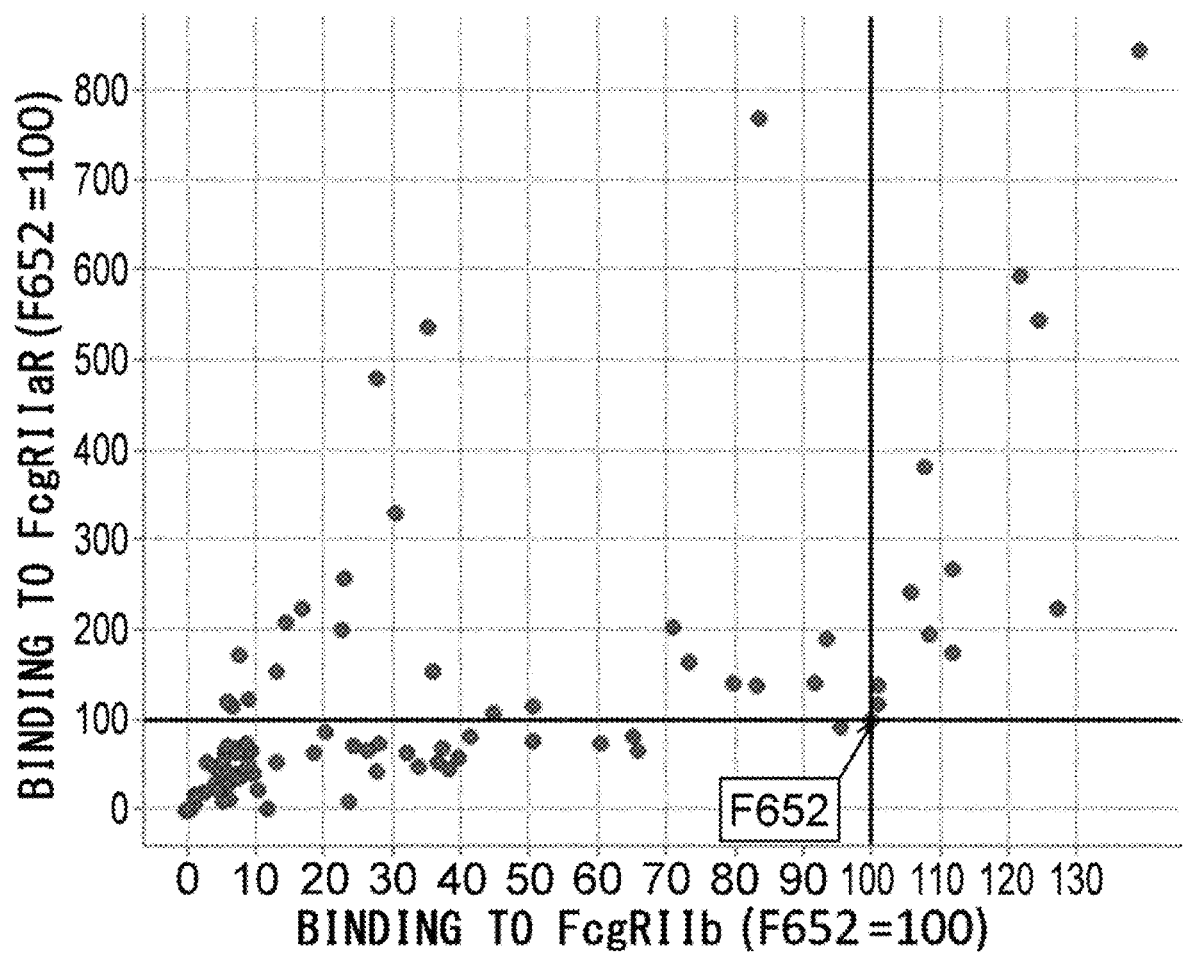
FIG. 22 shows a graph in which the horizontal axis shows the relative value of FcγRIIb-binding activity of each PD variant, and the vertical axis shows the relative value of FcγRIIa type R-binding activity of each PD variant. The value for the amount of binding of each PD variant to each FcγR was divided by the value for the amount of binding of IL6R-F652/IL6R-L, which is a control antibody prior to introduction of the alteration (altered Fc with substitution of Pro at position 238 (EU numbering) with Asp), to each FcγR; and then the obtained value was multiplied by 100, and used as the relative binding activity value for each PD variant to each FcγR. The F652 plot in the figure shows the value for IL6R-F652/IL6R-L.

With regard to the results of analyzing the interaction with the respective FcγRs, a figure was produced according to the following method. The value obtained by dividing the value for the amount of binding of each PD variant to each FcγR by the value for the amount of FcγR binding of the pre-altered antibody which is used as the control (IL6R-F652/IL6R-L, which has an alteration of substituting Pro at position 238 (EU numbering) with Asp) and then multiplying the result by 100, was used as the relative binding activity value of each PD variant to each FcγR. The horizontal axis shows relative values of the FcγRIIb-binding activity of each PD variant, and the vertical axis shows relative values of the FcγRIIa type R-binding activity values of each PD variant (FIG. 22).

As a result, eleven types of alterations were found to have the effects of enhancing FcγRIIb binding and maintaining or enhancing FcγRIIa type R-binding in comparison with the antibody before introducing alterations. The activities of these eleven variants to bind FcγRIIb and FcγRIIa R are summarized in Table 20. In the table, "alteration" refers to the alteration introduced into IL6R-F I(SEQ ID NO: 22).

TABLE 20

| VARIANT NAME | ALTERATION | RELATIVE BINDING ACTIVITY TO FcγRIIb | RELATIVE BINDING ACTIVITY TO FcγRIIaR |
|---|---|---|---|
| IL6R-F652/IL6R-L | P238D | 100 | 100 |
| IL6R-PD042/IL6R-L | P238D/L234W | 106 | 240 |
| IL6R-PD043/IL6R-L | P238D/L234Y | 112 | 175 |
| IL6R-PD079/IL6R-L | P238D/G237A | 101 | 138 |
| IL6R-PD080/IL6R-L | P238D/G237D | 127 | 222 |
| IL6R-PD081/IL6R-L | P238D/G237E | 101 | 117 |
| IL6R-PD082/IL6R-L | P238D/G237F | 108 | 380 |
| IL6R-PD086/IL6R-L | P238D/G237L | 112 | 268 |
| IL6R-PD087/IL6R-L | P238D/G237M | 109 | 196 |
| IL6R-PD094/IL6R-L | P238D/G237W | 122 | 593 |
| IL6R-PD095/IL6R-L | P238D/G237Y | 124 | 543 |
| IL6R-PD097/IL6R-L | P238D/S239D | 139 | 844 |

Figure 23:
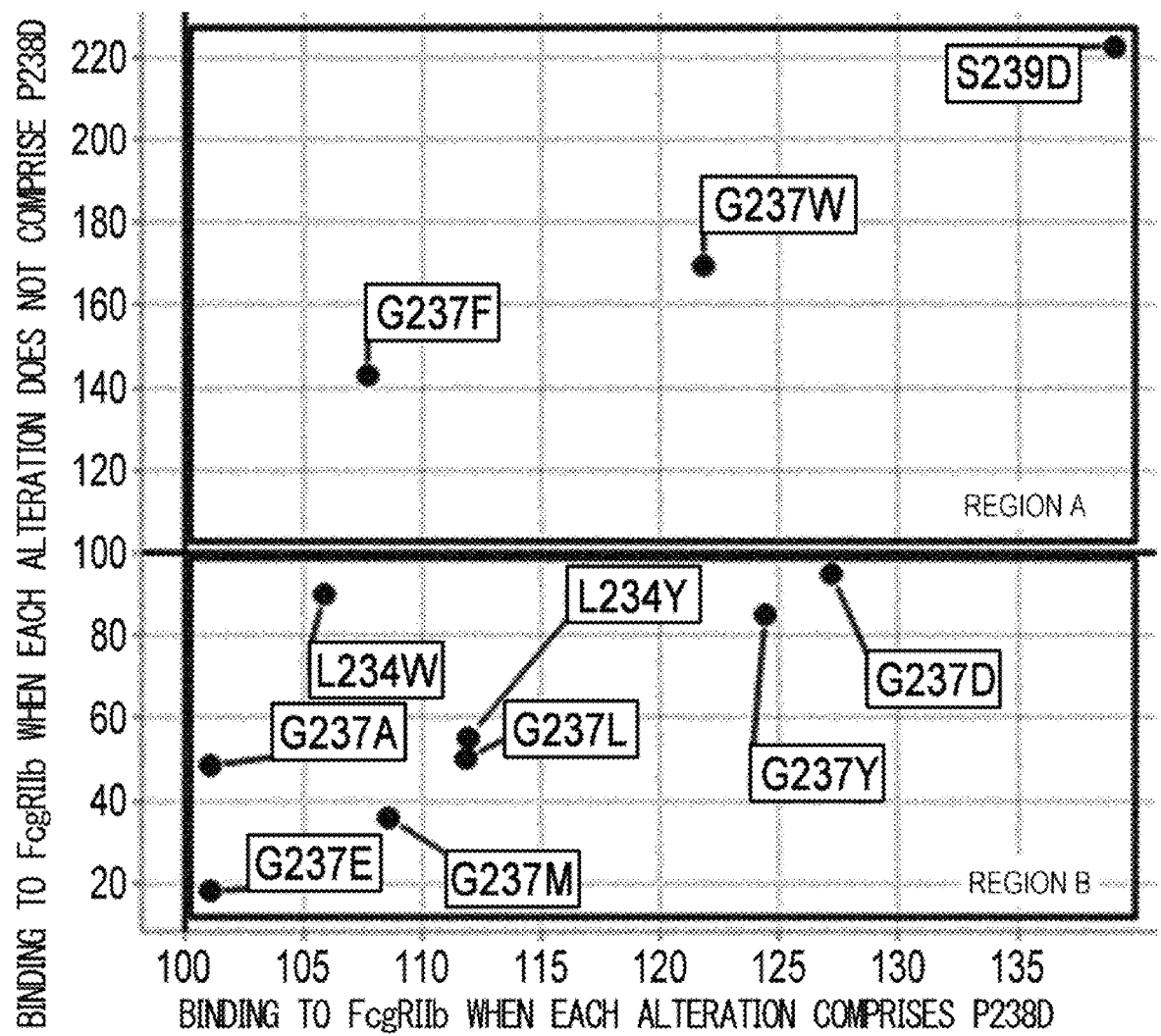
FIG. 23 shows a graph in which the vertical axis shows the relative value of FcγRIIb-binding activity of variants produced by introducing each alteration into GpH7-B3 which does not have the P238D alteration, and the horizontal axis shows the relative value of FcγRIIb-binding activity of variants produced by introducing each alteration into IL6R-F652 which has the P238D alteration. The value for the amount of FcγRIIb binding of each variant was divided by the value for the amount of FcγRIIb binding of the pre-altered antibody; and then the obtained value was multiplied by 100, and used as the value of relative binding activity. Here, region A contains alterations that exhibit the effect of enhancing FcγRIIb binding in both cases where an alteration is introduced into GpH7-B3 which does not have P238D and where an alteration is introduced into IL6R-F652 which has P238D. Region B contains alterations that exhibit the effect of enhancing FcγRIIb binding when introduced into GpH7-B3 which does not have P238D, but do not exhibit the effect of enhancing FcγRIIb binding when introduced into IL6R-F652 which has P238D.

FIG. 23 shows relative values for the FcγRIIb-binding activity obtained by additionally introducing these eleven alterations into a variant carrying the P238D alteration, and relative values for the FcγRIIb-binding activity obtained by introducing these alterations into an Fc that does not contain the P238D alteration in Reference Example 3. These eleven alterations enhanced the amount of FcγRIIb binding compared with before introduction when they were further introduced into the P238D variant, but on the contrary, the effect of lowering FcγRIIb binding was observed for eight of those alterations except G237F, G237W, and S239D, when they were introduced into the variant that does not contain P238D (GpH7-B3/GpL16-k0) used in Reference Example 3.

Reference Example 5 and these results showed that from the effects of introducing alterations into a naturally-occurring IgG1, it is difficult to predict the effects of introducing the same alterations into the variant containing an Fc with the P238D alteration. In other words, it would not have been possible to discover these eight alterations identified this time without this investigation.

The results of measuring KD values of the variants indicated in Table 20 for FcγRIa, FcγRIIaR, FcγRIIaH, FcγRIIb, and FcγRIIIaV by the method of Reference Example 2 are summarized in Table 21. In the table, "alteration" refers to the alteration introduced into IL6R-F11 (SEQ ID NO: 22). The template used for producing IL6R-F1, IL6R-G1d/IL6R-L, is indicated with an asterisk (*). Furthermore, "KD(IIaR)/KD(IIb)" and "KD(IIaH)/KD(IIb)" in the table respectively show the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD(IIb) of the parent polypeptide/KD(IIb) of the altered polypeptide refers to a value obtained by dividing the KD value of the parent polypeptide for FcγRIIb by the KD value of each variant for FcγRIIb. In addition, Table 21 shows KD values for the stronger of the FcγRIIaR- and FcγRIIaH-binding activities of each variant/KD values for the stronger of the FcγRIIaR- and FcγRIIaH-binding activities of the parent polypeptide. Here, parent polypeptide refers to a variant which has IL6R-F11 (SEQ ID NO: 22) as the H chain. It was determined that due to weak binding of FcγR to IgG, it was impossible to accurately analyze by kinetic analysis, and thus the values shown in bold italicized font in Table 21 were calculated by using Equation 2 of Reference Example 2.

$$KD = C \cdot R_{max}/(R_{eq}-RI)-C \qquad \text{[Equation 2]}$$

Table 21 shows that all variants improved their affinity for FcγRIIb in comparison with IL6R-F11, and the range of improvement was 1.9 fold to 5.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a larger value indicates a higher binding selectivity for FcγRIIb. For the parent polypeptide IL6R-F11/IL6R-L, the ratio of KD value for FcγRIIaR/KD value for FcγRIIb and the ratio of KD value for FcγRIIaH/KD value for FcγRIIb are both 0.7, and accordingly all variants in Table 21 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or reduced binding compared with the binding by the stronger of the FcγRIIaR- and FcγRIIaH-binding activities of the parent polypeptide. Since this value was 0.7 to 5.0 for the variants obtained this time, one may say that binding by the stronger of the FcγRIIaRand FcγRIIaH-binding activities of the variants obtained this time was nearly the same or decreased in comparison with the parent polypeptide. These results showed that compared with the parent polypeptide, the variants obtained this time have enhanced binding activity to FcγRIIb while having maintained or decreased binding activities to FcγRIIa type R and type H, and thus have improved selectivity for FcγRIIb. Furthermore, compared with IL6R-F11, all variants had lower affinity to FcγRIa and FcγRIIIaV.

2000, 400: 267-273; J. Biol. Chem. 2011, 276: 16469-16477), the Fc(WT)/FcγRIIIa extracellular region complex (Proc. Natl. Acad. Sci. USA, 2011, 108: 12669-126674), and the Fc(WT) /FcγRIIa extracellular region complex (J. Imunol. 2011, 187: 3208-3217) have been analyzed. While the three-dimensional structure of the Fc(WT)/FcγRIIb extracellular region complex has not been analyzed, the three-dimensional structure of a complex formed with Fc(WT) is known for FcγRIIa, and the extracellular regions of FcγRIIa

TABLE 21

| VARIANT NAME | ALTERATION | KD (mol/L) | | | | | KD(IIaR)/KD(IIb) |
|---|---|---|---|---|---|---|---|
| | | FcγRIa | FcgRIIaR | FcgRIIaH | FcgRIIb | FcgRIIIaV | |
| IL6R-G1d/IL6R-L | * | 3.2E−10 | 1.0E−06 | 6.7E−07 | 2.6E−06 | 3.5E−07 | 0.4 |
| IL6R-F11/IL6R-L | | 9.0E−10 | 5.0E−06 | 5.0E−06 | 6.8E−06 | 1.5E-06 | 0.7 |
| IL6R-PD042/IL6R-L | L234W/P238D | 6.3E−08 | 1.6E−05 | 1.9E-05 | 2.0E−06 | 3.7E-05 | 8.1 |
| IL6R-PD043/IL6R-L | L234Y/P238D | 7.5E−08 | 2.6E−05 | 2.3E-05 | 1.6E−06 | 4.5E-05 | 15.9 |
| IL6R-PD079/IL6R-L | G237A/P238D | 1.4E−07 | 3.2E−05 | 2.1E-05 | 3.0E−06 | 3.7E-05 | 10.5 |
| IL6R-PD080/IL6R-L | G237D/P238D | 1.4E−07 | 2.1E−05 | 2.5E-05 | 2.0E−06 | 4.3E-05 | 10.7 |
| IL6R-PD081/IL6R-L | G237E/P238D | 3.4E−07 | 3.8E−05 | 2.5E-05 | 3.6E−06 | 4.1E-05 | 10.6 |
| IL6R-PD082/IL6R-L | G237F/P238D | 5.2E−08 | 1.4E−05 | 1.6E-05 | 3.4E−06 | 4.3E-05 | 4.1 |
| IL6R-PD086/IL6R-L | G237L/P238D | 1.2E−07 | 1.8E−05 | 1.8E-05 | 2.6E−06 | 4.1E-05 | 6.9 |
| IL6R-PD087/IL6R-L | G237M/P238D | 5.2E−08 | 2.2E−05 | 2.0E-05 | 2.9E−06 | 3.7E-05 | 7.7 |
| IL6R-PD094/IL6R-L | G237W/P238D | 3.6E−08 | 7.2E−06 | 1.2E-05 | 2.3E−06 | 3.8E-05 | 3.1 |
| IL6R-PD095/IL6R-L | G237Y/P238D | 9.3E−08 | 7.9E−06 | 1.5E-05 | 2.3E−06 | 4.2E-05 | 3.4 |
| IL6R-PD097/IL6R-L | P238D/S239D | 4.9E−09 | 3.5E−06 | 1.9E-05 | 1.4E−06 | 1.7E-05 | 2.6 |

| VARIANT NAME | KD(IIaH)/KD(IIb) | KD(IIb) OF PARENT POLYPEPTIDE/KD(IIb) OF ALTERED POLYPEPTIDE | KD VALUE FOR THE STRONGER OF THE BINDING ACTIVITIES OF A VARIANT TO FcγRIIaR AND FcγRIIaH/KD VALUE FOR THE STRONGER OF THE BINDING ACTIVITIES OF THE PARENT POLYPEPTIDE TO FcγRIIaR AND FcγRIIaH |
|---|---|---|---|
| IL6R-G1d/IL6R-L | 0.3 | 2.6 | 0.1 |
| IL6R-F11/IL6R-L | 0.7 | 1.0 | 1.0 |
| IL6R-PD042/IL6R-L | 9.5 | 3.4 | 3.2 |
| IL6R-PD043/IL6R-L | 14.4 | 4.2 | 4.6 |
| IL6R-PD079/IL6R-L | 7.0 | 2.3 | 4.2 |
| IL6R-PD080/IL6R-L | 12.8 | 3.5 | 4.2 |
| IL6R-PD081/IL6R-L | 7.0 | 1.9 | 5.0 |
| IL6R-PD082/IL6R-L | 4.7 | 2.0 | 2.8 |
| IL6R-PD086/IL6R-L | 7.1 | 2.7 | 3.5 |
| IL6R-PD087/IL6R-L | 7.0 | 2.4 | 4.0 |
| IL6R-PD094/IL6R-L | 5.2 | 2.9 | 1.4 |
| IL6R-PD095/IL6R-L | 6.4 | 2.9 | 1.6 |
| IL6R-PD097/IL6R-L | 14.0 | 5.0 | 0.7 |

[Reference Example 7] X-Ray Structure Analysis of a Complex Formed Between an Fc Containing P238D and an Extracellular Region of FcγRIIb As indicated earlier in Reference Example 5, even though an alteration that improves FcγRIIb-binding activity or selectivity for FcγRIIb is introduced into an Fc containing P238D, the FcγRIIb-binding activity was found to decrease, and the reason for this may be that the structure of the interacting interface between Fc and FcγRIIb is changed due to introduction of P238D. Therefore, to pursue the reason for this phenomena, the three-dimensional structure of the complex formed between an IgG1 Fc containing the P238D mutation (hereinafter, Fc(P238D)) and the extracellular region of FcγRIIb was elucidated by X-ray crystal structure analysis, and the three-dimensional structure and binding mode were compared to those of the complex formed between the Fc of a naturally-occurring IgG1 (hereinafter, Fc(WT)) and the extracellular region of FcγRIIb. Many reports have been made on the three-dimensional structure of a complex formed between an Fc and an FcγR extracellular region; and the three-dimensional structures of the Fc(WT)/FcγRIIIb extracellular region complex (Nature, and FcγRIIb match 93% in amino acid sequence and have very high homology. Thus, the three-dimensional structure of the Fc(WT)/FcγRIIb extracellular region complex was predicted by modeling using the crystal structure of the Fc(WT)/FcγRIIa extracellular region complex.

Figure 24:
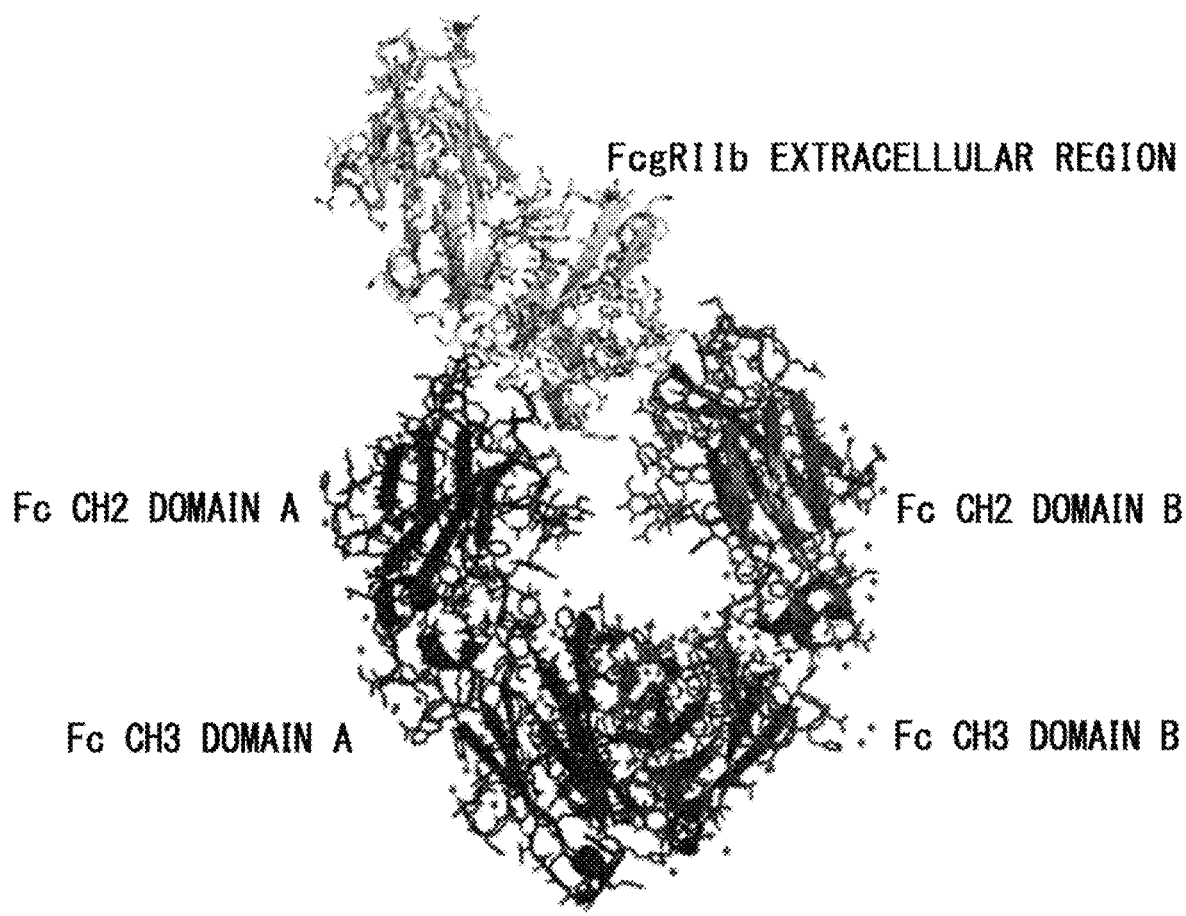
FIG. 24 shows a crystal structure of the Fc(P238D)/FcγRIIb extracellular region complex.

The three-dimensional structure of the Fc(P238D)/FcγRIIb extracellular region complex was determined by X-ray crystal structure analysis at 2.6 Å resolution. The structure obtained as a result of this analysis is shown in FIG. 24. The FcγRIIb extracellular region is bound between two Fc CH2 domains, and this is similar to the three-dimensional structures of complexes formed between Fc(WT) and the respective extracellular region of FcγRIIIa, FcγRIIIb, or FcγRIIa analyzed so far.

Figure 25:
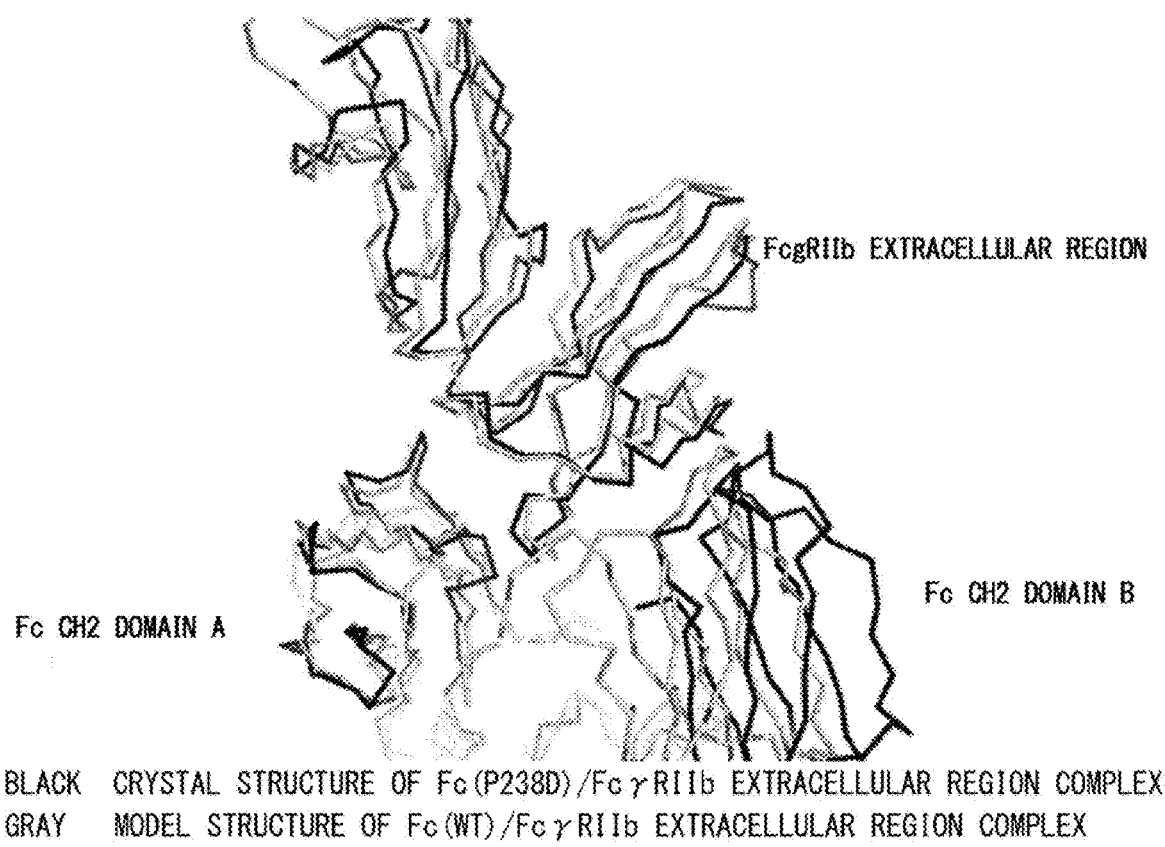
FIG. 25 shows an image of superimposing the crystal structure of the Fc(P238D)/FcγRIIb extracellular region complex and the model structure of the Fc(WT)/FcγRIIb extracellular region complex, with respect to the FcγRIIb extracellular region and the Fc CH2 domain A by least square fitting based on Cα atom pair distances.

Next, for detailed comparison, the crystal structure of the Fc(P238D)/FcγRIIb extracellular region complex and the model structure of the Fc(WT)/FcγRIIb extracellular region complex were superimposed by least square fitting based on Cα atom pair distances with respect to the FcγRIIb extracellular region and the Fc CH2 domain A (FIG. 25). In that case, the degree of overlap between Fc CH2 domains B was not satisfactory, and conformational differences were found in this portion. Furthermore, using the crystal structure of the Fc(P238D)/FcγRIIb extracellular region complex and the model structure of the Fc(WT)/FcγRIIb extracellular region complex, pairs of atoms that have a distance of 3.7 Å or less between the FcγRIIb extracellular region and Fc CH2 domain B were extracted and compared in order to observe the differences in interatomic interactions between FcγRIIb and Fc CH2 domain B in Fc(WT) and Fc(P238D). As shown in Table 22, the interatomic interactions between Fc CH2 domain B and FcγRIIb in Fc(P238D) and Fc(WT) do not match.

TABLE 22

| FcgRIIb ATOM | | | Fc(P238D) CH2 DOMAIN B INTERACTION PARTNER (DISTANCE BETWEEN ATOMS, A) | | | | Fc(WT) CH2 DOMAIN B INTERACTION PARTNER (DISTANCE BETWEEN ATOMS, A) | | | |
|---|---|---|---|---|---|---|---|---|---|---|
| Val | 116 | CG2 | | | | | Asp | 265 | OD2 | (3.47) |
| | | | | | | | Gly | 237 | O | (3.65) |
| Ser | 126 | OG | Ser | 298 | N | (3.31) | | | | |
| | | | Ser | 298 | CB | (3.32) | | | | |
| | | | Tyr | 296 | O | (3.05) | | | | |
| Lys | 128 | CA | Ser | 298 | OG | (3.50) | | | | |
| Phe | 129 | CB | Ser | 298 | O | (3.36) | | | | |
| Phe | 129 | CD2 | | | | | Asn | 297 | CB | (3.50) |
| | | | | | | | Asn | 297 | CG | (3.43) |
| Lys | 128 | C | Ser | 298 | OG | (3.47) | | | | |
| Phe | 129 | N | Ser | 298 | OG | (3.30) | | | | |
| Phe | 129 | O | Ser | 267 | OG | (3.54) | | | | |
| Arg | 131 | CB | | | | | Val | 266 | O | (3.02) |
| Arg | 131 | CG | | | | | Val | 266 | O | (3.22) |
| Arg | 131 | CD | | | | | Val | 266 | CG1 | (3.45) |
| | | | | | | | Val | 266 | C | (3.55) |
| | | | | | | | Val | 266 | O | (3.10) |
| Arg | 131 | NE | Ala | 327 | O | (3.60) | Val | 266 | C | (3.66) |
| | | | | | | | Val | 266 | O | (3.01) |
| | | | | | | | Val | 266 | N | (3.49) |
| Arg | 131 | CZ | Asp | 270 | CG | (3.64) | Val | 266 | N | (3.13) |
| | | | Asp | 270 | OD2 | (3.22) | | | | |
| | | | Asp | 270 | OD1 | (3.27) | | | | |
| | | | Ala | 327 | CB | (3.63) | | | | |
| Arg | 131 | NH1 | Asp | 270 | CG | (3.19) | Val | 266 | CG1 | (3.47) |
| | | | Asp | 270 | OD2 | (2.83) | Val | 266 | N | (3.43) |
| | | | Asp | 270 | OD1 | (2.99) | Thr | 299 | OG1 | (3.66) |
| | | | Ser | 267 | CB | (3.56) | Ser | 298 | O | (3.11) |

Furthermore, the X-ray crystal structure of the Fc(P238D)/FcγRIIb extracellular region complex and the model structure of the Fc(WT)/FcγRIIb extracellular region complex were superimposed by least square fitting based on Ca atom pair distances with respect to the only Fc CH2 domain A or the only Fc CH2 domain B, and the detailed structures near P238D were compared. The location of the amino acid residue at position 238 (EU numbering), which is the mutation introduction position, is changed between Fc(P238D) and Fc(WT), one can see that along with this change, the nearby loop structure continuing from the hinge region is changed between Fc(P238D) and Fc(WT) (FIG. 26). Originally in Fc(WT), Pro at position 238 (EU numbering) is present on the inner side of the protein, and forms a hydrophobic core with the surrounding residues. However, when this residue is changed to a charged and very hydrophilic Asp, the presence in the same hydrophobic core would cause energetical disadvantage in terms of desolvation. Therefore, in Fc(P238D), to cancel this energetically disadvantageous situation, the amino acid residue at position 238 (EU numbering) changes its orientation to face the solvent side, and this may have caused this change in the nearby loop structure. Furthermore, since this loop continues from the hinge region crosslinked by an S—S bond, its structural change will not be limited to a local change, and will affect the relative positioning of the FcCH2 domain A and domain B. As a result, the interatomic interactions between FcγRIIb and Fc CH2 domain B have been changed. Therefore, predicted effects could not be observed when alterations that improve selectivity and binding activity towards FcγRIIb in a naturally-occurring IgG were combined with an Fc containing the P238D alteration.

Furthermore, as a result of structural changes due to introduction of P238D in Fc CH2 domain A, a hydrogen bond has been found between the main chain of Gly at adjacent position 237 (EU numbering) and Tyr at position 160 in FcγRIIb (FIG. 27). The residue in FcγRIIa that corresponds to this Tyr 160 is Phe; and when the binding is to FcγRIIa, this hydrogen bond is not formed. The amino acid at position 160 is one of the few differences between FcγRIIa and FcγRIIb at the interface of interaction with Fc, the presence of this hydrogen bond which is specific to FcγRIIb is presumed to have led to improvement of FcγRIIb-binding activity and decrease of FcγRIIa-binding activity in Fc(P238D), and improvement of its selectivity. Furthermore, in Fc CH2 domain B, an electrostatic interaction is observed between Asp at position 270 (EU numbering) and Arg at position 131 in FcγRIIb (FIG. 28). In FcγRIIa type H, which is one of the allotypes of FcγRIIa, the corresponding residue is His, and therefore cannot form this electrostatic interaction. This can explain why the Fc(P238D)-binding activity is lowered in FcγRIIa type H compared with FcγRIIa type R. Observations based on such results of X-ray crystal structure analysis showed that the change of the loop structure beside P238D due to P238D introduction and the accompanying change in the relative domain positioning causes formation of new interactions not found in the naturally-occurring IgG, and this led to a selective binding profile of P238D variants for FcγRIIb.

[Expression and Purification of Fc(P238D)]

An Fc containing the P238D alteration was prepared as follows. First, Cys at position 220 (EU numbering) of hIL6R-IgG1-v1 (SEQ ID NO: 20) was substituted with Ser. Then, genetic sequence of Fc(P238D) from Glu at position 216 (EU numbering) to its C terminus was cloned by PCR. Using this cloned genetic sequence, production of expression vectors, and expression and purification of Fc(P238D) were carried out according to the method of Reference Example 1. Cys at position 220 (EU numbering) forms a disulfide bond with Cys of the L chain in general IgG1. The L chain is not co-expressed when Fc alone is prepared, and therefore, this residue was substituted with Ser to avoid formation of unnecessary disulfide bonds.

[Expression and Purification of the FcγRIIb Extracellular Region]

This was prepared according to the method of Reference Example 2.

[Purification of the Fc(P238D)/FcγRIIb Extracellular Region Complex]

To 2 mg of the FcγRIIb extracellular region sample obtained for crystallization, 0.29 mg of Endo F1 (Protein Science 1996, 5: 2617-2622) expressed and purified from *Escherichia coli* as a glutathione S-transferase fusion protein was added. This was allowed to remain at room temperature for three days in 0.1 M Bis-Tris buffer at pH 6.5, and the N-linked oligosaccharide was cleaved, leaving N-acetylglucosamine directly bound to Asn. Next, this FcγRIIb extracellular domain sample subjected to carbohydrate cleavage treatment was concentrated by ultrafiltration with 5000 MWCO, and purified by gel filtration chromatography (Superdex® 200 10/300 chromatography) using a column equilibrated in 20 mM HEPS at pH 7.5 containing 0.05 M NaCl. Furthermore, to the obtained carbohydrate-cleaved FcγRIIb extracellular region fraction, Fc(P238D) was added so that the molar ratio of the FcγRIIb extracellular region would be present in slight excess, and after concentration by ultrafiltration with 10000 MWCO, a sample of the Fc(P238D)/FcγRIIb extracellular region complex was obtained through purification by gel filtration chromatography (Superdex® 200 10/300 chromatography) using a column equilibrated in 20 mM HEPS at pH 7.5 containing 0.05 M NaCl.

[Crystallization of the Fc(P238D)/FcγRIIb Extracellular Region Complex]

A sample of the Fc(P238D)/FcγRIIb extracellular region complex was concentrated to approximately 10 mg/mL by ultrafiltration with 10000 MWCO, and crystallization was carried out by the sitting drop vapor diffusion method. A Hydra® II Plus One pipetting robot (MATRIX) was used for crystallization; and for a reservoir solution containing 100 mM Bis-Tris pH 6.5, 17% PEG3350, 0.2 M ammonium acetate, and 2.7% (w/v) D-Galactose, a crystallization drop was produced by mixing at a ratio of reservoir solution: crystallization sample=0.2 μL:0.2 μL, and after sealing, this was allowed to remain at 20° C., and thin plate-like crystals were successfully obtained.

[Measurement of X-Ray Diffraction Data from an Fc(P238D)/FcγRIIb Extracellular Region Complex Crystal]

One of the obtained single crystals of the Fc(P238D)/FcγRIIb extracellular region complex was soaked into a solution of 100 mM Bis-Tris pH 6.5, 20% PEG3350, ammonium acetate, 2.7% (w/v) D-Galactose, 22.5% (v/v) ethylene glycol. The crystal was fished out of the solution using a pin with attached tiny nylon loop, and frozen in liquid nitrogen; and then X-ray diffraction data was measured at synchrotron radiation facility Photon Factory BL-1A in High Energy Accelerator Research Organization. During the measurement, the crystal was constantly placed in a nitrogen stream at −178° C. to maintain in a frozen state, and a total of 225 X ray diffraction images were collected using Quantum 270 CCD detector (ADSC) attached to a beam line with rotating the crystal 0.8° at a time. Determination of cell parameters, indexing of diffraction spots, and diffraction data processing from the obtained diffraction images were performed using the Xia2 program (CCP4 Software Suite), XDS Package (Walfgang Kabsch) and Scala (CCP4 Software Suite); and finally, diffraction intensity data up to 2.46 Å resolution was obtained. The crystal belongs to the space group $P2_1$, and has the following cell parameters; a=48.85 Å, b=76.01 Å, c=115.09 Å, α=90°, β=100.70°, γ=90°.

[X Ray Structure Analysis of the Fc(P238D)/FcγRIIb Extracellular Region Complex]

Crystal structure of the Fc(P238D)/FcγRIIb extracellular region complex was determined by the molecular replacement method using the program Phaser (CCP4 Software Suite). From the size of the obtained crystal lattice and the molecular weight of the Fc(P238D)/FcγRIIb extracellular region complex, the number of complexes in the asymmetric unit was predicted to be one. From the structural coordinates of PDB code: 3SGJ which is the crystal structure of the Fc(WT)/FcγRIIIa extracellular region complex, the amino acid residue portions of the A chain positions 239-340 and the B chain positions 239-340 were taken out as separate coordinates, and they were used respectively as models for searching the Fc CH2 domains. The amino acid residue portions of the A chain positions 341-444 and the B chain positions 341-443 were taken out as a single set of coordinates from the same structural coordinates of PDB code: 3SGJ; and this was used as a model for searching the Fc CH3 domains. Finally, from the structural coordinates of PDB code: 2FCB which is a crystal structure of the FcγRIIb extracellular region, the amino acid residue portions of the A chain positions 6-178 was taken out and used as a model for searching the FcγRIIb extracellular region. The orientation and position of each search model in the crystal lattice were determined in the order of Fc CH3 domain, FcγRIIb extracellular region, and Fc CH2 domain, based on the rotation function and translation function to obtain the initial model for the crystal structure of the Fc(P238D)/FcγRIIb extracellular region complex. When rigid body refinement which moves the two Fc CH2 domains, the two Fc CH3 domains, and the FcγRIIb extracellular region was performed on the obtained initial model, the crystallographic reliability factor, R value became 40.4%, and the Free R value became 41.9% to diffraction intensity data from 25 Å to 3.0 Å at this point. Furthermore, structural refinement using the program Refmac5 (CCP4 Software Suite), and revision of the model to observe the electron density maps whose coefficient have 2Fo-Fc or Fo-Fc, which are calculated based on the experimentally determined structural factor Fo, the calculated structural factor Fc and the calculated phase using the model, was carried out by the Coot program (Paul Emsley), and model refinement was carried out by repeating these steps. Finally, as a result of incorporation of water molecules into the model based on the electron density maps which use 2Fo-Fc or Fo-Fc as the coefficient, and the following refinement, the crystallographic reliability factor, R values and the Free R value of the model containing 4846 non-hydrogen atoms became 23.7% and 27.6% to 24291 diffraction intensity data from 25 Å to 2.6 Å resolution, respectively.

[Production of a Model Structure of the Fc(WT)/FcγRIIb Extracellular Region Complex]

Based on the structural coordinates of PDB code: 3RY6 which is a crystal structure of the Fc(WT)/FcγRIIa extracellular region complex, the Build Mutants function of the Discovery Studio 3.1 program (Accelrys) was used to introduce mutations to match the amino acid sequence of FcγRIIb into FcγRIIa in this structural coordinates. In that case, the Optimization Level was set to High, Cut Radius was set to 4.5, five models were generated, and the one with the best energy score among them was employed as the model structure for the Fc(WT)/FcγRIIb extracellular region complex.

[Reference Example 8] Analysis of FcγR Binding of Fc Variants Whose Alteration Sites were Determined Based on Crystal Structures Based on the results of X-ray structure analysis on the complex formed between Fc(P238D) and the FcγRIIb extracellular region obtained in Reference Example 7, comprehensive alterations were introduced into sites on the Fc variant having substitution of Pro at position 238 (EU numbering) with Asp that were predicted to affect interaction with FcγRIIb, (residues of positions 233, 240, 241, 263, 265, 266, 267, 268, 271, 273, 295, 296, 298, 300, 323, 325, 326, 327, 328, 330, 332, and 334 (EU numbering)) and variants with a combination of alterations that enhance FcγRIIb binding were examined.

IL6R-B3 (SEQ ID NO: 23) was produced by introducing into IL6R-G1d (SEQ ID NO: 19) produced in Reference Example 4, the alteration produced by substituting Lys at position 439 (EU numbering) with Glu. Next, IL6R-BF648 was produced by introducing into IL6R-B3, the alteration produced by substituting Pro at position 238 (EU numbering) with Asp. IL6R-L (SEQ ID NO: 21) was utilized as the common antibody L chain for all of the antibodies. These antibody variants were expressed and purified according to the method of Reference Example 1, and binding to each of the FcγRs (FcγRIa, FcγRIIa type H, FcγRIIa type R, FcγRIIb, and FcγRIIIa type V) was comprehensively evaluated by the method of Reference Example 2.

A figure was produced according to the following method for the results of analyzing the interactions with the respective FcγRs. The value for the amount of binding of each variant to each FcγR was divided by the value for the amount of binding of the pre-altered control antibody (IL6R-BF648/IL6R-L with Pro at position 238 (EU numbering) substituted with Asp) to each FcγR, and the obtained was then multiplied by 100 and used as the relative binding activity value of each variant to each FcγR. The horizontal axis shows the relative binding activity value of each variant to FcγRIIb, and the vertical axis shows the relative binding activity value of each variant to FcγRIIa type R (FIG. 29).

Figure 29:
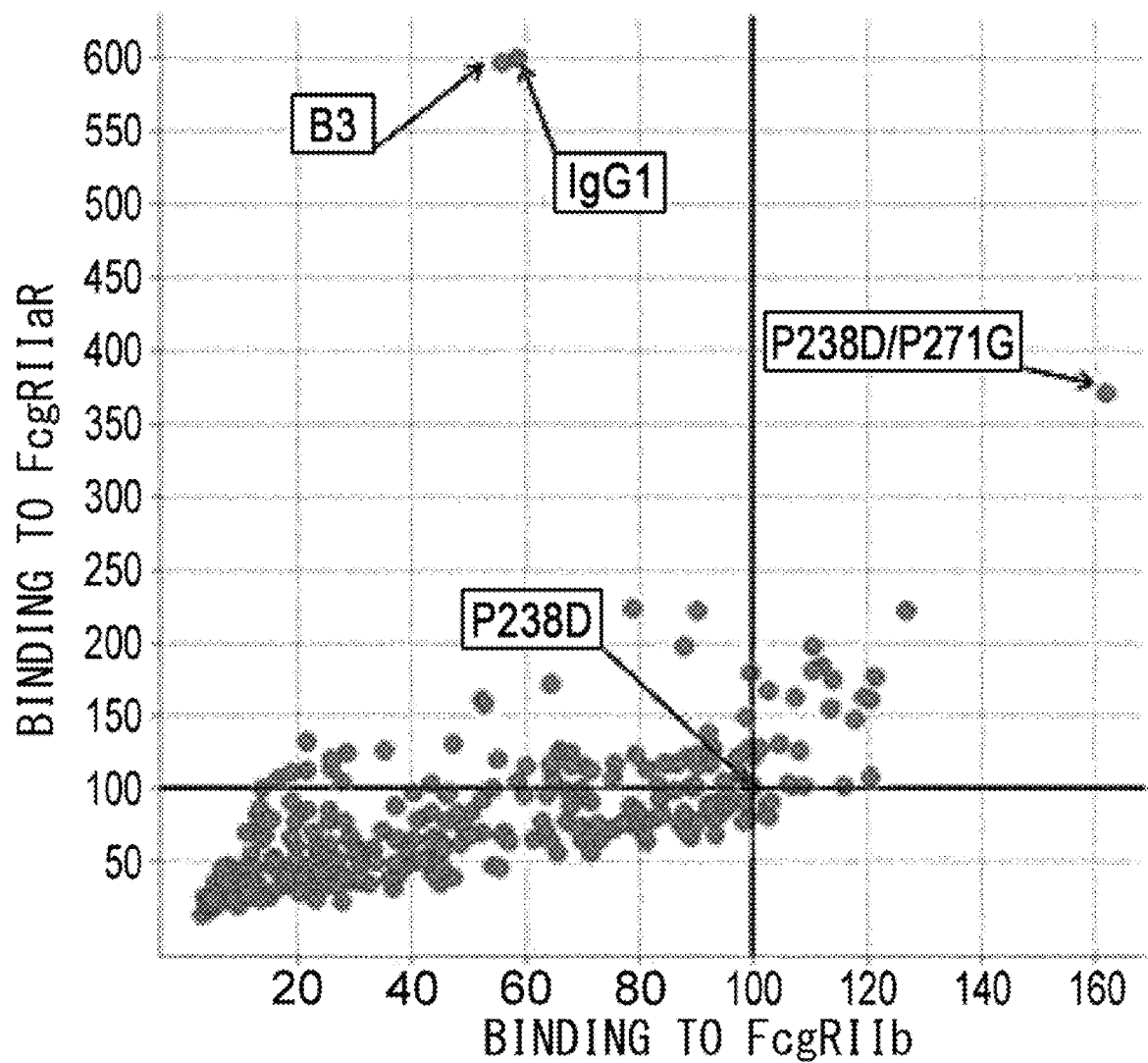
FIG. 29 shows a graph in which the horizontal axis shows the relative value of FcγRIIb-binding activity of each 2B variant, and the vertical axis shows the relative value of FcγRIIa type R-binding activity of each 2B variant. The value for the amount of binding of each 2B variant to each FcγR was divided by the value for the amount of binding of a control antibody prior to alteration (altered Fc with substitution of Pro at position 238 (EU numbering) with Asp) to each FcγR; and then the obtained value was multiplied by 100, and used as the value of relative binding activity of each 2B variant towards each FcγR.

As shown in FIG. 29, the results show that of all the alterations, 24 types of alterations were found to have an effect of maintaining or enhancing FcγRIIb binding in comparison with the pre-altered antibody. The binding of these variants to each of the FcγRs are shown in Table 23. In the table, "alteration" refers to the alteration introduced into IL6R-B3 (SEQ ID NO: 23; IL6R-2B999 in Table 23). The template used for producing IL6R-B3, IL6R-G1d/IL6R-L, is indicated with an asterisk (*).

TABLE 23

| VARIANT NAME | ALTERNATION | RELATIVE BINDING ACTIVITY TO FcgRIa | RELATIVE BINDING ACTIIVTY TO FcgRIIaR | RELATIVE BINDING ACTIVITY TO FcgRIIaH | RELATIVE BINDING ACTIVITY TO FcgRIIb | RELATIVE BINDING ACTIVITY TO FcgRIIIaV |
|---|---|---|---|---|---|---|
| IL6R-G1d/IL6R-L | * | 140 | 650 | 1670 | 62 | 3348 |
| IL6R-2B999/IL6R-L |  | 145 | 625 | 1601 | 58 | 3264 |
| IL6R-BF648/IL6R-L | P238D | 100 | 100 | 100 | 100 | 100 |
| IL6R-2B002/IL6R-L | P238D/E233D | 118 | 103 | 147 | 116 | 147 |
| IL6R-BP100/IL6R-L | P238D/S267A | 121 | 197 | 128 | 110 | 138 |
| IL6R-BP102/IL6R-L | P238D/S267Q | 104 | 165 | 66 | 106 | 86 |
| IL6R-BP103/IL6R-L | P238D/S267V | 56 | 163 | 69 | 107 | 77 |
| IL6R-BP106/IL6R-L | P238D/H268D | 127 | 150 | 110 | 116 | 127 |
| IL6R-BP107/IL6R-L | P238D/H268E | 123 | 147 | 114 | 118 | 129 |
| IL6R-BP110/IL6R-L | P238D/H268N | 105 | 128 | 127 | 101 | 127 |
| IL6R-BP112/IL6R-L | P238D/P271G | 119 | 340 | 113 | 157 | 102 |
| IL6R-2B128/IL6R-L | P238D/Y296D | 95 | 87 | 37 | 103 | 96 |
| IL6R-2B169/IL6R-L | P238D/V323I | 73 | 92 | 83 | 104 | 94 |
| IL6R-2B171/IL6R-L | P238D/V323L | 116 | 117 | 115 | 113 | 122 |
| IL6R-2B172/IL6R-L | P238D/V323M | 140 | 244 | 179 | 132 | 144 |
| IL6R-BP136/IL6R-L | P238D/K326A | 117 | 159 | 103 | 119 | 102 |
| IL6R-BP117/IL6R-L | P238D/K326D | 124 | 166 | 96 | 118 | 105 |
| IL6R-BP120/IL6R-L | P238D/K326E | 125 | 175 | 92 | 114 | 103 |
| IL6R-BP126/IL6R-L | P238D/K326L | 113 | 167 | 132 | 103 | 146 |
| IL6R-BP119/IL6R-L | P238D/K326M | 117 | 181 | 133 | 110 | 145 |
| IL6R-BP142/IL6R-L | P238D/K326N | 98 | 103 | 97 | 106 | 102 |
| IL6R-BP121/IL6R-L | P238D/K326Q | 118 | 155 | 135 | 113 | 157 |
| IL6R-BP118/IL6R-L | P238D/K326S | 101 | 132 | 128 | 104 | 144 |
| IL6R-BP116/IL6R-L | P238D/K326T | 110 | 126 | 110 | 108 | 114 |
| IL6R-BP911/IL6R-L | P238D/A330K | 52 | 101 | 108 | 119 | 120 |
| IL6R-BP078/IL6R-L | P238D/A330M | 106 | 101 | 89 | 105 | 91 |
| IL6R-BP912/IL6R-L | P238D/A330R | 60 | 81 | 93 | 103 | 97 |

The results of measuring KD values of the variants shown in Table 23 for FcgRIa, FcγRIIaR, FcγRIIaH, FcγRIIb, and FcγRIIIa type V by the method of Reference Example 2 are summarized in Table 24. In the table, "alteration" refers to the alteration introduced into IL6R-13 (SEQ ID NO: 23). The template used for producing IL6R-B3, IL6R-G1d/IL6R-L, is indicated with an asterisk (*). Furthermore, "KD(IIaR)/KD(IIb)" and "KD(IIaH)/KD(IIb)" in the table respectively represent the value obtained by dividing the KD value of each variant for FcγRIIaR by the KD value of each variant for FcγRIIb, and the value obtained by dividing the KD value of each variant for FcγRIIaH by the KD value of each variant for FcγRIIb. "KD(IIb) of the parent polypeptide/KD (IIb) of the altered polypeptide" refers to the value obtained by dividing the KD value of the parent polypeptide for FcγRIIb by the KD value of each variant for FcγRIIb. In addition, the "KD value for the stronger of the FcγRIIaR- and FcγRIIaH-binding activities of each variant/KD value for the stronger of the FcγRIIaR- and FcγRIIaH-binding activities of the parent polypeptide" are shown in Table 24. Here, parent polypeptide refers to the variant which has IL6R-B3 (SEQ ID NO: 23) as the H chain. It was determined that due to weak binding of FcγR to IgG, it was impossible to accurately analyze by kinetic analysis, and thus the values shown in bold italicized font in Table 24 were calculated by using Equation 2 of Reference Example 2.

$$KD = C \cdot R_{max}/(R_{eq}-RI) - C \quad \text{[Equation 2]}$$

Table 24 shows that in comparison with IL6R-B3 (IL6R-2B999 in Table 24), all variants showed improvement of affinity for FcγRIIb, and the range of improvement was 2.1 fold to 9.7 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb in the parent polypeptide IL6R-B3/IL6R-L were 0.3 and 0.2, respectively, all variants in Table 24 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 4.6 to 34.0 for the variants obtained this time, one may say that in comparison with the parent polypeptide, the variants obtained this time had reduced binding by the stronger of the FcγRIIaR- and FcγRIIaH-binding activities. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity to FcγRIa and FcγRIIIaV.

TABLE 24

| VARIANT NAME | ALTERATION | KD (mol/L) FcγRIa | FcgRIIaR | FcgRIIH | FcgRIIb | FcgRIIIaV | KD(IIaR)/KD(IIb) | KD(IIaH)/KD(IIb) | KD(IIb) OF THE PARENT POLYPEPTIDE/KD(IIb) OF ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| IL6R-G1d/IL6R-L | * | 3.2E−10 | 1.0E−06 | 6.7E−07 | 2.6E−06 | 3.5E−07 | 0.4 | 0.3 | 1.2 | 0.9 |
| IL6R-B3/IL6R-L | | 4.2E−10 | 1.1E−06 | 7.7E−07 | 3.1E−06 | 3.3E−07 | 0.3 | 0.2 | 1.0 | 1.0 |
| IL6R-BF648/IL6R-L | P238D | 1.1E−08 | 1.5E−05 | 4.0E-05 | 1.2E−06 | 7.1E-05 | 13.0 | 33.9 | 2.6 | 19.9 |
| IL6R-2B002/IL6R-L | P238D/E233D | 6.4E−09 | 1.9E-05 | 8.6E-05 | 9.3E−07 | 5.3E-05 | 20.4 | 92.3 | 3.3 | 24.7 |
| IL6R-BP100/IL6R-L | P238D/S267A | 1.1E−09 | 7.8E−06 | 4.6E-05 | 1.1E−06 | 5.9E-05 | 7.3 | 42.6 | 2.9 | 10.2 |
| IL6R-BP102/IL6R-L | P238D/S267Q | 8.2E−09 | 8.4E−06 | 6.1E-05 | 9.0E−07 | 8.2E-05 | 9.4 | 67.6 | 3.4 | 11.0 |
| IL6R-BP103/IL6R-L | P238D/S267V | 3.5E−08 | 1.1E−05 | 8.8E-05 | 1.2E−06 | 1.1E-04 | 9.0 | 71.5 | 2.5 | 14.4 |
| IL6R-BP106/IL6R-L | P238D/H268D | 4.0E−09 | 1.1E−05 | 3.6E-05 | 9.3E−07 | 5.5E-05 | 11.6 | 38.7 | 3.3 | 14.0 |
| IL6R-BP107/IL6R-L | P238D/H268E | 1.5E−09 | 1.2E−05 | 5.2E-05 | 9.3E−07 | 6.3E-05 | 12.7 | 56.1 | 3.3 | 15.3 |
| IL6R-BP110/IL6R-L | P238D/H268N | 7.3E−09 | 1.7E−05 | 4.7E-05 | 1.5E−06 | 6.4E-05 | 11.7 | 31.5 | 2.1 | 22.6 |
| IL6R-BP112/IL6R-L | P238D/P271G | 6.5E−09 | 3.5E−06 | 3.5E-05 | 3.2E−07 | 6.9E-05 | 11.0 | 109.4 | 9.7 | 4.6 |
| IL6R-2B128/IL6R-L | P238D/Y296D | 1.3E−08 | 2.6E−05 | 3.4E-05 | 1.4E−06 | 7.2E-05 | 17.7 | 23.6 | 2.1 | 33.1 |
| IL6R-2B169/L6R-L | P238D/V323I | 2.5E−08 | 1.9E−05 | 4.8E-05 | 1.2E−06 | 7.5E-05 | 15.8 | 40.7 | 2.6 | 24.3 |
| IL6R-2B171/IL6R-L | P238D/V323L | 9.1E−09 | 1.6E−05 | 3.4E-05 | 1.1E−06 | 5.7E-05 | 15.0 | 31.8 | 2.9 | 20.8 |
| IL6R-2B172/IL6R-L | P238D/V323M | 3.0E−09 | 6.1E−06 | 2.1E-05 | 7.7E−07 | 4.8E-05 | 8.0 | 27.3 | 4.0 | 8.0 |
| IL6R-BP136/IL6R-L | P238D/K326A | 6.6E−09 | 9.1E−06 | 3.8E-05 | 8.0E−07 | 6.9E-05 | 11.4 | 47.6 | 3.9 | 11.8 |
| IL6R-BP117/IL6R-L | P238D/K326D | 4.1E−09 | 9.2E−06 | 4.1E-05 | 8.0E−07 | 6.7E-05 | 11.6 | 51.4 | 3.9 | 12.0 |
| IL6R-BP120/IL6R-L | P238D/K326E | 6.6E−09 | 9.6E−06 | 6.5E-05 | 1.0E−06 | 7.9E-05 | 9.3 | 63.1 | 3.0 | 12.5 |

TABLE 24-continued

| VARIANT NAME | ALTERATION | KD (mol/L) | | | | | KD(IIaR)/ KD(IIb) | KD(IIaH)/ KD(IIb) | KD(IIb) OF THE PARENT POLYPEPTIDE/KD(IIb) OF ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| | | FcγRIa | FcγRIIaR | FcγRIIaH | FcγRIIb | FcγRIIIaV | | | | |
| IL6R-BP126/IL6R-L | P238D/K326L | 7.4E-09 | 1.1E-05 | *4.5E-05* | 1.4E-06 | *5.6E-05* | 7.8 | 31.7 | 2.2 | 14.4 |
| IL6R-BP119/IL6R-L | P238D/K326M | 7.0E-09 | 9.9E-06 | *4.5E-05* | 1.1E-06 | *5.6E-05* | 8.7 | 39.5 | 2.7 | 12.8 |
| IL6R-BP142/IL6R-L | P238D/K326N | 5.3E-09 | 1.8E-05 | *9.3E-05* | 1.2E-06 | *1.1E-04* | 15.5 | 79.5 | 2.6 | 23.5 |
| IL6R-BP121/IL6R-L | P238D/K326Q | 1.1E-08 | 1.3E-05 | *4.4E-05* | 1.1E-06 | *5.2E-05* | 11.7 | 40.4 | 2.8 | 16.6 |
| IL6R-BP118/IL6R-L | P238D/K326S | 1.2E-08 | 1.5E-05 | *4.6E-05* | 1.2E-06 | *5.6E-05* | 13.2 | 40.0 | 2.7 | 19.7 |
| IL6R-BP116/IL6R-L | P238D/K326T | 2.6E-09 | 1.5E-05 | *5.4E-05* | 1.1E-06 | *7.2E-05* | 13.3 | 48.2 | 2.8 | 19.4 |
| IL6R-BP911/IL6R-L | P238D/A330K | 4.9E-08 | 1.6E-05 | *3.7E-05* | 8.9E-07 | *5.8E-05* | 18.5 | 41.7 | 3.5 | 21.3 |
| IL6R-BP078/IL6R-L | P238D/A330M | 8.2E-09 | 1.5E-05 | *4.5E-05* | 1.1E-06 | *7.8E-05* | 13.4 | 41.3 | 2.8 | 19.0 |
| IL6R-BP912/IL6R-L | P238D/A330R | 3.8E-08 | 2.6E-05 | *3.8E-05* | 1.5E-06 | *7.8E-05* | 17.8 | 25.9 | 2.1 | 34.0 |

Figure 30:
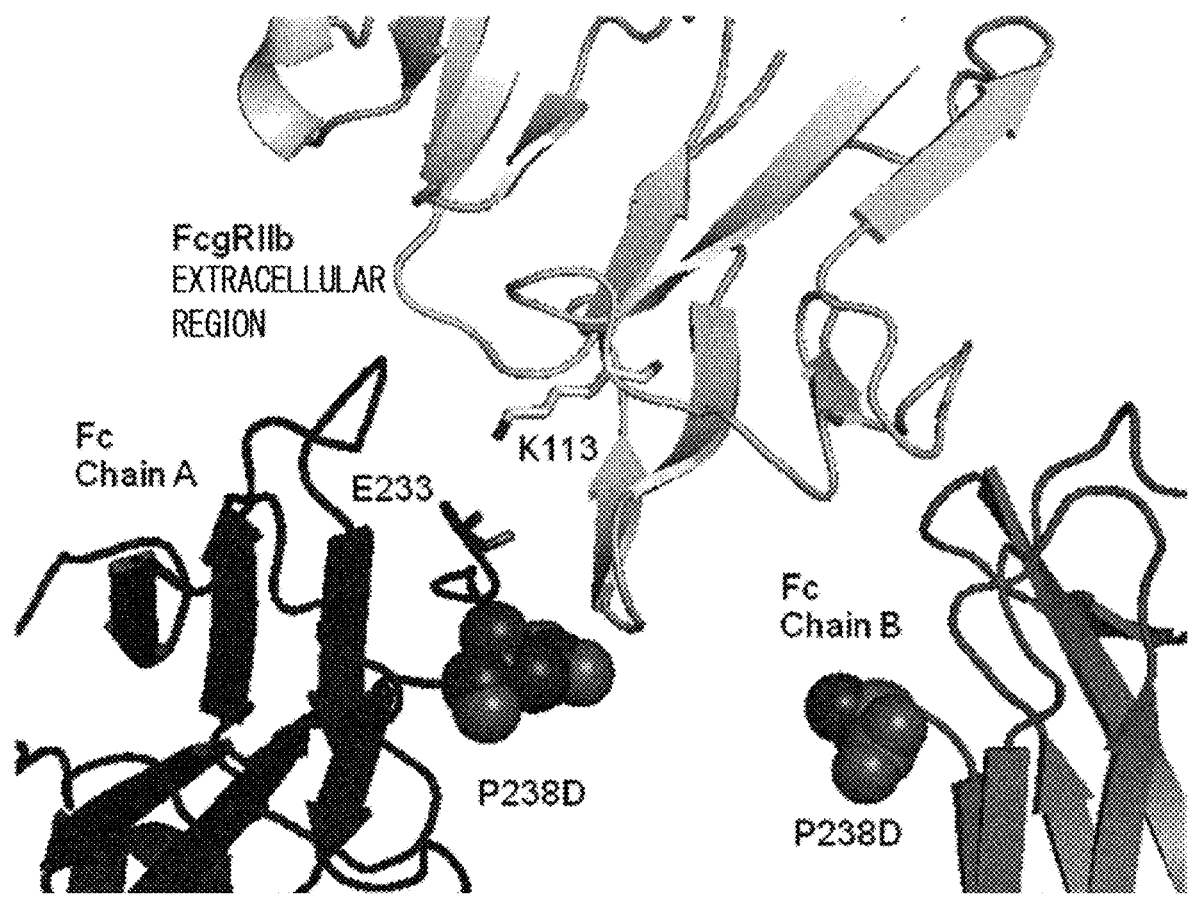
FIG. 30 shows Glu at position 233 (EU numbering) in Fc Chain A and the surrounding residues in the extracellular region of FcγRIIb in the crystal structure of the Fc(P238D)/FcγRIIb extracellular region complex.

With regard to the promising variants among the obtained combination variants, the factors leading to their effects were studied using the crystal structure. FIG. 30 shows the crystal structure of the Fc(P238D)/FcγRIIb extracellular region complex. In this figure, the H chain positioned on the left side is Fc Chain A, and the H chain positioned on the right side is Fc Chain B. Here, one can see that the site at position 233 (EU numbering) in Fe Chain A is located near Lys at position 113 (EU numbering) of FcγRIIb. However, in this crystal structure, the E233 side chain is in a condition of considerably high mobility, and its electron density is not well observed. Therefore, the alteration produced by substituting Glu at position 233 (EU numbering) with Asp leads to decrease in the degree of freedom of the side chain since the side chain becomes one carbon shorter. As a result, the entropy loss when forming an interaction with Lys at position 113 (EU numbering) of FcγRIIb may be decreased, and consequently this is speculated to contribute to improvement of binding free energy.

Figure 31:
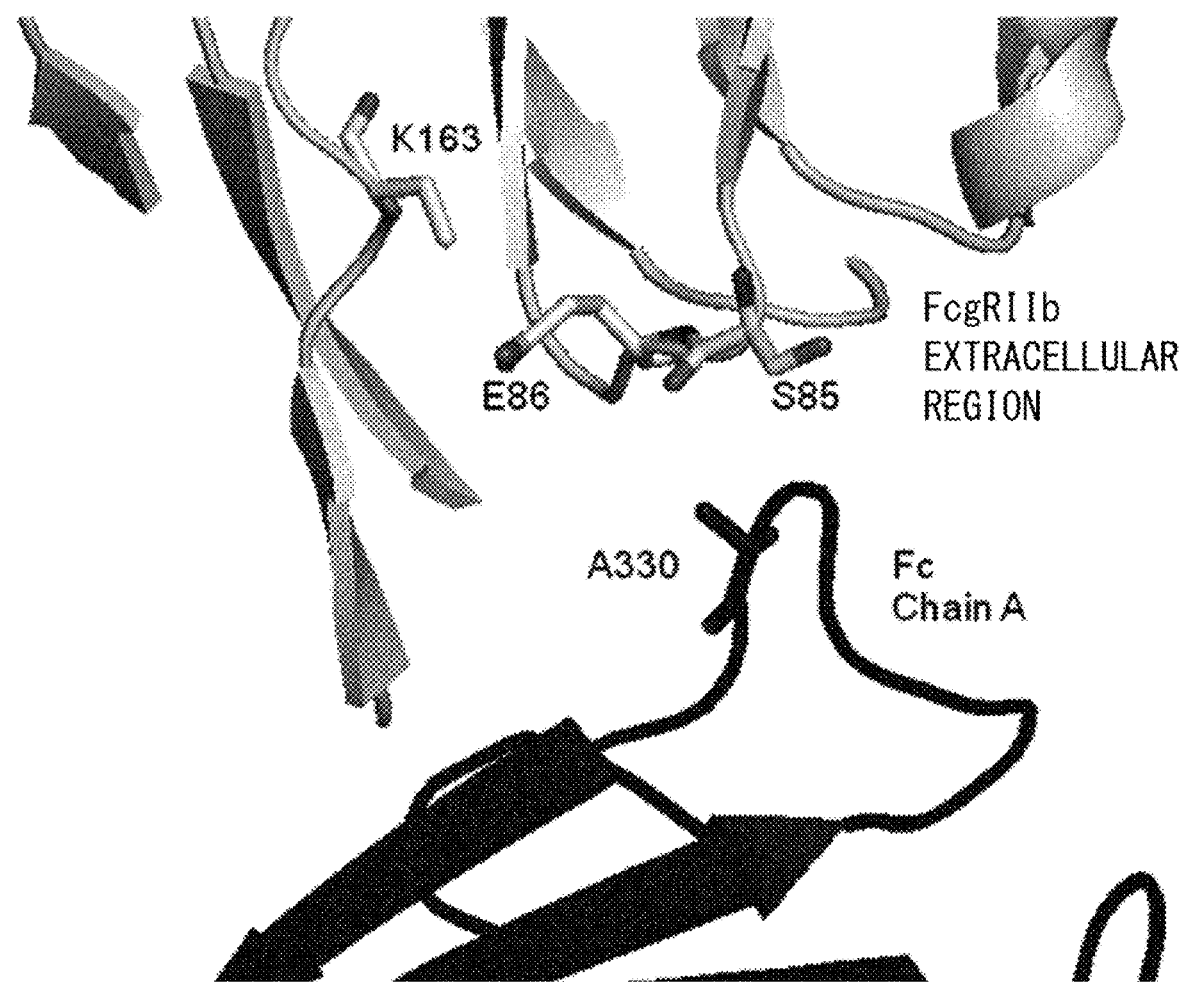
FIG. 31 shows Ala at position 330 (EU numbering) in Fc Chain A and the surrounding residues in the extracellular region of FcγRIIb in the crystal structure of the Fc(P238D)/FcγRIIb extracellular region complex.

Similarly, FIG. 31 shows the environment near the site at position 330 (EU numbering) in the structure of the Fc(P238D)/FcγRIIb extracellular region complex. This figure shows that the environment around the site at position 330 (EU numbering) of Fc Chain A of Fc(P238D) is a hydrophilic environment composed of Ser at position 85, Glu at position 86, Lys at position 163, and such (EU numbering) of FcγRIIb. Therefore, the alteration produced by substituting Ala at position 330 (EU numbering) with Lys or Arg is speculated to contribute to strengthening the interaction with Ser at position 85 (EU numbering) or Glu at position 86 (EU numbering) in FcγRIIb.

Figure 32:
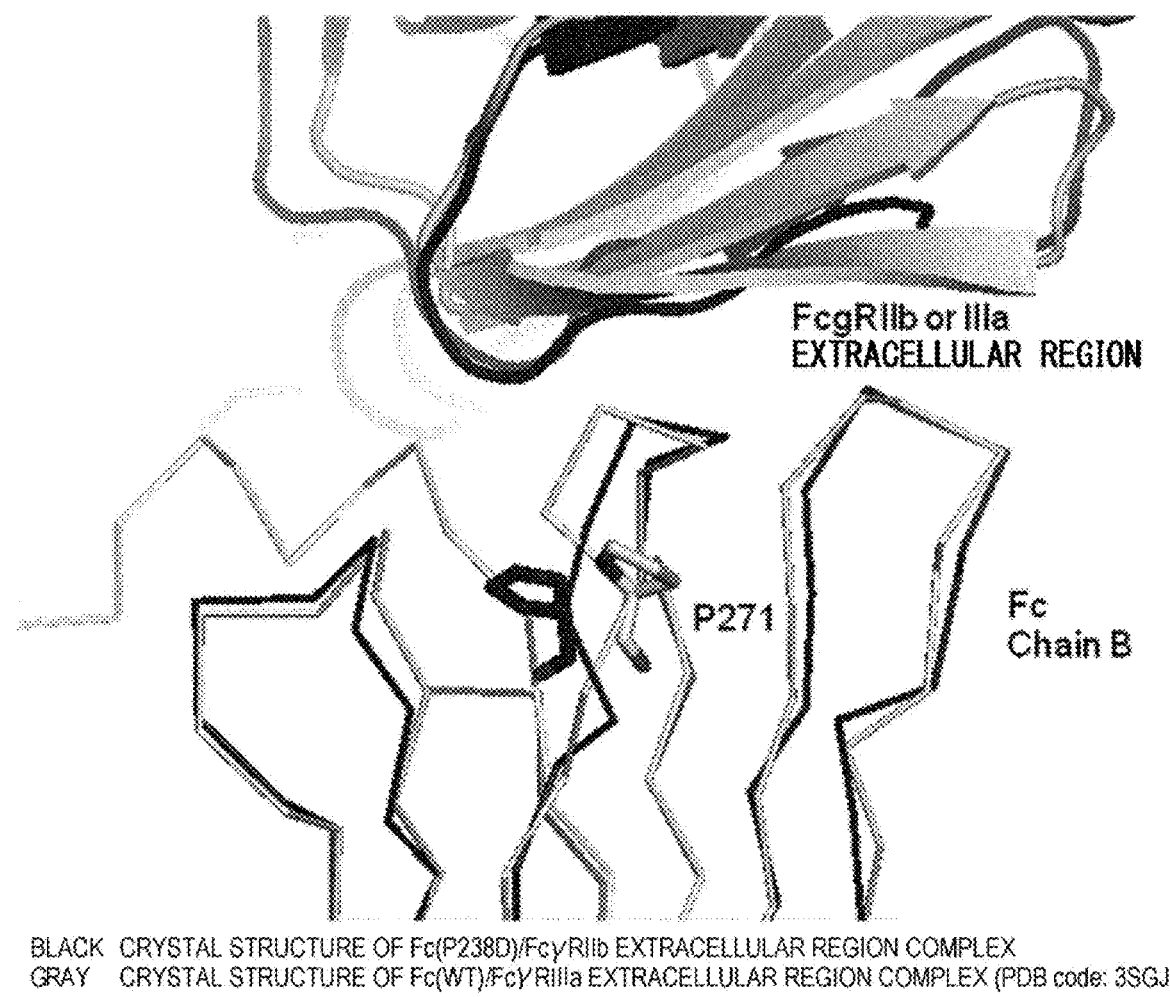
FIG. 32 shows the structures of Pro at position 271 (EU numbering) of Fc Chain B after superimposing the crystal structures of the Fc(P238D)/FcγRIIb extracellular region complex and the Fc(WT)/FcγRIIIa extracellular region complex by least square fitting based on Cα atom pair distances with respect to Fc Chain B.

FIG. 32 depicts the structures of Pro at position 271 (EU numbering) of Fc Chain B after superimposing the crystal structures of the Fc(P238D)/FcγRIIb extracellular region complex and the Fc(WT)/FcγRIIIa extracellular region complex by least square fitting based on Ca atom pair distances with respect to Fc Chain B. These two structures match well, but have different three-dimensional structures of Pro at position 271 (EU numbering). When the weak electron density around this area in the crystal structure of the Fc(P238D)/FcγRIIb extracellular region complex is also taken into consideration, it is suggested that there is possibility that Pro at position 271 (EU numbering) in Fc(P238D)/FcγRIIb causes a large strain on the structure, thus disturbing the loop structure to attain an optimal structure. Therefore, one may consider that the alteration produced by substituting Pro at position 271 (EU numbering) with Gly gives flexibility to this loop structure and contributes to enhancement of binding by reducing the energetic barrier when allowing to form an optimum structure upon interaction with FcγRIIb.

[Reference Example 9] Examination of the Combinatorial Effect of Alterations that Enhance FcγRIIb Binding when Combined with P238D Of the alterations obtained in Reference Examples 6 and 8, those that enhanced FcγRIIb binding or maintained FcγRIIb binding and showed effects of suppressing binding to other FcγRs were combined with each other, and their effects were examined.

Particularly good alterations were selected from Tables 19 and 22, and they were combined and introduced into the antibody H chain IL6R-BF648 in a similar manner to the method of Reference Example 8. IL6R-L was utilized as the common antibody L chain for all of the antibodies, the antibodies were expressed and purified according to the method of Reference Example 1, and binding to each of the FcγRs (FcγRIa, FcγRIIa type H, FcγRIa type R, FcγRIIb, and FcγRIIIa type V) was comprehensively evaluated by the method of Reference Example 2.

Relative binding activities were calculated for the results of analyzing interactions with the respective FcγRs according to the following method. The value for the amount of binding of each variant to each FcγR was divided by the value for the amount of binding of the pre-altered control antibody (IL6R-BF648/IL6R-L with substitution of Pro at position 238 (EU numbering) with Asp) to each FcγR, and multiplied by 100; and then the value was used as the relative binding activity value of each variant to each FcγR. The horizontal axis shows the relative binding activity value of each variant to FcγRIIb, and the vertical axis shows the relative binding activity value of each variant to FcγRIIa type R (Table 25).

In the table, "alteration" refers to the alteration introduced into IL6R-B3 (SEQ ID NO: 23). The template used for producing IL6R-B3, IL6R-G1d/IL6R-L, is indicated with an asterisk (*).

TABLE 25

| VARIANT NAME | ALTERATION | RELATIVE BINDING ACTIVITY TO FcgRIa | RELATIVE BINDING ACTIIVTY TO FcgRIIaR | RELATIVE BINDING ACTIVITY TO FcgRIIaH | RELATIVE BINDING ACTIVITY TO FcgRIIb | RELATIVE BINDING ACTIVITY TO FcgRIIIaV |
|---|---|---|---|---|---|---|
| IL6R-G1d/IL6R-L | * | 140 | 650 | 1670 | 62 | 3348 |
| IL6R-B3/IL5R-L |  | 145 | 625 | 1601 | 58 | 3264 |
| IL6R-BF648/IL6R-L | P238D | 100 | 100 | 100 | 100 | 100 |
| IL6R-2B253/IL6R-L | E233D/P238D/V323M | 155 | 288 | 207 | 156 | 126 |
| IL6R-2B261/IL6R-L | E233D/P238D/Y296D | 100 | 94 | 91 | 115 | 87 |
| IL6R-BP082/IL6R-L | E233D/P238D/A330K | 74 | 126 | 106 | 136 | 87 |
| IL6R-BP083/IL6R-L | P238D/Y296D/A330K | 50 | 87 | 91 | 122 | 107 |
| IL6R-BP084/IL6R-L | P238D/V323M/A330K | 109 | 203 | 162 | 141 | 106 |
| IL6R-BP085/IL6R-L | G237D/P238D/A330K | 19 | 279 | 158 | 152 | 104 |
| IL6R-BP086/IL6R-L | P238D/K326A/A330K | 72 | 155 | 116 | 137 | 123 |
| IL6R-BP087/IL6R-L | L234Y/P238D/A330K | 33 | 163 | 179 | 137 | 158 |
| IL6R-BP088/IL6R-L | G237D/P238D/K326A/A330K | 25 | 377 | 166 | 161 | 122 |
| IL6R-BP089/IL6R-L | L234Y/P238D/K326A/A330K | 43 | 222 | 186 | 147 | 136 |
| IL6R-BP129/IL6R-L | E233D/P238D/Y296D/A330K | 68 | 111 | 98 | 138 | 95 |
| IL6R-BP130/IL6R-L | E233D/P238D/V323M/A330K | 104 | 272 | 224 | 160 | 115 |
| IL6R-BP131/IL6R-L | E233D/G237D/P238D/A330K | 33 | 364 | 253 | 160 | 118 |
| IL6R-BP132/IL6R-L | E233D/P238D/K326A/A330K | 91 | 191 | 130 | 150 | 120 |
| IL6R-BP133/IL6R-L | E233D/L234Y/P238D/A330K | 41 | 174 | 151 | 137 | 114 |

TABLE 25-continued

| VARIANT NAME | ALTERATION | RELATIVE BINDING ACTIVITY TO FcgRIa | RELATIVE BINDING ACTIIVTY TO FcgRIIaR | RELATIVE BINDING ACTIVITY TO FcgRIIaH | RELATIVE BINDING ACTIVITY TO FcgRIIb | RELATIVE BINDING ACTIVITY TO FcgRIIIaV |
|---|---|---|---|---|---|---|
| IL6R-BP143/IL6R-L | L234Y/P238D/K326A | 86 | 238 | 143 | 133 | 114 |
| IL6R-BP144/IL6R-L | G237D/P238D/K326A | 64 | 204 | 108 | 121 | 128 |
| IL6R-BP145/IL6R-L | L234Y/G237D/P238D | 41 | 350 | 224 | 152 | 153 |
| IL6R-BP146/IL6R-L | L234Y/G237D/P238D/K326A | 50 | 445 | 203 | 156 | 180 |
| IL6R-BP147/IL6R-L | L234Y/G237D/P238D/K326A/A330K | 24 | 650 | 582 | 177 | 209 |
| IL6R-BP148/IL6R-L | E233D/L234Y/G237D/P238D/K326A/A330K | 33 | 603 | 462 | 176 | 227 |
| IL6R-BP149/IL6R-L | E233D/L234Y/G237D/P238D/Y296D/K326A/A330K | 29 | 539 | 401 | 173 | 186 |
| IL6R-BP150/IL6R-L | L234Y/G237D/P238D/K326A/A330R | 30 | 757 | 770 | 183 | 204 |
| IL6R-BP151/IL6R-L | E233D/L234Y/G237D/P238D/K326A/A330R | 39 | 705 | 621 | 180 | 221 |
| IL6R-BP152/IL6R-L | E233D/L234Y/G237D/P238D/Y296D/K326A/A330R | 34 | 638 | 548 | 178 | 146 |
| IL6R-BP176/IL6R-L | E233D/P238D/K326D/A330K | 102 | 201 | 128 | 147 | 131 |
| IL6R-BP177/IL6R-L | E233D/L234Y/G237D/P238D/P271G/K326D/A330K | 57 | 691 | 409 | 177 | 186 |
| IL6R-BP178/IL6R-L | E233D/G237D/P238D/P271G/A330K | 51 | 653 | 259 | 179 | 110 |
| IL6R-BP179/IL6R-L | G237D/P238D/P271G/K326A/A330K | 39 | 570 | 226 | 177 | 125 |
| IL6R-BP180/IL6R-L | G237D/P238D/P271G/A330K | 29 | 602 | 203 | 179 | 100 |
| IL6R-BP181/IL6R-L | E233D/P238D/P271G/K326A/A330K | 108 | 362 | 150 | 170 | 122 |
| IL6R-BP182/IL6R-L | E233D/P238D/P271G/Y296D/A330K | 95 | 413 | 139 | 173 | 120 |
| IL6R-BP183/IL6R-L | E233D/L234Y/P238D/P271G/K326A/A330K | 83 | 423 | 191 | 164 | 113 |
| IL6R-BP184/IL6R-L | E233D/P238D/P271G/A330K | 96 | 436 | 131 | 171 | 106 |
| IL6R-BP185/IL6R-L | E233D/L234Y/G237D/P238D/P271G/K326A/A330K | 47 | 670 | 446 | 179 | 191 |
| IL6R-BP186/IL6R-L | E233D/L234Y/G237D/P238D/P271G/Y296D/K326A/A330K | 43 | 614 | 368 | 175 | 143 |
| IL6R-BP187/IL6R-L | L234Y/P238D/P271G/K326A/A330K | 68 | 387 | 205 | 157 | 124 |
| IL6R-BP188/IL6R-L | E233D/G237D/P238D/H268D/P271G/A330K | 74 | 636 | 234 | 179 | 121 |
| IL6R-BP189/IL6R-L | G237D/P238D/H268D/P271G/K326A/A330K | 56 | 557 | 183 | 177 | 141 |
| IL6R-BP190/IL6R-L | G237D/P238D/H268D/P271G/A330K | 50 | 615 | 224 | 181 | 155 |
| IL6R-BP191/IL6R-L | E233D/P238D/H268D/P271G/K326A/A330K | 125 | 382 | 145 | 170 | 142 |
| IL6R-BP192/IL6R-L | E233D/P238D/H268D/P271G/Y296D/A330K | 109 | 406 | 122 | 172 | 118 |
| IL6R-BP193/IL6R-L | E233D/P238D/H268D/P271G/A330K | 113 | 449 | 154 | 173 | 135 |
| IL6R-BP194/IL6R-L | E233D/L234Y/G237D/P238D/H268D/P271G/K326A/A330K | 69 | 672 | 395 | 178 | 249 |
| IL6R-BP195/IL6R-L | E233D/L234Y/G237D/P238D/H268D/P271G/Y296D/K326A/A330K | 68 | 651 | 344 | 181 | 221 |
| IL6R-BP196/IL6R-L | L234Y/P238D/H268D/P271G/K326A/A330K | 89 | 402 | 195 | 157 | 137 |
| IL6R-BP197/IL6R-L | E233D/L234Y/G237D/P238D/H268D/P271G/Y296D/K326A/A330K | 71 | 642 | 294 | 179 | 206 |
| IL6R-BP198/IL6R-L | E233D/L234Y/P238D/H268D/P271G/K326A/A330K | 104 | 449 | 188 | 164 | 157 |
| IL6R-BP199/IL6R-L | E233D/P238D/K326A/A330R | 112 | 172 | 116 | 144 | 103 |
| IL6R-BP200/IL6R-L | E233D/L234Y/G237D/P238D/P271G/K326A/A330R | 60 | 754 | 517 | 188 | 164 |
| IL6R-BP201/IL6R-L | E233D/G237D/P238D/P271G/A330R | 57 | 696 | 359 | 186 | 121 |
| IL6R-BP202/IL6R-L | G237D/P238D/P271G/K326A/A330R | 43 | 615 | 285 | 185 | 108 |
| IL6R-BP203/IL6R-L | G237D/P238D/P271G/A330R | 35 | 637 | 255 | 185 | 88 |
| IL6R-BP204/IL6R-L | E233D/P238D/P271G/K326A/A330R | 110 | 301 | 137 | 165 | 121 |
| IL6R-BP205/IL6R-L | E233D/P238D/P271G/Y296D/A330R | 97 | 335 | 108 | 167 | 93 |
| IL6R-BP206/IL6R-L | E233D/P238D/P271G/A330R | 101 | 362 | 123 | 168 | 92 |
| IL6R-BP207/IL6R-L | E233D/P238D/A330R | 74 | 103 | 103 | 124 | 97 |
| IL6R-BP208/IL6R-L | E233D/G237D/P238D/H268D/P271G/A330R | 81 | 690 | 310 | 188 | 118 |
| IL6R-BP209/IL6R-L | G237D/P238D/H268D/P271G/K326A/A330R | 68 | 625 | 267 | 186 | 153 |
| IL6R-BP210/IL6R-L | G237D/P238D/H268D/P271G/A330R | 57 | 661 | 279 | 187 | 135 |
| IL6R-BP211/IL6R-L | E233D/P238D/H268D/P271G/K326A/A330R | 128 | 312 | 111 | 165 | 87 |
| IL6R-BP212/IL6R-L | E233D/P238D/H268D/P271G/Y296D/A330R | 117 | 363 | 135 | 173 | 122 |
| IL6R-BP213/IL6R-L | E233D/P238D/H268D/P271G/A330R | 118 | 382 | 123 | 169 | 100 |
| IL6R-BP214/IL6R-L | E233D/L234Y/G237D/P238D/Y296D/K326A/A330K | 36 | 498 | 285 | 174 | 165 |

The results of measuring KD values of the variants shown in Table 25 for FcγRIa, FcγRIIaR, FcγRIIaH, FcγRIb, and FcγRIIIa type V by the method of Reference Example 2are summarized in Table 26. In the table, "alteration" refers to the alteration introduced into IL6R-B3 (SEQ ID NO: 23). The template used for producing IL6R-B3, IL6R-G1d/IL6R-L, is indicated with an asterisk (*). Furthermore, "KD (IIaR)/KD (IIb)" and "KD (IIaH)/KD (IIb)" in the table respectively represent the value obtained by dividing the KD value of each variant for FcγRIIaR by the KD value of each variant for FcγRIIb, and the value obtained by dividing the KD value of each variant for FcγRIIaH by the KD value of each variant for FcγRIIb. "KD (IIb) of the parent polypeptide/KD (IIb) of the altered polypeptide" refers to the value obtained by dividing the KD value of the parent polypeptide for FcγRIIb by the KD value of each variant for FcγRIIb. In addition, the "KD value for the stronger of the FcγRIIaR- and FcγRIIaH-binding activities of each variant/KD value for the stronger of the FcγRIIaR- and FcγRIIaH-binding activities of the parent polypeptide" are shown in Table 26. Here, parent polypeptide refers to the variant which has IL6R-B3 (SEQ ID NO: 23) as the H chain. It was determined that due to weak binding of FcγR to IgG, it was impossible to accurately analyze by kinetic analysis, and thus the values shown in bold italicized font in Table 26 were calculated by using Equation 2 of Reference Example 2.

$$KD = C \cdot R_{max}/(R_{eq} - RI) - C \quad \text{[Equation 2]}$$

Table 26 shows that in comparison with IL6R-B3, all variants showed improvement of affinity for FcγRIIb, and the range of improvement was 3.0 fold to 99.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, those values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb of the parent polypeptide IL6R-B3/IL6R-L were 0.3 and 0.2, respectively, all variants in Table 26 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 0.7 to 29.9 for the variants obtained this time, one may say that binding by the stronger of the FcγRIIaR- and FcγRIIaH-binding activities of the variants obtained this time was nearly equivalent or decreased compared with that of the parent polypeptide. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity for FcγRIa and FcγRIIIaV.

TABLE 26

| VARIANT NAME | ALTERATION | KD (mol/L) FcγRIa | FcγRIIaR | FcγRIIaH | FcγRIIb | FcγRIIaV | KD(IIaR)/ KD(IIb) | KD(IIaH)/ KD(IIb) | KD(IIb) OF THE PARENT POLYPEPTIDE/KD(IIb) OF ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| IL6R-G1d/ IL6R-L | * | 3.2E-10 | 1.0E-06 | 6.7E-07 | 2.6E-06 | 3.5E-07 | 0.4 | 0.3 | 1.2 | 0.9 |
| IL6R-B3/ IL6R-L | | 4.2E-10 | 1.1E-06 | 7.7E-07 | 3.1E-06 | 3.3E-07 | 0.3 | 0.2 | 1.0 | 1.0 |
| IL6R-BF648/ IL6R-L | P238D | 1.1E-08 | 1.5E-05 | 4.0E-05 | 1.2E-06 | 7.1E-05 | 13.0 | 33.9 | 2.6 | 19.9 |
| IL6R-2B253/ IL6R-L | E233D/P238D/V323M | 1.4E-09 | 5.0E-06 | 1.3E-05 | 4.3E-07 | 5.0E-05 | 11.5 | 30.1 | 7.2 | 6.5 |
| IL6R-2B261/ IL6R-L | E233D/P238D/Y296D | 9.0E-09 | 2.2E-05 | 3.3E-05 | 1.0E-06 | 7.3E-05 | 21.8 | 32.4 | 3.0 | 28.8 |
| IL6R-BP082/ IL6R-L | E233D/P238D/A330K | 1.8E-08 | 1.2E-05 | 3.7E-05 | 5.4E-07 | 8.1E-05 | 22.8 | 69.0 | 5.8 | 15.8 |
| IL6R-BP083/ IL6R-L | P238D/Y296D/A330K | 3.8E-08 | 2.3E-05 | 4.4E-05 | 7.9E-07 | 6.6E-05 | 29.0 | 55.5 | 3.9 | 29.9 |
| IL6R-BP084/ IL6R-L | P238D/V323M/A330K | 7.0E-09 | 7.2E-06 | 2.4E-05 | 5.0E-07 | 6.7E-05 | 14.3 | 47.6 | 6.1 | 9.4 |
| IL6R-BP085/ IL6R-L | G237D/P238D/A330K | 2.9E-07 | 4.2E-06 | 2.4E-05 | 3.2E-07 | 6.8E-05 | 13.1 | 74.5 | 9.6 | 5.5 |
| IL6R-BP086/ IL6R-L | P238D/K326A/A330K | 2.7E-08 | 9.7E-06 | 3.4E-05 | 5.7E-07 | 5.7E-05 | 17.1 | 59.9 | 5.4 | 12.6 |
| IL6R-BP087/ IL6R-L | L234Y/P238D/A330K | 3.8E-08 | 9.7E-06 | 2.1E-05 | 6.1E-07 | 4.4E-05 | 16.0 | 34.7 | 5.1 | 12.6 |
| IL6R-BP088/ IL6R-L | G237D/P238D/K326A/ A330K | 3.9E-07 | 2.9E-06 | 2.3E-05 | 2.2E-07 | 5.7E-05 | 13.3 | 106.5 | 14.3 | 3.7 |
| IL6R-BP089/ IL6R-L | L234Y/P238D/K326A/ A330K | 6.3E-08 | 6.4E-06 | 2.0E-05 | 3.9E-07 | 1.6E-05 | 16.6 | 51.9 | 8.0 | 8.3 |
| IL6R-BP129/ IL6R-L | E233D/P238D/Y296D/ A330K | 2.5E-08 | 1.5E-05 | 4.0E-05 | 5.2E-07 | 7.5E-05 | 29.3 | 77.5 | 6.0 | 19.6 |

TABLE 26-continued

| VARIANT NAME | ALTERATION | KD (mol/L) FcγRIa | FcγRIIaR | FcγRIIaH | FcγRIIb | FcγRIIaV | KD(IIaR)/ KD(IIb) | KD(IIaH)/ KD(IIb) | KD(IIb) OF THE PARENT POLYPEPTIDE/KD(IIb) OF ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| IL6R-BP130/IL6R-L | E233D/P238D/V323M/A330K | 1.8E-09 | 5.3E-06 | 2.6E-05 | 3.0E-07 | 7.1E-05 | 17.5 | 85.5 | 10.2 | 6.9 |
| IL6R-BP131/IL6R-L | E233D/G237D/P238D/A330K | 1.2E-07 | 3.1E-06 | 1.4E-05 | 2.5E-07 | 5.9E-05 | 12.5 | 56.9 | 12.6 | 4.0 |
| IL6R-BP132/IL6R-L | E233D/P238D/K326A/A330K | 1.5E-08 | 8.0E-06 | 3.0E-05 | 3.7E-07 | 5.8E-05 | 21.5 | 81.1 | 8.4 | 10.3 |
| IL6R-BP133/IL6R-L | E233D/L234Y/P238D/A330K | 1.3E-07 | 8.6E-06 | 2.6E-05 | 5.6E-07 | 6.2E-05 | 15.5 | 46.8 | 5.6 | 11.2 |
| IL6R-BP143/IL6R-L | L234Y/P238D/K326A | 1.6E-08 | 5.7E-06 | 2.7E-05 | 5.7E-07 | 6.2E-05 | 10.0 | 47.1 | 5.4 | 7.5 |
| IL6R-BP144/IL6R-L | G237D/P238D/K326A | 3.7E-08 | 6.9E-06 | 3.6E-05 | 7.9E-07 | 5.5E-05 | 8.7 | 45.8 | 3.9 | 8.9 |
| IL6R-BP145/IL6R-L | L234Y/G237D/P238D | 1.2E-07 | 3.4E-06 | 1.7E-05 | 3.4E-07 | 4.5E-05 | 9.9 | 49.9 | 9.1 | 4.4 |
| IL6R-BP146/IL6R-L | L234Y/G237D/P238D/K326A | 7.4E-08 | 2.1E-06 | 1.8E-05 | 2.3E-07 | 3.8E-05 | 9.3 | 80.0 | 13.7 | 2.7 |
| IL6R-BP147/IL6R-L | L234Y/G237D/P238D/K326A/A330K | 1.4E-07 | 8.9E-07 | 5.1E-06 | 6.6E-08 | 3.3E-05 | 13.6 | 77.7 | 47.1 | 1.2 |
| IL6R-BP148/IL6R-L | E233D/L234Y/G237D/P238D/K326A/A330K | 8.9E-08 | 1.1E-06 | 7.0E-06 | 7.5E-08 | 3.0E-05 | 14.5 | 93.8 | 41.4 | 1.4 |
| IL6R-BP149/IL6R-L | E233D/L234Y/G237D/P238D/Y296D/K326A/A330K | 1.2E-07 | 1.4E-06 | 8.4E-06 | 9.3E-08 | 3.7E-05 | 15.0 | 89.9 | 33.1 | 1.8 |
| IL6R-BP150/IL6R-L | L234Y/G237D/P238D/K326A/A330R | 3.2E-07 | 5.5E-07 | 3.4E-06 | 3.1E-08 | 3.4E-05 | 17.7 | 109.0 | 99.0 | 0.7 |
| IL6R-BP151/IL6R-L | E233D/L234Y/G237D/P238D/K326A/A330R | 8.4E-08 | 6.7E-07 | 4.7E-06 | 4.0E-08 | 3.1E-05 | 16.9 | 117.8 | 77.4 | 0.9 |
| IL6R-BP152/IL6R-L | E233D/L234Y/G237D/P238D/V296D/K326A/A330R | 7.3E-08 | 8.1E-07 | 5.6E-06 | 4.1E-08 | 4.8E-05 | 19.5 | 135.9 | 75.0 | 1.0 |

TABLE 26-continued

| VARIENT NAME | ALTERATION | KD (mol/L) FcγRIa | FcγRIIaR | FcγRIIaH | FcγRIIb | FcγRIIaV | KD(IIaR)/ KD(IIb) | KD(IIaH)/ KD(IIb) | KD(IIb) OF THE PARENT POLYPEPTIDE/KD(IIb) OF ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| IL6R-BP176/IL6R-L | E233D/P238D/K326D/A330K | 7.3E-09 | 6.9E-06 | 3.0E-05 | 3.6E-07 | 5.4E-05 | 19.1 | 83.1 | 8.6 | 8.9 |
| IL6R-BP177/IL6R-L | E233D/L234Y/G237D/P238D/P271G/K326D/A330K | 3.3E-08 | 7.1E-07 | 8.2E-06 | 5.2E-08 | 3.7E-05 | 13.8 | 159.2 | 60.0 | 0.9 |
| IL6R-BP178/IL6R-L | E233D/G237D/P238D/P271G/A330K | 4.3E-08 | 9.3E-07 | 1.4E-05 | 5.1E-08 | 6.4E-05 | 18.1 | 272.4 | 60.1 | 1.2 |
| IL6R-BP179/IL6R-L | G237D/P238D/P271G/K326A/A330K | 6.4E-08 | 1.4E-06 | 1.6E-05 | 8.4E-08 | 5.6E-05 | 16.7 | 190.9 | 36.9 | 1.8 |
| IL6R-BP180/IL6R-L | G237D/P238D/P271G/A330K | 9.8E-08 | 1.2E-06 | 1.8E-05 | 6.2E-08 | 7.0E-05 | 18.6 | 290.8 | 49.9 | 1.5 |
| IL6R-BP181/IL6R-L | E233D/P238D/P271G/K326A/A330K | 7.5E-09 | 3.2E-06 | 2.6E-05 | 1.6E-07 | 5.7E-05 | 20.3 | 162.5 | 19.3 | 4.2 |
| IL6R-BP182/IL6R-L | E233D/P238D/P271G/Y296D/A330K | 1.0E-08 | 2.6E-06 | 2.8E-05 | 1.1E-07 | 5.8E-05 | 23.5 | 256.9 | 28.3 | 3.3 |
| IL6R-BP183/IL6R-L | E233D/L234Y/P238D/P271G/K326A/A330K | 1.7E-08 | 2.6E-06 | 1.5E-05 | 2.4E-07 | 5.6E-05 | 10.7 | 62.5 | 12.9 | 3.3 |
| IL6R-BP184/IL6R-L | E233D/P238D/P271G/A330K | 1.1E-08 | 2.3E-06 | 3.0E-05 | 1.3E-07 | 6.6E-05 | 18.2 | 238.1 | 24.5 | 3.0 |
| IL6R-BP185/IL6R-L | E233D/L234Y/G237D/P238D/P271G/K326A/A330K | 6.3E-08 | 8.8E-07 | 7.3E-06 | 6.9E-08 | 3.6E-05 | 12.6 | 105.2 | 44.5 | 1.1 |
| IL6R-BP186/IL6R-L | E233D/L234Y/G237D/P238D/P271G/Y296D/K326A/A330K | 4.5E-08 | 9.6E-07 | 9.3E-06 | 6.1E-08 | 4.9E-05 | 15.8 | 152.5 | 50.7 | 1.3 |
| IL6R-BP187/IL6R-L | L234Y/P238D/P271G/K326A/A330K | 2.5E-08 | 2.8E-06 | 1.8E-05 | 2.9E-07 | 5.6E-05 | 9.7 | 62.3 | 10.7 | 3.6 |
| IL6R-BP188/IL6R-L | E233D/G237D/P238D/H268D/P271G/A330K | 2.1E-08 | 1.0E-06 | 1.6E-05 | 4.6E-08 | 5.8E-05 | 21.9 | 350.1 | 67.6 | 1.3 |
| IL6R-BP189/IL6R-L | G237D/P238D/H268D/P271G/K326A/A330K | 4.2E-08 | 1.4E-06 | 2.1E-05 | 7.4E-08 | 4.9E-05 | 18.5 | 283.8 | 41.8 | 1.8 |

TABLE 26-continued

| VARIANT NAME | ALTERATION | KD (mol/L) | | | | KD(IIaR)/ KD(IIb) | KD(IIaH)/ KD(IIb) | KD(IIb) OF THE PARENT POLYPEPTIDE/KD(IIb) OF ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|
| | | FcγRIa | FcγRIIaR | FcγRIIaH | FcγRIIb | FcγRIIaV | | | | |
| IL6R-BP190/IL6R-L | G237D/P238D/H268D/ P271G/A330K | 6.3E-08 | 1.1E-06 | 1.7E-05 | 5.8E-08 | 4.5E-05 | 19.3 | 292.6 | 53

TABLE 26-continued

| VARIANT NAME | ALTERATION | KD (mol/L) FcγRIa | FcγRIIaR | FcγRIIaH | FcγRIIb | FcγRIIaV | KD(IIaR)/ KD(IIb) | KD(IIaH)/ KD(IIb) | KD(IIb) OF THE PARENT POLYPEPTIDE/KD(IIb) OF ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| IL6R-BP204/IL6R-L | E233D/P238D/P271G/K326A/A330R | 7.6E-09 | 4.5E-06 | 2.1E-05 | 2.5E-07 | 5.2E-05 | 17.6 | 82.7 | 12.2 | 5.8 |
| IL6R-BP205/IL6R-L | E233D/P238D/P271G/Y296D/A330R | 7.7E-09 | 3.5E-06 | 2.8E-05 | 1.6E-07 | 6.8E-05 | 21.8 | 176.1 | 19.4 | 4.5 |
| IL6R-BP206/IL6R-L | E233D/P238D/P271G/A330R | 8.2E-09 | 3.1E-06 | 2.4E-05 | 2.0E-07 | 6.9E-05 | 16.1 | 123.1 | 15.8 | 4.1 |
| IL6R-BP207/IL6R-L | E233D/P238D/A330R | 2.2E-08 | 1.9E-05 | 2.9E-05 | 8.4E-07 | 6.5E-05 | 23.0 | 34.5 | 3.7 | 25.1 |
| IL6R-BP208/IL6R-L | E233D/G237D/P238D/H268D/P271G/A330R | 1.9E-08 | 8.5E-07 | 8.3E-06 | 3.2E-08 | 5.3E-05 | 26.3 | 256.2 | 95.4 | 1.1 |
| IL6R-BP209/IL6R-L | G237D/P238D/H268D/P271G/K326A/A330R | 3.9E-08 | 1.2E-06 | 1.0E-05 | 5.1E-08 | 4.1E-05 | 22.7 | 195.3 | 60.4 | 1.5 |
| IL6R-BP210/IL6R-L | G237D/P238D/H268D/P271G/A330R | 6.5E-08 | 1.0E-06 | 9.5E-06 | 3.9E-08 | 4.6E-05 | 25.4 | 241.1 | 78.4 | 1.3 |
| IL6R-BP211/IL6R-L | E233D/P238D/H268D/P271G/K326A/A330R | 4.2E-09 | 4.1E-06 | 2.7E-05 | 2.2E-07 | 7.3E-05 | 18.5 | 120.5 | 13.8 | 5.4 |
| IL6R-BP212/IL6R-L | E233D/P238D/H268D/P271G/Y296D/A330R | 5.2E-09 | 3.5E-06 | 2.2E-05 | 1.7E-07 | 5.2E-05 | 21.1 | 133.3 | 18.7 | 4.5 |
| IL6R-BP213/IL6R-L | E233D/P238D/H268D/P271G/A330R | 4.1E-09 | 3.1E-06 | 2.4E-05 | 1.8E-07 | 6.3E-05 | 17.7 | 136.4 | 17.6 | 4.0 |
| IL6R-BP214/IL6R-L | E233D/L234Y/G237D/P238D/Y296D/K326D/A330K | 5.9E-08 | 1.7E-06 | 9.2E-06 | 1.2E-07 | 3.8E-05 | 14.5 | 78.0 | 26.2 | 2.2 |

The variable region and constant region in the sequence of the respective SEQ ID NOs are summarized in the following Table. In the table, "B3" refers to "2B999(B3)", "omlizH" refers to "omalizumab_VH", and "omlizL" refers to "omalizumab_VL".

TABLE 27

| SEQ ID NO | VARIABLE REGION | CONSTANT REGION |
|---|---|---|
| 15 | GpH7 | |
| 16 | GpL16 | k0 |
| 17 | GpH7 | B3 |
| 18 | IL6R | |
| 19 | IL6R | G1d |
| 20 | IL6R | IgG1-v1 |
| 21 | IL6R-L | k0 |
| 22 | IL6R | F11 |
| 23 | IL6R | B3 |
| 24 | IL6R | BP208 |
| 25 | omlizH | G1d |
| 26 | omlizL | CK |
| 27 | IL6R | BP230 |
| 28 | IL6R | BP264 |
| 29 | IL6R | BP267 |
| 30 | IL6R | G4d |
| 31 | IL6R | BP478 |
| 32 | IL6R | BP253 |
| 33 | IL6R | BP423 |
| 34 | GpH7 | G1d |
| 35 | GpH7 | A5 |
| 36 | IL6R | BP404 |
| 37 | IL6R | BP408 |
| 38 | IL6R | BP419 |
| 39 | IL6R | BP407 |
| 40 | IL6R | BP409 |
| 41 | IL6R | BP410 |
| 42 | IL6R | AP029 |
| 43 | | BP230 |
| 44 | | BP231 |
| 45 | | BP265 |
| 46 | | BP391 |
| 47 | | BP429 |
| 48 | | BP436 |
| 49 | | BP437 |
| 50 | | BP445 |
| 51 | | BP473 |
| 52 | | BP478 |
| 53 | | BP481 |

TABLE 27-continued

| SEQ ID NO | VARIABLE REGION | CONSTANT REGION |
|---|---|---|
| 54 | | BP487 |
| 55 | | BP488 |
| 56 | | BP489 |
| 57 | | BP490 |
| 58 | | BP491 |
| 59 | | BP492 |
| 60 | | BP493 |
| 61 | | BP494 |
| 62 | | BP495 |
| 63 | | BP498 |
| 64 | | BP499 |
| 65 | | BP503 |
| 66 | | BP509 |
| 67 | | BP510 |
| 68 | | BP511 |
| 69 | IL6R | A5 |
| 70 | | Fc(P587) |
| 71 | | Fc(P588) |
| 72 | IL6R | P587 |
| 73 | IL6R | P587-LS |
| 74 | IL6R-L2 | k0 |
| 75 | | BP557 |
| 76 | | BP559 |
| 77 | | BP567 |
| 78 | | Fc(DLE) |
| 79 | | Fc(YTE) |
| 80 | | Fc(EF) |
| 81 | | Fc(P208) |

INDUSTRIAL APPLICABILITY

An Fc region variant with enhanced FcγRIIb-binding activity, and enhanced binding selectivity to FcγRIIb compared to FcγRIIa (type R), as compared to those of a polypeptide comprising an Fc region to which amino acid alteration(s) have not been introduced; and a polypeptide which comprises the Fc region variant. Use of the polypeptide enables transmission of an inhibitory signal of inflammatory immune response mediated by phosphorylation of ITIM of FcγRIIb. Furthermore, by conferring an antibody Fc with the property of selective FcγRIIb binding, anti-drug antibody production may be suppressed through FcγRIIb-mediated immunosuppressive actions.

The invention claimed is:

1. A protein comprising an IgG Fc region variant in which the amino acid at position 238 (EU numbering) is Asp, wherein the IgG Fc region variant further comprises one of the following combinations (i) to (xxiv) (all positions by EU numbering):

(i) Asp at position 233, Asp at position 237, Asp at position 268, Gly at position 271, Asp at position 296, and Arg at position 330;

(ii) Asp at position 237, Asp or Glu at position 268, Gly at position 271, Asp at position 296, and Arg at position 330;

(iii) Asp at position 233, Asp at position 237, Asp at position 268, Gly at position 271, Asp at position 296, Arg at position 330, and Thr at position 332;

(iv) Asp at position 233, Asp at position 237, Ile at position 264, Gly or Ala at position 267, Glu at position 268, Gly at position 271, and Arg at position 330;

(v) Asp at position 233, Asp at position 237, Ala at position 267, Glu at position 268, Gly at position 271, Asp at position 296, Arg at position 330, and Thr at position 332;

(vi) Asp at position 237, Ala at position 267, Glu at position 268, Gly at position 271, Asp at position 296, Arg at position 330, and Thr at position 332;

(vii) Asp at position 233, Asp at position 237, Ile at position 264, Ala at position 267, Glu at position 268, and Gly at position 271;

(viii) Asp at position 233, Asp at position 237, Ile at position 264, Ala at position 267, Glu at position 268, Gly at position 271, Asp at position 296, and Arg at position 330;

(ix) Asp at position 233, Asp at position 237, Ile at position 264, Ala at position 267, Glu at position 268, Gly at position 271, Asp at position 296, Arg at position 330, and Met or Leu at position 396;

(x) Asp at position 237, Ile at position 264, Ala at position 267, Glu at position 268, Gly at position 271, and Arg at position 330;

(xi) Asp at position 237, Ile at position 264, Ala at position 267, Glu at position 268, Gly at position 271, Asp at position 296, and Arg at position 330;

(xii) Ile at position 264, Ala at position 267, Glu at position 268, and Gly at position 271;

(xiii) Ile at position 264, Ala at position 267, Glu at position 268, Gly at position 271, and Asp at position 296;

(xiv) Asp at position 237, Ala or Gly at position 267, Glu at position 268, Gly at position 271, Asp at position 296, and Arg at position 330;

(xv) Asp at position 233, Asp at position 237, Ile at position 264, Ala at position 267, Glu at position 268, Gly at position 271, Arg at position 330, and Met or Leu at position 396;

(xvi) Asp at position 233, Asp at position 237, Ile at position 264, Ala at position 267, Glu at position 268, Gly at position 271, Asp at position 296, Gly at position 327, Arg at position 330, and Met at position 396;

(xvii) Asp at position 233, Asp at position 237, Ile at position 264, Ala at position 267, Glu at position 268, Gly at position 271, Asp at position 272, and Asp at position 296;

(xviii) Asp at position 237, Ile at position 264, Ala at position 267, Glu at position 268, Gly at position 271, Pro at position 272, and Arg at position 330;

(xix) Asp at position 237, Ile at position 264, Ala at position 267, Glu at position 268, Gly at position 271, Pro at position 272, Asp at position 296, and Arg at position 330;

(xx) Asp at position 233, Ile at position 264, Ala at position 267, Glu at position 268, and Gly at position 271;

(xxi) Asp at position 237, Gly at position 267, Asp at position 268, Gly at position 271, Asp at position 296, and Arg at position 330;

(xxii) Ile at position 264, Ala at position 267, Glu at position 268, Gly at position 271, Asp at position 272, Asp at position 296;

(xxiii) Asp at position 233, Ile at position 264, Ala at position 267, Glu at position 268, Gly at position 271, and Asp at position 296; or (xxiv) Asp at position 233, Tyr at position 234, Phe at position 235, Asp at position 237, Ile at position 264, Glu at position 265, Phe at position 266, Ala at position 267, Asp at position 268, Asp at position 269, Gly at position 271, Asp at position 272, Gln at position 274, Asp at position 296, Ala at position 326, Gly at position 327, Lys at position 330, Ser at position 331, Lys at position 332, Lys at position 333, Arg at position 334, Ala at position 355, Glu at position 356, Met at position 358, Ala at position 396, Arg at position 409, and Glu at position 419.

2. The protein of claim 1, wherein the ratio of [KD value for FcγRIIa (type R) of a polypeptide comprising the Fc region variant]/[KD value for FcγRIIb of the polypeptide comprising the Fc region variant] is 10.0 or more, and wherein the respective KD values are determined using a surface plasmon resonance technique in which the polypeptide comprising the Fc region variant is immobilized, an extracellular domain of the respective Fcγ receptor serves as analyte, and the following conditions are used: 0.01 M HEPES pH 7.4, 0.15 M NaCl, 3 mM ethylene diamine tetraacetic acid (EDTA), 0.05% polysorbate 20, at 25° C.

3. The protein of claim 2, wherein the ratio of [KD value for FcγRIIa (type R) of the polypeptide comprising the Fc region variant]/[KD value for FcγRIIb of the polypeptide comprising the Fc region variant] is 20.0 or more.

4. The protein of claim 1, wherein the ratio of [KD value for FcγRIIb of a first polypeptide comprising an Fc region of SEQ ID NO: 11/[KD value for FcγRIIb of a second polypeptide comprising the Fc region variant] is 15.0 or more, wherein the first and second polypeptides are identical to each other except in their Fc regions, and wherein the respective KD values are determined using a surface plasmon resonance technique in which the first or second polypeptide, respectively, is immobilized, an extracellular domain of the respective Fcγ receptor serves as analyte, and the following conditions are used: 0.01 M HEPES pH 7.4, 0.15 M NaCl, 3 mM ethylene diamine tetraacetic acid (EDTA), 0.05% polysorbate 20, at 25° C.

5. The protein of claim 4, wherein the ratio of [KD value for FcγRIIb of the first polypeptide/[KD value for FcγRIIb of the second polypeptide] is 50.0 or more.

6. The protein of claim 4, wherein the ratio of [KD value for FcγRIIb of the first polypeptide/[KD value for FcγRIIb of the second polypeptide] is 100.0 or more.

7. The protein of any of claims 1 to 6, wherein the protein comprises an IgG antibody.

8. A pharmaceutical composition comprising the protein of claim 7.

* * * * *